US009505829B2

(12) United States Patent
Lacy et al.

(10) Patent No.: US 9,505,829 B2
(45) Date of Patent: Nov. 29, 2016

(54) ANTI-NGF ANTIBODIES AND THEIR USE

(75) Inventors: Susan E. Lacy, Westborough, MA (US); Jeffrey A. Barbon, Groton, MA (US); Meha Chhaya, Shrewsbury, MA (US); Emma Fung, Northborough, MA (US); Charles W. Hutchins, Green Oaks, IL (US); Diane M. Lang, Hope Valley, RI (US); Eve H. Barlow, Wellesley, MA (US); Mary Leddy, North Atteboro, MA (US); Ravi Chari, Norwich, CT (US)

(73) Assignee: ZOETIS BELGIUM S.A., Louvain-la-Neuve (BE)

( * ) Notice: Subject to any disclaimer, the term of this patent is extended or adjusted under 35 U.S.C. 154(b) by 0 days.

(21) Appl. No.: 13/817,721

(22) PCT Filed: Aug. 19, 2011

(86) PCT No.: PCT/US2011/048518
§ 371 (c)(1),
(2), (4) Date: Aug. 27, 2013

(87) PCT Pub. No.: WO2012/024650
PCT Pub. Date: Feb. 23, 2012

(65) Prior Publication Data
US 2013/0330348 A1    Dec. 12, 2013

Related U.S. Application Data

(60) Provisional application No. 61/375,193, filed on Aug. 19, 2010.

(51) Int. Cl.
*C07K 16/22* (2006.01)
*A61K 39/395* (2006.01)

(52) U.S. Cl.
CPC ........... *C07K 16/22* (2013.01); *C07K 2317/24* (2013.01); *C07K 2317/31* (2013.01); *C07K 2317/50* (2013.01); *C07K 2317/54* (2013.01); *C07K 2317/55* (2013.01); *C07K 2317/565* (2013.01); *C07K 2317/569* (2013.01); *C07K 2317/60* (2013.01); *C07K 2317/622* (2013.01); *C07K 2317/624* (2013.01); *C07K 2317/626* (2013.01); *C07K 2317/64* (2013.01); *C07K 2317/73* (2013.01); *C07K 2317/76* (2013.01); *C07K 2317/92* (2013.01); *C07K 2317/94* (2013.01)

(58) Field of Classification Search
CPC ............................... C07K 14/48; A61K 38/18
See application file for complete search history.

(56) References Cited

U.S. PATENT DOCUMENTS

| 4,230,691 | A | 10/1980 | Young |
| 4,526,938 | A | 7/1985 | Churchill et al. |
| 4,554,101 | A | 11/1985 | Hopp |
| 4,676,980 | A | 6/1987 | Segal et al. |
| 4,816,567 | A | 3/1989 | Cabilly et al. |
| 4,946,778 | A | 8/1990 | Ladner et al. |
| 4,980,286 | A | 12/1990 | Morgan et al. |
| 5,128,326 | A | 7/1992 | Balasz et al. |
| 5,130,311 | A | 7/1992 | Guillaumet et al. |
| 5,147,294 | A | 9/1992 | Smith et al. |
| 5,223,409 | A | 6/1993 | Ladner et al. |
| 5,225,539 | A | 7/1993 | Winter |
| 5,258,498 | A | 11/1993 | Huston |
| 5,290,540 | A | 3/1994 | Prince et al. |
| 5,342,942 | A | 8/1994 | Jaen et al. |
| 5,350,576 | A | 9/1994 | Payne et al. |
| 5,403,484 | A | 4/1995 | Ladner et al. |
| 5,409,944 | A | 4/1995 | Black et al. |
| 5,427,908 | A | 6/1995 | Dower et al. |
| 5,436,265 | A | 7/1995 | Black et al. |
| 5,500,362 | A | 3/1996 | Robinson et al. |
| 5,510,368 | A | 4/1996 | Lau et al. |
| 5,516,637 | A | 5/1996 | Huang et al. |
| 5,530,101 | A | 6/1996 | Queen et al. |
| 5,536,752 | A | 7/1996 | Ducharme et al. |
| 5,545,806 | A | 8/1996 | Lonberg et al. |
| 5,545,807 | A | 8/1996 | Surani et al. |
| 5,550,142 | A | 8/1996 | Ducharme et al. |
| 5,552,422 | A | 9/1996 | Gauthier et al. |
| 5,565,332 | A | 10/1996 | Hoogenboom et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,593,994 | A | 1/1997 | Batt et al. |

(Continued)

FOREIGN PATENT DOCUMENTS

| WO | 89/09225 A1 | 10/1989 |
| WO | 90/02809 A1 | 3/1990 |

(Continued)

OTHER PUBLICATIONS

Examination Report for Australian Application No. 2011291462 mailed Feb. 18, 2014.
International Search Report and Written Opinion for Application No. PCT/US20111048518, mailed on Apr. 12, 2012, 30 pages.
Examination report for European Application No. 11 767 319.4, date Apr. 9, 2014, 7 pages.
Okragly, et al., J. Urology 6: 438-441 (1999).
Otten et al., Eur J Pharm 106(1): 199-201 (1985).
Otten et al., PNAS 86: 10059-10063 (1989).

(Continued)

*Primary Examiner* — Robert C Hayes
(74) *Attorney, Agent, or Firm* — Kelly M. Sullivan

(57) ABSTRACT

The present disclosure encompasses NGF binding proteins, specifically to antibodies that are chimeric, CDR grafted and canonized antibodies, and methods of making and uses thereof. The antibodies, or antibody portions, of the disclosure are useful for detecting NGF and for inhibiting NGF activity, e.g., in a mammal subject suffering from a disorder in which NGF activity is detrimental.

13 Claims, 46 Drawing Sheets

(56) References Cited

U.S. PATENT DOCUMENTS

| | | |
|---|---|---|
| 5,604,253 A | 2/1997 | Lau et al. |
| 5,604,260 A | 2/1997 | Guay et al. |
| 5,616,601 A | 4/1997 | Khanna et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,639,780 A | 6/1997 | Lau et al. |
| 5,648,260 A | 7/1997 | Winter et al. |
| 5,656,435 A | 8/1997 | Nakahama et al. |
| 5,658,727 A | 8/1997 | Barbas et al. |
| 5,679,377 A | 10/1997 | Bernstein et al. |
| 5,693,761 A | 12/1997 | Queen et al. |
| 5,693,762 A | 12/1997 | Queen et al. |
| 5,698,426 A | 12/1997 | Huse |
| 5,712,100 A | 1/1998 | Nakahama et al. |
| 5,714,352 A | 2/1998 | Jakobovits |
| 5,723,323 A | 3/1998 | Kauffman et al. |
| 5,733,743 A | 3/1998 | Johnson et al. |
| 5,750,373 A | 5/1998 | Garrard et al. |
| 5,763,192 A | 6/1998 | Kauffman et al. |
| 5,766,886 A | 6/1998 | Studnicka et al. |
| 5,780,225 A | 7/1998 | Wigler et al. |
| 5,807,715 A | 9/1998 | Morrison et al. |
| 5,814,476 A | 9/1998 | Kauffman et al. |
| 5,817,483 A | 10/1998 | Kauffman et al. |
| 5,821,047 A | 10/1998 | Garrard et al. |
| 5,821,337 A | 10/1998 | Carter et al. |
| 5,824,514 A | 10/1998 | Kauffman et al. |
| 5,843,942 A | 12/1998 | Breault et al. |
| 5,844,092 A | 12/1998 | Presta et al. |
| 5,852,183 A | 12/1998 | Maeda |
| 5,855,913 A | 1/1999 | Hanes |
| 5,866,692 A | 2/1999 | Shitara et al. |
| 5,874,064 A | 2/1999 | Edwards et al. |
| 5,877,016 A | 3/1999 | Presta et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jokobovits et al. |
| 6,017,878 A | 1/2000 | Saragovi et al. |
| 6,019,968 A | 2/2000 | Platz et al. |
| 6,027,927 A | 2/2000 | Presta et al. |
| 6,054,297 A | 4/2000 | Carter et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,153,189 A | 11/2000 | Presta et al. |
| 6,180,370 B1 | 1/2001 | Queen et al. |
| 6,180,377 B1 | 1/2001 | Morgan et al. |
| 6,194,167 B1 | 2/2001 | Browse et al. |
| 6,204,023 B1 | 3/2001 | Robinson et al. |
| 6,265,150 B1 | 7/2001 | Terstappen et al. |
| 6,291,247 B1 | 9/2001 | Riopelle et al. |
| 6,350,861 B1 | 2/2002 | Co et al. |
| 6,399,780 B1 | 6/2002 | Hudkins |
| 6,492,380 B1 | 12/2002 | Ross et al. |
| 6,548,062 B2 | 4/2003 | Buchkovich et al. |
| 6,548,640 B1 | 4/2003 | Winter |
| 6,649,605 B2 | 11/2003 | Olesen et al. |
| 6,656,465 B2 | 12/2003 | Clary et al. |
| 6,699,658 B1 | 3/2004 | Wittrup et al. |
| 6,774,107 B1 | 8/2004 | Strittmatter et al. |
| 6,790,639 B2 | 9/2004 | Brown et al. |
| 6,797,492 B2 | 9/2004 | Daugherty et al. |
| 6,919,426 B2 | 7/2005 | Boone et al. |
| 7,022,484 B2 | 4/2006 | High et al. |
| 7,029,872 B2 | 4/2006 | Gerngross |
| 7,117,096 B2 | 10/2006 | Luo et al. |
| 7,220,840 B2 | 5/2007 | Ruben et al. |
| 7,252,822 B2 | 8/2007 | Shelton et al. |
| 7,255,860 B2 | 8/2007 | Shelton et al. |
| 7,261,890 B2 | 8/2007 | Krah, III et al. |
| 7,393,648 B2 | 7/2008 | Rother et al. |
| 7,425,329 B2 | 9/2008 | Shelton et al. |
| 7,449,308 B2 | 11/2008 | Gerngross et al. |
| 7,449,616 B2 | 11/2008 | Pons et al. |
| 7,569,364 B2 | 8/2009 | Rosenthal et al. |
| 7,601,352 B1 | 10/2009 | Novak |
| 7,612,181 B2 | 11/2009 | Wu et al. |
| 7,655,231 B2 | 2/2010 | Shelton et al. |
| 7,655,232 B2 | 2/2010 | Pons et al. |
| 7,727,527 B2 | 6/2010 | Shelton |
| 2003/0031671 A1 | 2/2003 | Welt et al. |
| 2009/0041717 A1 | 2/2009 | MacDonald et al. |

FOREIGN PATENT DOCUMENTS

| | | |
|---|---|---|
| WO | 90/10700 A1 | 9/1990 |
| WO | 90/14424 A1 | 11/1990 |
| WO | 90/14443 A1 | 11/1990 |
| WO | 91/05548 A1 | 5/1991 |
| WO | 91/09966 A1 | 7/1991 |
| WO | 91/09967 A1 | 7/1991 |
| WO | 91/10737 A1 | 7/1991 |
| WO | 91/10741 A1 | 7/1991 |
| WO | 92/02551 A1 | 8/1991 |
| WO | 91/14430 A1 | 10/1991 |
| WO | 91/17271 A1 | 11/1991 |
| WO | 92/01047 A1 | 1/1992 |
| WO | 92/03461 A1 | 3/1992 |
| WO | 92/09631 A1 | 6/1992 |
| WO | 92/09690 A2 | 6/1992 |
| WO | 95/15982 A1 | 6/1992 |
| WO | 92/11272 A1 | 7/1992 |
| WO | 92/15679 A1 | 9/1992 |
| WO | 92/18619 A1 | 10/1992 |
| WO | 92/19244 A1 | 11/1992 |
| WO | 92/20791 A1 | 11/1992 |
| WO | 92/22324 A1 | 12/1992 |
| WO | 93/01288 A1 | 1/1993 |
| WO | 93/06213 A1 | 4/1993 |
| WO | 93/11236 A1 | 6/1993 |
| WO | 94/02602 A1 | 2/1994 |
| WO | 94/18219 A1 | 8/1994 |
| WO | 95/20401 A1 | 8/1995 |
| WO | 95/25795 A1 | 9/1995 |
| WO | 96/20698 A1 | 7/1996 |
| WO | 96/33735 A1 | 10/1996 |
| WO | 96/34096 A1 | 10/1996 |
| WO | 97/15593 A1 | 5/1997 |
| WO | 97/20032 A1 | 6/1997 |
| WO | 97/21732 A1 | 6/1997 |
| WO | 97/29131 A1 | 8/1997 |
| WO | 97/32572 A1 | 9/1997 |
| WO | 97/44013 A1 | 11/1997 |
| WO | 98/06048 A2 | 2/1998 |
| WO | 98/16654 A1 | 4/1998 |
| WO | 98/17278 A1 | 4/1998 |
| WO | 98/24893 A2 | 6/1998 |
| WO | 98/31346 A1 | 7/1998 |
| WO | 98/31700 A1 | 7/1998 |
| WO | 98/50433 A2 | 11/1998 |
| WO | 99/06834 A2 | 2/1999 |
| WO | 99/15154 A1 | 4/1999 |
| WO | 99/20253 A1 | 4/1999 |
| WO | 99/45031 A1 | 9/1999 |
| WO | 99/53049 A1 | 10/1999 |
| WO | 99/53055 A2 | 10/1999 |
| WO | 99/58572 A1 | 11/1999 |
| WO | 00/37504 A2 | 12/1999 |
| WO | 99/66903 A2 | 12/1999 |
| WO | 00/09560 A2 | 2/2000 |
| WO | 00/56772 A1 | 9/2000 |
| WO | 00/69828 A1 | 11/2000 |
| WO | 00/73344 A2 | 12/2000 |

(56) References Cited

FOREIGN PATENT DOCUMENTS

| | | |
|---|---|---|
| WO | 01/64247 A2 | 9/2001 |
| WO | 01/77332 A2 | 10/2001 |
| WO | 01/78698 A2 | 10/2001 |
| WO | 01/83525 A2 | 11/2001 |
| WO | 02/072636 A2 | 9/2002 |
| WO | 02/102232 A2 | 12/2002 |
| WO | 02096458 A1 | 12/2002 |
| WO | 03/022261 A1 | 3/2003 |
| WO | 03/029456 A1 | 4/2003 |
| WO | 03060080 A2 | 7/2003 |
| WO | 2004/026329 A1 | 4/2004 |
| WO | 2004/032852 A2 | 4/2004 |
| WO | 2004/032870 A2 | 4/2004 |
| WO | 2004/256385 A2 | 7/2004 |
| WO | 2004058184 A2 | 7/2004 |
| WO | 2004/065560 A2 | 8/2004 |
| WO | 2004/073653 A2 | 9/2004 |
| WO | 2004/096122 A2 | 11/2004 |
| WO | 2005/000194 A2 | 1/2005 |
| WO | 2005/019266 A2 | 3/2005 |
| WO | 2005/061540 A2 | 7/2005 |
| WO | 2005/111077 A2 | 11/2005 |
| WO | 2005/035575 A3 | 4/2006 |
| WO | 2006/077441 A1 | 7/2006 |
| WO | 2006/110883 A2 | 10/2006 |
| WO | 2006/121558 A2 | 11/2006 |
| WO | 2006/131951 A2 | 12/2006 |
| WO | 2006/131952 A2 | 12/2006 |
| WO | 2008/046033 A2 | 8/2008 |
| WO | 2009/023540 A1 | 2/2009 |
| WO | 2009/077993 A2 | 6/2009 |
| WO | 2009/091972 A2 | 7/2009 |
| WO | 2009150623 A1 | 12/2009 |
| WO | 2010/027488 A2 | 3/2010 |

OTHER PUBLICATIONS

Owens et al J Immunol Methods 168(2):149-165 (1994).
Padlan FASEB J. 9: 133-139 (1995).
Paulus et al., Arthritis and Rheumatism 33(4): 477-485 (1990).
Pearce, et al., J. Physiol, 372:379-393 (1986).
Pearson Arthritis-Rheum 2: 440-459 (1959).
Pelat et al., mAbs 1: 377-381 (2009).
Petersen et al., Neuroscience 83: 161-168 (1998).
Petty et al., Annals Neuro 36: 244-246 (1994).
Poljak RJ, Structure 15(2): 1121-1123 (1994).
Pollack J Immunol Meth 231: 147-157 (1999).
Pons et al., Protein Science 8: 958-968 (1999).
Pozza et al., J Rheumatol 27(5): 1121-1127 (2000).
Presta, Current Opin Immunol 5-6: 640-656 (2006).
Prodromou and Pearl, Protein Engineering 5(8) 827-829) (1992).
Puigdellivol-Sanchez et al., Neuro Lett 251(3): 169-172 (1998).
Ramer and Bisby, Eur J Neuro 11:837-846 (1999).
Ravetch and Kinet, 1991, Ann. Rev. Immunol., 9:457-92 (1991).
Raychaudhuri Acta Derm Venereol 78: 84-86 (1998).
Riechmann et al., nature 332: 323-327 (1988).
Ro et al., Neuro Letters 218:87-90 (1996).
Ro et al., Pain 79: 265-274 (1999).
Rosak et al., J Biol Chem 271:22611-22618 (1996).
Roubenoff et al., J Clin Inves 93: 2379-2386 (1994).
Roubenoff et al.,Arthritis Rheum 40(3): 534-539 (1997).
Ruberti et al. (1993) Cell. Molec. Neurobiol. 13(5): 559-568 (1993).
Rudikoff et al., PNAS 79: 1979-1963 (1982).
Saragovi et al., Trends Pharmacol Sci. 21: 93-98 (2000).
Schwartz, et al., J Photochem. Photobiol., B66: 195-200 (2002).
Schwei et al., J Neuro 19(24): 10886-10897 (1999).
Sevcik et al., Pain 115: 128-141 (2005).
Shapiro et al., Crit. Rev. Immunol. 22(3): 183-200 (2002).
Shaw et al., J Immunol 138(12): 4534-4538 (1987).
Sheets et al., PNAS 95: 6157-6162 (1998).
Shelton and Reichardt, PNAS 81: 7951-7955 (1984).
Shelton et al., Rest Neurol and Neuro 8: 99-100 (1995).
Shih et al., J Biol Chem 269: 27679-27686 (1994).
Smeyne, et al, Nature 368:246-249 (1994).
Stanisz., Annals of NY Acad Sci 917(1): 268-272 (2000).
Steiner, et al., Am. J. Physiol., 261 :F792-798 (1991).
Szekanecz et al., Arth Rheum 43 (6): 1266-1277 (2000).
Taglialatela et al., J Neurochem 66: 1826-1835 (1996).
Taylor, L. D., et al. (1992) Nucl. Acids Res. 20:6287-6295 (1992).
Torcia, et al, Cell 85:345-356 (1996).
Ueyama, et al, J Hypertens. 11: 1061-1065 (1993).
Ullrich et al., Nature 303: 821-825 (1983).
Umana etl al Nature Biotech 17:176-180 (1999).
Urfer et al., Biochemisry 36: 4775-4781 (1997).
Adey et al. Phage Display of Peptides and Proteins: 277-291 (1996).
Aley et al., Neuroscience 71: 1083-1090 (1996).
Al-Lazikani et al., 273-927-948 (1997).
Aloe et al., Growth Factors 9: 149-155 (1993).
Aloe et al., Int. J. Tiss. Reac XV(4) 139-143 (1993).
Aloe et al., Rheumatol. Int. 14: 249-252 (1995).
Aloe, Clin and Exp Rheum 10: 203-204 (1992).
Aloe, Clin Exp Theumatol 17: 632-633 (1999).
Aloe, et al., Arch. Rheum. 35:351-355 (1992).
Amann et al., Pain 64: 323-329 (1995).
Andreev et al., Pain 63: 109-115 (1995).
Apfel et al., Mol and Cell. Neuro 7: 134-142 (1996).
Apfel, S.C. et al., Neurology, 51: 695-702 (1998).
Armour et al., Eur J. Immunol 29: 2613-2624 (1999).
Azzazy et al., Clin. Biochem., 35: 425-445 (2002).
Balint et al., Gene, 137: 109-118 (1993).
Bellamy et al., J. Rheumatol., 15: 1833-1840 (1988).
Bellamy, N., Semin Arthritis Rheum, 18: 14-17 (1989).
Bellini and Viola, Intern J Neuroscience, 51: 329-330 (1990).
Berrera et al., Biophys J, 91: 2063-2071 (2006).
Bibel et al., Genes Dev, 14(23): 2919-2937 (2000).
Bird et al., Science, 242: 423-426 (1988).
Bischoff et al., Blood 79: 2662-2669 (1992).
Boerner et al., J Immuno 147: 86-95 (1991).
Borsani et al., Nucleic Acids Research 18(13) 4020 (1990).
Bracci-Laudiero, et al, Neurosci. Lett. 147:9-12 (1992).
Bracci-Laudiero, et al., Neuroreport 4:563-565 (1993).
Braun, et al., Eur. J. Immunol., 28:3240-3251 (1998).
Brennan et al., Anesthesiology Clin N Am 23: 1-20 (2005).
Brennan et al., ILAR Journal 40(3): 129-136 (1999).
Brennan, Soc Neurosci Abstract 349.4 (1998).
Brosseau et al., The Cochrane Database of Systematic Reviews 4: Art No. CD004522 (2003).
Brown et al., Cancer Res 47: 3577-3583 (1987).
Buchman et al., Development 118: 989-1001 (1993).
Calissano et al., Cell Death and Differentiation, 17: 1126-1133 (2010).
Capel et al. Immunomethods, 4:25-34 (1994).
Caraceni J Pain Symptom Management 23: 239-255 (2002).
Chao, et al, Science 232:518-521 (1986).
Chaplan et al., J Neuro Methods 53: 55-63 (1994).
Choi et al., Life Sciences 73: 471-485 (2003).
Chothia and Lesk J. Mol. Biol. 196:901-917 (1987).
Chothia et al. Nature 342:877-883 (1989).
Chothia et al., J. Mol. Biol., 227:799 (1992).
Christensen and Hulsebosch, Experimental Neurology147(2):463-475 (1997).
Chun et al., J Cell Biol 75: 705-711 (1977).
Clackson et al., Nature 352:624 628 (1991).
Clohisy et al., Clin Ortho and Rel Res 415S: S279-S288 (2003).
Clynes et al., 1998, PNAS (USA), 95:652-656 (1998).
Covaceuzach et al., J Mol Bio 4: 881-896 (2008).
Covaceuzach et al., PLoS One 7: 1-12 (2012).
Cromartie et al., J Exp Med 146: 1585-1602 (1977).
Crowley et al. Cell 76:1001-1011 (1994).
Kabat et al., Ann. NY Acad, Sci., 190:382-391 (1971).
Kassel, et al., Clin, Exp. Allergy, 31: 1432-40 (2001).
Katz and Melzack, Surg Clin North Am 79: 231-252 (1999).
Kawamoto et al., J Immunol 168: 6412-6419 (2002).
Kazemier et al., J Immunol Methods 194: 201-209 (1996).

(56) References Cited

OTHER PUBLICATIONS

Kellermann et al., Current Opinion in Biotechnology, 13: 593-597 (2002).
Kidd et al, Br J Anaesthesia 87 (1) 3-11 (2001).
Kim et al., Eur J. Immunol 24: 2429-2434 (1994).
Kipriyanov, et al., Mol. Immunol., 31: 1047-1058 (1994).
Kipriyanov, S.M., et al., Human Antibodies and Hybridomas, 6: 93-101 (1995).
Klein et al, Cell 61: 647-656 (1990).
Knusel et al., J Neurochem 57: 955-962 (1990).
Knusel et al., J Neurochem 59: 715-721 (1992).
Koizumi et al., J.Neurosci 8: 715-721 (1988).
Kryger, et al., J. Hand Surg. (Am.), 26: 635-644 (2001).
Kuzuna and Kawai, Chem Pharm Bulletin 23: 1184-1191 (1975).
Lamballe et al., EMBO J 12(8): 3083-3094 (1993).
Lane et al., New England Journal of Medicine 363: 1521-1531 (2010).
Lane, N., Osteoarthritis and Cartilage Abstracts 20: S1-S9(2012).
Lefranc et al., Nucleic Acids Res, 27:209-212 (1999).
Leon et al., PNAS 81: 3739-3743 (1994).
Levi-Montalcini and Angeletti, Physiol Rev 48; 534-569 (1968).
Levi-Montalcini, Science 187: 113 (1975).
Lewin et al Eur J Neuroscience 6: 1903-1912 (1994).
Lewin et al., J Neuroscience 13: 2136-2148 (1993).
Li et al., PNAS 95: 10884-10889 (1998).
Linday, R., J Neuroscience 8(7): 2394-2405 (1988).
Lindsholm, et al., Eur. J. Neurosci. 2:795-801 (1990).
Lindsay, et al, Nature 337:362-364 (1989).
Little et al., Immunology Today, 21: 364-370 (2000).
LoBuglio et al., PNAS 86: 4220-4224 (1989).
Lonberg et al., In Rev Immunol 13:65-93 (1995).
Luger et al. Cancer Research 61: 4038-4047 (2001).
MacCallum (J Mol Biol 262(5):732-45 (1996).
Mach et al., Neuroscience 113(1): 155-166 (2002).
Manni et al., Rheumatol Int 18: 97-102 (1998).
Mantyh et al., Nature Reviews Cancer 2(3): 201-209 (2002).
Marchalonis et al, Adv Exp MedBiol. 484: 13-30 (2001).
Marks et al., Bio Technol 10:779-783 (1992).
Marks et al., J. Mol. Biol. 222:581 597 (1991).
Martin, et al., Proc. Natl. Acad. Sci. USA, 86:9268-9272 (1989).
Matsuda et al., PNAS 85(17):6508-6512 (1988).
McCafferty et al., Nature 348:552-554 (1990).
McDonald et al., Nature 354:411-414 (1991).
McMahon et al., Nature Medicine 1:774-780 (1995).
McMahon et al., Phil. Trans R. Soc. Land B 351(1338):431-440 (1996).
Meenan et al., Arthritis Rheumatism 25: 1048-1053 (1982).
Milstein, Nature 305: 537-540 (1983).
Moiniche et al., Anesthesiology 96: 725-741 (2002).
Molander and Grant, J Comp Neuro 260: 246-255 (1987).
Molnar et al., Eur J Neuro 10:3127-3140 (1998).
Morrison et al., PNAS 81: 6851-6855 (1984).
Muyldermans Rev Mol Biotech 74: 277-302 (2001).
Myers and Miller, CABIOS 4: 11-17 (1988).
Nanduri et al., J Neuro Res 37: 433-444 (1994).
Niissalo et al., Ann NY Acad Sci 966:384-399 (2002).
Daughtery, Nucleic Acids Research 19: 2471-2476 (1991).
De Haas et al., J. Lab. Clin. Med., 126:330-41 (1995).
DeKock et al., Pain 92:373-380 (2001).
Devereux et al., Nucl Acid. Res., 12:387 (1984).
Dicou et al., Autoimmunity 24: 1-9 (1996).
Dicou et al., J Neuroimmun 47(159-167 (1993).
Dicou et al., J. Neuroimmun 75: 200-203 (1997).
Dicou et al., NeuroReport 5: 321-324 (1993).
DiMarco et al., J Biol Chem 268(30) 22838-22846 (1993).
Donnerer et al., Neuroscience 49(3): 693-698 (1992).
Eide et al., J. Neuroscience 16(10) 3123-3129 (1996).
Falcini et al., Ann Rheum Dis 55: 745-748 (1996).
Felson et al., Arthritis Rheumatism 36: 729-740 (1993).
Fjell et al., J. Neurophysiol 81: 803-810 (1999).
Foote and Winter, J Mol Biol 224: 487-499 (1992).
Foster et al., J. Pathol 197: 245-255 (2002).
Fries, J.Rheumatol 9:789-793 (1982).
Garaci et al., PNAS 96(24) 14013-14018 (1999).
Garcia-Castellano et al., Iowa Orthop J 20: 49-58 (2000).
Garrett et al., Neurosci Lett 230: 5-8 (1997).
Gavilondo and Larrick, BioTechniques 29: 128-145 (2000).
Gould et al., Brain Research 854: 19-29 (2000).
Griffiths et al., EMBO 12(2): 725-734 (1993).
Grosschedl et al., 41 Cell 885 (1985).
Gwak et al., Neurosci Lett 336: 117-120 (2003).
Halvorson et al., Cancer Res 65: 9426-9435 (2005).
Haynes et al., Clinical Immunology 105(3): 315-325 (2002).
Hefti et al., Trends in Pharmacological Sciences 27(2): 85-91 (2006).
Hein, J., Meth Enzymol 183: 626-645 (1990).
Higgins and Sharp, CABIOS Comm 5: 151-153 (1989).
Hill et al., Trends Pharmacol Sci 21(7): 244-246 (2000).
Holliger et al., PNAS 90:6444-6448 (1993).
Hongo et al., Hybridoma 19(3): 215-227 (2000).
Honore et al., Nature med 6: 521-528 (2000).
Honore et al., Neuroscience 98(3): 585--598 (2000).
Honore et al., Prog Brain Res 129: 389-397 (2000).
Hoogenboom and Winter, J Mol Biol 227: 381-388 (1992).
Hoogenboom et al., Immunology Today, 21: 371-378 (2000).
Hoogenboom, TIB Tech., 15: 62-70 (1997).
Horigome, et al., J. Bioi. Chem. 268:14881-14887 (1993).
Huang and Reichardt, Ann Rev. Neurosci 24: 677-736 (2001).
Huse et al.,Intern Rev Immunol 10: 129-137 (1993).
Iannone et al., Rheumatology 41: 1413-1418 (2002).
Jefferis, Chem Immunol 65: 111-128 (1997).
Johnson and Chiswell, Curr Opin Structural Biol 3: 564-571 (1993).
Jones et al., Nature 321: 522-525 (1986).
Jones et al., Pain 79: 21-29 (1999).
Jonsson, et al. Ann. Biol. Clin. 51: 19-26 (1993).
Vajdos et al., J Mol Biol 320: 415-428 (2002).
Vanderah et al., pain 92: 5-9 (2001).
Vaughn et al., Nat Biotech 14: 309-314 (1996).
Verhoeyen et al., Science 239: 1534-1536 (1988).
Vigneti et al., Year Immunol 7: 146-149 (2000).
Waterhouse et al., Nucleic Acids Res 21: 2265-2266 (1993).
Wiesmann et al., Nature 401: 184-188 (1999).
Wilbur and Lipman PNAS 80: 726-730 (1983).
Winter and Milstein, Nature 349: 293-299 (1991).
Winter et al., Ann Rev Immunol 12: 433-455 (1994).
Winter et al., Arth Rheum 9: 394-404 (1966).
Woolf et al., J Neurosci 16(8): 2716-2723 (1996).
Woolf et al., J Neurosci 21(3): 1047-1055 (2001).
Woolf et al, Neuroscience 62: 327-331 (1994).
Wright and Morrison, TibTech 15: 26-32(1997).
Wu et al, J Mol Biol 294:151-162 (1999).
Wyss and Wagner, Curr Opin Biotech 7: 409-416 (1996).
Yamamoto et al., Brain Res 909: 138-144 (2001).
Yan et al., Clinical Science 80: 565-569 (1991).
Yelton et al., JImmunol 155: 1994-2004 (1995).
Yu et al., J Neurosci Meth 115: 107-113 (2002).
Zahn et al., J Pain 5(3): 157-163 (2004).
Zahn et al., Reg Anesth Pain Med 27: 514-516 (2002).
Zhu, Z. et al., J Clin. Oncol., 17: 241-228 (1999).

Figure 1

Mouse Anti-NGF Antibodies

SEQ ID NO: 1 (PR-1254972 VH nucleotide sequence)

GAAGTGCACCTGGTGGAGTCTGGGGGAGGCTTAGTGAAGCCTGGAGGGTTCC
TGATACTCTCCTGTGCAGCCTCTGGATTCACTTTCAGTGACTATTACATGTTTT
GGATTCGCCAGACTCCGGGAAAGAGGCTGGAGTGGGTCGCAACCATTAGTGA
TGGTGGTAGTTACACCTACTACACAGACAATGTAAAGGGCCGATTCACCATC
TCCAGAGACAATGTCAAGAACAACCTGTACCTGCAAATGAGCCATCTGAAGT
CTGCGGACACAGCCATGTATTACTGTGCAAGAGATTGGAGTGACTCCGAGGG
GTTTGCTTACTGGGGCCAAGGGACTCTGGTCACTGTCTCTGCA

Figure 2

SEQ ID NO: 2 (PR-1254972 VH amino acid)

EVHLVESGGGLVKPGGFLILSCAASGFTFS<u>DYYMF</u>WIRQTPGKRLEWVA<u>TISDGG
SYTYYTDNVKG</u>RFTISRDNVKNNLYLQMSHLKSADTAMYYCAR<u>DWSDSEGFA
Y</u>WGQGTLVTVSA

Figure 3

SEQ ID NO: 3 (PR-1254972 VL nucleotide sequence)

GATGTTTTGATGACCCAAACTCCACTCTCCCTGCCTGTCAGTCTTGGAGATCA
AGCCTCCATCTCTTGCAGATCTAGTCAGAGTATTGTACAAAGTAATGGAAAC
ACCTATTTAGAATGGTACCTGCAGAAACCAGGCCAGTCTCCAAAGCTCCTGA
TCTACAAAGTTTCCAACCGATTTTCTGGGGTCCCAGACAGGTTCAGTGGCAGT
GGATCAGGGACAGATTTCACACTCAAGATCAGCAGAGTGGAGGCTGAGGATC
TGGGAGTTTATTACTGCTTTCAAGGTTCACATGTTCCATTCACGTTCGGCTCG
GGGACAAAGTTGGAAATAAAACGG

Figure 4

SEQ ID NO: 4 (PR-1254972 VL amino acid)

DVLMTQTPLSLPVSLGDQASISCRSSQSIVQSNGNTYLEWYLQKPGQSPKLLIYK
VSNRFSGVPDRFSGSGSGTDFTLKISRVEAEDLGVYYCFQGSHVPFTFGSGTKLEI
KRC

Figure 5

SEQ ID NO: 5 (PR-1254973 VH nucleotide sequence)

CAGGTCCAACTGCAGCAGCCTGGGGCTGAGCTTGTGAAGCCTGGGGCTTCAG
TGAAGCTGTCCTGTAAGGCTTCTGGCTACACCTTCACCAACTACTGGATGCAC
TGGGTGAAGCAGAGGCCTGGACAAGGCCTTGAGTGGATTGGAAGGATTGATC
CTTATGGTGGTGGTACTAAGCACAATGAGAAGTTCAAGAGGAAGGCCACAGT
GACTGCAGACAAATCCTCCAGCACAGCCTACATCCTGCTCAGCAGCCTGACA
TCTGAGGACTCTGCGGTCTATTATTGTACAAGATCTGGTTACGACTATTACTT
CGATGTCTGGGGCACAGGGACCACGGTCACCGTCTCCTCA

Figure 6

SEQ ID NO: 6 (PR-1254973 VH amino acid)

QVQLQQPGAELVKPGASVKLSCKASGYTFTNYWMHWVKQRPGQGLEWIGRIDP
YGGGTKHNEKFKRKATVTADKSSSTAYILLSSLTSEDSAVYYCTRSGYDYYFDV
WGTGTTVTVSS

Figure 7

SEQ ID NO: 7 (PR-1254973 VL nucleotide sequence)

GACATCCAGATGACTCAGTCTCCAGCCTCCCTATCTGCATCTGTGGGAGAAA
CTGTCACCGTCACATGTCGAGCAAGTGAAAATATTTACAGTTTTTTAGCATGG
CATCAGCAGAAACAGGGAAAATCTCCTCAGCTCCTGGTCTATAATGCAAATA
CCTTAGCAGAGGGTGTGCCATCAAGGTTCAGTGGCAGTGGATCAGGCACACA
GTTTTCTCTGAAGATCAACAGCCTGCAGCCTGAAGATTTGGGAGTTATTACT
GTCAACATCATTTTGGGACTCCATTCACGTTCGGCTCGGGGACAAAGTTGGA
AATAAAACGG

Figure 8

SEQ ID NO: 8 (PR-1254973 VL amino acid)

DIQMTQSPASLSASVGETVTVTCRASENIYSFLAWHQQKQGKSPQLLVYNANTL
AEGVPSRFSGSGSGTQFSLKINSLQPEDFGSYYCQHHFGTPFTFGSGTKLEIKR

Figure 9

SEQ ID NO: 9 (PR-1254977 VH nucleotide sequence)

GAGGTTCAGCTGCAGCAGTCTGGGGCAGAGCTTGTGAAGCCAGGGGCCTCAG
TCAAGTTGTCCTGCACAGCTTCTGGCTTCAACATTAAAGACACCTATATATAC
TGGGTGAAACAGAGGCCTGAACAGGGCCTGGAGTGGATTGGAAGGATTGAT
CCTGCGAATGGAAATACTATATATGCCTCAAAGTTCCAGGGCAAGGCCTCTA
TAACAGCAGACACATCATCCAACACAGCCTACATGCAGCTCAGCAGCCTGAC
ATCTGGGGACACTGCCGTCTATTACTGTGCTGGTTATGGTTACTACGCCTACT
GGGGCCAAGGCACCACTCTCACAGTCTCCTCA

Figure 10

SEQ ID NO: 10 (PR-1254977 VH amino acid)

EVQLQQSGAELVKPGASVKLSCTASGFNIKDTYIYWVKQRPEQGLEWIGRIDPAN
GNTIYASKFQGKASITADTSSNTAYMQLSSLTSGDTAVYYCAGYGYYAYWGQG
TTLTVSS

Figure 11

SEQ ID NO: 11 (PR-1254977VL nucleotide sequence)

GATGTTGTTCTGACCCAAACTCCACTCTCTCTGCCTGTCAATATTGGAGATCA
AGCCTCTATCTCTTGCAAGTCTACTAAGAGTCTTCTGAATGGTGATGGATTCA
CTTATTTGGACTGGTACTTGCAGAAGCCAGGCCAGTCTCCACAGCTCCTAATA
TATTTGGTTTCTAATCGATTTCTGGAGTTCCAGACAGGTTCAGTGGCAGTGG
GTCAGGAACAGATTTCACACTCAAGATCAGCAGAGTGGAGGCTGAGGATTTG
GGAGTTTATTATTGCTTCGAGAGTAACTATCTATTCACGTTCGGCTCGGGGAC
AAAGTTGGAAATGAAACGG

Figure 12

SEQ ID NO: 12 (PR-1254977 VL amino acid)

DVVLTQTPLSLPVNIGDQASISCKSTKSLLNGDGFTYLDWYLQKPGQSPQLLIYL
VSNRFSGVPDRFSGSGSGTDFTLKISRVEAEDLGVYYCFESNYLFTFGSGTKLEM
KR

Figure 13

SEQ ID NO: 13 (PR-1254980 VH nucleotide sequence)

GAGGTTCAGCTGCAGCAGTCTGGGGCAGAGCTTGTGAAGCCAGGGGCCTCAG
TCAAGTTGTCCTGCACAGCTTCTGGCTTCAACATTAAAGACACCTATATATAT
TGGGTGAAACAGAGGCCTGAACAGGGCCTGGAATGGATTGGAAGGATTGAT
CCTGCGAATGGAAATACTATATATGCCTCAAAGTTCCAGGGCAAGGCCACTA
TAACAGCAGACACATCATCCAACACAGCCTACATGCAGCTCAGCAGCCTGAC
ATCTGGGGACACTGCCGTCTATTACTGTGCTGGTTATGGTTACTACGCCTACT
GGGGCCAAGGCACCACTCTCACAGTCTCCTCA

Figure 14

SEQ ID NO: 14 (PR-1254980 VH amino acid)

EVQLQQSGAELVKPGASVKLSCTASGFNIKDTYIYWVKQRPEQGLEWIGRIDPAN
GNTIYASKFQGKATITADTSSNTAYMQLSSLTSGDTAVYYCAGYGYYAYWGQG
TTLTVSS

Figure 15

SEQ ID NO: 15 (PR-1254980 VL nucleotide sequence)

GATGTTGTTCTGACCCAAACTCCACTCTCTCTGCCTGTCAATATTGGAGATCA
AGCCTCTATCTCTTGCAAGTCTACTAAGAGTCTTCTGAATGGTGATGGATTCA
CTTATTTGGACTGGTACTTGCAGAAGCCAGGCCAGTCTCCACAGCTCCTAATA
TATTTGGTTTCTAATCGATTTTCTGGAGTTCCGGACAGGTTCAGTGGCAGTGG
GTCAGGAACAGATTTCACACTCAAGATCAGCAGAGTGGAGGCTGAGGATTTG
GGAGTTTATTATTGCTTCGAGAGTAACTATCTATTCACGTTCGGCTCGGGGAC
AAAGTTGGAAATGAAACGG

Figure 16

SEQ ID NO: 16 (PR-1254980 VL amino acid)

DVVLTQTPLSLPVNIGDQASISC<u>KSTKSLLNGDGFTYLD</u>WYLQKPGQSPQLLIY<u>L</u>
<u>VSNRFS</u>GVPDRFSGSGSGTDFTLKISRVEAEDLGVYYC<u>FESNYLFT</u>FGSGTKLEM
KR

Figure 17

SEQ ID NO: 17 (PR-1254981 VH nucleotide sequence)

GAAGTGCAACTGGTGGAGTCTGGGGGAGGCGCAGTGAAGCCTGGAGGGTCC
CTGACACTCTCCTGTGCAGCCTCTGGATTCACTTTCAGTAACCATTACATGTA
TTGGGTTCGCCAGACTCCGGAAAAGAGGCTGGAGTGGGTCGCGTCCATTAGT
GATGGTGGTGCTTACACCTTCTATCCAGACACTGTCAAGGGCCGATTCACCAT
CTCCAGAGACAATGTCAACAACAACCTGTACCTGCAAATGCGCCATCTGAAG
TCTGAGGACACAGCCATGTATTACTGTACAAGAGAGGAGAGTGCTAACAACG
GGTTTGCTTTCTGGGGCCAAGGGACTCTGGTCACTGTCTCTGCA

Figure 18

SEQ ID NO: 18 (PR-1254981 VH amino acid)

EVQLVESGGGAVKPGGSLTLSCAASGFTFS<u>NHYMY</u>WVRQTPEKRLEWVA<u>SISD</u>
<u>GGAYTFYPDTVKGR</u>FTISRDNVNNNLYLQMRHLKSEDTAMYYCTR<u>EESANNGF</u>
<u>AF</u>WGQGTLVTVSA

Figure 19

SEQ ID NO: 19 (PR-1254981 VL nucleotide sequence)

GATGTTTTGATGACCCAAACTCCACTCTCCCTGCCTGTCAGTCTTGGAGATCA
AGCCTCCATCTCTTGCAGATCTAGTCAGAGCATTCTACATAGTAATGGAAACA
CCTATTTAGAATGGTACCTGCAGAAACCAGGCCAGTCTCCAAACCTCCTGAT
CTACAGAGTTTCCAACCGATTTTCTGGGGTCCCCGACAGGTTCAGTGGCAGTG
GATCAGGGACAGATTTCACACTCAAGATCAGCAGAGTGGAGGCTGAGGATCT
GGGAGTTTATTACTGCTTTCAAGGTGCACATGTTCCATTCACGTTCGGCTCGG
GGACAAAGTTAGAAATAAAACGG

Figure 20

SEQ ID NO: 20 (PR-1254981 VL amino acid)

DVLMTQTPLSLPVSLGDQASISCRSSQSILHSNGNTYLEWYLQKPGQSPNLLIYRV
SNRFSGVPDRFSGSGSGTDFTLKISRVEAEDLGVYYCFQGAHVPFTFGSGTKLEIK
R

Figure 21

SEQ ID NO: 21 (PR-1254982 VH nucleotide sequence)

CAGGTGCAGCTGAAGGAGTCAGGACCTGGCCTGGTGGCGCCCTCACAGAGCC
TGTCCATCACATGCACCGTCTCAGGGTTCTCATTAACCGGCTATAATATAAAC
TGCGTTCGCCAGCCTCCAGGAAAGGGTCTGGAGTGGCTGGGAATGATATGGG
GTTATGGAGACACAGACTATAATTCAGCTCTCAAATCCAGACTGAGCATCAG
CAAGGACAACTCCAAGAGCCAAGTTTTCTTAAAAATGAACAGTCTGCAAACT
GATGACACAGCCAGGTATTATTGTGCCAGAGATCACTATGGTGGTAACGACT
GGTACTTCGATGTCTGGGGCACAGGGACCACGGTCACCGTCTCCTCA

Figure 22

SEQ ID NO: 22 (PR-1254982 VH amino acid)

QVQLKESGPGLVAPSQSLSITCTVSGFSLTGYNINWVRQPPGKGLEWLGMIWGY
GDTDYNSALKSRLSISKDNSKSQVFLKMNSLQTDDTARYYCARDHYGGNDWYF
DVWGTGTTVTVSS

Figure 23

SEQ ID NO: 23 (PR-1254982 VL nucleotide sequence)

GATATCCAGATGACACAGACTACATCCTCCCTGTCTGCCTCTCTGGGAGACA
GAGTCACCATCACTTGCAGGGCAAGTCAGGACATTACCAATTATTTAAACTG
GTATCAGCAGAAACCAGATGGAACTGTTAAACTCCTGATCTACTACACATCA
AGATTACACTCAGGAGTCCCATCAAGGTTCAGTGGCAGTGGGTCTGGAACAG
ATTATTCTCTCACCATTAGCAACCTGGATCAAGAAGATATTGCCACTTACTTT
TGCCAACAGGGTAAAACGCTTCCTCGGACGTTCGGTGGAGGCACCAAGCTGG
AAATCAAACGG

Figure 24

SEQ ID NO: 24 (PR-1254982 VL amino acid)

DIQMTQTTSSLSASLGDRVTITCRASQDITNYLNWYQQKPDGTVKLLIYYTSRLH
SGVPSRFSGSGSGTDYSLTISNLDQEDIATYFCQQGKTLPRTFGGGTKLEIKR

Mouse Anti-NGF mAb CDRs Grafted onto Canine Ig Frameworks (CDR-Grafted Anti-NGF Abs); CDRs are underlined

Figure 25

SEQ ID NO: 25 (72.1 VH amino acid)

EVQLVESGGDLVKPGGSLRLSCVASGFTFSDYYMFWVRHSPGKGLQWVATISD
GGSYTYYTDNVKGRFTISRDDANNTLYLQMNSLRAEDTAVYYCAKDWSDSEGF
AYWGQGTLVTVSS

Figure 26

SEQ ID NO: 26 (72.1 VL amino acid)

DIVMTQTPPSLSVSPREPASISCRSSQSIVQSNGNTYLEWYLQKPGQSPQLLIYKVS
NRFSGVSDRFSGSGSGTDFTLRISRVEADDTGVYYCFQGSHVPFTFGAGTKVELK
R

Figure 27

SEQ ID NO: 27 (73.1 VH amino acid)

EVQLVQSAAEVKKPGASVKVSCKTSGYIFINYWMHWVQQAPGAGLEWMGRIDP
YGGGTKHNEKFKRRVTLTADTSTNTVYMELSNLRTEDTAVYYCARSGYDYYFD
VWGQGTLVTVSS

Figure 28

SEQ ID NO: 28 (73.1 VL amino acid)

IIVMTQTPLSLSASPGESASISCRASENIYSFLAWFRQKPGQSPQRLIYNANTLAEG
VPDRFSGSGSGTDFTLRISRVEDEDAGLYYCQHHFGTPFTFGQGTKLEIKR

Figure 29

SEQ ID NO: 29 (77.1 VH amino acid)

EVQLVQSAAEVKKPGASVKVSCKTSGYIFIDTYIYWVQQAPGAGLEWMGR
IDPANGNTIYASKFQGRVTLTADTSTNTVYMELSNLRTEDTAVYYCARYGYYAY
WGQGTLVTVSS

Figure 30

SEQ ID NO: 30 (77.1 VL amino acid)

DLVLTQTPRSLSVSPGETASISCKSTKSLLNGDGFTYLDWFRQKPGQSPQRLIYLV
SNRFSGVPDRFSGSGSGTDFTLRISRVEADDTGLYYCFESNYLFTFSQGTNLEMK
R

Figure 31A

SEQ ID NO: 31 (81.1 VH amino acid)

EVQLVESGGDLMKPGGSLRLSCVASGFTFSNHYMYWVRQAPGKGLQWVGSISD
GGAYTFYPDTVKGRFTISRDNAKNTLYLQMNSLRTEDTGRVLLCEGEESANNGF
AFWGHGTLVTVSS

Figure 31B

SEQ ID NO: 177 (81.1B VH amino acid)

EVQLEESGGDLVKPGGSLRLSCVASGFTFSNHYMYWVRQSPGKGLQWVASISD
GGAYTFYPDTVKGRFTISRDNAKNTLFLQMNSLRAEDTAVYFCVKEESANNGFA
FWGQGTLVTVSS

Figure 32

SEQ ID NO: 32 (81.1 VL amino acid)

DVVMTQAPPSLSVSPREPASISCRSSQSILHSNGNTYLEWFRQKPGQSPQRLIYRV
SNRFSGVPDRFSGSGSGTDFTLRISRVEADDLGVYYCFQGAHVPFTFGQGTKLEI
KR

Figure 33

SEQ ID NO: 33 (82.1 VH amino acid)

EVILQESGPGLVKPSQTLSLTCTVSGGSVT<u>GYNIN</u>WIRQRPDRGLEWMG<u>MIWGY
GDTDYNSALKS</u>RISITADGTKNHLSLQLTSTTTEDTAVYYCTR<u>DHYGGNDWYFD
Y</u>WGQGTLVTVSS

Figure 34

SEQ ID NO: 34 (82.1 VL amino acid)

DVMTQTPLSLSASPGESASISC<u>RASQDITNYLN</u>WFRQKPGQSPQRLIY<u>YTSRLHS</u>G
VPDRFSGSGSGTDFTLRISRVEDEDAGLYYC<u>QQGKTLPRT</u>FGQGTKLEIKR

**Caninized Anti-NGF Antibodies Containing Back Mutation Residues
(backmutation residues shown in bold)**

Figure 35

SEQ ID NO: 35 (72.2 VH amino acid)

EVHLVESGGDLVKPGGSLRLSCVASGFTFS<u>DYYMF</u>WIRHSPGKGLEWVA<u>TISDG
GSYTYYTDNVKG</u>RFTISRDNANNNLYLQMNSLKAEDTAVYYCAK<u>DWSDSEGF
AY</u>WGQGTLVTVSS

Figure 36A

SEQ ID NO: 36 (72.2 VL amino acid)

DVLMTQTPPSLSVSPREPASISC<u>RSSQSIVQSNGNTYLE</u>WYLQKPGQSPKLLIY<u>KV
SNRFS</u>GVPDRFSGSGSGTDFTLRISRVEADDTGVYYC<u>FQGSHVPFT</u>FGAGTKVEL
KR

Figure 36B

SEQ ID NO: 179 (72.3 VH amino acid)

EVHLVESGGDLVKPGGSLRLSCVASGFTFS<u>DYYMF</u>WIRQSPGKGLEWVA<u>TISDG
GSYTYYTDNVKG</u>RFTISRDNANNNLYLQMNSLKAEDTAVYYCAK<u>DWSDSEGFA
Y</u>WGQGTLVTVSS

Figure 36C

SEQ ID NO: 180 (72.4 VH amino acid)

EVHLVESGGDLVKPGGSLRLSCVASGFTFSDYYMFWVRHSPGKGLEWVATISD
GGSYTYYTDNVKGRFTISRDNANNTLYLQMNSLRAEDTAVYYCAKDWSDSEGF
AYWGQGTLVTVSS

Figure 36D

SEQ ID NO: 181 (72.4 VL amino acid)

DIVMTQTPPSLSVSPREPASISCRSSQSIVQSNGNTYLEWYLQKPGQSPKLLIYKVS
NRFSGVPDRFSGSGSGTDFTLRISRVEADDTGVYYCFQGSHVPFTFGAGTKVELK
R

Figure 37

SEQ ID NO: 37 (73.2 VH amino acid)

QVQLVQSAAEVKKPGASVKVSCKASGYTFTNYWMHWVQQAPGAGLEWIGRID
PYGGGTKHNEKFKRRATVTADKSTSTAYMELSNLRTEDTAVYYCTRSGYDYYF
DVWGQGTLVTVSS

Figure 38A

SEQ ID NO: 38 (73.2 VL amino acid)

DIQMTQTPLSLSASPGESASITCRASENIYSFLAWHRQKPGQSPQLLVYNANTLA
EGVPSRFSGSGSGTQFTLRISRVEDEDAGLYYCQHHFGTPFTFGQGTKLEIKR

Figure 38B

SEQ ID NO:182 (73.4 VH amino acid)

EVQLVQSAAEVKKPGASVKVSCKASGYIFINYWMHWVQQAPGAGLEWMGRID
PYGGGTKHNEKFKRRVTLTADKSTSTVYMELSNLRTEDTAVYYCTRSGYDYYF
DVWGQGTLVTVSS

Figure 38C

SEQ ID NO:183 (73.4 VL amino acid)

DIQMTQTPLSLSASPGESASISCRASENIYSFLAWHRQKPGQSPQLLIYNANTLAE
GVPSRFSGSGSGTQFTLRISRVEDEDAGLYYCQHHFGTPFTFCQGTKLEIKR

Figure 39

SEQ ID NO: 39 (77.2 VH amino acid)

EVQLVQSAAEVKKPGASVKVSCKASGFNIKDTYIYWVKQAPGAGLEWIGRIDPA
NGNTIYASKFQGKASITADTSTNTAYMELSNLRTEDTAVYYCARYGYYAYWGQ
GTLVTVSS

Figure 40A

SEQ ID NO: 40 (77.2 VL amino acid)

DVVLTQTPRSLSVSPGETASISCKSTKSLLNGDGFTYLDWYRQKPGQSPQLLIYL
VSNRFSGVPDRFSGSGSGTDFTLRISRVEADDTGLYYCFESNYLFTFGQGTNLEM
KR

Figure 40B

SEQ ID NO: 184 (77.3 VH amino acid)

EVQLVQSAAEVKKPGASVKVSCKASGFNIKDTYIYWVKQAPGAGLEWIGRIDPA
NGNTIYASKFQGKASITADTSTNTAYMELSNLRTEDTAVYYCAGYGYYAYWGQ
GTLVTVSS

Figure 40C

SEQ ID NO: 185 (77.4 VH amino acid)

EVQLVQSAAEVKKPGASVKVSCKASGYIFIDTYIYWVKQAPGAGLEWMGRIDPA
NGNTIYASKFQGRVTLTADTSTNTVYMELSNLRTEDTAVYYCAGYGYYAYWG
QGTLVTVSS

Figure 40D

SEQ ID NO: 186 (77.4 VL amino acid)
DLVLTQTPRSLSVSPGETASISCKSTKSLLNGDGFTYLDWYRQKPGQSPQLLIYLV
SNRFSGVPDRFSGSGSGTDFTLRISRVEADDTGLYYCFESNYL
FTFSQGTNLEMKR

Figure 41

SEQ ID NO: 41 (81.2 VH amino acid)
EVQLVESGGDLMKPGGSLRLSCVASGFTFSNHYMYWVRQAPGKGLEWVASISD
GGAYTFYPDTVKGRFTISRDNAKNNLYLQMNSLKTEDTGRVLYCTGEESANNG
FAFWGHGTLVTVSS

Figure 42A

SEQ ID NO: 42 (81.2 VL amino acid)
DVLMTQTPPSLSVSPREPASISCRSSQSILHSNGNTYLEWYRQKPGQSPQLLIYRV
SNRFSGVPDRFSGSGSGTDFTLKISRVEAEDLGVYYCFQGAHVPFTFGQGTKLEI
KR

Figure 42B

SEQ ID NO: 187 (81.4 VH amino acid)
EVQLVESGGDLMKPGGSLRLSCVASGFTFSNHYMYWVRQAPGKGLEWVASISD
GGAYTFYPDTVKGRFTISRDNAKNTLYLQMNSLRTEDTGRVLYCTGEESANNGF
AFWGHGTLVTVSS

Figure 42C

SEQ ID NO: 188 (81.4 VL amino acid)
DVLMTQAPPSLSVSPREPASISCRSSQSILHSNGNTYLEWYRQKPGQSPQLLIYRV
SNRFSGVPDRFSGSGSGTDFTLRISRVEADDLGVYYCFQGAHVPFTFGQGTKLEI
KR

Figure 42D

SEQ ID NO: 189 (81.2B VH amino acid)

EVQLEESGGDLVKPGGSLRLSCVASGFTFSNHYMYWVRQSPGKGLEWVASISDG
GAYTFYPDTVKGRFTISRDNAKNNLYLQMNSLKKEDTAVYYCTREESANNGFA
FWGQGTLVTVSS

Figure 42E

SEQ ID NO: 190 (81.4B VH amino acid)

EVQLEESGGDLVKPGGSLRLSCVASGFTFSNHYMYWVRQSPGKGLEWVASISD
GGAYTFYPDTVKGRFTISRDNAKNTLYLQMNSLRKEDTAVYYCTKEESANNGF
AFWGQGTLVTVSS

Figure 42F

SEQ ID NO: 206 (81.5B VH amino acid)

EVQLEESGGDLVKPGGSLRLSCVASGFTFSNHYMYWVRQSPGKGLEWVASISDG
GAYTFYPDTVKGRFTISRDNAKNNLYLQMNSLKAEDTAVYYCTREESANNGFA
FWGQGTLVTVSS

Figure 42G

SEQ ID NO: 207 (81.6B VH amino acid)

EVQLEESGGDLVKPGGSLRLSCVASGFTFSNHYMYWVRQSPGKGLEWVASISD
GGAYTFYPDTVKGRFTISRDNAKNTLYLQMNSLRAEDTAVYYCTKEESANNGF
AFWGQGTLVTVSS

Figure 43

SEQ ID NO: 43 (82.2 VH amino acid)

EVQLQESGPGLVKPSQTLSLTCTVSGFSLTGYNINWVRQRPDRGLEWLGMIWGY
GDTDYNSALKSRLSISKDNTKSQVFLQLTSTTTEDTAVYYCARDHYGGNDWYF
DVWGQGTLVTVSS

Figure 44A

SEQ ID NO: 44 (82.2 VL amino acid)

DIQMTQTPLSLSASPGESASITCRASQDITNYLNWYRQKPGQSPKLLIYYTSRLHS
GVPSRFSGSGSGTDYSLRISRVEDEDAGLYFCQQGKTLPRTFGQGTKLEIKR

Figure 44B

SEQ ID NO: 191 (82.3 VL amino acid)

DIQMTQTPLSLSASPGESASITCRASQDITNYLNWYRQKPGQSVKLLIYYTSRLHS
GVPSRFSGSGSGTDYSLRISRVEDEDAGLYFCQQGKTLPRTFGQGTKLEIKR

Figure 44C

SEQ ID NO: 192 (82.4 VH amino acid)

EVQLQESGPGLVKPSQTLSLTCTVSGGSVTGYNIKWIRQRPDRGLEWMGMIWGY
GDTDYNSALKSRISITKDNTKSQLFLQLTSTTTEDTAVYYCARDHYGGNDWYFD
VWGQGTLVTVSS

Figure 44D

SEQ ID NO: 193 (82.4 VL amino acid)

DIQMTQTPLSLSASPGESASISCRASQDITNYLNWYRQKPGQSPKLLIYYTSRLHS
GVPSRFSGSGSGTDYTLRISRVEDEDAGLYFCQQGKTLPRTFGQGTKLEIKR

Canine NGF

Figure 45

SEQ ID NO: 45 (NGF-Dog-S primer)

5'-GGC AGG GTA CCG CCG CCA CCATGT CCATGT TGT TCT ACA C-3'

Figure 46

SEQ ID NO: 46 (NGF-Dog-AS primer)

5'-GGC AGT CTA GAT CAGTGA TGA TGA TGATGG GCT CGT CTC CCG
GCCTTC C-3'

Figure 47

SEQ ID NO: 47 (NGF-d-Ec-S primer)

5'-GGC AGC ATA TGG AAC CGC ATC CAG AGA GCC AT-3'

Figure 48

SEQ ID NO: 48 (NGF-d-Ec-AS primer)

5'-GGC AGC TCG AGC TAG GCT CGT CTC CCG GCC TTC CT-3'

Figure 49

SEQ ID NO: 49 (Canine NGF C-terminal 6His fusion nucleotide sequence)

ATGTCCATGTTGTTCTACACTCTGATCACAGCTCTTCTGATCGGCATCCGGGC
AGAACCGCATCCAGAGAGCCATGTCCCAGCAGGACACGCCATCCCCCACGCC
CACTGGACTAAGCTTCAGCATTCCCTTGACACAGCCCTCCGCAGAGCCCGCA
GCGCCCCGGCCGGGGCAATAGCTGCCAGGGTGACAGGGCAGACCCGCAACA
TCACTGTGGATCCCAAACTCTTTAAAAAGCGGCGACTGCGTTCGCCCCGCGT
GCTGTTCAGCACGCACCCCCACCTGTGGCTGCGGACGCTCAGGACCTGGAC
CTGGAGGCCGGCAGCACCGCCTCCGTCAACAGGACTCACAGGAGCAAGCGG
TCTTCGTCCCACCCTGTCTTCCACCGGGGGGAGTTCTCGGTGTGCGACAGCGT
CAGCGTGTGGGTGGGCGACAAGACCACAGCCACCGACATCAAGGGCAAGGA
GGTGATGGTGCTGGGAGAGGTGAACATTAACAACAGTGTGTTCAAACAGTAC
TTCTTTGAGACCAAGTGCCGGGACCCCACCCCCGTGGACAGCGGGTGCAGGG
GCATCGACTCCAAGCACTGGAACTCCTACTGCACCACCACCCACACCTTCGTC
AAGGCGCTGACCATGGACGGCAAGCAGGCTGCCTGGCGGTTCATCCGGATCG
ACACGGCCTGCGTGTGCGTGCTCAGCAGGAAGGCCGGGAGACGAGCCCATC
ATCATCATCATCAC

Figure 50

SEQ ID NO: 50 (Canine NGF C-terminal 6-His amino acid sequence)
MSMLFYTLITALLIGIRAEPHPESHVPAGHAIPHAHWTKLQHSLDTALRRARSAP
AGAIAARVTGQTRNITVDPKLFKKRRLRSPRVLFSTHPPPVAADAQDLDLEAGST
ASVNRTHRSKRSSSHPVFHRGEFSVCDSVSVWVGDKTTATDIKGKEVMVLGEV
NINNSVFKQYFFETKCRDPTPVDSGCRGIDSKHWNSYCTTTHTFVKALTMDGKQ
AAWRFIRIDTACVCVLSRKAGRRAHHHHHH Canine heavy and light chain constant domains

Figure 51

SEQ ID NO: 51 (Canine IgG constant region nucleotide sequence)
GCGTCGACCACAGCCCCGTCAGTCTTCCCATTGGCCCCCAGCTGCGGGTCAA
CTAGCGGGTCTACCGTCGCTCTGGCTTGTCTGGTGTCCGGCTACTTCCCTGAG
CCTGTGACCGTCAGCTGGAACTCTGGTAGCCTGACCAGCGGCGTGCATACTTT
TCCAAGCGTCCTTCAGAGCTCCGGACTCCACTCCCTTAGTTCCATGGTAACCG
TGCCAAGTAGTCGGTGGCCATCCGAGACATTTACCTGTAACGTGGTCCATCCC
GCTAGTAATACCAAGGTGGATAAGCCTGTCTTTAACGAGTGCCGGTGCACAG
ACACACCACCTTGTCCCGTGCCTGAGCCTCTCGGCGGCCCCTCAGTCCTGATC
TTTCCTCCAAAGCCAAAAGATATCCTCCGGATTACCCGGACTCCTGAAGTGA
CATGTGTAGTTCTGGACTTGGGCCGGGAAGACCCAGAGGTACAGATTAGCTG
GTTCGTAGACGGCAAAGAGGTGCACACAGCCAAAACGCAATCAAGGGAACA
GCAGTTCAATGGTACTTATCGGGTCGTGTCAGTACTGCCGATCGAACATCAG
GATTGGCTTACTGGCAAGGAATTCAAATGCCGCGTGAACCACATTGACCTGC
CAAGCCCCATCGAGAGGACCATATCAAAGGCCAGGGGGCGGGCACACAAGC
CGAGCGTTTATGTCCTGCCCCTTCCCCTAAGGAACTTAGCTCTTCAGACACT
GTGAGCATTACATGTCTGATCAAGGATTTCTATCCACCGGACATAGATGTAG
AGTGGCAGTCCAACGGGCAACAGGAGCCTGAACGGAAACATAGAATGACTC
CTCCACAGCTCGATGAGGATGGTTCTTACTTTCTTACTCCAAACTGTCAGTG
GACAAATCACGATGGCAGCAGGGCGATCCATTCACATGTGCCGTTATGCACG
AGACGCTTCAGAACCACTATACTGATCTGTCCCTCTCACATAGCCCGGGCAA
ATGA

Figure 52

SEQ ID NO: 52 (Canine IgG constant region amino acid sequence)
ASTTAPSVFPLAPSCGSTSGSTVALACLVSGYFPEPVTVSWNSGSLTSGVHTFPSV
LQSSGLHSLSSMVTVPSSRWPSETFTCNVVHPASNTKVDKPVFNECRCTDTPPCP
VPEPLGGPSVLIFPPKPKDILRITRTPEVTCVVLDLGREDPEVQISWFVDGKEVHT
AKTQSREQQFNGTYRVVSVLPIEHQDWLTGKEFKCRVNHIDLPSPIERTISKARG
RAHKPSVYVLPPSPKELSSSDTVSITCLIKDFYPPDIDVEWQSNGQQEPERKHRMT
PPQLDEDGSYFLYSKLSVDKSRWQQGDPFTCAVMHETLQNHYTDLSLSHSPGK

Figure 53

SEQ ID NO: 53 (Canine kappa constant region nucleotide sequence)
AATGATGCCCAGCCTGCAGTGTACCTGTTCCAACCTAGCCCTGACCAGCTCCA
CACAGGCTCTGCTAGCGTCGTCTGCCTGCTCAATTCTTTCTACCCAAAGGATA
TCAACGTGAAGTGGAAGGTCGATGGCGTGATTCAAGACACCGGCATTCAAGA
GTCAGTGACCGAACAGGATAAAGATTCTACATATAGCTTGAGCAGCACACTG
ACCATGAGCTCCACCGAGTATCTCAGTCATGAGCTGTATTCCTGCGAGATCAC
ACACAAGTCATTGCCCAGTACGCTCATAAAAAGCTTCCAGAGGTCCGAATGC
CAGCGCGTGGATTGA

Figure 54

SEQ ID NO: 54 (Canine kappa constant region amino acid sequence)
NDAQPAVYLFQPSPDQLHTGSASVVCLLNSFYPKDINVKWKVDGVIQDTGIQES
VTEQDKDSTYSLSSTLTMSSTEYLSHELYSCEITHKSLPSTLIKSFQRSECQRVD Caninized mAb variable domain CDRs

Figure 55

SEQ ID NO: 55 (72.1 VH amino acid; CDR1)
DYYMF

Figure 56

SEQ ID NO: 56 (72.1 VH amino acid; CDR2)

TISDGGSYTYYTDNVKG

Figure 57

SEQ ID NO: 57 (72.1 VH amino acid; CDR3)

DWSDSEGFAY

Figure 58

SEQ ID NO: 58 (72.1 VL amino acid; CDR1)

RSSQSIVQSNGNTYLE

Figure 59

SEQ ID NO: 59 (72.1 VL amino acid; CDR2)

KVSNRFS

Figure 60

SEQ ID NO: 60 (72.1 VL amino acid; CDR3)

FQGSHVPFT

Figure 61

SEQ ID NO: 61 (73.1 VH amino acid; CDR1)

NYWMH

Figure 62

SEQ ID NO: 62 (73.1 VH amino acid; CDR2)

RIDPYGGGTKHNEKFKR

Figure 63

SEQ ID NO: 63 (73.1 VH amino acid; CDR3)

SGYDYYFDV

Figure 64

SEQ ID NO: 64 (73.1 VL amino acid; CDR1)

RASENIYSFLA

Figure 65

SEQ ID NO: 65 (73.1 VL amino acid; CDR2)

NANTLAE

Figure 66

SEQ ID NO: 66 (73.1 VL amino acid; CDR3)

QHHFGTPFT

Figure 67

SEQ ID NO: 67 (77.1 VH amino acid; CDR1)

DTYIY

Figure 68

SEQ ID NO: 68 (77.1 VH amino acid; CDR2)

RIDPANGNTIYASKFQG

Figure 69

SEQ ID NO: 69 (77.1 VH amino acid; CDR3)

YGYYAY

Figure 70

SEQ ID NO: 70 (77.1 VL amino acid; CDR1)

KSTKSLLNGDGFTYLD

Figure 71

SEQ ID NO: 71 (77.1 VL amino acid; CDR2)

LVSNRFS

Figure 72

SEQ ID NO: 72 (77.1 VL amino acid; CDR3)

FESNYLFT

Figure 73

SEQ ID NO: 73 (81.1 VH amino acid; CDR1)

NHYMY

Figure 74

SEQ ID NO: 74 (81.1 VH amino acid; CDR2)

SISDGGAYTFYPDTVKG

Figure 75

SEQ ID NO: 75 (81.1 VH amino acid; CDR3)

EESANNGFAF

Figure 76

SEQ ID NO: 76 (81.1 VL amino acid; CDR1)

RSSQSILHSNGNTYLE

Figure 77

SEQ ID NO: 77 (81.1 VL amino acid; CDR2)

RVSNRFS

Figure 78

SEQ ID NO: 78 (81.1 VL amino acid; CDR3)

FQGAHVPFT

Figure 79

SEQ ID NO: 79 (82.1 VH amino acid; CDR1)

GYNIN

Figure 80

SEQ ID NO: 80 (82.1 VH amino acid; CDR2)

MIWGYGDTDYNSALKS

Figure 81

SEQ ID NO: 81 (82.1 VH amino acid; CDR3)

DHYGGNDWYFDV

Figure 82

SEQ ID NO: 82 (82.1 VL amino acid; CDR1)

RASQDITNYLN

Figure 83

SEQ ID NO: 83 (82.1 VL amino acid; CDR2)

YTSRLHS

Figure 84

SEQ ID NO: 84 (82.1 VL amino acid; CDR3)

QQGKTLPRT

Human NGF

Figure 85

SEQ ID NO: 85 (Human βNGF)

SSSHPIFHRGEFSVCDSVSVWVGDKTTATDIKGKEVMVLGEVNINNSVFKQYFFE
TKCRDPNPVDSGCRGIDSKHWNSYCTTTHTFVKALTMDGKQAAWRFIRIDTACV
CVLSRKAVRRA

Figure 86 - Tables

Canine heavy chain variable domain sequences derived from canine PBMC

Table 14
SEQ ID NO:178 (Ca-1005)
EVQLEESGGDLVKPGGSLRLSCVASGFSIGSYGMSWVRQSPGKGLQWVAWIKY
DGSRTFYADAVKGRFTISRDNAKNTLFLQMNSLRAEDTAVYFCVKGPNSSWLPS
TYFASWGQGTLVTVSS Table 14
SEQ ID NO: 86 (Ca-2301)

EMQLVESGGDLVRPGGSLRLSCVASGFTFSTYGMTWVRQSPGKGLQWVATIGP
GGRNTYYADAVKGRFTISRDDAENTLFLQMNSLRAEDTAVYYCAQAFDATYYT
SFDCWGRGSLVAVSS

Table 14
SEQ ID NO: 87 (Ca-2302)

MESVLSWVFLVALLQGIQGEIRLVESGGDLVKPGGSLRLSCVASGFIFGNYDMS
WVRQAPGKGLQWVAAVRYDGSSTYYSDAVKGRITISRDDPGNTVYLQLDSLRA
EDTATYYCVRGGYYSSSFYIGGAFGHWGPGTLITVSS

Table 14
SEQ ID NO: 88 (Ca-2303)

MECVLGWVFLVAILRGVQGEVQLVESGGDLVKPGGSLRLSCVASGFTFSDYYM
SWIRQAPGKGLQWVADISDGGDGTGYAGAVKGRFTVSRENVKNTLYLQMNDL
RAEDTAIYYCTKAREMYGYRDFDSWGPGTLVTVSS

FIG 86A

Table 14

SEQ ID NO: 89 (Ca-2304)

MESVLGLVALLTILKGVQGEVQLVESGGDLVKPGGSLRLSCVASGFTFSNYYMT
WVRQAPGKGLEWVGYIHNGGTYTYYADAVKGRFTISRDDAKNTLYLEMNSLR
AEDTAVYYCGKMIFDYWGQGTLVTVSS

Table 14

SEQ ID NO: 90 (Ca-2305)

MESALSWVFLVTILKGVQGEVLLVESGGDLVKPGGSLRLSCLTSGFTFNTYDWG
WVRQAPGKGLQWIAYIKKGGSDVRYADAVKGRFTISRDDAKNTLYLQMNSLRA
EDTAVYYCARSAWDSFDYWGQGTLVTVSS

Table 14

SEQ ID NO: 91 (Ca-2306)

MESVFCWVFLVAILKGVRGVQGEVQLVESGGDLVKPAGSLRLSCVASGFTFTDY
SMNWVRQAPGKGLQWVATISNDGTSTDYTDAVKGRFTVSRDSARNTVYLQMT
SLRADDTATYYCVSRHSYSLLADYWGQGTLVTVSS

Table 14

SEQ ID NO: 92 (Ca-2307)

MQMPWSLLCLLAAPLGVLSEVTLQESGPGLVKPSQTLSLTCAVSGGSVIRNYYW
HWIRQRPGRGLEWMGCWSETTYYSPAFRGRISITIDAATDQFSLHLNSMTTDDT
AVYYCARALYPTSSWYDGMDYWGHGASVVVSS

Table 14

SEQ ID NO: 93 (Ca-2308)

EVQLVESGGDLVKPGGSLRLSCESSGFIFSQYAMNWVRQAPGKGLQWVAYIGG
AGFITYHADDVKGRFTISRDNAKNTLYLQMNSLTINDTAVYYCVRSNSRIPDYW
GQGTLVAVSS

FIG 86B
Table 14

SEQ ID NO: 94 (Ca-2309)

MESVFCWVFLVAILKGVQGEVQLVESGGDLVKPGGSLRLSCVASGFTFSSVYMS
WVRQAPGKGLQWVARITTDGTDTFYADAVKGRFTISRDNVKNMLYLEMNSLR
AEDTAIYYCGDPWQPAYPDLWGQGTMVTVSS

Table 14

SEQ ID NO: 95 (Ca-2310)

MESVLCWVFLVAILKGVQGEVHLVESGGDLVKPGGTLRLSCVASGFTFSQYDM
SWVRQSPGKGLQWVALSRYHGGGTYYADAVKGRFTISRDNAKNMLYLQMNSL
RAEDTAVYYCVKEGSRWDLRGDYDYWGQGTLVTVSS

Table 14

SEQ ID NO: 96 (Ca-2311)

MQMPWSLLCLLAAPLGVLSELTLQESGPGLVKPSQTLSLTCVVSGGSVTSSHYW
NWIRQRPGRGLEWMGYWTGNVNYNPAFQGRISIIGDAAKNQFSLILSSMTTDDT
AVYYCARCGIVAPGFLPIGDFDFWGQGTLVTVSS

Table 14

SEQ ID NO: 97 (Ca-2312)

MESVFCWVFLVAILKGVQGEVQLVESGGDLVKPGGSLRLSCVASGFSFSNYFMF
WGRQAPGKGLQWVARIRSDGGSTYYADAVKGRFTISRDNARNTLYLQMNSLRA
EDTATYYCAKADIIKLPEYRGQGTLVTVSS

Table 14

SEQ ID NO: 98 (Ca-2401)

ESVLGWIFLATILKGVQGEVQLVESGGDLVKPGGSLRLSCVGSGFTFSSSWMNW
VRQAPGKGLQWIAEISGTGSSTNYADAVKGRFTISRDNDKNTLYLQMNSLRAED
TAMYYCARAAYYGNYRNDLDYWGQGTLVTVSS

FIG 86C
Table 14

SEQ ID NO: 99 (Ca-2402)

KPAGSLRLSCVASGFTFSSHSVTWVRQAPGKGLQFVAGITSGGNNRYYTDAVRG
RFTLSRDNAKNTVYLQMNSLRAEDTAMYFCALGSYEWLSGEFDYWGQGTLVT
VSS

Table 14

SEQ ID NO: 100 (Ca-2403)

MESVFCWVFLVAILKGVQGEVQLVESGGDLVKPGGSLRLSCVASGFTLNNYFM
YWVRQAPGKGLQWVARLNSNGDSTFYADAVKGRFTISRDNAKNTLYLQMNSL
RAEDTSMYYCAKDLIYGYTLWGQGTLVTVSS

Table 14

SEQ ID NO: 101 (Ca-2404)

MASVLSWVFLVAIVKGVQGEVQLVESGGDLVKPGGSLRLSCVASGFIFNKYEVY
WVRQAPGKGLEWVARILESGNPTYYAEAVEGRFTISRDNAKNMAYLQMNSLRA
DDTAVYYCATPSVSSTVAIDYWGQGALVTVSS

Table 14
SEQ ID NO: 102 (Ca-2405)

MQMPWSLLCLLATPLGVLSELTLQESGPGLVKPSQTLSLTCVVSRGSVTSDYYW
NWIRQRPGRGLEWMGHWIGSTAYNPAFQGRISITADTAKNQLSLQLRSMTTEDT
AVYFCARGSSWTPSGDSWGQGTLVTVSS

FIG 86D

Table 14

SEQ ID NO: 103 (Ca-2406)

MASVLKLGFSCRYCKKVSRVRCNXVESGGDLVKPGGSLRLSCVASGFIFNKYEV
YWVRQAPGKGLEWVARILESGNPTYYAEAVEGRFTISRDNAKNMAYLQMNSLR
ADDTAVYYCATPSVSSTVAIDYWGQGALVTVSS

Table 14

SEQ ID NO: 104 (Ca-2407)

MDCSWRIFFLLALATGVHSEVQLVQSAAEVKKPGASVKVSCKTSGYTLTDYYIH
WVQQAPGTGLHWMGWIDPEXGTTDYAQKFQGXVTLTADTSTNTAYMELSGLR
AEDTAVYYCARFPRSLDYGSFPFDYWGQGTLVTVSS

Table 14

SEQ ID NO: 105 (Ca-2408)

MESVLCWVFLVAILKGVQGEVRLVESGGDLVKPGGSLRLSCVASGFTFRNYGM
SWVRQRPGKGLQWVAAIRSDGVTYYADDLKVRFTVSRDDARNTLYLQLNSLGA
EDTAVYYCAKAPWGLYDAWGQGTLVTVSS

Table 14

SEQ ID NO: 106 (Ca-2409)

MESVLSWVFLVAILQGVQGEVQVVESGGDLVKPAGSLRLSCVASGYSISTYTMT
WVRQVPGKGLQLVAGINGDGSSTYYTDAVKGRFTISRDNARNTVYLQMNSLRA
EDTAMYYCLGEYSWFYYWGQGTLVTVSS

Table 14

SEQ ID NO: 107 (Ca-2410)

MQMPWSLLCLLAAPLGVLSELTLQESGPRLVKPSQTLSLTCAVSGGSVTTTSYW
SWIRQRPGRGLEWVGYWTGTTNYSPAFQGRISISADTAKNQFSLHLSSVTTEDTA
LYFCASKSASTSWYFSLFESWGQGTLVTVSS

FIG 86E

Table 14

<u>SEQ ID NO: 108 (Ca-2411)</u>

MESVLGLVFLLTILKGVQEVQLVESGGDLVKPGGSLRLSCVASGFTFSSYSMS
WVRQAPGKGLQWVGYIDNGGTSTYYADAVKGRFTISRDNAKNTLYLQMNSLR
AEDTAVYYCGRGSYGMEYWGHGTSLFVSS

Table 14

<u>SEQ ID NO: 109 (Ca-2412)</u>

MESVLGLLFLVAILKGVQGEIQLVESGGDLLKPGGSLRLSCVASGFTFSGSDMN
WIRQAPGKGLQWVAHITHEGIGTSYVGSVKGRFTISRDNAKNTLYLQMNDLRAE
DTAMYYCAYSPWNYYSFDSWGQGTLVTVSS

Figure 87

Canine lambda light chain variable domain sequences derived from canine PBMC RNA Table 15

SEQ ID NO: 110 (Ca-1001)

MTSTMAWSPLLLTLLTHCTVSWAQTVLTQSPSVSAVLGRRVTISCTGSDTNIGSH
RDVQWYQLVPGKSPKTLIYGTDNRPSGIPVRFSGSKSGNSGTLTITGIQAEDEAD
YYCQSYDDDLSMNVFGGGTHLTVLG

Table 15

SEQ ID NO: 111 (Ca-1002)

MDWVPFYILPFIFSTGFCALPVLTQPTNASASLEESVKLTCTLSSEHSNYIVRWYQ
QQPGKAPRYLMYVRSDGSYKRGDGIPSRFSGSSSGADRYLTISNIKSEDEDDYYY
CGADYTISGQYGSVFGGGTHLTVLG

Table 15

SEQ ID NO: 204 (Ca-1003)

LWISGGSALGTPTMAWTHLLLPVLTLCTGSVASSVLTQPPSVSVSLGQTATISCSG
ESL
SKYYAQWFQQKAGQVPVLVIYKDTERPSGIPDRFSGSSSGNTHTLTISRARAEDE
ADYYCESEVSTGTYCVRRRHPSNRPRSAQGLPLGHTLPALL

Table 15

SEQ ID NO: 112 (Ca-1006)

MTSTMAWSPLLLTLLTHCTGSWAQSVLTQPASLSGSLGQRVTISCTGSSSNIGGY
SVNWLQQLPGTGPRTIIYNNSNRPSGVPDRFSGSRSGTTATLTISGLQAEDEADYY
CSTWDSNLRTIVFGGGTHLTVLG

FIG 87A

Table 15

SEQ ID NO: 113 (Ca-1007)

MTSTMDWSPLLLTLLAHCTGSWAQSVLTQPASVSGSLGQRVTISCTGSTSNLGT
YNVGWLQQVPGTGPRTVIYTNIYRPSGVPDRFSGSESGSTATLTISDLQAEDEAE
YYCTAWDSSLNAYVFGSGTQLTVLG

Table 15

SEQ ID NO: 114 (Ca-1008)

MTSNMAWCPFLLTLLAYCTGSWAQSVLTQPTSVSGSLGQRVTISCSGSTNNIGIV
GASWYQQLPGKAPKLLVYSDGDRPSGVPDRFSGSNSGNSDTLTITGLQAEDEAD
YYCQSFDTTLDAAVFGGGTHLTVLG

Table 15

SEQ ID NO: 115 (Ca-1009)

MTSTMAWSPLLLTLLAHCTVSWAQAVLTQPPSVSAALGQRVTISCTGSDTNIGS
GYEVHWYRQVPGKSPAIIIYGNSNRPSGVPVRFSGSKSGSTATLTITGIEAEDEAD
YHCQSYDGNLDGGVFGGGTIILTVLG

Table 15

SEQ ID NO: 116 (Ca-1010)

MTSTMGWFPLILTLLAHCAGSWAQSVLTQPASVSGSLGQRVTISCTGSSPNVGY
GDFVAWYQQVPGTSPRTLIYNTRSPSGVPDRFSASRSGNTATLTISGLQAEDEA
DYYCSSYDNTLIGIVFGGGTHLTVLG

Table 15

SEQ ID NO: 117 (Ca-1011)

MTSTMGWSPLLLTLLAHCTGSWAQSVLTQPASVSGSLGQRVTITCTGSSSNIGRA
NVAWFQQVPGTGPRTVIYTSVKRPSGVPDRFSGSKSGSTATLTISGLQAEDEADY
YCSSWDNSLDAGVFGGGTHLTVLG

FIG 87B

Table 15

SEQ ID NO: 118 (Ca-1012)

MTSTMGWFPLLLTLLAHSTGSWAQSVLTQPASVSGSLGQRVTITCTGGTSNIGRG
FVSWFQQVPGIGPKILIFDAYRRPSGVPDRFSGSRSGNTATLTISGLQAEDEADYY
CAVYDSRLDVGVFGSGSQLTVLS

Table 15

SEQ ID NO: 119 (Ca-1202)

MTSNMAWCPFLLTLLTYCTGSWARSVLTQPASVSGSPGQKVTIYCSGTMSDIGV
LGANWYQQLPGKAPKLLVDNDGDRPSGVPDRFSASKSGHSDTLTITGLQPEDEG
DYYCQSFDSSLDAAIFGEGTHLTVLG

Table 15

SEQ ID NO: 120 (Ca-1203)

SVASYVLTQSPSQNVTLRQAAIITCEGHINIGTKSVHWYQQKQGQAPVLIIYDDK
SRPSGIPERFSGANSGNTATLTISGALAEDEADYYCLVWDSSAIWVFGEGTHLTV
LG

Table 15

SEQ ID NO: 121 (Ca-1204)

MTSTMAWSPLLLTLLAIIFTGSWAQSVLTQPTSVSGSLGQRVTISCTASSSNIDRD
YVAWYQQLPGTRPRALIYANSNRPSGVPDRFSGSKSGSTATLTISGLQAEDEADY
YCSTWDNSLTYVFGSGTQLTVLG

Table 15

SEQ ID NO: 122 (Ca-1205)

SVASYVLTQVPSVSVNLGKTATITCEGDNVGEKYTHWYQQEYGQAPVLIIYEDS
RRPSGIPERFSGSNSGNTATLTISGARAEDETDYYCQVWDDSGNVFGGGTHLTVL
G

FIG 87C
Table 15

SEQ ID NO: 123 (Ca-1206)

MTSTMGWFPLILTLLAHCAGSWAQSVLTQPASVSGSLGQRVTISCTGSDSNVGY
GDSIAYGDSVAWYQQVPGTSPRTLIYDVTSRPSGVPDRFSGSRSGTTATLTISGLQ
AEDEADYYCSSFDKTLNGLIVGGGTHLTVLG

Table 15

SEQ ID NO: 124 (Ca-1207)

MTSNMAWSPLLLTLLAYCTGSWAQSALTQPTSVSGSLGQRVSISCSGGIHNIGSV
GATWYQQLPGKAPKLLVSSDGDRPSGIPDRFSGSRSGNSVTLTITGLQAEDEAEY
YCQSFDSTLGVHVVFGGGTHLTVLG

Table 15

SEQ ID NO: 205 (Ca-1208)

LCSAVGPPKTESVMTSTMGWSPLLLTLLAHCTGSWAQSVLTQPASVSGSLGQRV
TIPCTGSSSNIDRYNVAWFQQLPGTGPKPSSIVLLTDPQGSLIDSLAPSQAA

Table 15

SEQ ID NO: 125 (Ca-1209)

MTSTMAWFPLLLTLLAHYTGSWARSDLTQPASVSGSLGQRITISCTGSSSNIGRN
YVGWYQQLPGRGPRTVVYGINSRPSGVPDRFSGSKSGSTVTLTISGLQAEDEADY
YCSTWDDSLSVVVFGGGTHLTVLG

Table 15

SEQ ID NO: 126 (Ca-1210)

MTSTMGWSPLLLTLTHWTGSWAQSVLSQPASMSGSLGLRITICCTGKNSNINNS
YVDWNQPLAGTGPRTVIHDDGDRPSGVPDQFSGSKSGNTATLTISRLQAEDEAD
YNGASFETSFNAVFGGGTHVTVLG

Figure 88

Canine Kappa Light Chain Variable Domain Sequences Derived from Canine PBMC RNA

Table 16

SEQ. ID NO. 127 (Ca Ka016-A1)

LSWLRQKPGHSPQRLIHQVSSRD?GVPDRFSGSGSGTDFTLTISRVEADDGGVYY
CGQGSQSIPTFGQGTKVEIKR

Table 16

SEQ. ID NO. 128 (Ca Ka016-A2)

MRFPSQLLGLLMLWIPGSAGDIVMTQTPLSLSVSPGEPASISCKASQSLLHSNGNT
YLYWFRQKPGQSPQRLIYKVSNRDPGVPDRFSGSGSGTDFTLRISRVETDDAGVY
YCGQVIQDPWTFGVGTKLELKR

Table 16

SEQ. ID NO. 129 (Ca Ka016-A3)

MRFPSQLLGLLMLWIPGSSGDIVMTQTPLSLSVSPGETASISCRASQTLLYSNGKN
YLFWYRQKPGQSPQRLIDLASNRDPGVPDRFSGSGSGTDFTLRISRVEADDAGVY
YCGQGMEIPWTFGAGTKVELKR

Table 16

SEQ. ID NO. 130 (Ca Ka016-A4)

MKFPSLLLGLLMLWIPGSTGEAVMTQTPLSLAVTPGEVATISCRASQSLLHSDGK
SYLNWYLQKPGQTPRPLIYEASKRFSGVSDRFSGSGSGTDFTLKINRVEAEDVGV
YYCQQSLHFPPTFGPGTKVELKR

Table 16

SEQ. ID NO. 131 (Ca Ka016-A5)

PDRFSGSGSGTDFTLTISRVEADDAGIYYCGQATQTPPTFGAGTKLDLKR

FIG 88A

Table 16

SEQ. ID NO. 132 (Ca Ka016-A6)

MRFPSQLLGLLMLWIPGSSGDIVMTQTPLSLSVRPGESASISCKASQSLLHSGGGT
YLNWFRQRPGQSPQRLIYEVSKRDTGVPDRFSGSGSGTDFTLRITRVEADDTGIY
YCGQNTQLPLTFGQGTKVEIKR

Table 16

SEQ. ID NO. 133 (Ca Ka016-A7)

MRFPSQLLGLLMLWIPGSTGDIVMTQTPLSLSVSPGEPASISCKASQSLLHSNGNT
YLFWLRQKPGQSPQRLIYRVSNRDPGVPDRFSGSGSGTDFTLRISRVEADDAGVY
YCGQRVRSPWTFGAGTKVEVKR

Table 16

SEQ. ID NO. 134 (Ca Ka016-A8)

MRFPSQLLGLLMLWIPGSAGDIVMTQTPLSLSVSPGEPASISCKASQSLLHSNGNT
YLYWFRQKPGQSPQRLIYKVSNRDPGVPDRFSGSGSGTDFTLRISRVETDDAGVY
YCGQVIQDPWTFGVGTKLELKR

Table 16

SEQ. ID NO. 135 (Ca Ka016-A9)

MRFPSQLLGLLMLWIPGSSGDVVMAQTPLSLSVSPGETASISCRASQSLLHSNGN
TFLFWFRQKPGQSPQRLINFLSNRDPGVPDRFSGSGSGTDFTLRINRVEADDAGL
YYCGQGLQAPLTFGQGTKLEIKR

Table 16

SEQ. ID NO. 136 (Ca Ka016-A10)

MRFPSQLLGLLMLWIPGSNGDDVLTQTPLSLSVRPGETVSILCKASESLLHSDGN
TYLSWVRQKAGQSPQRLMYRVSDRDTGVPDRFSGSGSGTDFTLTISGVEADDAG
IYYCGQATHYPLEFGQGTRVEIKR

FIG 88B

Table 16

SEQ. ID NO. 137 (Ca Ka016-A11)

LMLWIPGSTGEIVLTQTPLSLSVSPGEPASISCKASQSLLHPNGVTYLYWFRQKPG
QSPQRLIYKVSNRDPGVPDRFSGSGSEIDFTLIISRVEADDGGIYYCGQGIQNPFTF
GQGTKLEIKR

Table 16

SEQ. ID NO. 138 (Ca Ka016-A12)

MRFPSQLLGLLMLWIPGSIGDIVMTQTPLSLSVSPGESASISCKASQSLLHSNGNT
YLYWFRQKPGHSPQRLIHQVSSRDPGVPDRFSGSGSGTDFTLRISRVEADDAGLY
YCGQGTQFPFTFGQGTKVEIKR

Table 16

SEQ. ID NO. 139 (Ca Ka016-B1)

MRFPSQLLGLLMLWIPGSIGDIVMTQTPLSLSVSPGESASISCKASQSLLHSNGNT
YLYWFRQKPGHSPQRLIHQVSSRDPGVPDRFSGSGSGTDFTLRISRVEADDAGLY
YCGQGTQFPFTFGQGTKVEIKR

Table 16

SEQ. ID NO. 140 (Ca Ka016-B2)

MRFPSQLLGLLMLWIPGSSGDIVMTQTPLSLSVSPGETASISCRASQSLLHSNGNT
YSFWFRQKPGQSPQRLINLVSSRGPGVPDRFSGSGSGTDFTLIISRVEADDAGVYY
CGHGKEAPYTFSQGTKLEIKR

Table 16

SEQ. ID NO. 141 (Ca Ka016-B3)

MRFPSQLLGLLMLWIPGSVGDIVMTQSPMSLSVGPGESASMSCKANQSLLYSDGI
TYLSWFLQRPGQSPQRLIYEVSKRDTGVPGRFIGSGAGTDFTLRISRVEADDAGV
YYCGQALQFPLTFSQGAKLEIER

FIG 88C

Table 16

<u>SEQ. ID NO. 142 (Ca Ka016-B4)</u>

MRFPSQLLGLLMLWIPGSSGDVVMTQTPLSLSVRPGETASISCRASQSLLHSSGIT
KLFWYRQKPGQSPQRLVYWVSNRDPGVPDRFTGSGSGTDFTLRISRLEADDAGI
YYCGHAIGFPLTFGQGTKVEIKR

Table 16

<u>SEQ. ID NO. 143 (Ca Ka016-B5)</u>

MRFPSQLLGLLMLWIPGSSGDIVMTQTPLSLSVRPGESASISCKASQSLLHSGGGT
YLNWFRQRPGQSPQRLIYEVSKRDTGVPDRFSGSGSGTDFTLRITRVEADDTGIY
YCGQNTQFPLTFGQGTKVEIKR

Table 16

<u>SEQ. ID NO. 144 (Ca Ka016-B6)</u>

MRFPSQLLGLLMLWIPGSSGGIVMTQTPLSLSVRPGETASISCRASQSLLYSDGNT
YLFWFRQKPGQSPQRLMYRVSDRDTGVPDRFSGSGSGTDFTLTISGVEADDAGI
YYCGQATHYPLEFGQGTXVEIKR

Table 16

<u>SEQ. ID NO. 145 (Ca Ka016-B7)</u>

MRFPSQLLGLLMLWIPGSSGDIVMTQTPLSLSVRPGESASISCKASQSLLHSGGGT
YLNWFRQRPGQSPQRLIYEVSKRDTGVPDRFIGSGAGTDFTLRISRVEADDAGVY
YCGQGVQGPWTIGAGTKLELQR

Table 16

<u>SEQ. ID NO. 146 (Ca Ka016-B8)</u>

MRFPSQLLGLLMLWIPGSSGDIVMTQTPLSVSVSPGETASISCKASQSLLSHDGNT
YLHWFRQKPGQSPQRLIYKVSNRDTGVPDRFSGSGSGTDFTLKISRVEADDTGV
YYCGQITQDPFTFGQGTKLEIKR

FIG 88D

Table 16

SEQ. ID NO. 147 (Ca Ka016-B9)

MRFPSQLLGLLMLWIPGSSGDIVMTQTPLSLSVSPGETASISCRASQSLLHSNGNT
YLFWFRQKPGQSPQRLINWVSNRDPGVPDRFGGSGSGTDFTLRISRVEADDAGIY
YCGQGIQGPYTFSQGTKLEIKR

Table 16

SEQ. ID NO. 148 (Ca Ka016-B10)

MRFPSQFLGLLMLWIPGSSGDIAMTQTPLSLSVGPGETASITCKASQSLLHSNGNT
YLFWFRQKPGQSPQRLIYLVSNRDPGVPDRFSGSGSGTDFTLTISRVEADDAGIY
YCGQATQTPPTFGAGTKLDLKR

Table 16

SEQ. ID NO. 149 (Ca Ka016-B11)

MRFPSQLLGLLMLWIPGSSGDIVMAQTPLSLSVSPGEPASISCKASQSLLHSDGRT
CLSWFRQKSGQSPQRLIYEVSNRDTGVPDRFSGSGSGTDFTLRISRVEADDTGIYY
CGQTVQFPLTFGQGTKLEIKR

Table 16

(SEQ. ID NO. 150) (Ca Ka016-B12)

GQSPQRLIYKVSNRDPGVPDRFSGSGSGTDFTLRISRVEPEDVGVYYCGQGTLNP
WTFGAGTKVELKR

Table 16

SEQ. ID NO. 151 (Ca Ka017-1)

MRFPSQLLGLLMLWIPGSSGDVVMTQTPLSLSVSPGETASISCRASQSLLISNGN
TFLFWFRQ*PGQSPQRLNFVSNRDPGVPDRFSGSGSGTDFTLRISRVEADDAGIY
YCGQGLLAPPTFGQGTKVEIRR    Note: * indicates a stop codon

FIG 88E

Table 16

SEQ. ID NO. 152 (Ca Ka017-2)

MRFPSQLLGLLMLWIPGSGGDIVMTQTPPSLSVSPREPASISCKASQSLLRSNGNT
YLYWFRQKPGQSPEGLIYRVSNRFTGVSDRFSGSGSGTDFTLRISTVEADDAGVY
YCGQATQFPSTFSQGTKLEIKR

Table 16

SEQ. ID NO. 153 (Ca Ka017-3)

MRFPSQLLGLLMLWIPGSXGDIVLTQTPLSLSVSPGEPASISCKASQSLLHSNGITY
LNWYRQRPGQSPQXLIYKVSNRDTGVPDRFSGSGSGTDFTLRXSKVEADDTGIY
YCGQDTQFPLTLGXGTHXEIKR

Table 16

SEQ. ID NO. 154 (Ca Ka017-5)

MRFPSQLLGLLMLWIPGSTGDIVMTQTPLSLSVSPGEPASIYCKASQSLLHSNGKT
FLYWFRQKPGQSPQRLIYRVSNRDPGVPDRFSGSGSGTDFTLRISRVEADDAGIY
YCGQGIQDPTFGQGTKVEIKR

Table 16

SEQ. ID NO. 155 (Ca Ka017-6)

MRFPSQLLGLLMLWIPGSGGDIVMTQTPPSLSVSPREAASISCKASQSLLKSNGNT
YFYWFRQKPGQVSEGLIYKVSSRFTGVSDRFSGSGSGTDFTLRISRVEADDAGVY
FCGQALQFPYTFSQGTKLDIKR

Table 16

SEQ. ID NO. 156 (Ca Ka017-10)

MRFPSQLLGLLMLWIPESGGDVVLTQTPPSLSLSPGETASISCKASRSLLNSDGST
YLDWYLQKPGQSPRLLIYLVSNRFSGVSDRFSGSGSGTDFTLTISRVEADDAGVY
YCGQGSRVPLTFGQGTKVEIKR

FIG 88F

Table 16

SEQ. ID NO. 157 (Ca Ka017-11)

MRFPSQLLGLLMLWIPGSSGDIVMTQTPLSLSVSPGETASISCRASQSLLHRNGIT
YLSWFRQRPGQSPQRLINLVSNRDPGVPDRFSGSGSGTDFTLRISRVEADDVGVY
YCGHGLQTPYTFGQGTSLEIER

Table 16

SEQ. ID NO. 158 (a Ka017-12)

MRFPSQLLGLLVLWIPGSSGDIVMTQTPLSLSVSPGETVSISCRASQSLLYSDGNIY
LFWFRRKPGQSPQHLINLVSNRDPGVPDRFSGSGSGTDFTLRISRVEADDAGVYY
CGQGTQPPYTFSQGTKVEIKR

Table 16

SEQ. ID NO. 159 (Ca Ka017-13)

MRFPSQLLGLLMLWIPESGGDVVLTQTPPSLSLSPGETASISCKASRSLLNSDGST
YLDWYLQKPGQSPRLLIYLVSNRFSGVSDRFSGSGSGTDFTLTISRVEADDAGVY
YCGQGSRVPLTFGQGTKVEIKR

Table 16

SEQ. ID NO. 160 (Ca Ka017-14)

MRFPSQLLGLLMLWIPGSSGDIVMAQTPLSLSVSPGETASISCRASQSLLHSNGIT
YLFWYRQKPGQSPQRLISMVFNRDPGVPDRFGGSGSGTDFTLRISRVEADDAGL
YFCGHGTQIPYSFSQGTKLEIKR

Table 16
SEQ. ID NO. 161 (Ca Ka017-16)

MRFPSQLLGLLMLWIPGSSGDIVMTQTPLSLSISPGEPASISCKASQSLLHSGGDTY
LNWFRQRPGQSPQLLINRVSSRKKGVPDRFSGSGSGTEFTLRISRVEADDAGIYFC
GQGTQFPYTFSQGTKLEIKR

FIG 88G

Table 16

SEQ. ID NO. 162 (Ca Ka017-20)

MRFPSQLLGLLMLWIPGSGGDIVMTQTPPSLSVSPGEPASMSCKASQSLLHSNGN
TYLYWFRQKPGQSPEALIYKVSNRFTGVSDRFSGSGSGTDFTLRINRVEADDVGV
YYCGQGIQIPYTFSQGTKLEIKR

Table 16

SEQ. ID NO. 163 (Ca Ka017-23)

MRFPSQLLGLLMLWIPGSTGEIVLTQTPLSLSVSPGESASISCKASQSLLYSNGNT
YLYWFRQKAGQSPQRVIYRVSNRDPGVPDRFSGSGSGTDFTLRISSVENDDAGV
YYCGQGSEDPPTFGAGTKVELKR

Table 16

SEQ. ID NO. 164 (Ca Ka017-24)

MRFPSQLLGLLTLWIPGSTGDIVMTQTPLSLSVSPGEPASISCKASQSLLHSNGNT
YLYWFRQKPGQSPQRLIYKVSNRDPGVPXRFSGSGSGTDFTLRVSXVEADDAGV
YYCGQGVQDPFTFGQGTKLEIKR

Figure 89

Mouse Anti-NGF mAb CDRs Grafted onto Human Ig Frameworks (CDR-Grafted Anti-NGF Abs); CDRs underlined Table 17

SEQ ID NO: 165 (Hu72 VH; CDR-GRAFT VH3-13/JH5)

EVQLVESGGGLVQPGGSLRLSCAASGFTFSDYYMFWVRQATGKGLEWVSTISD
GGSYTYYTDNVKGRFTISRENAKNSLYLQMNSLRAGDTAVYYCARDWSDSEGF
AYWGQGTLVTVSS

Table 17

SEQ ID NO: 166 (Hu73 VH (CDR-GRAFT VH1-18/JH6)

QVQLVQSGAEVKKPGASVKVSCKASGYTFTNYWMHWVRQAPGQGLEWMGRI
DPYGGGTKHNEKFKRRVTMTTDTSTSTAYMELRSLRSDDTAVYYCARSGYDYY
FDVWGQGTTVTVSS

Table 17

SEQ ID NO: 167 (HU77 VH (CDR-GRAFT VH1-69/JH6)

QVQLVQSGAEVKKPGSSVKVSCKASGFNIKDTYIYWVRQAPGQGLEWMGRIDP
ANGNTIYASKFQGRVTITADKSTSTAYMELSSLRSEDTAVYYCARYGYYAYWG
QGTTVTVSS

Table 17

SEQ ID NO: 168 HU80 VH (CDR-GRAFT VH1-18/JH6)

QVQLVQSGAEVKKPGASVKVSCKASGFNIKDTYIYWVRQAPGQGLEWMGRIDP
ANGNTIYASKFQGRVTMTTDTSTSTAYMELRSLRSDDTAVYYCARYGYYAYWG
QGTTVTVSS

FIG 89A

Table 17

SEQ ID NO: 169 HU81 VH (CDR-GRAFT VH3-15/JH1)

EVQLVESGGGLVKPGGSLRLSCAASGFTFSNHYMYWVRQAPGKGLEWVGSISD
GGAYTFYPDTVKGRFTISRDDSKNTLYLQMNSLKTEDTAVYYCTTEESANNGFA
FWGQGTLVTVSS

Table 17

SEQ ID NO: 170 HU82 VH (CDR-GRAFT VH2-26/JH6)

QVTLKESGPVLVKPTETLTLTCTVSGFSLTGYNINWIRQPPGKALEWLAMIWGY
GDTDYNSALKSRLTISKDTSKSQVVLTMTNMDPVDTATYYCARDHYGGNDWY
FDVWGQGTTVTVSS

Table 17

SEQ ID NO: 171 HU72 VL (CDR-GRAFT O1/JK2)

DIVMTQTPLSLPVTPGEPASISCRSSQSIVQSNGNTYLEWYLQKPGQSPQLLIYKV
SNRFSGVPDRFSGSGSGTDFTLKISRVEAEDVGVYYCFQGSHVPFTFGQGTKLEIK
R

Table 17

SEQ ID NO: 172 HU73 VL (CDR-GRAFT L22/JK2)

DIQMIQSPSFLSASVGDRVSIICRASENIYSFLAWYLQKPGKSPKLFLYNANTLAE
GVSSRFSGRGSGTDFTLTIISLKPEDFAAYYCQHHFGTPFTFGQGTKLEIKR

Table 17

SEQ ID NO: 173 HU77 VL (CDR-GRAFT O1/JK2)

DIVMTQTPLSLPVTPGEPASISCKSTKSLLNGDGFTYLDWYLQKPGQSPQLLIYLV
SNRFSGVPDRFSGSGSGTDFTLKISRVEAEDVGVYYCFESNYLFTFGQGTKLEIKR

FIG 89B

Table 17

SEQ ID NO: 174 HU80 VL (CDR-GRAFT 01/JK2)

DIVMTQTPLSLPVTPGEPASISC<u>KSTKSLLNGDGFTYLD</u>WYLQKPGQSPQLLIY<u>LV
SNRFS</u>GVPDRFSGSGSGTDFTLKISRVEAEDVGVYYC<u>FESNYLFT</u>FGQGTKLEIKR

Table 17

SEQ ID NO: 175 HU81 VL (CDR-GRAFT 01/JK2)

DIVMTQTPLSLPVTPGEPASISC<u>RSSQSILHSNGNTYLE</u>WYLQKPGQSPQLLIY<u>RVS
NRFS</u>GVPDRFSGSGSGTDFTLKISRVEAEDVGVYYC<u>FQGAHVPFT</u>FGQGTKLEIK
R

Table 17

SEQ ID NO: 176 HU82 VL (CDR-GRAFT 08/JK2)

DIQMTQSPSSLSASVGDRVTITC<u>RASQDITNYLN</u>WYQQKPGKAPKLLIY<u>YTSRLH</u>
SGVPSRFSGSGSGTDFTFTISSLQPEDIATYYC<u>QQGKTLPRT</u>FGQGTKLEIKR

Figure 90

Mouse/Canine Chimeric Antibody sequences

Table 18
PR-1290646 light chain amino acid sequence (SEQ ID NO:194)
DVLMTQTPLSLPVSLGDQASISC<u>RSSQSIVQSNGNTY</u>LEWYLQKPGQSPKLLIY<u>K
VSNRFS</u>GVPDRFSGSGSGTDFTLKISREAEDLGVYYC<u>FQGSHVPFT</u>FGSGTKLEIK
RNDAQPAVYLFQPSPDQLIITGSASVVCLLNSFYPKDINVKWKVDGVIQDTGIQE
SVTEQDKDSTYSLSSTLTMSSTEYLSHELYSCEITHKSLPSTLIKSFQRSECQRVD
(SEQ ID NO:194)

Table 18
PR-1290646 heavy chain amino acid sequence (SEQ ID NO:195)
EVHLVESGGGLVKPGGFLILSCAASGFTFS<u>DYYMF</u>WIRQTPGKRLEWVA<u>TISDGG
SYTYYTDNVKG</u>RFTISRDNVKNNLYLQMSHLKSADTAMYYCAR<u>DWSDSEGFA
Y</u>WGQGTLVTVSAASTTAPSVFPLAPSCGSTSGSTVALACLVSGYFPEPVTVSWNS
GSLTSGVHTFPSVLQSSGLHSLSSMVTVPSSRWPSETFTCNVVHPASNTKVDKPV
FNECRCTDTPPCPVPEPLGGPSVLIFPPKPKDILRITRTPEVTCVVLDLGREDPEVQI
SWFVDGKEVHTAKTQSREQQFNGTYRVVSVLPIEHQDWLTGKEFKCRVNHIDLP
SPIERTISKARGRAHKPSVYVLPPSPKELSSSDTVSITCLIKDFYPPDIDVEWQSNG
QQEPERKHRMTPPQLDEDGSYFLYSKLSVDKSRWQQGDPFTCAVMHETLQNHY
TDLSLSHSPGK (SEQ ID NO:195)

Table 18
PR-1290654 light chain amino acid sequence (SEQ ID NO:196)
DIQMTQSPASLSASVGETVTVTC<u>RASENIYSFLA</u>WHQQKQGKSPQLLVY<u>NANTL
AEG</u>VPSRFSGSGSGTQFSLKINSLQPEDFGSYYC<u>QHHFGTPFT</u>FGSGTKLEIKRND
AQPAVYLFQPSPDQLHTGSASVVCLLNSFYPKDINVKWKVDGVIQDTGIQESVTE
QDKDSTYSLSSTLTMSSTEYLSHELYSCEITHKSLPSTLIKSFQR SECQRVD (SEQ
ID NO:196)

FIG 90A

Table 18

PR-1290654 heavy chain amino acid sequence (SEQ ID NO:197)

QVQLQQPGAELVKPGASVKLSCKASGYTFT<u>NYWMH</u>WVKQRPGQGLEWIG<u>RIDP
YGGGTKHNEKFKRK</u>ATVTADKSSSTAYILLSSLTSEDSAVYYCTR<u>SGYDYYFDV</u>
WGTGTTVTVSSASTTAPSVFPLAPSCGSTSGSTVALACLVSGYFPEPVTVSWNSG
SLTSGVHTFPSVLQSSGLHSLSSMVTVPSSRWPSETFTCNVVHPASNTKVDKPVF
NECRCTDTPPCPVPEPLGGPSVLIFPPKPKDILRITRTPEVTCVVLDLGREDPEVQIS
WFVDGKEVHTAKTQSREQQFNGTYRVVSVLPIEHQDWLTGKEFKCRVNHIDLPS
PIERTISKARGRAHKPSVYVLPPSPKELSSSDTVSITCLIKDFYPPDIDVEWQSNGQ
QEPERKHRMTPPQLDEDGSYFLYSKLSVDKSRWQQGDPFTCAVMHETLQNHYT
DLSLSHSPGV (SEQ ID NO:197)

Table 18

PR-1290656 light chain amino acid sequence (SEQ ID NO:198)

DVVLTQTPLSLPVNIGDQASISCKST<u>KSLLNGDGFTYLD</u>WYLQKPGQSPQLLIY<u>L
VSNRFS</u>GVPDRFSGSGSGTDFTLKISRVEAEDLGVYYC<u>FESNYLFT</u>FGSGTKLEM
KRNDAQPAVYLFQPSPDQLHTGSASVVCLLNSFYPKDINVKWKVDGVIQDTGIQ
ESVTEQDKDSTYSLSSTLTMSSTEYLSHELYSCEITHKSLPSTLIKSFQRSECQRVD
(SEQ ID NO:198)

Table 18

PR-1290656 heavy chain amino acid sequence (SEQ ID NO:199)

EVQLQQSGAELVKPGASVKLSCTASGFNIK<u>DIYIY</u>WVKQRPEQGLEWIG<u>RIDPAN
GNTIYASKFQG</u>KASITADTSSNTAYMQLSSLTSGDTAVYYCAG<u>YGYYAY</u>WGQG
TTLTVSSASTTAPSVFPLAPSCGSTSGSTVALACLVSGYFPEPVTVSWNSGSLTSG
VHTFPSVLQSSGLHSLSSMVTVPSSRWPSETFTCNVVHPASNTKVDKPVFNECRC
TDTPPCPVPEPLGGPSVLIFPPKPKDILRITRTPEVTCVVLDLGREDPEVQISWFVD
GKEVHTAKTQSREQQFNGTYRVVSVLPIEHQDWLTGKEFKCRVNHIDLPSPIERT
ISKARGRAHKPSVYVLPPSPKELSSSDTVSITCLIKDFYPPDIDVEWQSNGQQEPER
KHRMTPPQLDEDGSYFLYSKLSVDKSRWQQGDPFTCAVMHETLQNHYTDLSLS
HSPGK (SEQ ID NO:199)

FIG 90B

Table 18

PR-1290657 light chain amino acid sequence (SEQ ID NO:200)
DVLMTQTPLSLPVSLGDQASISC<u>RSSQSILHSNGNTYLE</u>WYLQKPGQSPNLLIY<u>RV
SNRFS</u>GVPDRFSGSGSGTDFTLKISRVEAEDLGVYYC<u>FQGAHVPFT</u>FGSGTKLEIK
RNDAQPAVYLFQPSPDQLHTGSASVVCLLNSFYPKDINVKWKVDGVIQDTGIQE
SVTEQDKDSTYSLSSTLTMSSTEYLSHELYSCEITHKSLPSTLIKSFQRSECQRVD
(SEQ ID NO:200)

Table 18

PR-1290657 heavy chain amino acid sequence (SEQ ID NO:201)
EVQLVESGGGAVKPGGSLTLSCAASGFTFS<u>NHYMY</u>WVRQTPEKRLEWVA<u>SISD
GGAYTYYPDTVKGR</u>FTISRDNVNNNLYLQMRHLKSEDTAMYYC<u>TREESANNGF
AF</u>WGQGTLVTVSAASTTAPSVFPLAPSCGSTSGSTVALACLVSGYFPEPVTVSWN
SGSLTSGVHTFPSVLQSSGLHSLSSMVTVPSSRWPSETFTCNVVHPASNTKVDKP
VFNECRCTDTPPCPVPEPLGGPSVLIFPPKPKDILRITRTPEVTCVVLDLGREDPEV
QISWFVDGKEVHTAKTQSREQQFNGTYRVVSVLPIEHQDWLTGKEFKCRVNHID
LPSPIERTISKARGRAHKPSVYVLPPSPKELSSSDTVSITCLIKDFYPPDIDVEWQSN
GQQEPERKHRMTPPQLDEDGSYFLYSKLSVDKSRWQQGDPFTCAVMHETLQNH
YTDLSLSHSPGV (SEQ ID NO:201)

Table 18

PR-1290658 light chain amino acid sequence (SEQ ID NO:202)
DIQMTQTTSSLSASLGDRVTITC<u>RASQDITNYLN</u>WYQQKPDGTVKLLIY<u>YTSRLH</u>
SGVPSRFSGSGSGTDYSLTISNLDQEDIATYFC<u>QQGKTLPRT</u>FGGGTKLEIKRNDA
QPAVYLFQPSPDQLHTGSASVVCLLNSFYPKDINVKWKVDGVIQDTGIQESVTEQ
DKDSTYSLSSTLTMSSTEYLSHELYSCEITHKSLPSTLIKSFQRSECQRVD (SEQ ID
NO:202)

FIG 90C

Table 18

PR-1290658 heavy chain amino acid sequence (SEQ ID NO:203)

QVQLKESGPGLVAPSQSLSITCTVSGFSLT<u>GYNIN</u>WVRQPPGKGLEWLG<u>MIWGY
GDTDYNSALKS</u>RLSISKDNSKSQVFLKMNSLQTDDTARYYCAR<u>DHYGGNDWYF
DV</u>WGTGTTVTVSSASTTAPSVFPLAPSCGSTSGSTVALACLVSGYFPEPVTVSWN
SGSLTSGVHTFPSVLQSSGLHSLSSMVTVPSSRWPSETFTCNVVHPASNTKVDKP
VFNECRCTDTPPCPVPEPLGGPSVLIFPPKPKDILRITRTPEVTCVVLDLGREDPEV
QISWFVDGKEVHTAKTQSREQQFNGTYRVVSVLPIEHQDWLTGKEFKCRVNHID
LPSPIERTISKARGRAHKPSVYVLPPSPKELSSSDTVSITCLIKDFYPPDIDVEWQSN
GQQEPERKHRMTPPQLDEDGSYFLYSKLSVDKSRWQQGDPFTCAVMHETLQNH
YTDLSLSHSPGK (SEQ ID NO:203)

SEQUENCE LISTING

```
<160> NUMBER OF SEQ ID NOS: 210

<210> SEQ ID NO 1
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaagtgcacc tggtggagtc tgggggaggc ttagtgaagc ctggagggtt cctgatactc      60
tcctgtgcag cctctggatt cactttcagt gactattaca tgtttggat tcgccagact     120 ccgggaaaga ggctggagtg ggtcgcaacc attagtgatg gtggtagtta cacctactac     180
acagacaatg taaagggccg attcaccatc tccagagaca atgtcaagaa caacctgtac     240
ctgcaaatga gccatctgaa gtctgcggac acagccatgt attactgtgc aagagattgg     300
agtgactccg aggggtttgc ttactggggc caagggactc tggtcactgt ctctgca        357

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val His Leu Val Glu Ser Gly Gly Gly Leu Val Lys Pro Gly Gly
1               5                   10                  15

Phe Leu Ile Leu Ser Cys Ala Ala Ser Gly Phe Thr Phe Ser Asp Tyr
            20                  25                  30

Tyr Met Phe Trp Ile Arg Gln Thr Pro Gly Lys Arg Leu Glu Trp Val
        35                  40                  45

Ala Thr Ile Ser Asp Gly Gly Ser Tyr Thr Tyr Tyr Thr Asp Asn Val
    50                  55                  60

Lys Gly Arg Phe Thr Ile Ser Arg Asp Asn Val Lys Asn Asn Leu Tyr
65                  70                  75                  80

Leu Gln Met Ser His Leu Lys Ser Ala Asp Thr Ala Met Tyr Tyr Cys
                85                  90                  95

Ala Arg Asp Trp Ser Asp Ser Glu Gly Phe Ala Tyr Trp Gly Gln Gly
            100                 105                 110

Thr Leu Val Thr Val Ser Ala
        115

<210> SEQ ID NO 3
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
```

```
gatgttttga tgacccaaac tccactctcc ctgcctgtca gtcttggaga tcaagcctcc    60
atctcttgca gatctagtca gagtattgta caaagtaatg gaaacaccta tttagaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttcca   300
ttcacgttcg gctcggggac aaagttggaa ataaaacgg                          339
```

<210> SEQ ID NO 4
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg Cys
```

<210> SEQ ID NO 5
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
caggtccaac tgcagcagcc tggggctgag cttgtgaagc ctggggcttc agtgaagctg    60
tcctgtaagg cttctggcta caccttcacc aactactgga tgcactgggt gaagcagagg   120
cctggacaag gccttgagtg gattggaagg attgatcctt atggtggtgg tactaagcac   180
aatgagaagt tcaagaggaa ggccacagtg actgcagaca atcctccag cacagcctac    240 atcctgctca gcagcctgac atctgaggac tctgcggtct attattgtac aagatctggt   300
tacgactatt acttcgatgt ctggggcaca gggaccacgg tcaccgtctc ctca          354
```

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
                20                  25                  30

Trp Met His Trp Val Lys Gln Arg Pro Gly Gln Gly Leu Glu Trp Ile
            35                  40                  45

Gly Arg Ile Asp Pro Tyr Gly Gly Thr Lys His Asn Glu Lys Phe
        50                  55                  60

Lys Arg Lys Ala Thr Val Thr Ala Asp Lys Ser Ser Thr Ala Tyr
65                  70                  75                  80

Ile Leu Leu Ser Ser Leu Thr Ser Glu Asp Ser Ala Val Tyr Tyr Cys
                85                  90                  95

Thr Arg Ser Gly Tyr Asp Tyr Tyr Phe Asp Val Trp Gly Thr Gly Thr
            100                 105                 110

Thr Val Thr Val Ser Ser
            115

<210> SEQ ID NO 7
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gacatccaga tgactcagtc tccagcctcc ctatctgcat ctgtgggaga aactgtcacc     60
gtcacatgtc gagcaagtga aaatatttac agttttttag catggcatca gcagaaacag    120
ggaaaatctc ctcagctcct ggtctataat gcaaatacct tagcagaggg tgtgccatca    180
aggttcagtg gcagtggatc aggcacacag ttttctctga agatcaacag cctgcagcct    240
gaagattttg ggagttatta ctgtcaacat cattttggga ctccattcac gttcggctcg    300
gggacaaagt tggaaataaa acgg                                            324

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ala Ser Leu Ser Ala Ser Val Gly
1               5                   10                  15

Glu Thr Val Thr Val Thr Cys Arg Ala Ser Glu Asn Ile Tyr Ser Phe
                20                  25                  30

Leu Ala Trp His Gln Gln Lys Gln Gly Lys Ser Pro Gln Leu Leu Val
            35                  40                  45

Tyr Asn Ala Asn Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Phe Gly Thr Pro Phe
            85                  90                  95

Thr Phe Gly Ser Gly Thr Lys Leu Glu Ile Lys Arg
            100                 105
```

<210> SEQ ID NO 9
<211> LENGTH: 345
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 9
gaggttcagc tgcagcagtc tggggcagag cttgtgaagc caggggcctc agtcaagttg    60
tcctgcacag cttctggctt caacattaaa gacacctata tatactgggt gaaacagagg    120
cctgaacagg gcctggagtg gattggaagg attgatcctg cgaatggaaa tactatatat    180
gcctcaaagt tccagggcaa ggcctctata acagcagaca catcatccaa cacagcctac    240
atgcagctca gcagcctgac atctggggac actgccgtct attactgtgc tggttatggt    300
tactacgcct actggggcca aggcaccact ctcacagtct cctca    345

<210> SEQ ID NO 10
<211> LENGTH: 115
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 10

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile Tyr Trp Val Lys Gln Arg Pro Glu Gln Gly Leu Glu Trp Ile
        35                  40                  45

Gly Arg Ile Asp Pro Ala Asn Gly Asn Thr Ile Tyr Ala Ser Lys Phe
    50                  55                  60

Gln Gly Lys Ala Ser Ile Thr Ala Asp Thr Ser Ser Asn Thr Ala Tyr
65                  70                  75                  80

Met Gln Leu Ser Ser Leu Thr Ser Gly Asp Thr Ala Val Tyr Tyr Cys
                85                  90                  95

Ala Gly Tyr Gly Tyr Tyr Ala Tyr Trp Gly Gln Gly Thr Thr Leu Thr
            100                 105                 110

Val Ser Ser
        115

<210> SEQ ID NO 11
<211> LENGTH: 336
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 11
gatgttgttc tgacccaaac tccactctct ctgcctgtca atattggaga tcaagcctct    60
atctcttgca gtctactaa gagtcttctg aatggtgatg gattcactta tttggactgg    120
tacttgcaga agccaggcca gtctccacag ctcctaatat atttggtttc taatcgattt    180
tctggagttc cagacaggtt cagtggcagt gggtcaggaa cagatttcac actcaagatc    240
agcagagtgg aggctgagga tttgggagtt tattattgct tcgagagtaa ctatctattc    300
acgttcggct cggggacaaa gttggaaatg aaacgg                               336

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Val Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Gly
            20                  25                  30

Asp Gly Phe Thr Tyr Leu Asp Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Glu Ser
                85                  90                  95

Asn Tyr Leu Phe Thr Phe Gly Ser Gly Thr Lys Leu Glu Met Lys Arg
            100                 105                 110

<210> SEQ ID NO 13
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gaggttcagc tgcagcagtc tggggcagag cttgtgaagc caggggcctc agtcaagttg    60
tcctgcacag cttctggctt caacattaaa gacacctata tatattgggt gaaacagagg   120
cctgaacagg gcctggaatg gattggaagg attgatcctg cgaatggaaa tactatatat   180
gcctcaaagt tccagggcaa ggccactata acagcagaca catcatccaa cacagcctac   240
atgcagctca gcagcctgac atctggggac actgccgtct attactgtgc tggttatggt   300
tactacgcct actggggcca aggcaccact ctcacagtct cctca                   345

<210> SEQ ID NO 14
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile Tyr Trp Val Lys Gln Arg Pro Glu Gln Gly Leu Glu Trp Ile
        35                  40                  45

Gly Arg Ile Asp Pro Ala Asn Gly Asn Thr Ile Tyr Ala Ser Lys Phe

Gln Gly Lys Ala Thr Ile Thr Ala Asp Thr Ser Ser Asn Thr Ala Tyr
65                  70                  75                  80

Met Gln Leu Ser Ser Leu Thr Ser Gly Asp Thr Ala Val Tyr Tyr Cys
                85                  90                  95

Ala Gly Tyr Gly Tyr Tyr Ala Tyr Trp Gly Gln Gly Thr Thr Leu Thr
            100                 105                 110

Val Ser Ser
        115

<210> SEQ ID NO 15
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gatgttgttc tgacccaaac tccactctct ctgcctgtca atattggaga tcaagcctct     60
atctcttgca agtctactaa gagtcttctg aatggtgatg gattcactta tttggactgg    120
tacttgcaga agccaggcca gtctccacag ctcctaatat atttggtttc taatcgattt    180
tctggagttc cggacaggtt cagtggcagt gggtcaggaa cagatttcac actcaagatc    240
agcagagtgg aggctgagga tttgggagtt tattattgct tcgagagtaa ctatctattc    300
acgttcggct cggggacaaa gttggaaatg aaacgg                              336

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Val Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Gly
            20                  25                  30

Asp Gly Phe Thr Tyr Leu Asp Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Glu Ser
                85                  90                  95

Asn Tyr Leu Phe Thr Phe Gly Ser Gly Thr Lys Leu Glu Met Lys Arg
            100                 105                 110

<210> SEQ ID NO 17
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gaagtgcaac tggtggagtc tgggggaggc gcagtgaagc ctggagggtc cctgacactc      60
tcctgtgcag cctctggatt cactttcagt aaccattaca tgtattgggt tcgccagact     120
ccggaaaaga ggctggagtg ggtcgcgtcc attagtgatg gtggtgctta caccttctat     180
ccagacactg tcaagggccg attcaccatc tccagagaca atgtcaacaa caacctgtac     240
ctgcaaatgc gccatctgaa gtctgaggac acagccatgt attactgtac aagagaggag     300
agtgctaaca acgggtttgc tttctggggc caagggactc tggtcactgt ctctgca        357
```

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

```
Glu Val Gln Leu Val Glu Ser Gly Gly Gly Ala Val Lys Pro Gly Gly
1               5                   10                  15

Ser Leu Thr Leu Ser Cys Ala Ala Ser Gly Phe Thr Phe Ser Asn His
            20                  25                  30

Tyr Met Tyr Trp Val Arg Gln Thr Pro Glu Lys Arg Leu Glu Trp Val
        35                  40                  45

Ala Ser Ile Ser Asp Gly Gly Ala Tyr Thr Phe Tyr Pro Asp Thr Val
    50                  55                  60

Lys Gly Arg Phe Thr Ile Ser Arg Asp Asn Val Asn Asn Asn Leu Tyr
65                  70                  75                  80

Leu Gln Met Arg His Leu Lys Ser Glu Asp Thr Ala Met Tyr Tyr Cys
                85                  90                  95

Thr Arg Glu Glu Ser Ala Asn Asn Gly Phe Ala Phe Trp Gly Gln Gly
            100                 105                 110

Thr Leu Val Thr Val Ser Ala
        115
```

<210> SEQ ID NO 19
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19

```
gatgttttga tgacccaaac tccactctcc ctgcctgtca gtcttggaga tcaagcctcc      60
atctcttgca gatctagtca gagcattcta catagtaatg gaaacaccta tttagaatgg     120
tacctgcaga accaggcca gtctccaaac ctcctgatct acagagtttc caaccgattt     180
tctggggtcc ccgacaggtt cagtggcagt ggatcaggga cagatttcac actcaagatc     240
agcagagtgg aggctgagga tctgggagtt tattactgct ttcaaggtgc acatgttcca     300
ttcacgttcg gctcggggac aaagttagaa ataaaacgg                            339
```

<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 20

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Asn Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ala His Val Pro Phe Thr Phe Gly Ser Gly Thr Lys Leu Glu Ile Lys
            100                 105                 110

Arg

<210> SEQ ID NO 21
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caggtgcagc tgaaggagtc aggacctggc ctggtggcgc cctcacagag cctgtccatc      60
acatgcaccg tctcagggtt ctcattaacc ggctataata aaactgggt tcgccagcct     120 ccaggaaagg gtctggagtg gctgggaatg atatgggtt atggagacac agactataat     180
tcagctctca aatccagact gagcatcagc aaggacaact ccaagagcca agttttctta     240
aaaatgaaca gtctgcaaac tgatgacaca gccaggtatt attgtgccag agatcactat     300
ggtggtaacg actggtactt cgatgtctgg ggcacaggga ccacggtcac cgtctcctca     360

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Asn Ile Asn Trp Val Arg Gln Pro Pro Gly Lys Gly Leu Glu Trp Leu
        35                  40                  45

Gly Met Ile Trp Gly Tyr Gly Asp Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp His Tyr Gly Gly Asn Asp Trp Tyr Phe Asp Val Trp Gly Thr

Gly Thr Thr Val Thr Val Ser Ser
        115                 120

<210> SEQ ID NO 23
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gatatccaga tgacacagac tacatcctcc ctgtctgcct ctctgggaga cagagtcacc        60
atcacttgca gggcaagtca ggacattacc aattatttaa actggtatca gcagaaacca       120
gatggaactg ttaaactcct gatctactac acatcaagat tacactcagg agtcccatca       180
aggttcagtg gcagtgggtc tggaacagat tattctctca ccattagcaa cctggatcaa       240
gaagatattg ccacttactt ttgccaacag ggtaaaacgc ttcctcggac gttcggtgga       300
ggcaccaagc tggaaatcaa acgg                                              324

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Thr Thr Ser Ser Leu Ser Ala Ser Leu Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Asp Gln
65                  70                  75                  80

Glu Asp Ile Ala Thr Tyr Phe Cys Gln Gln Gly Lys Thr Leu Pro Arg
                85                  90                  95

Thr Phe Gly Gly Gly Thr Lys Leu Glu Ile Lys Arg
            100                 105

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Phe Trp Val Arg His Ser Pro Gly Lys Gly Leu Gln Trp Val
        35                  40                  45

```
Ala Thr Ile Ser Asp Gly Gly Ser Tyr Thr Tyr Tyr Thr Asp Asn Val
        50                  55                  60

Lys Gly Arg Phe Thr Ile Ser Arg Asp Asp Ala Asn Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Trp Ser Asp Ser Glu Gly Phe Ala Tyr Trp Gly Gln Gly
            100                 105                 110

Thr Leu Val Thr Val Ser Ser
            115
```

<210> SEQ ID NO 26
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Ile Val Met Thr Gln Thr Pro Ser Leu Ser Val Ser Pro Arg
 1               5                  10                  15

Glu Pro Ala Ser Ile Ser Cys Arg Ser Ser Gln Ser Ile Val Gln Ser
                20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Ser
 50                  55                  60

Asp Arg Phe Ser Gly Ser Gly Ser Gly Thr Asp Phe Thr Leu Arg Ile
 65                  70                  75                  80

Ser Arg Val Glu Ala Asp Asp Thr Gly Val Tyr Tyr Cys Phe Gln Gly
                 85                  90                  95

Ser His Val Pro Phe Thr Phe Gly Ala Gly Thr Lys Val Glu Leu Lys
            100                 105                 110

Arg
```

<210> SEQ ID NO 27
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Glu Val Gln Leu Val Gln Ser Ala Ala Glu Val Lys Lys Pro Gly Ala
 1               5                  10                  15

Ser Val Lys Val Ser Cys Lys Thr Ser Gly Tyr Ile Phe Ile Asn Tyr
                20                  25                  30

Trp Met His Trp Val Gln Gln Ala Pro Gly Ala Gly Leu Glu Trp Met
             35                  40                  45

Gly Arg Ile Asp Pro Tyr Gly Gly Thr Lys His Asn Glu Lys Phe
 50                  55                  60

Lys Arg Arg Val Thr Leu Thr Ala Asp Thr Ser Thr Asn Thr Val Tyr
 65                  70                  75                  80

Met Glu Leu Ser Asn Leu Arg Thr Glu Asp Thr Ala Val Tyr Tyr Cys
                 85                  90                  95
```

```
Ala Arg Ser Gly Tyr Asp Tyr Tyr Phe Asp Val Trp Gly Gln Gly Thr
            100                 105                 110

Leu Val Thr Val Ser Ser
        115

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ile Ile Val Met Thr Gln Thr Pro Leu Ser Leu Ser Ala Ser Pro Gly
1               5                   10                  15

Glu Ser Ala Ser Ile Ser Cys Arg Ala Ser Glu Asn Ile Tyr Ser Phe
            20                  25                  30

Leu Ala Trp Phe Arg Gln Lys Pro Gly Gln Ser Pro Gln Arg Leu Ile
        35                  40                  45

Tyr Asn Ala Asn Thr Leu Ala Glu Gly Val Pro Asp Arg Phe Ser Gly
    50                  55                  60

Ser Gly Ser Gly Thr Asp Phe Thr Leu Arg Ile Ser Arg Val Glu Asp
65                  70                  75                  80

Glu Asp Ala Gly Leu Tyr Tyr Cys Gln His His Phe Gly Thr Pro Phe
                85                  90                  95

Thr Phe Gly Gln Gly Thr Lys Leu Glu Ile Lys Arg
            100                 105

<210> SEQ ID NO 29
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Gln Ser Ala Ala Glu Val Lys Lys Pro Gly Ala
1               5                   10                  15

Ser Val Lys Val Ser Cys Lys Thr Ser Gly Tyr Ile Phe Ile Asp Thr
            20                  25                  30

Tyr Ile Tyr Trp Val Gln Gln Ala Pro Gly Ala Gly Leu Glu Trp Met
        35                  40                  45

Gly Arg Ile Asp Pro Ala Asn Gly Asn Thr Ile Tyr Ala Ser Lys Phe
    50                  55                  60

Gln Gly Arg Val Thr Leu Thr Ala Asp Thr Ser Thr Asn Thr Val Tyr
65                  70                  75                  80

Met Glu Leu Ser Asn Leu Arg Thr Glu Asp Thr Ala Val Tyr Tyr Cys
                85                  90                  95

Ala Arg Tyr Gly Tyr Tyr Ala Tyr Trp Gly Gln Gly Thr Leu Val Thr
            100                 105                 110

Val Ser Ser
        115

<210> SEQ ID NO 30
<211> LENGTH: 112
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 30

Asp Leu Val Leu Thr Gln Thr Pro Arg Ser Leu Ser Val Ser Pro Gly
1               5                   10                  15

Glu Thr Ala Ser Ile Ser Cys Lys Ser Thr Lys Ser Leu Leu Asn Gly
            20                  25                  30

Asp Gly Phe Thr Tyr Leu Asp Trp Phe Arg Gln Lys Pro Gly Gln Ser
        35                  40                  45

Pro Gln Arg Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Thr Gly Leu Tyr Tyr Cys Phe Glu Ser
                85                  90                  95

Asn Tyr Leu Phe Thr Phe Ser Gln Gly Thr Asn Leu Glu Met Lys Arg
            100                 105                 110

<210> SEQ ID NO 31
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Asp Leu Met Lys Pro Gly Gly
1               5                   10                  15

Ser Leu Arg Leu Ser Cys Val Ala Ser Gly Phe Thr Phe Ser Asn His
            20                  25                  30

Tyr Met Tyr Trp Val Arg Gln Ala Pro Gly Lys Gly Leu Gln Trp Val
        35                  40                  45

Gly Ser Ile Ser Asp Gly Gly Ala Tyr Thr Phe Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Thr Glu Asp Thr Gly Arg Val Leu Leu
                85                  90                  95

Cys Glu Gly Glu Glu Ser Ala Asn Asn Gly Phe Ala Phe Trp Gly His
            100                 105                 110

Gly Thr Leu Val Thr Val Ser Ser
            115                 120

<210> SEQ ID NO 32
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Val Val Met Thr Gln Ala Pro Pro Ser Leu Ser Val Ser Pro Arg
1               5                   10                  15

Glu Pro Ala Ser Ile Ser Cys Arg Ser Ser Gln Ser Ile Leu His Ser
            20                  25                  30

Asn Gly Asn Thr Tyr Leu Glu Trp Phe Arg Gln Lys Pro Gly Gln Ser

```
                35                  40                  45
Pro Gln Arg Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Arg Ile
 65                  70                  75                  80

Ser Arg Val Glu Ala Asp Asp Leu Gly Val Tyr Tyr Cys Phe Gln Gly
                85                  90                  95

Ala His Val Pro Phe Thr Phe Gly Gln Gly Thr Lys Leu Glu Ile Lys
            100                 105                 110

Arg
```

```
<210> SEQ ID NO 33
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Ile Leu Gln Glu Ser Gly Pro Gly Leu Val Lys Pro Ser Gln
 1               5                   10                  15

Thr Leu Ser Leu Thr Cys Thr Val Ser Gly Ser Val Thr Gly Tyr
                20                  25                  30

Asn Ile Asn Trp Ile Arg Gln Arg Pro Asp Arg Gly Leu Glu Trp Met
                35                  40                  45

Gly Met Ile Trp Gly Tyr Gly Asp Thr Asp Tyr Asn Ser Ala Leu Lys
        50                  55                  60

Ser Arg Ile Ser Ile Thr Ala Asp Gly Thr Lys Asn His Leu Ser Leu
 65                  70                  75                  80

Gln Leu Thr Ser Thr Thr Glu Asp Thr Ala Val Tyr Tyr Cys Thr
                85                  90                  95

Arg Asp His Tyr Gly Gly Asn Asp Trp Tyr Phe Asp Val Trp Gly Gln
            100                 105                 110

Gly Thr Leu Val Thr Val Ser Ser
        115                 120
```

```
<210> SEQ ID NO 34
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ile Ile Val Met Thr Gln Thr Pro Leu Ser Leu Ser Ala Ser Pro Gly
 1               5                   10                  15

Glu Ser Ala Ser Ile Ser Cys Arg Ala Ser Gln Asp Ile Thr Asn Tyr
                20                  25                  30

Leu Asn Trp Phe Arg Gln Lys Pro Gly Gln Ser Pro Gln Arg Leu Ile
                35                  40                  45

Tyr Tyr Thr Ser Arg Leu His Ser Gly Val Pro Asp Arg Phe Ser Gly
        50                  55                  60

Ser Gly Ser Gly Thr Asp Phe Thr Leu Arg Ile Ser Arg Val Glu Asp
 65                  70                  75                  80

Glu Asp Ala Gly Leu Tyr Tyr Cys Gln Gln Gly Lys Thr Leu Pro Arg
                85                  90                  95
```

Thr Phe Gly Gln Gly Thr Lys Leu Glu Ile Lys Arg
            100                 105

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val His Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Phe Trp Ile Arg His Ser Pro Gly Lys Gly Leu Glu Trp Val
        35                  40                  45

Ala Thr Ile Ser Asp Gly Gly Ser Tyr Thr Tyr Tyr Thr Asp Asn Val
50                  55                  60

Lys Gly Arg Phe Thr Ile Ser Arg Asp Asn Ala Asn Asn Leu Tyr
65                  70                  75                  80

Leu Gln Met Asn Ser Leu Lys Ala Glu Asp Thr Ala Val Tyr Tyr Cys
            85                  90                  95

Ala Lys Asp Trp Ser Asp Ser Glu Gly Phe Ala Tyr Trp Gly Gln Gly
            100                 105                 110

Thr Leu Val Thr Val Ser Ser
        115

<210> SEQ ID NO 36
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Val Leu Met Thr Gln Thr Pro Pro Ser Leu Ser Val Ser Pro Arg
1               5                   10                  15

Glu Pro Ala Ser Ile Ser Cys Arg Ser Ser Gln Ser Ile Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Arg Ile
65                  70                  75                  80

Ser Arg Val Glu Ala Asp Asp Thr Gly Val Tyr Tyr Cys Phe Gln Gly
            85                  90                  95

Ser His Val Pro Phe Thr Phe Gly Ala Gly Thr Lys Val Glu Leu Lys
            100                 105                 110

Arg

<210> SEQ ID NO 37
<211> LENGTH: 118
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 37

Gln Val Gln Leu Val Gln Ser Ala Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Gln Gln Ala Pro Gly Ala Gly Leu Glu Trp Ile
            35                  40                  45

Gly Arg Ile Asp Pro Tyr Gly Gly Thr Lys His Asn Glu Lys Phe
        50                  55                  60

Lys Arg Arg Ala Thr Val Thr Ala Asp Lys Ser Thr Ser Thr Ala Tyr
65                  70                  75                  80

Met Glu Leu Ser Asn Leu Arg Thr Glu Asp Thr Ala Val Tyr Tyr Cys
                85                  90                  95

Thr Arg Ser Gly Tyr Asp Tyr Tyr Phe Asp Val Trp Gly Gln Gly Thr
                100                 105                 110

Leu Val Thr Val Ser Ser
        115

<210> SEQ ID NO 38
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Thr Pro Leu Ser Leu Ser Ala Ser Pro Gly
1               5                   10                  15

Glu Ser Ala Ser Ile Thr Cys Arg Ala Ser Glu Asn Ile Tyr Ser Phe
                20                  25                  30

Leu Ala Trp His Arg Gln Lys Pro Gly Gln Ser Pro Gln Leu Leu Val
            35                  40                  45

Tyr Asn Ala Asn Thr Leu Ala Glu Gly Val Pro Ser Arg Phe Ser Gly
        50                  55                  60

Ser Gly Ser Gly Thr Gln Phe Thr Leu Arg Ile Ser Arg Val Glu Asp
65                  70                  75                  80

Glu Asp Ala Gly Leu Tyr Tyr Cys Gln His His Phe Gly Thr Pro Phe
                85                  90                  95

Thr Phe Gly Gln Gly Thr Lys Leu Glu Ile Lys Arg
                100                 105

<210> SEQ ID NO 39
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Gln Ser Ala Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile Tyr Trp Val Lys Gln Ala Pro Gly Ala Gly Leu Glu Trp Ile

```
                    35                  40                  45
Gly Arg Ile Asp Pro Ala Asn Gly Asn Thr Ile Tyr Ala Ser Lys Phe
 50                  55                  60

Gln Gly Lys Ala Ser Ile Thr Ala Asp Thr Ser Thr Asn Thr Ala Tyr
 65                  70                  75                  80

Met Glu Leu Ser Asn Leu Arg Thr Glu Asp Thr Ala Val Tyr Tyr Cys
                 85                  90                  95

Ala Arg Tyr Gly Tyr Tyr Ala Tyr Trp Gly Gln Gly Thr Leu Val Thr
                100                 105                 110

Val Ser Ser
        115

<210> SEQ ID NO 40
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Val Val Leu Thr Gln Thr Pro Arg Ser Leu Ser Val Ser Pro Gly
 1               5                  10                  15

Glu Thr Ala Ser Ile Ser Cys Lys Ser Thr Lys Ser Leu Leu Asn Gly
                 20                  25                  30

Asp Gly Phe Thr Tyr Leu Asp Trp Tyr Arg Gln Lys Pro Gly Gln Ser
             35                  40                  45

Pro Gln Leu Leu Ile Tyr Leu Val Ser Asn Arg Phe Ser Gly Val Pro
 50                  55                  60

Asp Arg Phe Ser Gly Ser Gly Ser Gly Thr Asp Phe Thr Leu Arg Ile
 65                  70                  75                  80

Ser Arg Val Glu Ala Asp Asp Thr Gly Leu Tyr Tyr Cys Phe Glu Ser
                 85                  90                  95

Asn Tyr Leu Phe Thr Phe Gly Gln Gly Thr Asn Leu Glu Met Lys Arg
                100                 105                 110

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Asp Leu Met Lys Pro Gly Gly
 1               5                  10                  15

Ser Leu Arg Leu Ser Cys Val Ala Ser Gly Phe Thr Phe Ser Asn His
                 20                  25                  30

Tyr Met Tyr Trp Val Arg Gln Ala Pro Gly Lys Gly Leu Glu Trp Val
             35                  40                  45

Ala Ser Ile Ser Asp Gly Gly Ala Tyr Thr Phe Tyr Pro Asp Thr Val
 50                  55                  60

Lys Gly Arg Phe Thr Ile Ser Arg Asp Asn Ala Lys Asn Asn Leu Tyr
 65                  70                  75                  80

Leu Gln Met Asn Ser Leu Lys Thr Glu Asp Thr Gly Arg Val Leu Tyr
                 85                  90                  95

Cys Thr Gly Glu Glu Ser Ala Asn Asn Gly Phe Ala Phe Trp Gly His
```

```
                    100                 105                 110

Gly Thr Leu Val Thr Val Ser Ser
            115                 120

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Val Leu Met Thr Gln Thr Pro Ser Leu Ser Val Ser Pro Arg
1               5                   10                  15

Glu Pro Ala Ser Ile Ser Cys Arg Ser Ser Gln Ser Ile Leu His Ser
            20                  25                  30

Asn Gly Asn Thr Tyr Leu Glu Trp Tyr Arg Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ala His Val Pro Phe Thr Phe Gly Gln Gly Thr Lys Leu Glu Ile Lys
            100                 105                 110

Arg

<210> SEQ ID NO 43
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Gly Tyr
            20                  25                  30

Asn Ile Asn Trp Val Arg Gln Arg Pro Asp Arg Gly Leu Glu Trp Leu
        35                  40                  45

Gly Met Ile Trp Gly Tyr Gly Asp Thr Asp Tyr Asn Ser Ala Leu Lys
    50                  55                  60

Ser Arg Leu Ser Ile Ser Lys Asp Asn Thr Lys Ser Gln Val Phe Leu
65                  70                  75                  80

Gln Leu Thr Ser Thr Thr Thr Glu Asp Thr Ala Val Tyr Tyr Cys Ala
                85                  90                  95

Arg Asp His Tyr Gly Gly Asn Asp Trp Tyr Phe Asp Val Trp Gly Gln
            100                 105                 110

Gly Thr Leu Val Thr Val Ser Ser
            115                 120

<210> SEQ ID NO 44
<211> LENGTH: 108
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 44

Asp Ile Gln Met Thr Gln Thr Pro Leu Ser Leu Ser Ala Ser Pro Gly
1               5                   10                  15

Glu Ser Ala Ser Ile Thr Cys Arg Ala Ser Gln Asp Ile Thr Asn Tyr
            20                  25                  30

Leu Asn Trp Tyr Arg Gln Lys Pro Gly Gln Ser Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Arg Ile Ser Arg Val Glu Asp
65                  70                  75                  80

Glu Asp Ala Gly Leu Tyr Phe Cys Gln Gln Gly Lys Thr Leu Pro Arg
                85                  90                  95

Thr Phe Gly Gln Gly Thr Lys Leu Glu Ile Lys Arg
            100                 105

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggcagggtac cgccgccacc atgtccatgt tgttctacac                          40

<210> SEQ ID NO 46
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggcagtctag atcagtgatg atgatgatga tgggctcgtc tcccggcctt cc           52

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggcagcatat ggaaccgcat ccagagagcc at                                  32

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggcagctcga gctaggctcg tctcccggcc ttcct                               35
```

<210> SEQ ID NO 49
<211> LENGTH: 741
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
atgtccatgt tgttctacac tctgatcaca gctcttctga tcggcatccg ggcagaaccg      60
catccagaga gccatgtccc agcaggacac gccatccccc acgcccactg gactaagctt     120
cagcattccc ttgacacagc cctccgcaga gcccgcagcg ccccggccgg ggcaatagct     180
gccagggtga cagggcagac ccgcaacatc actgtggatc ccaaactctt taaaaagcgg     240
cgactgcgtt cgccccgcgt gctgttcagc acgcaccccc cacctgtggc tgcggacgct     300
caggacctgg acctggaggc cggcagcacc gcctccgtca acaggactca caggagcaag     360
cggtcttcgt cccaccctgt cttccaccgg ggggagttct cggtgtgcga cagcgtcagc     420
gtgtgggtgg gcgacaagac cacagccacc gacatcaagg gcaaggaggt gatggtgctg     480
ggagaggtga acattaacaa cagtgtgttc aaacagtact ctttgagac caagtgccgg     540
gaccccaccc ccgtggacag cgggtgcagg ggcatcgact ccaagcactg gaactcctac     600
tgcaccacca cccacacctt cgtcaaggcg ctgaccatgg acggcaagca ggctgcctgg     660
cggttcatcc ggatcgacac cggcctgcgt gtgcgtgctca gcaggaaggc cgggagacga     720
gcccatcatc atcatcatca c                                               741
```

<210> SEQ ID NO 50
<211> LENGTH: 247
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Met Ser Met Leu Phe Tyr Thr Leu Ile Thr Ala Leu Leu Ile Gly Ile
1               5                   10                  15

Arg Ala Glu Pro His Pro Glu Ser His Val Pro Ala Gly His Ala Ile
                20                  25                  30

Pro His Ala His Trp Thr Lys Leu Gln His Ser Leu Asp Thr Ala Leu
            35                  40                  45

Arg Arg Ala Arg Ser Ala Pro Ala Gly Ala Ile Ala Ala Arg Val Thr
        50                  55                  60

Gly Gln Thr Arg Asn Ile Thr Val Asp Pro Lys Leu Phe Lys Lys Arg
65                  70                  75                  80

Arg Leu Arg Ser Pro Arg Val Leu Phe Ser Thr His Pro Pro Val
                85                  90                  95

Ala Ala Asp Ala Gln Asp Leu Asp Leu Glu Ala Gly Ser Thr Ala Ser
                100                 105                 110

Val Asn Arg Thr His Arg Ser Lys Arg Ser Ser His Pro Val Phe
            115                 120                 125

His Arg Gly Glu Phe Ser Val Cys Asp Ser Val Ser Val Trp Val Gly
        130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
```

```
                165                 170                 175
Thr Lys Cys Arg Asp Pro Thr Pro Val Asp Ser Gly Cys Arg Gly Ile
            180                 185                 190

Asp Ser Lys His Trp Asn Ser Tyr Cys Thr Thr Thr His Thr Phe Val
            195                 200                 205

Lys Ala Leu Thr Met Asp Gly Lys Gln Ala Ala Trp Arg Phe Ile Arg
            210                 215                 220

Ile Asp Thr Ala Cys Val Cys Val Leu Ser Arg Lys Ala Gly Arg Arg
225                 230                 235                 240

Ala His His His His His His
            245

<210> SEQ ID NO 51
<211> LENGTH: 996
<212> TYPE: DNA
<213> ORGANISM: Canis lupus

<400> SEQUENCE: 51
gcgtcgacca cagccccgtc agtcttccca ttggccccca gctgcgggtc aactagcggg      60
tctaccgtcg ctctggcttg tctggtgtcc ggctacttcc ctgagcctgt gaccgtcagc     120
tggaactctg gtagcctgac cagcggcgtg catactttc caagcgtcct tcagagctcc     180
ggactccact cccttagttc catggtaacc gtgccaagta gtcggtggcc atccgagaca     240
tttacctgta acgtggtcca tcccgctagt aataccaagg tggataagcc tgtctttaac     300
gagtgccggt gcacagacac accaccttgt cccgtgcctg agcctctcgg cggcccctca     360
gtcctgatct ttcctccaaa gccaaaagat atcctccgga ttacccggac tcctgaagtg     420
acatgtgtag ttctggactt gggccgggaa gacccagagg tacagattag ctggttcgta     480
gacggcaaag aggtgcacac agccaaaacg caatcaaggg aacagcagtt caatggtact     540
tatcgggtcg tgtcagtact gccgatcgaa catcaggatt ggcttactgg caaggaattc     600
aaatgccgcg tgaaccacat tgacctgcca agccccatcg agaggaccat atcaaaggcc     660 aggggggcggg cacacaagcc gagcgtttat gtcctgcccc cttcccctaa ggaacttagc     720
tcttcagaca ctgtgagcat acatgtctg atcaaggatt tctatccacc ggacatagat     780
gtagagtggc agtccaacgg gcaacaggag cctgaacgga acatagaat gactcctcca     840 cagctcgatg aggatggttc ttactttctt tactccaaac tgtcagtgga caaatcacga     900
tggcagcagg gcgatccatt cacatgtgcc gttatgcacg agacgcttca gaaccactat     960
actgatctgt ccctctcaca tagcccgggc aaatga                               996

<210> SEQ ID NO 52
<211> LENGTH: 331
<212> TYPE: PRT
<213> ORGANISM: Canis lupus

<400> SEQUENCE: 52

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
            35                  40                  45

Gly Val His Thr Phe Pro Ser Val Leu Gln Ser Ser Gly Leu His Ser
        50                  55                  60
```

```
Leu Ser Ser Met Val Thr Val Pro Ser Ser Arg Trp Pro Ser Glu Thr
 65                  70                  75                  80

Phe Thr Cys Asn Val Val His Pro Ala Ser Asn Thr Lys Val Asp Lys
                 85                  90                  95

Pro Val Phe Asn Glu Cys Arg Cys Thr Asp Thr Pro Pro Cys Pro Val
            100                 105                 110

Pro Glu Pro Leu Gly Gly Pro Ser Val Leu Ile Phe Pro Pro Lys Pro
        115                 120                 125

Lys Asp Ile Leu Arg Ile Thr Arg Thr Pro Glu Val Thr Cys Val Val
130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Ser Arg Glu Gln Gln
                165                 170                 175

Phe Asn Gly Thr Tyr Arg Val Val Ser Val Leu Pro Ile Glu His Gln
            180                 185                 190

Asp Trp Leu Thr Gly Lys Glu Phe Lys Cys Arg Val Asn His Ile Asp
        195                 200                 205

Leu Pro Ser Pro Ile Glu Arg Thr Ile Ser Lys Ala Arg Gly Arg Ala
210                 215                 220

His Lys Pro Ser Val Tyr Val Leu Pro Pro Ser Pro Lys Glu Leu Ser
225                 230                 235                 240

Ser Ser Asp Thr Val Ser Ile Thr Cys Leu Ile Lys Asp Phe Tyr Pro
                245                 250                 255

Pro Asp Ile Asp Val Glu Trp Gln Ser Asn Gly Gln Gln Glu Pro Glu
            260                 265                 270

Arg Lys His Arg Met Thr Pro Pro Gln Leu Asp Glu Asp Gly Ser Tyr
        275                 280                 285

Phe Leu Tyr Ser Lys Leu Ser Val Asp Lys Ser Arg Trp Gln Gln Gly
290                 295                 300

Asp Pro Phe Thr Cys Ala Val Met His Glu Thr Leu Gln Asn His Tyr
305                 310                 315                 320

Thr Asp Leu Ser Leu Ser His Ser Pro Gly Lys
                325                 330

<210> SEQ ID NO 53
<211> LENGTH: 330
<212> TYPE: DNA
<213> ORGANISM: Canis lupus

<400> SEQUENCE: 53
aatgatgccc agcctgcagt gtacctgttc caacctagcc ctgaccagct ccacacaggc      60
tctgctagcg tcgtctgcct gctcaattct ttctacccaa aggatatcaa cgtgaagtgg     120
aaggtcgatg gcgtgattca agacaccggc attcaagagt cagtgaccga acaggataaa     180
gattctacat atagcttgag cagcacactg accatgagct ccaccgagta tctcagtcat     240
gagctgtatt cctgcgagat cacacacaag tcattgccca gtacgctcat aaaaagcttc     300
cagaggtccg aatgccagcg cgtggattga                                      330

<210> SEQ ID NO 54
<211> LENGTH: 109
<212> TYPE: PRT
<213> ORGANISM: Canis lupus

<400> SEQUENCE: 54
```

-continued

```
Asn Asp Ala Gln Pro Ala Val Tyr Leu Phe Gln Pro Ser Pro Asp Gln
1               5                   10                  15

Leu His Thr Gly Ser Ala Ser Val Val Cys Leu Leu Asn Ser Phe Tyr
            20                  25                  30

Pro Lys Asp Ile Asn Val Lys Trp Lys Val Asp Gly Val Ile Gln Asp
        35                  40                  45

Thr Gly Ile Gln Glu Ser Val Thr Glu Gln Asp Lys Asp Ser Thr Tyr
    50                  55                  60

Ser Leu Ser Ser Thr Leu Thr Met Ser Ser Thr Glu Tyr Leu Ser His
65                  70                  75                  80

Glu Leu Tyr Ser Cys Glu Ile Thr His Lys Ser Leu Pro Ser Thr Leu
                85                  90                  95

Ile Lys Ser Phe Gln Arg Ser Glu Cys Gln Arg Val Asp
            100                 105
```

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Asp Tyr Tyr Met Phe
1               5
```

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Thr Ile Ser Asp Gly Gly Ser Tyr Thr Tyr Tyr Thr Asp Asn Val Lys
1               5                   10                  15

Gly
```

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Asp Trp Ser Asp Ser Glu Gly Phe Ala Tyr
1               5                   10
```

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Arg Ser Ser Gln Ser Ile Val Gln Ser Asn Gly Asn Thr Tyr Leu Glu
1               5                   10                  15
```

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Val Ser Asn Arg Phe Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Phe Gln Gly Ser His Val Pro Phe Thr
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Tyr Trp Met His
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ile Asp Pro Tyr Gly Gly Gly Thr Lys His Asn Glu Lys Phe Lys
1               5                   10                  15

Arg

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Gly Tyr Asp Tyr Tyr Phe Asp Val
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Arg Ala Ser Glu Asn Ile Tyr Ser Phe Leu Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn Ala Asn Thr Leu Ala Glu
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln His His Phe Gly Thr Pro Phe Thr
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Thr Tyr Ile Tyr
1               5

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ile Asp Pro Ala Asn Gly Asn Thr Ile Tyr Ala Ser Lys Phe Gln
1               5                   10                  15

Gly

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Tyr Gly Tyr Tyr Ala Tyr
1               5

```
<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Ser Thr Lys Ser Leu Leu Asn Gly Asp Gly Phe Thr Tyr Leu Asp
1               5                   10                  15

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Val Ser Asn Arg Phe Ser
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Phe Glu Ser Asn Tyr Leu Phe Thr
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asn His Tyr Met Tyr
1               5

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Ile Ser Asp Gly Gly Ala Tyr Thr Phe Tyr Pro Asp Thr Val Lys
1               5                   10                  15

Gly

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 75

Glu Glu Ser Ala Asn Asn Gly Phe Ala Phe
1               5                   10

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ser Ser Gln Ser Ile Leu His Ser Asn Gly Asn Thr Tyr Leu Glu
1               5                   10                  15

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Val Ser Asn Arg Phe Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Phe Gln Gly Ala His Val Pro Phe Thr
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Tyr Asn Ile Asn
1               5

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Met Ile Trp Gly Tyr Gly Asp Thr Asp Tyr Asn Ser Ala Leu Lys Ser
1               5                   10                  15

<210> SEQ ID NO 81

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp His Tyr Gly Gly Asn Asp Trp Tyr Phe Asp Val
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Ala Ser Gln Asp Ile Thr Asn Tyr Leu Asn
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Tyr Thr Ser Arg Leu His Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gln Gly Lys Thr Leu Pro Arg Thr
1               5

<210> SEQ ID NO 85
<211> LENGTH: 120
<212> TYPE: PRT
<213> ORGANISM: Homo sapiens

<400> SEQUENCE: 85

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95
```

```
Ala Ala Trp Arg Phe Ile Arg Ile Asp Thr Ala Cys Val Cys Val Leu
            100                 105                 110

Ser Arg Lys Ala Val Arg Ala
            115                 120

<210> SEQ ID NO 86
<211> LENGTH: 121
<212> TYPE: PRT
<213> ORGANISM: Canis lupus

<400> SEQUENCE: 86

Glu Met Gln Leu Val Glu Ser Gly Gly Asp Leu Val Arg Pro Gly Gly
1               5                   10                  15

Ser Leu Arg Leu Ser Cys Val Ala Ser Gly Phe Thr Phe Ser Thr Tyr
            20                  25                  30

Gly Met Thr Trp Val Arg Gln Ser Pro Gly Lys Gly Leu Gln Trp Val
        35                  40                  45

Ala Thr Ile Gly Pro Gly Gly Arg Asn Thr Tyr Tyr Ala Asp Ala Val
    50                  55                  60

Lys Gly Arg Phe Thr Ile Ser Arg Asp Asp Ala Glu Asn Thr Leu Phe
65                  70                  75                  80

Leu Gln Met Asn Ser Leu Arg Ala Glu Asp Thr Ala Val Tyr Tyr Cys
            85                  90                  95

Ala Gln Ala Phe Asp Ala Thr Tyr Tyr Thr Ser Phe Asp Cys Trp Gly
            100                 105                 110

Arg Gly Ser Leu Val Ala Val Ser Ser
            115                 120

<210> SEQ ID NO 87
<211> LENGTH: 144
<212> TYPE: PRT
<213> ORGANISM: Canis lupus

<400> SEQUENCE: 87

Met Glu Ser Val Leu Ser Trp Val Phe Leu Val Ala Leu Leu Gln Gly
1               5                   10                  15

Ile Gln Gly Glu Ile Arg Leu Val Glu Ser Gly Gly Asp Leu Val Lys
            20                  25                  30

Pro Gly Gly Ser Leu Arg Leu Ser Cys Val Ala Ser Gly Phe Ile Phe
        35                  40                  45

Gly Asn Tyr Asp Met Ser Trp Val Arg Gln Ala Pro Gly Lys Gly Leu
    50                  55                  60

Gln Trp Val Ala Ala Val Arg Tyr Asp Gly Ser Ser Thr Tyr Tyr Ser
65                  70                  75                  80

Asp Ala Val Lys Gly Arg Ile Thr Ile Ser Arg Asp Asp Pro Gly Asn
            85                  90                  95

Thr Val Tyr Leu Gln Leu Asp Ser Leu Arg Ala Glu Asp Thr Ala Thr
            100                 105                 110

Tyr Tyr Cys Val Arg Gly Gly Tyr Tyr Ser Ser Ser Phe Tyr Ile Gly
            115                 120                 125

Gly Ala Phe Gly His Trp Gly Pro Gly Thr Leu Ile Thr Val Ser Ser
        130                 135                 140

<210> SEQ ID NO 88
<211> LENGTH: 140
<212> TYPE: PRT
<213> ORGANISM: Canis lupus
```

<400> SEQUENCE: 88

Met Glu Cys Val Leu Gly Trp Val Phe Leu Val Ala Ile Leu Arg Gly
1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Ser Asp Tyr Tyr Met Ser Trp Ile Arg Gln Ala Pro Gly Lys Gly Leu
    50                  55                  60

Gln Trp Val Ala Asp Ile Ser Asp Gly Gly Thr Gly Tyr Ala
65                  70                  75                  80

Gly Ala Val Lys Gly Arg Phe Thr Val Ser Arg Glu Asn Val Lys Asn
                85                  90                  95

Thr Leu Tyr Leu Gln Met Asn Asp Leu Arg Ala Glu Asp Thr Ala Ile
            100                 105                 110

Tyr Tyr Cys Thr Lys Ala Arg Glu Met Tyr Gly Tyr Arg Asp Phe Asp
        115                 120                 125

Ser Trp Gly Pro Gly Thr Leu Val Thr Val Ser Ser
    130                 135                 140

<210> SEQ ID NO 89
<211> LENGTH: 136
<212> TYPE: PRT
<213> ORGANISM: Canis lupus

<400> SEQUENCE: 89

Met Glu Ser Ala Leu Ser Trp Val Phe Leu Val Thr Ile Leu Lys Gly
1               5                   10                  15

Val Gln Gly Glu Val Leu Leu Val Glu Ser Gly Gly Asp Leu Val Lys
            20                  25                  30

Pro Gly Gly Ser Leu Arg Leu Ser Cys Leu Thr Ser Gly Phe Thr Phe
        35                  40                  45

Asn Thr Tyr Asp Trp Gly Trp Val Arg Gln Ala Pro Gly Lys Gly Leu
    50                  55                  60

Gln Trp Ile Ala Tyr Ile Lys Lys Gly Gly Ser Asp Val Arg Tyr Ala
65                  70                  75                  80

Asp Ala Val Lys Gly Arg Phe Thr Ile Ser Arg Asp Asp Ala Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ser Ala Trp Asp Ser Phe Asp Tyr Trp Gly Gln
        115                 120                 125

Gly Thr Leu Val Thr Val Ser Ser
    130                 135

<210> SEQ ID NO 90
<211> LENGTH: 136
<212> TYPE: PRT
<213> ORGANISM: Canis lupus

<400> SEQUENCE: 90

Met Glu Ser Ala Leu Ser Trp Val Phe Leu Val Thr Ile Leu Lys Gly
1               5                   10                  15

Val Gln Gly Glu Val Leu Leu Val Glu Ser Gly Gly Asp Leu Val Lys
            20                  25                  30

```
Pro Gly Gly Ser Leu Arg Leu Ser Cys Leu Thr Ser Gly Phe Thr Phe
            35                  40                  45

Asn Thr Tyr Asp Trp Gly Trp Val Arg Gln Ala Pro Gly Lys Gly Leu
 50                      55                  60

Gln Trp Ile Ala Tyr Ile Lys Lys Gly Gly Ser Asp Val Arg Tyr Ala
 65                  70                  75                  80

Asp Ala Val Lys Gly Arg Phe Thr Ile Ser Arg Asp Ala Lys Asn
                85                  90                  95

Thr Leu Tyr Leu Gln Met Asn Ser Leu Arg Ala Glu Asp Thr Ala Val
                100                 105                 110

Tyr Tyr Cys Ala Arg Ser Ala Trp Asp Ser Phe Asp Tyr Trp Gly Gln
            115                 120                 125

Gly Thr Leu Val Thr Val Ser Ser
        130                 135

<210> SEQ ID NO 91
<211> LENGTH: 141
<212> TYPE: PRT
<213> ORGANISM: Canis lupus

<400> SEQUENCE: 91

Met Glu Ser Val Phe Cys Trp Val Phe Leu Val Ala Ile Leu Lys Gly
 1               5                  10                  15

Val Arg Gly Val Gln Gly Glu Val Gln Leu Val Glu Ser Gly Gly Asp
                20                  25                  30

Leu Val Lys Pro Ala Gly Ser Leu Arg Leu Ser Cys Val Ala Ser Gly
            35                  40                  45

Phe Thr Phe Thr Asp Tyr Ser Met Asn Trp Val Arg Gln Ala Pro Gly
 50                      55                  60

Lys Gly Leu Gln Trp Val Ala Thr Ile Ser Asn Asp Gly Thr Ser Thr
 65                  70                  75                  80

Asp Tyr Thr Asp Ala Val Lys Gly Arg Phe Thr Val Ser Arg Asp Ser
                85                  90                  95

Ala Arg Asn Thr Val Tyr Leu Gln Met Thr Ser Leu Arg Ala Asp Asp
                100                 105                 110

Thr Ala Thr Tyr Tyr Cys Val Ser Arg His Ser Tyr Ser Leu Leu Ala
            115                 120                 125

Asp Tyr Trp Gly Gln Gly Thr Leu Val Thr Val Ser Ser
        130                 135                 140

<210> SEQ ID NO 92
<211> LENGTH: 140
<212> TYPE: PRT
<213> ORGANISM: Canis lupus

<400> SEQUENCE: 92

Met Gln Met Pro Trp Ser Leu Leu Cys Leu Leu Ala Ala Pro Leu Gly
 1               5                  10                  15

Val Leu Ser Glu Val Thr Leu Gln Glu Ser Gly Pro Gly Leu Val Lys
                20                  25                  30

Pro Ser Gln Thr Leu Ser Leu Thr Cys Ala Val Ser Gly Gly Ser Val
            35                  40                  45

Ile Arg Asn Tyr Tyr Trp His Trp Ile Arg Gln Arg Pro Gly Arg Gly
 50                      55                  60

Leu Glu Trp Met Gly Cys Trp Ser Glu Thr Thr Tyr Tyr Ser Pro Ala
 65                  70                  75                  80
```

```
Phe Arg Gly Arg Ile Ser Ile Thr Ile Asp Ala Ala Thr Asp Gln Phe
                85                  90                  95

Ser Leu His Leu Asn Ser Met Thr Thr Asp Asp Thr Ala Val Tyr Tyr
            100                 105                 110

Cys Ala Arg Ala Leu Tyr Pro Thr Ser Trp Tyr Asp Gly Met Asp
            115                 120                 125

Tyr Trp Gly His Gly Ala Ser Val Val Ser Ser
130                 135                 140

<210> SEQ ID NO 93
<211> LENGTH: 117
<212> TYPE: PRT
<213> ORGANISM: Canis lupus

<400> SEQUENCE: 93

Glu Val Gln Leu Val Glu Ser Gly Gly Asp Leu Val Lys Pro Gly Gly
1               5                   10                  15

Ser Leu Arg Leu Ser Cys Glu Ser Ser Gly Phe Ile Phe Ser Gln Tyr
            20                  25                  30

Ala Met Asn Trp Val Arg Gln Ala Pro Gly Lys Gly Leu Gln Trp Val
            35                  40                  45

Ala Tyr Ile Gly Gly Ala Gly Phe Ile Thr Tyr His Ala Asp Asp Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Thr Ile Asn Asp Thr Ala Val Tyr Tyr Cys
                85                  90                  95

Val Arg Ser Asn Ser Arg Ile Pro Asp Tyr Trp Gly Gln Gly Thr Leu
            100                 105                 110

Val Ala Val Ser Ser
        115

<210> SEQ ID NO 94
<211> LENGTH: 137
<212> TYPE: PRT
<213> ORGANISM: Canis lupus

<400> SEQUENCE: 94

Met Glu Ser Val Phe Cys Trp Val Phe Leu Val Ala Ile Leu Lys Gly
1               5                   10                  15

Val Gln Gly Glu Val Gln Leu Val Glu Ser Gly Gly Asp Leu Val Lys
            20                  25                  30

Pro Gly Gly Ser Leu Arg Leu Ser Cys Val Ala Ser Gly Phe Thr Phe
            35                  40                  45

Ser Ser Val Tyr Met Ser Trp Val Arg Gln Ala Pro Gly Lys Gly Leu
            50                  55                  60

Gln Trp Val Ala Arg Ile Thr Thr Asp Gly Thr Asp Thr Phe Tyr Ala
65                  70                  75                  80

Asp Ala Val Lys Gly Arg Phe Thr Ile Ser Arg Asp Asn Val Lys Asn
                85                  90                  95

Met Leu Tyr Leu Glu Met Asn Ser Leu Arg Ala Glu Asp Thr Ala Ile
            100                 105                 110

Tyr Tyr Cys Gly Asp Pro Trp Gln Pro Ala Tyr Pro Asp Leu Trp Gly
            115                 120                 125

Gln Gly Thr Met Val Thr Val Ser Ser
130                 135
```

-continued

<210> SEQ ID NO 95
<211> LENGTH: 141
<212> TYPE: PRT
<213> ORGANISM: Canis lupus

<400> SEQUENCE: 95

Met Glu Ser Val Leu Cys Trp Val Phe Leu Val Ala Ile Leu Lys Gly
1               5                   10                  15

Val Gln Gly Glu Val His Leu Val Glu Ser Gly Gly Asp Leu Val Lys
            20                  25                  30

Pro Gly Gly Thr Leu Arg Leu Ser Cys Val Ala Ser Gly Phe Thr Phe
        35                  40                  45

Ser Gln Tyr Asp Met Ser Trp Val Arg Gln Ser Pro Gly Lys Gly Leu
    50                  55                  60

Gln Trp Val Ala Leu Ser Arg Tyr His Gly Gly Thr Tyr Tyr Ala
65                  70                  75                  80

Asp Ala Val Lys Gly Arg Phe Thr Ile Ser Arg Asp Asn Ala Lys Asn
                85                  90                  95

Met Leu Tyr Leu Gln Met Asn Ser Leu Arg Ala Glu Asp Thr Ala Val
            100                 105                 110

Tyr Tyr Cys Val Lys Glu Gly Ser Arg Trp Asp Leu Arg Gly Asp Tyr
        115                 120                 125

Asp Tyr Trp Gly Gln Gly Thr Leu Val Thr Val Ser Ser
    130                 135                 140

<210> SEQ ID NO 96
<211> LENGTH: 142
<212> TYPE: PRT
<213> ORGANISM: Canis lupus

<400> SEQUENCE: 96

Met Gln Met Pro Trp Ser Leu Leu Cys Leu Leu Ala Ala Pro Leu Gly
1               5                   10                  15

Val Leu Ser Glu Leu Thr Leu Gln Glu Ser Gly Pro Gly Leu Val Lys
            20                  25                  30

Pro Ser Gln Thr Leu Ser Leu Thr Cys Val Val Ser Gly Gly Ser Val
        35                  40                  45

Thr Ser Ser His Tyr Trp Asn Trp Ile Arg Gln Arg Pro Gly Arg Gly
    50                  55                  60

Leu Glu Trp Met Gly Tyr Trp Thr Gly Asn Val Asn Tyr Asn Pro Ala
65                  70                  75                  80

Phe Gln Gly Arg Ile Ser Ile Ile Gly Asp Ala Ala Lys Asn Gln Phe
                85                  90                  95

Ser Leu His Leu Ser Ser Met Thr Thr Asp Asp Thr Ala Val Tyr Tyr
            100                 105                 110

Cys Ala Arg Cys Gly Ile Val Ala Pro Gly Phe Leu Pro Ile Gly Asp
        115                 120                 125

Phe Asp Phe Trp Gly Gln Gly Thr Leu Val Thr Val Ser Ser
    130                 135                 140

<210> SEQ ID NO 97
<211> LENGTH: 137
<212> TYPE: PRT
<213> ORGANISM: Canis lupus

<400> SEQUENCE: 97

Met Glu Ser Val Phe Cys Trp Val Phe Leu Val Ala Ile Leu Lys Gly

```
                1               5                   10                  15
Val Gln Gly Glu Val Gln Leu Val Glu Ser Gly Gly Asp Leu Val Lys
                    20                  25                  30

Pro Gly Gly Ser Leu Arg Leu Ser Cys Val Ala Ser Gly Phe Ser Phe
                35                  40                  45

Ser Asn Tyr Phe Met Phe Trp Gly Arg Gln Ala Pro Gly Lys Gly Leu
            50                  55                  60

Gln Trp Val Ala Arg Ile Arg Ser Asp Gly Ser Thr Tyr Tyr Ala
65                  70                  75                  80

Asp Ala Val Lys Gly Arg Phe Thr Ile Ser Arg Asp Asn Ala Arg Asn
                    85                  90                  95

Thr Leu Tyr Leu Gln Met Asn Ser Leu Arg Ala Glu Asp Thr Ala Thr
                100                 105                 110

Tyr Tyr Cys Ala Lys Ala Asp Ile Ile Lys Leu Pro Glu Tyr Arg Gly
            115                 120                 125

Gln Gly Thr Leu Val Thr Val Ser Ser
        130                 135
```

<210> SEQ ID NO 98
<211> LENGTH: 140
<212> TYPE: PRT
<213> ORGANISM: Canis lupus

<400> SEQUENCE: 98

```
Glu Ser Val Leu Gly Trp Ile Phe Leu Ala Thr Ile Leu Lys Gly Val
1               5                   10                  15

Gln Gly Glu Val Gln Leu Val Glu Ser Gly Gly Asp Leu Val Lys Pro
                    20                  25                  30

Gly Gly Ser Leu Arg Leu Ser Cys Val Gly Ser Gly Phe Thr Phe Ser
                35                  40                  45

Ser Ser Trp Met Asn Trp Val Arg Gln Ala Pro Gly Lys Gly Leu Gln
            50                  55                  60

Trp Ile Ala Glu Ile Ser Gly Thr Gly Ser Ser Thr Asn Tyr Ala Asp
65                  70                  75                  80

Ala Val Lys Gly Arg Phe Thr Ile Ser Arg Asp Asn Asp Lys Asn Thr
                    85                  90                  95

Leu Tyr Leu Gln Met Asn Ser Leu Arg Ala Glu Asp Thr Ala Met Tyr
                100                 105                 110

Tyr Cys Ala Arg Ala Ala Tyr Tyr Gly Asn Tyr Arg Asn Asp Leu Asp
            115                 120                 125

Tyr Trp Gly Gln Gly Thr Leu Val Thr Val Ser Ser
        130                 135                 140
```

<210> SEQ ID NO 99
<211> LENGTH: 109
<212> TYPE: PRT
<213> ORGANISM: Canis lupus

<400> SEQUENCE: 99

```
Lys Pro Ala Gly Ser Leu Arg Leu Ser Cys Val Ala Ser Gly Phe Thr
1               5                   10                  15

Phe Ser Ser His Ser Val Thr Trp Val Arg Gln Ala Pro Gly Lys Gly
                    20                  25                  30

Leu Gln Phe Val Ala Gly Ile Thr Ser Gly Gly Asn Asn Arg Tyr Tyr
                35                  40                  45

Thr Asp Ala Val Arg Gly Arg Phe Thr Leu Ser Arg Asp Asn Ala Lys
```

```
                    50                  55                  60
Asn Thr Val Tyr Leu Gln Met Asn Ser Leu Arg Ala Glu Asp Thr Ala
 65                  70                  75                  80

Met Tyr Phe Cys Ala Leu Gly Ser Tyr Glu Trp Leu Ser Gly Glu Phe
                 85                  90                  95

Asp Tyr Trp Gly Gln Gly Thr Leu Val Thr Val Ser Ser
            100                 105

<210> SEQ ID NO 100
<211> LENGTH: 136
<212> TYPE: PRT
<213> ORGANISM: Canis lupus

<400> SEQUENCE: 100

Met Glu Ser Val Phe Cys Trp Val Phe Leu Val Ala Ile Leu Lys Gly
  1               5                  10                  15

Val Gln Gly Glu Val Gln Leu Val Glu Ser Gly Gly Asp Leu Val Lys
                 20                  25                  30

Pro Gly Gly Ser Leu Arg Leu Ser Cys Val Ala Ser Gly Phe Thr Leu
             35                  40                  45

Asn Asn Tyr Phe Met Tyr Trp Val Arg Gln Ala Pro Gly Lys Gly Leu
         50                  55                  60

Gln Trp Val Ala Arg Leu Asn Ser Asn Gly Asp Ser Thr Phe Tyr Ala
 65                  70                  75                  80

Asp Ala Val Lys Gly Arg Phe Thr Ile Ser Arg Asp Asn Ala Lys Asn
                 85                  90                  95

Thr Leu Tyr Leu Gln Met Asn Ser Leu Arg Ala Glu Asp Thr Ser Met
                100                 105                 110

Tyr Tyr Cys Ala Lys Asp Leu Ile Tyr Gly Tyr Thr Leu Trp Gly Gln
            115                 120                 125

Gly Thr Leu Val Thr Val Ser Ser
        130                 135

<210> SEQ ID NO 101
<211> LENGTH: 139
<212> TYPE: PRT
<213> ORGANISM: Canis lupus

<400> SEQUENCE: 101

Met Ala Ser Val Leu Ser Trp Val Phe Leu Val Ala Ile Val Lys Gly
  1               5                  10                  15

Val Gln Gly Glu Val Gln Leu Val Glu Ser Gly Gly Asp Leu Val Lys
                 20                  25                  30

Pro Gly Gly Ser Leu Arg Leu Ser Cys Val Ala Ser Gly Phe Ile Phe
             35                  40                  45

Asn Lys Tyr Glu Val Tyr Trp Val Arg Gln Ala Pro Gly Lys Gly Leu
         50                  55                  60

Glu Trp Val Ala Arg Ile Leu Glu Ser Gly Asn Pro Thr Tyr Tyr Ala
 65                  70                  75                  80

Glu Ala Val Glu Gly Arg Phe Thr Ile Ser Arg Asp Asn Ala Lys Asn
                 85                  90                  95

Met Ala Tyr Leu Gln Met Asn Ser Leu Arg Ala Asp Asp Thr Ala Val
                100                 105                 110

Tyr Tyr Cys Ala Thr Pro Ser Val Ser Ser Thr Val Ala Ile Asp Tyr
            115                 120                 125

Trp Gly Gln Gly Ala Leu Val Thr Val Ser Ser
```

<210> SEQ ID NO 102
<211> LENGTH: 136
<212> TYPE: PRT
<213> ORGANISM: Canis lupus

<400> SEQUENCE: 102

Met Gln Met Pro Trp Ser Leu Leu Cys Leu Leu Ala Thr Pro Leu Gly
1               5                   10                  15

Val Leu Ser Glu Leu Thr Leu Gln Glu Ser Gly Pro Gly Leu Val Lys
            20                  25                  30

Pro Ser Gln Thr Leu Ser Leu Thr Cys Val Val Ser Arg Gly Ser Val
        35                  40                  45

Thr Ser Asp Tyr Tyr Trp Asn Trp Ile Arg Gln Arg Pro Gly Arg Gly
    50                  55                  60

Leu Glu Trp Met Gly His Trp Ile Gly Ser Thr Ala Tyr Asn Pro Ala
65                  70                  75                  80

Phe Gln Gly Arg Ile Ser Ile Thr Ala Asp Thr Ala Lys Asn Gln Leu
                85                  90                  95

Ser Leu Gln Leu Arg Ser Met Thr Thr Glu Asp Thr Ala Val Tyr Phe
            100                 105                 110

Cys Ala Arg Gly Ser Ser Trp Thr Pro Ser Gly Asp Ser Trp Gly Gln
        115                 120                 125

Gly Thr Leu Val Thr Val Ser Ser
    130                 135

<210> SEQ ID NO 103
<211> LENGTH: 140
<212> TYPE: PRT
<213> ORGANISM: Canis lupus
<220> FEATURE:
<221> NAME/KEY: MOD_RES
<222> LOCATION: (24)..(24)
<223> OTHER INFORMATION: Any amino acid

<400> SEQUENCE: 103

Met Ala Ser Val Leu Lys Leu Gly Phe Ser Cys Arg Tyr Cys Lys Lys
1               5                   10                  15

Val Ser Arg Val Arg Cys Asn Xaa Val Glu Ser Gly Gly Asp Leu Val
            20                  25                  30

Lys Pro Gly Gly Ser Leu Arg Leu Ser Cys Val Ala Ser Gly Phe Ile
        35                  40                  45

Phe Asn Lys Tyr Glu Val Tyr Trp Val Arg Gln Ala Pro Gly Lys Gly
    50                  55                  60

Leu Glu Trp Val Ala Arg Ile Leu Glu Ser Gly Asn Pro Thr Tyr Tyr
65                  70                  75                  80

Ala Glu Ala Val Glu Gly Arg Phe Thr Ile Ser Arg Asp Asn Ala Lys
                85                  90                  95

Asn Met Ala Tyr Leu Gln Met Asn Ser Leu Arg Ala Asp Asp Thr Ala
            100                 105                 110

Val Tyr Tyr Cys Ala Thr Pro Ser Val Ser Ser Thr Val Ala Ile Asp
        115                 120                 125

Tyr Trp Gly Gln Gly Ala Leu Val Thr Val Ser Ser
    130                 135                 140

<210> SEQ ID NO 104
<211> LENGTH: 142

```
<212> TYPE: PRT
<213> ORGANISM: Canis lupus
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (86)..(86)
<223> OTHER INFORMATION: Any amino acid

<400> SEQUENCE: 104

Met Asp Cys Ser Trp Arg Ile Phe Phe Leu Leu Ala Leu Ala Thr Gly
1               5                   10                  15

Val His Ser Glu Val Gln Leu Val Gln Ser Ala Ala Glu Val Lys Lys
            20                  25                  30

Pro Gly Ala Ser Val Lys Val Ser Cys Lys Thr Ser Gly Tyr Thr Leu
        35                  40                  45

Thr Asp Tyr Tyr Ile His Trp Val Gln Gln Ala Pro Gly Thr Gly Leu
    50                  55                  60

His Trp Met Gly Trp Ile Asp Pro Glu Xaa Gly Thr Thr Asp Tyr Ala
65                  70                  75                  80

Gln Lys Phe Gln Gly Xaa Val Thr Leu Thr Ala Asp Thr Ser Thr Asn
                85                  90                  95

Thr Ala Tyr Met Glu Leu Ser Gly Leu Arg Ala Glu Asp Thr Ala Val
            100                 105                 110

Tyr Tyr Cys Ala Arg Phe Pro Arg Ser Leu Asp Tyr Gly Ser Phe Pro
        115                 120                 125

Phe Asp Tyr Trp Gly Gln Gly Thr Leu Val Thr Val Ser Ser
    130                 135                 140

<210> SEQ ID NO 105
<211> LENGTH: 135
<212> TYPE: PRT
<213> ORGANISM: Canis lupus

<400> SEQUENCE: 105

Met Glu Ser Val Leu Cys Trp Val Phe Leu Val Ala Ile Leu Lys Gly
1               5                   10                  15

Val Gln Gly Glu Val Arg Leu Val Glu Ser Gly Gly Asp Leu Val Lys
            20                  25                  30

Pro Gly Gly Ser Leu Arg Leu Ser Cys Val Ala Ser Gly Phe Thr Phe
        35                  40                  45

Arg Asn Tyr Gly Met Ser Trp Val Arg Gln Arg Pro Gly Lys Gly Leu
    50                  55                  60

Gln Trp Val Ala Ala Ile Arg Ser Asp Gly Val Thr Tyr Tyr Ala Asp
65                  70                  75                  80

Asp Leu Lys Val Arg Phe Thr Val Ser Arg Asp Ala Arg Asn Thr
                85                  90                  95

Leu Tyr Leu Gln Leu Asn Ser Leu Gly Ala Glu Asp Thr Ala Val Tyr
            100                 105                 110

Tyr Cys Ala Lys Ala Pro Trp Gly Leu Tyr Asp Ala Trp Gly Gln Gly
        115                 120                 125

Thr Leu Val Thr Val Ser Ser
    130                 135

<210> SEQ ID NO 106
<211> LENGTH: 135
<212> TYPE: PRT
```

<213> ORGANISM: Canis lupus

<400> SEQUENCE: 106

Met Glu Ser Val Leu Ser Trp Val Phe Leu Val Ala Ile Leu Gln Gly
1               5                   10                  15

Val Gln Gly Glu Val Gln Val Glu Ser Gly Gly Asp Leu Val Lys
            20                  25                  30

Pro Ala Gly Ser Leu Arg Leu Ser Cys Val Ala Ser Gly Tyr Ser Ile
        35                  40                  45

Ser Thr Tyr Thr Met Thr Trp Val Arg Gln Val Pro Gly Lys Gly Leu
    50                  55                  60

Gln Leu Val Ala Gly Ile Asn Gly Asp Gly Ser Ser Thr Tyr Tyr Thr
65                  70                  75                  80

Asp Ala Val Lys Gly Arg Phe Thr Ile Ser Arg Asp Asn Ala Arg Asn
                85                  90                  95

Thr Val Tyr Leu Gln Met Asn Ser Leu Arg Ala Glu Asp Thr Ala Met
            100                 105                 110

Tyr Tyr Cys Leu Gly Glu Tyr Ser Trp Phe Tyr Tyr Trp Gly Gln Gly
        115                 120                 125

Thr Leu Val Thr Val Ser Ser
    130                 135

<210> SEQ ID NO 107
<211> LENGTH: 140
<212> TYPE: PRT
<213> ORGANISM: Canis lupus

<400> SEQUENCE: 107

Met Gln Met Pro Trp Ser Leu Leu Cys Leu Leu Ala Ala Pro Leu Gly
1               5                   10                  15

Val Leu Ser Glu Leu Thr Leu Gln Glu Ser Gly Pro Arg Leu Val Lys
            20                  25                  30

Pro Ser Gln Thr Leu Ser Leu Thr Cys Ala Val Ser Gly Gly Ser Val
        35                  40                  45

Thr Thr Thr Ser Tyr Trp Ser Trp Ile Arg Gln Arg Pro Gly Arg Gly
    50                  55                  60

Leu Glu Trp Val Gly Tyr Trp Thr Gly Thr Thr Asn Tyr Ser Pro Ala
65                  70                  75                  80

Phe Gln Gly Arg Ile Ser Ile Ser Ala Asp Thr Ala Lys Asn Gln Phe
                85                  90                  95

Ser Leu His Leu Ser Ser Val Thr Thr Glu Asp Thr Ala Leu Tyr Phe
            100                 105                 110

Cys Ala Ser Lys Ser Ala Ser Thr Ser Trp Tyr Phe Ser Leu Phe Glu
        115                 120                 125

Ser Trp Gly Gln Gly Thr Leu Val Thr Val Ser Ser
    130                 135                 140

<210> SEQ ID NO 108
<211> LENGTH: 135
<212> TYPE: PRT
<213> ORGANISM: Canis lupus

<400> SEQUENCE: 108

Met Glu Ser Val Leu Gly Leu Val Phe Leu Leu Thr Ile Leu Lys Gly
1               5                   10                  15

Val Gln Gly Glu Val Gln Leu Val Glu Ser Gly Gly Asp Leu Val Lys
            20                  25                  30

-continued

```
Pro Gly Gly Ser Leu Arg Leu Ser Cys Val Ala Ser Gly Phe Thr Phe
            35                  40                  45

Ser Ser Tyr Ser Met Ser Trp Val Arg Gln Ala Pro Gly Lys Gly Leu
 50                  55                  60

Gln Trp Val Gly Tyr Ile Asp Asn Gly Gly Thr Ser Thr Tyr Tyr Ala
 65                  70                  75                  80

Asp Ala Val Lys Gly Arg Phe Thr Ile Ser Arg Asp Asn Ala Lys Asn
                 85                  90                  95

Thr Leu Tyr Leu Gln Met Asn Ser Leu Arg Ala Glu Asp Thr Ala Val
                100                 105                 110

Tyr Tyr Cys Gly Arg Gly Ser Tyr Gly Met Glu Tyr Trp Gly His Gly
            115                 120                 125

Thr Ser Leu Phe Val Ser Ser
            130                 135

<210> SEQ ID NO 109
<211> LENGTH: 138
<212> TYPE: PRT
<213> ORGANISM: Canis lupus

<400> SEQUENCE: 109

Met Glu Ser Val Leu Gly Leu Leu Phe Leu Val Ala Ile Leu Lys Gly
  1               5                  10                  15

Val Gln Gly Glu Ile Gln Leu Val Glu Ser Gly Gly Asp Leu Leu Lys
                 20                  25                  30

Pro Gly Gly Ser Leu Arg Leu Ser Cys Val Ala Ser Gly Phe Thr Phe
            35                  40                  45

Ser Gly Ser Asp Met Asn Trp Ile Arg Gln Ala Pro Gly Lys Gly Leu
 50                  55                  60

Gln Trp Val Ala His Ile Thr His Glu Gly Ile Gly Thr Ser Tyr Val
 65                  70                  75                  80

Gly Ser Val Lys Gly Arg Phe Thr Ile Ser Arg Asp Asn Ala Lys Asn
                 85                  90                  95

Thr Leu Tyr Leu Gln Met Asn Asp Leu Arg Ala Glu Asp Thr Ala Met
                100                 105                 110

Tyr Tyr Cys Ala Tyr Ser Pro Trp Asn Tyr Tyr Ser Phe Asp Ser Trp
            115                 120                 125

Gly Gln Gly Thr Leu Val Thr Val Ser Ser
            130                 135

<210> SEQ ID NO 110
<211> LENGTH: 135
<212> TYPE: PRT
<213> ORGANISM: Canis lupus

<400> SEQUENCE: 110

Met Thr Ser Thr Met Ala Trp Ser Pro Leu Leu Leu Thr Leu Leu Thr
  1               5                  10                  15

His Cys Thr Val Ser Trp Ala Gln Thr Val Leu Thr Gln Ser Pro Ser
                 20                  25                  30

Val Ser Ala Val Leu Gly Arg Arg Val Thr Ile Ser Cys Thr Gly Ser
            35                  40                  45

Asp Thr Asn Ile Gly Ser His Arg Asp Val Gln Trp Tyr Gln Leu Val
 50                  55                  60

Pro Gly Lys Ser Pro Lys Thr Leu Ile Tyr Gly Thr Asn Arg Pro
 65                  70                  75                  80
```

```
Ser Gly Ile Pro Val Arg Phe Ser Gly Ser Lys Ser Gly Asn Ser Gly
            85                  90                  95

Thr Leu Thr Ile Thr Gly Ile Gln Ala Glu Asp Glu Ala Asp Tyr Tyr
            100                 105                 110

Cys Gln Ser Tyr Asp Asp Leu Ser Met Asn Val Phe Gly Gly Gly
            115                 120                 125

Thr His Leu Thr Val Leu Gly
            130                 135

<210> SEQ ID NO 111
<211> LENGTH: 136
<212> TYPE: PRT
<213> ORGANISM: Canis lupus

<400> SEQUENCE: 111

Met Asp Trp Val Pro Phe Tyr Ile Leu Pro Phe Ile Phe Ser Thr Gly
1               5                   10                  15

Phe Cys Ala Leu Pro Val Leu Thr Gln Pro Thr Asn Ala Ser Ala Ser
            20                  25                  30

Leu Glu Glu Ser Val Lys Leu Thr Cys Thr Leu Ser Ser Glu His Ser
            35                  40                  45

Asn Tyr Ile Val Arg Trp Tyr Gln Gln Pro Gly Lys Ala Pro Arg
50                  55                  60

Tyr Leu Met Tyr Val Arg Ser Asp Gly Ser Tyr Lys Arg Gly Asp Gly
65                  70                  75                  80

Ile Pro Ser Arg Phe Ser Gly Ser Ser Ser Gly Ala Asp Arg Tyr Leu
            85                  90                  95

Thr Ile Ser Asn Ile Lys Ser Glu Asp Glu Asp Asp Tyr Tyr Tyr Cys
            100                 105                 110

Gly Ala Asp Tyr Thr Ile Ser Gly Gln Tyr Gly Ser Val Phe Gly Gly
            115                 120                 125

Gly Thr His Leu Thr Val Leu Gly
            130                 135

<210> SEQ ID NO 112
<211> LENGTH: 134
<212> TYPE: PRT
<213> ORGANISM: Canis lupus

<400> SEQUENCE: 112

Met Thr Ser Thr Met Ala Trp Ser Pro Leu Leu Leu Thr Leu Leu Thr
1               5                   10                  15

His Cys Thr Gly Ser Trp Ala Gln Ser Val Leu Thr Gln Pro Ala Ser
            20                  25                  30

Leu Ser Gly Ser Leu Gly Gln Arg Val Thr Ile Ser Cys Thr Gly Ser
            35                  40                  45

Ser Ser Asn Ile Gly Gly Tyr Ser Val Asn Trp Leu Gln Gln Leu Pro
            50                  55                  60

Gly Thr Gly Pro Arg Thr Ile Ile Tyr Asn Asn Ser Asn Arg Pro Ser
65                  70                  75                  80

Gly Val Pro Asp Arg Phe Ser Gly Ser Arg Ser Gly Thr Thr Ala Thr
            85                  90                  95

Leu Thr Ile Ser Gly Leu Gln Ala Glu Asp Glu Ala Asp Tyr Tyr Cys
            100                 105                 110

Ser Thr Trp Asp Ser Asn Leu Arg Thr Ile Val Phe Gly Gly Gly Thr
            115                 120                 125
```

```
His Leu Thr Val Leu Gly
        130

<210> SEQ ID NO 113
<211> LENGTH: 134
<212> TYPE: PRT
<213> ORGANISM: Canis lupus

<400> SEQUENCE: 113

Met Thr Ser Thr Met Asp Trp Ser Pro Leu Leu Thr Leu Leu Ala
1               5                   10                  15

His Cys Thr Gly Ser Trp Ala Gln Ser Val Leu Thr Gln Pro Ala Ser
            20                  25                  30

Val Ser Gly Ser Leu Gly Gln Arg Val Thr Ile Ser Cys Thr Gly Ser
        35                  40                  45

Thr Ser Asn Leu Gly Thr Tyr Asn Val Gly Trp Leu Gln Gln Val Pro
    50                  55                  60

Gly Thr Gly Pro Arg Thr Val Ile Tyr Thr Asn Ile Tyr Arg Pro Ser
65                  70                  75                  80

Gly Val Pro Asp Arg Phe Ser Gly Ser Glu Ser Gly Ser Thr Ala Thr
                85                  90                  95

Leu Thr Ile Ser Asp Leu Gln Ala Glu Asp Glu Ala Glu Tyr Tyr Cys
            100                 105                 110

Thr Ala Trp Asp Ser Ser Leu Asn Ala Tyr Val Phe Gly Ser Gly Thr
        115                 120                 125

Gln Leu Thr Val Leu Gly
        130

<210> SEQ ID NO 114
<211> LENGTH: 134
<212> TYPE: PRT
<213> ORGANISM: Canis lupus

<400> SEQUENCE: 114

Met Thr Ser Asn Met Ala Trp Cys Pro Phe Leu Leu Thr Leu Leu Ala
1               5                   10                  15

Tyr Cys Thr Gly Ser Trp Ala Gln Ser Val Leu Thr Gln Pro Thr Ser
            20                  25                  30

Val Ser Gly Ser Leu Gly Gln Arg Val Thr Ile Ser Cys Ser Gly Ser
        35                  40                  45

Thr Asn Asn Ile Gly Ile Val Gly Ala Ser Trp Tyr Gln Gln Leu Pro
    50                  55                  60

Gly Lys Ala Pro Lys Leu Leu Val Tyr Ser Asp Gly Asp Arg Pro Ser
65                  70                  75                  80

Gly Val Pro Asp Arg Phe Ser Gly Ser Asn Ser Gly Asn Ser Asp Thr
                85                  90                  95

Leu Thr Ile Thr Gly Leu Gln Ala Glu Asp Glu Ala Asp Tyr Tyr Cys
            100                 105                 110

Gln Ser Phe Asp Thr Thr Leu Asp Ala Ala Val Phe Gly Gly Gly Thr
        115                 120                 125

His Leu Thr Val Leu Gly
        130

<210> SEQ ID NO 115
<211> LENGTH: 135
<212> TYPE: PRT
<213> ORGANISM: Canis lupus
```

<400> SEQUENCE: 115

Met Thr Ser Thr Met Ala Trp Ser Pro Leu Leu Leu Thr Leu Leu Ala
1               5                   10                  15

His Cys Thr Val Ser Trp Ala Gln Ala Val Leu Thr Gln Pro Pro Ser
            20                  25                  30

Val Ser Ala Ala Leu Gly Gln Arg Val Thr Ile Ser Cys Thr Gly Ser
        35                  40                  45

Asp Thr Asn Ile Gly Ser Gly Tyr Glu Val His Trp Tyr Arg Gln Val
50                  55                  60

Pro Gly Lys Ser Pro Ala Ile Ile Ile Tyr Gly Asn Ser Asn Arg Pro
65                  70                  75                  80

Ser Gly Val Pro Val Arg Phe Ser Gly Ser Lys Ser Gly Ser Thr Ala
                85                  90                  95

Thr Leu Thr Ile Thr Gly Ile Glu Ala Glu Asp Glu Ala Asp Tyr His
            100                 105                 110

Cys Gln Ser Tyr Asp Gly Asn Leu Asp Gly Gly Val Phe Gly Gly Gly
        115                 120                 125

Thr His Leu Thr Val Leu Gly
130                 135

<210> SEQ ID NO 116
<211> LENGTH: 135
<212> TYPE: PRT
<213> ORGANISM: Canis lupus

<400> SEQUENCE: 116

Met Thr Ser Thr Met Gly Trp Phe Pro Leu Ile Leu Thr Leu Leu Ala
1               5                   10                  15

His Cys Ala Gly Ser Trp Ala Gln Ser Val Leu Thr Gln Pro Ala Ser
            20                  25                  30

Val Ser Gly Ser Leu Gly Gln Arg Val Thr Ile Ser Cys Thr Gly Ser
        35                  40                  45

Ser Pro Asn Val Gly Tyr Gly Asp Phe Val Ala Trp Tyr Gln Gln Val
50                  55                  60

Pro Gly Thr Ser Pro Arg Thr Leu Ile Tyr Asn Thr Arg Ser Arg Pro
65                  70                  75                  80

Ser Gly Val Pro Asp Arg Phe Ser Ala Ser Arg Ser Gly Asn Thr Ala
                85                  90                  95

Thr Leu Thr Ile Ser Gly Leu Gln Ala Glu Asp Glu Ala Asp Tyr Tyr
            100                 105                 110

Cys Ser Ser Tyr Asp Asn Thr Leu Ile Gly Ile Val Phe Gly Gly Gly
        115                 120                 125

Thr His Leu Thr Val Leu Gly
130                 135

<210> SEQ ID NO 117
<211> LENGTH: 134
<212> TYPE: PRT
<213> ORGANISM: Canis lupus

<400> SEQUENCE: 117

Met Thr Ser Thr Met Gly Trp Ser Pro Leu Leu Leu Thr Leu Leu Ala
1               5                   10                  15

His Cys Thr Gly Ser Trp Ala Gln Ser Val Leu Thr Gln Pro Ala Ser
            20                  25                  30

```
Val Ser Gly Ser Leu Gly Gln Arg Val Thr Ile Thr Cys Thr Gly Ser
         35                  40                  45

Ser Ser Asn Ile Gly Arg Ala Asn Val Ala Trp Phe Gln Gln Val Pro
 50                      55                  60

Gly Thr Gly Pro Arg Thr Val Ile Tyr Thr Ser Val Lys Arg Pro Ser
 65                  70                  75                  80

Gly Val Pro Asp Arg Phe Ser Gly Ser Lys Ser Gly Ser Thr Ala Thr
                 85                  90                  95

Leu Thr Ile Ser Gly Leu Gln Ala Glu Asp Glu Ala Asp Tyr Tyr Cys
             100                 105                 110

Ser Ser Trp Asp Asn Ser Leu Asp Ala Gly Val Phe Gly Gly Gly Thr
         115                 120                 125

His Leu Thr Val Leu Gly
    130

<210> SEQ ID NO 118
<211> LENGTH: 134
<212> TYPE: PRT
<213> ORGANISM: Canis lupus

<400> SEQUENCE: 118

Met Thr Ser Thr Met Gly Trp Phe Pro Leu Leu Thr Leu Leu Leu Ala
 1               5                  10                  15

His Ser Thr Gly Ser Trp Ala Gln Ser Val Leu Thr Gln Pro Ala Ser
             20                  25                  30

Val Ser Gly Ser Leu Gly Gln Arg Val Thr Ile Thr Cys Thr Gly Gly
         35                  40                  45

Thr Ser Asn Ile Gly Arg Gly Phe Val Ser Trp Phe Gln Gln Val Pro
 50                      55                  60

Gly Ile Gly Pro Lys Ile Leu Ile Phe Asp Ala Tyr Arg Arg Pro Ser
 65                  70                  75                  80

Gly Val Pro Asp Arg Phe Ser Gly Ser Arg Ser Gly Asn Thr Ala Thr
                 85                  90                  95

Leu Thr Ile Ser Gly Leu Gln Ala Glu Asp Glu Ala Asp Tyr Tyr Cys
             100                 105                 110

Ala Val Tyr Asp Ser Arg Leu Asp Val Gly Val Phe Gly Ser Gly Ser
         115                 120                 125

Gln Leu Thr Val Leu Ser
    130

<210> SEQ ID NO 119
<211> LENGTH: 134
<212> TYPE: PRT
<213> ORGANISM: Canis lupus

<400> SEQUENCE: 119

Met Thr Ser Asn Met Ala Trp Cys Pro Phe Leu Leu Thr Leu Leu Thr
 1               5                  10                  15

Tyr Cys Thr Gly Ser Trp Ala Arg Ser Val Leu Thr Gln Pro Ala Ser
             20                  25                  30

Val Ser Gly Ser Pro Gly Gln Lys Val Thr Ile Tyr Cys Ser Gly Thr
         35                  40                  45

Met Ser Asp Ile Gly Val Leu Gly Ala Asn Trp Tyr Gln Gln Leu Pro
 50                      55                  60

Gly Lys Ala Pro Lys Leu Leu Val Asp Asn Asp Gly Asp Arg Pro Ser
 65                  70                  75                  80
```

```
Gly Val Pro Asp Arg Phe Ser Ala Ser Lys Ser Gly His Ser Asp Thr
                85                  90                  95

Leu Thr Ile Thr Gly Leu Gln Pro Glu Asp Glu Gly Asp Tyr Tyr Cys
            100                 105                 110

Gln Ser Phe Asp Ser Ser Leu Asp Ala Ala Ile Phe Gly Glu Gly Thr
            115                 120                 125

His Leu Thr Val Leu Gly
            130

<210> SEQ ID NO 120
<211> LENGTH: 111
<212> TYPE: PRT
<213> ORGANISM: Canis lupus

<400> SEQUENCE: 120

Ser Val Ala Ser Tyr Val Leu Thr Gln Ser Pro Ser Gln Asn Val Thr
1               5                   10                  15

Leu Arg Gln Ala Ala His Ile Thr Cys Glu Gly His Asn Ile Gly Thr
            20                  25                  30

Lys Ser Val His Trp Tyr Gln Gln Lys Gln Gly Gln Ala Pro Val Leu
        35                  40                  45

Ile Ile Tyr Asp Asp Lys Ser Arg Pro Ser Gly Ile Pro Glu Arg Phe
    50                  55                  60

Ser Gly Ala Asn Ser Gly Asn Thr Ala Thr Leu Thr Ile Ser Gly Ala
65                  70                  75                  80

Leu Ala Glu Asp Glu Ala Asp Tyr Tyr Cys Leu Val Trp Asp Ser Ser
                85                  90                  95

Ala Ile Trp Val Phe Gly Glu Gly Thr His Leu Thr Val Leu Gly
            100                 105                 110

<210> SEQ ID NO 121
<211> LENGTH: 133
<212> TYPE: PRT
<213> ORGANISM: Canis lupus

<400> SEQUENCE: 121

Met Thr Ser Thr Met Ala Trp Ser Pro Leu Leu Thr Leu Leu Ala
1               5                   10                  15

His Phe Thr Gly Ser Trp Ala Gln Ser Val Leu Thr Gln Pro Thr Ser
            20                  25                  30

Val Ser Gly Ser Leu Gly Gln Arg Val Thr Ile Ser Cys Thr Ala Ser
        35                  40                  45

Ser Ser Asn Ile Asp Arg Asp Tyr Val Ala Trp Tyr Gln Gln Leu Pro
    50                  55                  60

Gly Thr Arg Pro Arg Ala Leu Ile Tyr Ala Asn Ser Asn Arg Pro Ser
65                  70                  75                  80

Gly Val Pro Asp Arg Phe Ser Gly Ser Lys Ser Gly Ser Thr Ala Thr
                85                  90                  95

Leu Thr Ile Ser Gly Leu Gln Ala Glu Asp Glu Ala Asp Tyr Tyr Cys
            100                 105                 110

Ser Thr Trp Asp Asn Ser Leu Thr Tyr Val Phe Gly Ser Gly Thr Gln
            115                 120                 125

Leu Thr Val Leu Gly
            130

<210> SEQ ID NO 122
<211> LENGTH: 110
```

```
<212> TYPE: PRT
<213> ORGANISM: Canis lupus

<400> SEQUENCE: 122

Ser Val Ala Ser Tyr Val Leu Thr Gln Val Pro Ser Val Ser Val Asn
1               5                   10                  15

Leu Gly Lys Thr Ala Thr Ile Thr Cys Glu Gly Asp Asn Val Gly Glu
            20                  25                  30

Lys Tyr Thr His Trp Tyr Gln Gln Glu Tyr Gly Gln Ala Pro Val Leu
        35                  40                  45

Ile Ile Tyr Glu Asp Ser Arg Arg Pro Ser Gly Ile Pro Glu Arg Phe
    50                  55                  60

Ser Gly Ser Asn Ser Gly Asn Thr Ala Thr Leu Thr Ile Ser Gly Ala
65                  70                  75                  80

Arg Ala Glu Asp Glu Thr Asp Tyr Tyr Cys Gln Val Trp Asp Asp Ser
                85                  90                  95

Gly Asn Val Phe Gly Gly Gly Thr His Leu Thr Val Leu Gly
            100                 105                 110

<210> SEQ ID NO 123
<211> LENGTH: 141
<212> TYPE: PRT
<213> ORGANISM: Canis lupus

<400> SEQUENCE: 123

Met Thr Ser Thr Met Gly Trp Phe Pro Leu Ile Leu Thr Leu Leu Ala
1               5                   10                  15

His Cys Ala Gly Ser Trp Ala Gln Ser Val Leu Thr Gln Pro Ala Ser
            20                  25                  30

Val Ser Gly Ser Leu Gly Gln Arg Val Thr Ile Ser Cys Thr Gly Ser
        35                  40                  45

Asp Ser Asn Val Gly Tyr Gly Asp Ser Ile Ala Tyr Gly Asp Ser Val
    50                  55                  60

Ala Trp Tyr Gln Gln Val Pro Gly Thr Ser Pro Arg Thr Leu Ile Tyr
65                  70                  75                  80

Asp Val Thr Ser Arg Pro Ser Gly Val Pro Arg Phe Ser Gly Ser
                85                  90                  95

Arg Ser Gly Thr Thr Ala Thr Leu Thr Ile Ser Gly Leu Gln Ala Glu
            100                 105                 110

Asp Glu Ala Asp Tyr Tyr Cys Ser Ser Phe Asp Lys Thr Leu Asn Gly
        115                 120                 125

Leu Ile Val Gly Gly Gly Thr His Leu Thr Val Leu Gly
    130                 135                 140

<210> SEQ ID NO 124
<211> LENGTH: 135
<212> TYPE: PRT
<213> ORGANISM: Canis lupus

<400> SEQUENCE: 124

Met Thr Ser Asn Met Ala Trp Ser Pro Leu Leu Leu Thr Leu Leu Ala
1               5                   10                  15

Tyr Cys Thr Gly Ser Trp Ala Gln Ser Ala Leu Thr Gln Pro Thr Ser
            20                  25                  30

Val Ser Gly Ser Leu Gly Gln Arg Val Ser Ile Ser Cys Ser Gly Gly
        35                  40                  45

Ile His Asn Ile Gly Ser Val Gly Ala Thr Trp Tyr Gln Gln Leu Pro
```

```
                   50                  55                  60
Gly Lys Ala Pro Lys Leu Leu Val Ser Ser Asp Gly Arg Pro Ser
 65                  70                  75                  80

Gly Ile Pro Asp Arg Phe Ser Gly Ser Arg Gly Asn Ser Val Thr
                 85                  90                  95

Leu Thr Ile Thr Gly Leu Gln Ala Glu Asp Glu Ala Glu Tyr Tyr Cys
                100                 105                 110

Gln Ser Phe Asp Ser Thr Leu Gly Val His Val Val Phe Gly Gly Gly
            115                 120                 125

Thr His Leu Thr Val Leu Gly
        130                 135

<210> SEQ ID NO 125
<211> LENGTH: 134
<212> TYPE: PRT
<213> ORGANISM: Canis lupus

<400> SEQUENCE: 125

Met Thr Ser Thr Met Ala Trp Phe Pro Leu Leu Thr Leu Leu Ala
  1               5                  10                  15

His Tyr Thr Gly Ser Trp Ala Arg Ser Asp Leu Thr Gln Pro Ala Ser
                 20                  25                  30

Val Ser Gly Ser Leu Gly Gln Arg Ile Thr Ile Ser Cys Thr Gly Ser
             35                  40                  45

Ser Ser Asn Ile Gly Arg Asn Tyr Val Gly Trp Tyr Gln Gln Leu Pro
     50                  55                  60

Gly Arg Gly Pro Arg Thr Val Val Tyr Gly Ile Asn Ser Arg Pro Ser
 65                  70                  75                  80

Gly Val Pro Asp Arg Phe Ser Gly Ser Lys Ser Gly Ser Thr Val Thr
                 85                  90                  95

Leu Thr Ile Ser Gly Leu Gln Ala Glu Asp Glu Ala Asp Tyr Tyr Cys
                100                 105                 110

Ser Thr Trp Asp Asp Ser Leu Ser Val Val Val Phe Gly Gly Gly Thr
            115                 120                 125

His Leu Thr Val Leu Gly
        130

<210> SEQ ID NO 126
<211> LENGTH: 132
<212> TYPE: PRT
<213> ORGANISM: Canis lupus

<400> SEQUENCE: 126

Met Thr Ser Thr Met Gly Trp Ser Pro Leu Leu Leu Thr Leu Thr His
  1               5                  10                  15

Trp Thr Gly Ser Trp Ala Gln Ser Val Leu Ser Gln Pro Ala Ser Met
                 20                  25                  30

Ser Gly Ser Leu Gly Leu Arg Ile Thr Ile Cys Cys Thr Gly Lys Asn
             35                  40                  45

Ser Asn Ile Asn Asn Ser Tyr Val Asp Trp Asn Gln Pro Leu Ala Gly
     50                  55                  60

Thr Gly Pro Arg Thr Val Ile His Asp Asp Gly Asp Arg Pro Ser Gly
 65                  70                  75                  80

Val Pro Asp Gln Phe Ser Gly Ser Lys Ser Gly Asn Thr Ala Thr Leu
                 85                  90                  95

Thr Ile Ser Arg Leu Gln Ala Glu Asp Glu Ala Asp Tyr Asn Gly Ala
```

```
                100                 105                 110
Ser Phe Glu Thr Ser Phe Asn Ala Val Phe Gly Gly Gly Thr His Val
            115                 120                 125

Thr Val Leu Gly
        130

<210> SEQ ID NO 127
<211> LENGTH: 76
<212> TYPE: PRT
<213> ORGANISM: Canis lupus

<400> SEQUENCE: 127

Leu Ser Trp Leu Arg Gln Lys Pro Gly His Ser Pro Gln Arg Leu Ile
1               5                   10                  15

His Gln Val Ser Ser Arg Asp Pro Gly Val Pro Asp Arg Phe Ser Gly
            20                  25                  30

Ser Gly Ser Gly Thr Asp Phe Thr Leu Thr Ile Ser Arg Val Glu Ala
            35                  40                  45

Asp Asp Gly Gly Val Tyr Tyr Cys Gly Gln Gly Ser Gln Ser Ile Pro
        50                  55                  60

Thr Phe Gly Gln Gly Thr Lys Val Glu Ile Lys Arg
65                  70                  75

<210> SEQ ID NO 128
<211> LENGTH: 133
<212> TYPE: PRT
<213> ORGANISM: Canis lupus

<400> SEQUENCE: 128

Met Arg Phe Pro Ser Gln Leu Leu Gly Leu Leu Met Leu Trp Ile Pro
1               5                   10                  15

Gly Ser Ala Gly Asp Ile Val Met Thr Gln Thr Pro Leu Ser Leu Ser
            20                  25                  30

Val Ser Pro Gly Glu Pro Ala Ser Ile Ser Cys Lys Ala Ser Gln Ser
            35                  40                  45

Leu Leu His Ser Asn Gly Asn Thr Tyr Leu Tyr Trp Phe Arg Gln Lys
        50                  55                  60

Pro Gly Gln Ser Pro Gln Arg Leu Ile Tyr Lys Val Ser Asn Arg Asp
65                  70                  75                  80

Pro Gly Val Pro Asp Arg Phe Ser Gly Ser Gly Ser Gly Thr Asp Phe
                85                  90                  95

Thr Leu Arg Ile Ser Arg Val Glu Thr Asp Asp Ala Gly Val Tyr Tyr
            100                 105                 110

Cys Gly Gln Val Ile Gln Asp Pro Trp Thr Phe Gly Val Gly Thr Lys
        115                 120                 125

Leu Glu Leu Lys Arg
        130

<210> SEQ ID NO 129
<211> LENGTH: 133
<212> TYPE: PRT
<213> ORGANISM: Canis lupus

<400> SEQUENCE: 129

Met Arg Phe Pro Ser Gln Leu Leu Gly Leu Leu Met Leu Trp Ile Pro
1               5                   10                  15

Gly Ser Ser Gly Asp Ile Val Met Thr Gln Thr Pro Leu Ser Leu Ser
            20                  25                  30
```

```
Val Ser Pro Gly Glu Thr Ala Ser Ile Ser Cys Arg Ala Ser Gln Thr
         35                  40                  45

Leu Leu Tyr Ser Asn Gly Lys Asn Tyr Leu Phe Trp Tyr Arg Gln Lys
 50                  55                  60

Pro Gly Gln Ser Pro Gln Arg Leu Ile Asp Leu Ala Ser Asn Arg Asp
 65                  70                  75                  80

Pro Gly Val Pro Asp Arg Phe Ser Gly Ser Gly Ser Gly Thr Asp Phe
                 85                  90                  95

Thr Leu Arg Ile Ser Arg Val Glu Ala Asp Asp Ala Gly Val Tyr Tyr
                100                 105                 110

Cys Gly Gln Gly Met Glu Ile Pro Trp Thr Phe Gly Ala Gly Thr Lys
                115                 120                 125

Val Glu Leu Lys Arg
    130

<210> SEQ ID NO 130
<211> LENGTH: 133
<212> TYPE: PRT
<213> ORGANISM: Canis lupus

<400> SEQUENCE: 130

Met Lys Phe Pro Ser Leu Leu Gly Leu Leu Met Leu Trp Ile Pro
 1               5                  10                  15

Gly Ser Thr Gly Glu Ala Val Met Thr Gln Thr Pro Leu Ser Leu Ala
                 20                  25                  30

Val Thr Pro Gly Glu Val Ala Thr Ile Ser Cys Arg Ala Ser Gln Ser
         35                  40                  45

Leu Leu His Ser Asp Gly Lys Ser Tyr Leu Asn Trp Tyr Leu Gln Lys
 50                  55                  60

Pro Gly Gln Thr Pro Arg Pro Leu Ile Tyr Glu Ala Ser Lys Arg Phe
 65                  70                  75                  80

Ser Gly Val Ser Asp Arg Phe Ser Gly Ser Gly Ser Gly Thr Asp Phe
                 85                  90                  95

Thr Leu Lys Ile Asn Arg Val Glu Ala Glu Asp Val Gly Val Tyr Tyr
                100                 105                 110

Cys Gln Gln Ser Leu His Phe Pro Pro Thr Phe Gly Pro Gly Thr Lys
                115                 120                 125

Val Glu Leu Lys Arg
    130

<210> SEQ ID NO 131
<211> LENGTH: 50
<212> TYPE: PRT
<213> ORGANISM: Canis lupus

<400> SEQUENCE: 131

Pro Asp Arg Phe Ser Gly Ser Gly Ser Gly Thr Asp Phe Thr Leu Thr
 1               5                  10                  15

Ile Ser Arg Val Glu Ala Asp Asp Ala Gly Ile Tyr Tyr Cys Gly Gln
                 20                  25                  30

Ala Thr Gln Thr Pro Pro Thr Phe Gly Ala Gly Thr Lys Leu Asp Leu
         35                  40                  45

Lys Arg
 50

<210> SEQ ID NO 132
```

```
<211> LENGTH: 133
<212> TYPE: PRT
<213> ORGANISM: Canis lupus

<400> SEQUENCE: 132

Met Arg Phe Pro Ser Gln Leu Leu Gly Leu Leu Met Leu Trp Ile Pro
1               5                   10                  15

Gly Ser Ser Gly Asp Ile Val Met Thr Gln Thr Pro Leu Ser Leu Ser
            20                  25                  30

Val Arg Pro Gly Glu Ser Ala Ser Ile Ser Cys Lys Ala Ser Gln Ser
        35                  40                  45

Leu Leu His Ser Gly Gly Gly Thr Tyr Leu Asn Trp Phe Arg Gln Arg
    50                  55                  60

Pro Gly Gln Ser Pro Gln Arg Leu Ile Tyr Glu Val Ser Lys Arg Asp
65                  70                  75                  80

Thr Gly Val Pro Asp Arg Phe Ser Gly Ser Gly Ser Gly Thr Asp Phe
                85                  90                  95

Thr Leu Arg Ile Thr Arg Val Glu Ala Asp Asp Thr Gly Ile Tyr Tyr
            100                 105                 110

Cys Gly Gln Asn Thr Gln Leu Pro Leu Thr Phe Gly Gln Gly Thr Lys
        115                 120                 125

Val Glu Ile Lys Arg
    130

<210> SEQ ID NO 133
<211> LENGTH: 133
<212> TYPE: PRT
<213> ORGANISM: Canis lupus

<400> SEQUENCE: 133

Met Arg Phe Pro Ser Gln Leu Leu Gly Leu Leu Met Leu Trp Ile Pro
1               5                   10                  15

Gly Ser Thr Gly Asp Ile Val Met Thr Gln Thr Pro Leu Ser Leu Ser
            20                  25                  30

Val Ser Pro Gly Glu Pro Ala Ser Ile Ser Cys Lys Ala Ser Gln Ser
        35                  40                  45

Leu Leu His Ser Asn Gly Asn Thr Tyr Leu Phe Trp Leu Arg Gln Lys
    50                  55                  60

Pro Gly Gln Ser Pro Gln Arg Leu Ile Tyr Arg Val Ser Asn Arg Asp
65                  70                  75                  80

Pro Gly Val Pro Asp Arg Phe Ser Gly Ser Gly Ser Gly Thr Asp Phe
                85                  90                  95

Thr Leu Arg Ile Ser Arg Val Glu Ala Asp Asp Ala Gly Val Tyr Tyr
            100                 105                 110

Cys Gly Gln Arg Val Arg Ser Pro Trp Thr Phe Gly Ala Gly Thr Lys
        115                 120                 125

Val Glu Val Lys Arg
    130

<210> SEQ ID NO 134
<211> LENGTH: 133
<212> TYPE: PRT
<213> ORGANISM: Canis lupus

<400> SEQUENCE: 134

Met Arg Phe Pro Ser Gln Leu Leu Gly Leu Leu Met Leu Trp Ile Pro
1               5                   10                  15
```

```
Gly Ser Ala Gly Asp Ile Val Met Thr Gln Thr Pro Leu Ser Leu Ser
            20                  25                  30

Val Ser Pro Gly Glu Pro Ala Ser Ile Ser Cys Lys Ala Ser Gln Ser
        35                  40                  45

Leu Leu His Ser Asn Gly Asn Thr Tyr Leu Tyr Trp Phe Arg Gln Lys
    50                  55                  60

Pro Gly Gln Ser Pro Gln Arg Leu Ile Tyr Lys Val Ser Asn Arg Asp
65                  70                  75                  80

Pro Gly Val Pro Asp Arg Phe Ser Gly Ser Gly Ser Gly Thr Asp Phe
                85                  90                  95

Thr Leu Arg Ile Ser Arg Val Glu Thr Asp Asp Ala Gly Val Tyr Tyr
            100                 105                 110

Cys Gly Gln Val Ile Gln Asp Pro Trp Thr Phe Gly Val Gly Thr Lys
            115                 120                 125

Leu Glu Leu Lys Arg
        130
```

<210> SEQ ID NO 135
<211> LENGTH: 133
<212> TYPE: PRT
<213> ORGANISM: Canis lupus

<400> SEQUENCE: 135

```
Met Arg Phe Pro Ser Gln Leu Leu Gly Leu Leu Met Leu Trp Ile Pro
1               5                   10                  15

Gly Ser Ser Gly Asp Val Val Met Ala Gln Thr Pro Leu Ser Leu Ser
            20                  25                  30

Val Ser Pro Gly Glu Thr Ala Ser Ile Ser Cys Arg Ala Ser Gln Ser
        35                  40                  45

Leu Leu His Ser Asn Gly Asn Thr Phe Leu Phe Trp Phe Arg Gln Lys
    50                  55                  60

Pro Gly Gln Ser Pro Gln Arg Leu Ile Asn Phe Leu Ser Asn Arg Asp
65                  70                  75                  80

Pro Gly Val Pro Asp Arg Phe Ser Gly Ser Gly Ser Gly Thr Asp Phe
                85                  90                  95

Thr Leu Arg Ile Asn Arg Val Glu Ala Asp Asp Ala Gly Leu Tyr Tyr
            100                 105                 110

Cys Gly Gln Gly Leu Gln Ala Pro Leu Thr Phe Gly Gly Gly Thr Lys
            115                 120                 125

Leu Glu Ile Lys Arg
        130
```

<210> SEQ ID NO 136
<211> LENGTH: 133
<212> TYPE: PRT
<213> ORGANISM: Canis lupus

<400> SEQUENCE: 136

```
Met Arg Phe Pro Ser Gln Leu Leu Gly Leu Leu Met Leu Trp Ile Pro
1               5                   10                  15

Gly Ser Asn Gly Asp Asp Val Leu Thr Gln Thr Pro Leu Ser Leu Ser
            20                  25                  30

Val Arg Pro Gly Glu Thr Val Ser Ile Leu Cys Lys Ala Ser Glu Ser
        35                  40                  45

Leu Leu His Ser Asp Gly Asn Thr Tyr Leu Ser Trp Val Arg Gln Lys
    50                  55                  60
```

```
Ala Gly Gln Ser Pro Gln Arg Leu Met Tyr Arg Val Ser Asp Arg Asp
 65                  70                  75                  80

Thr Gly Val Pro Asp Arg Phe Ser Gly Ser Gly Ser Gly Thr Asp Phe
                 85                  90                  95

Thr Leu Thr Ile Ser Gly Val Glu Ala Asp Asp Ala Gly Ile Tyr Tyr
            100                 105                 110

Cys Gly Gln Ala Thr His Tyr Pro Leu Glu Phe Gly Gln Gly Thr Arg
            115                 120                 125

Val Glu Ile Lys Arg
            130
```

<210> SEQ ID NO 137
<211> LENGTH: 123
<212> TYPE: PRT
<213> ORGANISM: Canis lupus

<400> SEQUENCE: 137

```
Leu Met Leu Trp Ile Pro Gly Ser Thr Gly Glu Ile Val Leu Thr Gln
 1               5                  10                  15

Thr Pro Leu Ser Leu Ser Val Ser Pro Gly Glu Pro Ala Ser Ile Ser
             20                  25                  30

Cys Lys Ala Ser Gln Ser Leu Leu His Pro Asn Gly Val Thr Tyr Leu
         35                  40                  45

Tyr Trp Phe Arg Gln Lys Pro Gly Gln Ser Pro Gln Arg Leu Ile Tyr
     50                  55                  60

Lys Val Ser Asn Arg Asp Pro Gly Val Pro Asp Arg Phe Ser Gly Ser
 65                  70                  75                  80

Gly Ser Glu Ile Asp Phe Thr Leu Ile Ile Ser Arg Val Glu Ala Asp
                 85                  90                  95

Asp Gly Gly Ile Tyr Tyr Cys Gly Gln Gly Ile Gln Asn Pro Phe Thr
            100                 105                 110

Phe Gly Gln Gly Thr Lys Leu Glu Ile Lys Arg
            115                 120
```

<210> SEQ ID NO 138
<211> LENGTH: 133
<212> TYPE: PRT
<213> ORGANISM: Canis lupus

<400> SEQUENCE: 138

```
Met Arg Phe Pro Ser Gln Leu Leu Gly Leu Leu Met Leu Trp Ile Pro
 1               5                  10                  15

Gly Ser Ile Gly Asp Ile Val Met Thr Gln Thr Pro Leu Ser Leu Ser
             20                  25                  30

Val Ser Pro Gly Glu Ser Ala Ser Ile Ser Cys Lys Ala Ser Gln Ser
         35                  40                  45

Leu Leu His Ser Asn Gly Asn Thr Tyr Leu Tyr Trp Phe Arg Gln Lys
     50                  55                  60

Pro Gly His Ser Pro Gln Arg Leu Ile His Gln Val Ser Ser Arg Asp
 65                  70                  75                  80

Pro Gly Val Pro Asp Arg Phe Ser Gly Ser Gly Ser Gly Thr Asp Phe
                 85                  90                  95

Thr Leu Arg Ile Ser Arg Val Glu Ala Asp Asp Ala Gly Leu Tyr Tyr
            100                 105                 110

Cys Gly Gln Gly Thr Gln Phe Pro Phe Thr Phe Gly Gln Gly Thr Lys
            115                 120                 125
```

Val Glu Ile Lys Arg
    130

<210> SEQ ID NO 139
<211> LENGTH: 133
<212> TYPE: PRT
<213> ORGANISM: Canis lupus

<400> SEQUENCE: 139

Met Arg Phe Pro Ser Gln Leu Leu Gly Leu Leu Met Leu Trp Ile Pro
1               5                   10                  15

Gly Ser Ile Gly Asp Ile Val Met Thr Gln Thr Pro Leu Ser Leu Ser
            20                  25                  30

Val Ser Pro Gly Glu Ser Ala Ser Ile Ser Cys Lys Ala Ser Gln Ser
        35                  40                  45

Leu Leu His Ser Asn Gly Asn Thr Tyr Leu Tyr Trp Phe Arg Gln Lys
    50                  55                  60

Pro Gly His Ser Pro Gln Arg Leu Ile His Gln Val Ser Ser Arg Asp
65                  70                  75                  80

Pro Gly Val Pro Asp Arg Phe Ser Gly Ser Gly Ser Gly Thr Asp Phe
                85                  90                  95

Thr Leu Arg Ile Ser Arg Val Glu Ala Asp Asp Ala Gly Leu Tyr Tyr
            100                 105                 110

Cys Gly Gln Gly Thr Gln Phe Pro Phe Thr Phe Gly Gln Gly Thr Lys
        115                 120                 125

Val Glu Ile Lys Arg
    130

<210> SEQ ID NO 140
<211> LENGTH: 133
<212> TYPE: PRT
<213> ORGANISM: Canis lupus

<400> SEQUENCE: 140

Met Arg Phe Pro Ser Gln Leu Leu Gly Leu Leu Met Leu Trp Ile Pro
1               5                   10                  15

Gly Ser Ser Gly Asp Ile Val Met Thr Gln Thr Pro Leu Ser Leu Ser
            20                  25                  30

Val Ser Pro Gly Glu Thr Ala Ser Ile Ser Cys Arg Ala Ser Gln Ser
        35                  40                  45

Leu Leu His Ser Asn Gly Asn Thr Tyr Ser Phe Trp Phe Arg Gln Lys
    50                  55                  60

Pro Gly Gln Ser Pro Gln Arg Leu Ile Asn Leu Val Ser Ser Arg Gly
65                  70                  75                  80

Pro Gly Val Pro Asp Arg Phe Ser Gly Ser Gly Ser Gly Thr Asp Phe
                85                  90                  95

Thr Leu Ile Ile Ser Arg Val Glu Ala Asp Asp Ala Gly Val Tyr Tyr
            100                 105                 110

Cys Gly His Gly Lys Glu Ala Pro Tyr Thr Phe Ser Gln Gly Thr Lys
        115                 120                 125

Leu Glu Ile Lys Arg
    130

<210> SEQ ID NO 141
<211> LENGTH: 133
<212> TYPE: PRT
<213> ORGANISM: Canis lupus -continued

```
<400> SEQUENCE: 141

Met Arg Phe Pro Ser Gln Leu Leu Gly Leu Leu Met Leu Trp Ile Pro
1               5                   10                  15

Gly Ser Val Gly Asp Ile Val Met Thr Gln Ser Pro Met Ser Leu Ser
            20                  25                  30

Val Gly Pro Gly Glu Ser Ala Ser Met Ser Cys Lys Ala Asn Gln Ser
        35                  40                  45

Leu Leu Tyr Ser Asp Gly Ile Thr Tyr Leu Ser Trp Phe Leu Gln Arg
    50                  55                  60

Pro Gly Gln Ser Pro Gln Arg Leu Ile Tyr Glu Val Ser Lys Arg Asp
65                  70                  75                  80

Thr Gly Val Pro Gly Arg Phe Ile Gly Ser Gly Ala Gly Thr Asp Phe
                85                  90                  95

Thr Leu Arg Ile Ser Arg Val Glu Ala Asp Asp Ala Gly Val Tyr Tyr
            100                 105                 110

Cys Gly Gln Ala Leu Gln Phe Pro Leu Thr Phe Ser Gln Gly Ala Lys
        115                 120                 125

Leu Glu Ile Glu Arg
    130

<210> SEQ ID NO 142
<211> LENGTH: 133
<212> TYPE: PRT
<213> ORGANISM: Canis lupus

<400> SEQUENCE: 142

Met Arg Phe Pro Ser Gln Leu Leu Gly Leu Leu Met Leu Trp Ile Pro
1               5                   10                  15

Gly Ser Ser Gly Asp Val Val Met Thr Gln Thr Pro Leu Ser Leu Ser
            20                  25                  30

Val Arg Pro Gly Glu Thr Ala Ser Ile Ser Cys Arg Ala Ser Gln Ser
        35                  40                  45

Leu Leu His Ser Ser Gly Ile Thr Lys Leu Phe Trp Tyr Arg Gln Lys
    50                  55                  60

Pro Gly Gln Ser Pro Gln Arg Leu Val Tyr Trp Val Ser Asn Arg Asp
65                  70                  75                  80

Pro Gly Val Pro Asp Arg Phe Thr Gly Ser Gly Ser Gly Thr Asp Phe
                85                  90                  95

Thr Leu Arg Ile Ser Arg Leu Glu Ala Asp Asp Ala Gly Ile Tyr Tyr
            100                 105                 110

Cys Gly His Ala Ile Gly Phe Pro Leu Thr Phe Gly Gln Gly Thr Lys
        115                 120                 125

Val Glu Ile Lys Arg
    130

<210> SEQ ID NO 143
<211> LENGTH: 133
<212> TYPE: PRT
<213> ORGANISM: Canis lupus

<400> SEQUENCE: 143

Met Arg Phe Pro Ser Gln Leu Leu Gly Leu Leu Met Leu Trp Ile Pro
1               5                   10                  15

Gly Ser Ser Gly Asp Ile Val Met Thr Gln Thr Pro Leu Ser Leu Ser
            20                  25                  30

Val Arg Pro Gly Glu Ser Ala Ser Ile Ser Cys Lys Ala Ser Gln Ser
```

```
                35                  40                  45
Leu Leu His Ser Gly Gly Gly Thr Tyr Leu Asn Trp Phe Arg Gln Arg
         50                  55                  60

Pro Gly Gln Ser Pro Gln Arg Leu Ile Tyr Glu Val Ser Lys Arg Asp
 65                  70                  75                  80

Thr Gly Val Pro Asp Arg Phe Ser Gly Ser Gly Ser Gly Thr Asp Phe
                 85                  90                  95

Thr Leu Arg Ile Thr Arg Val Glu Ala Asp Asp Thr Gly Ile Tyr Tyr
            100                 105                 110

Cys Gly Gln Asn Thr Gln Phe Pro Leu Thr Phe Gly Gln Gly Thr Lys
        115                 120                 125

Val Glu Ile Lys Arg
    130
```

<210> SEQ ID NO 144
<211> LENGTH: 133
<212> TYPE: PRT
<213> ORGANISM: Canis lupus
<220> FEATURE:
<221> NAME/KEY: MOD_RES
<222> LOCATION: (128)..(128)
<223> OTHER INFORMATION: Any amino acid

<400> SEQUENCE: 144

```
Met Arg Phe Pro Ser Gln Leu Leu Gly Leu Leu Met Leu Trp Ile Pro
 1               5                  10                  15

Gly Ser Ser Gly Gly Ile Val Met Thr Gln Thr Pro Leu Ser Leu Ser
                20                  25                  30

Val Arg Pro Gly Glu Thr Ala Ser Ile Ser Cys Arg Ala Ser Gln Ser
            35                  40                  45

Leu Leu Tyr Ser Asp Gly Asn Thr Tyr Leu Phe Trp Phe Arg Gln Lys
         50                  55                  60

Pro Gly Gln Ser Pro Gln Arg Leu Met Tyr Arg Val Ser Asp Arg Asp
 65                  70                  75                  80

Thr Gly Val Pro Asp Arg Phe Ser Gly Ser Gly Ser Gly Thr Asp Phe
                 85                  90                  95

Thr Leu Thr Ile Ser Gly Val Glu Ala Asp Asp Ala Gly Ile Tyr Tyr
            100                 105                 110

Cys Gly Gln Ala Thr His Tyr Pro Leu Glu Phe Gly Gln Gly Thr Xaa
        115                 120                 125

Val Glu Ile Lys Arg
    130
```

<210> SEQ ID NO 145
<211> LENGTH: 133
<212> TYPE: PRT
<213> ORGANISM: Canis lupus

<400> SEQUENCE: 145

```
Met Arg Phe Pro Ser Gln Leu Leu Gly Leu Leu Met Leu Trp Ile Pro
 1               5                  10                  15

Gly Ser Ser Gly Asp Ile Val Met Thr Gln Thr Pro Leu Ser Leu Ser
                20                  25                  30

Val Arg Pro Gly Glu Ser Ala Ser Ile Ser Cys Lys Ala Ser Gln Ser
            35                  40                  45

Leu Leu His Ser Gly Gly Gly Thr Tyr Leu Asn Trp Phe Arg Gln Arg
         50                  55                  60
```

```
Pro Gly Gln Ser Pro Gln Arg Leu Ile Tyr Glu Val Ser Lys Arg Asp
 65                  70                  75                  80

Thr Gly Val Pro Asp Arg Phe Ile Gly Ser Gly Ala Gly Thr Asp Phe
                 85                  90                  95

Thr Leu Arg Ile Ser Arg Val Glu Ala Asp Asp Ala Gly Val Tyr Tyr
                100                 105                 110

Cys Gly Gln Gly Val Gln Gly Pro Trp Thr Ile Gly Ala Gly Thr Lys
            115                 120                 125

Leu Glu Leu Gln Arg
    130

<210> SEQ ID NO 146
<211> LENGTH: 133
<212> TYPE: PRT
<213> ORGANISM: Canis lupus

<400> SEQUENCE: 146

Met Arg Phe Pro Ser Gln Leu Leu Gly Leu Leu Met Leu Trp Ile Pro
1               5                   10                  15

Gly Ser Ser Gly Asp Ile Val Met Thr Gln Thr Pro Leu Ser Val Ser
                20                  25                  30

Val Ser Pro Gly Glu Thr Ala Ser Ile Ser Cys Lys Ala Ser Gln Ser
            35                  40                  45

Leu Leu Ser His Asp Gly Asn Thr Tyr Leu His Trp Phe Arg Gln Lys
    50                  55                  60

Pro Gly Gln Ser Pro Gln Arg Leu Ile Tyr Lys Val Ser Asn Arg Asp
 65                  70                  75                  80

Thr Gly Val Pro Asp Arg Phe Ser Gly Ser Gly Ser Gly Thr Asp Phe
                 85                  90                  95

Thr Leu Lys Ile Ser Arg Val Glu Ala Asp Asp Thr Gly Val Tyr Tyr
                100                 105                 110

Cys Gly Gln Ile Thr Gln Asp Pro Phe Thr Phe Gly Gly Gly Thr Lys
            115                 120                 125

Leu Glu Ile Lys Arg
    130

<210> SEQ ID NO 147
<211> LENGTH: 133
<212> TYPE: PRT
<213> ORGANISM: Canis lupus

<400> SEQUENCE: 147

Met Arg Phe Pro Ser Gln Leu Leu Gly Leu Leu Met Leu Trp Ile Pro
1               5                   10                  15

Gly Ser Ser Gly Asp Ile Val Met Thr Gln Thr Pro Leu Ser Leu Ser
                20                  25                  30

Val Ser Pro Gly Glu Thr Ala Ser Ile Ser Cys Arg Ala Ser Gln Ser
            35                  40                  45

Leu Leu His Ser Asn Gly Asn Thr Tyr Leu Phe Trp Phe Arg Gln Lys
    50                  55                  60

Pro Gly Gln Ser Pro Gln Arg Leu Ile Asn Trp Val Ser Asn Arg Asp
 65                  70                  75                  80

Pro Gly Val Pro Asp Arg Phe Gly Gly Ser Gly Ser Gly Thr Asp Phe
                 85                  90                  95

Thr Leu Arg Ile Ser Arg Val Glu Ala Asp Asp Ala Gly Ile Tyr Tyr
                100                 105                 110
```

Cys Gly Gln Gly Ile Gln Gly Pro Tyr Thr Phe Ser Gln Gly Thr Lys
            115                 120                 125

Leu Glu Ile Lys Arg
    130

<210> SEQ ID NO 148
<211> LENGTH: 133
<212> TYPE: PRT
<213> ORGANISM: Canis lupus

<400> SEQUENCE: 148

Met Arg Phe Pro Ser Gln Phe Leu Gly Leu Leu Met Leu Trp Ile Pro
1               5                   10                  15

Gly Ser Ser Gly Asp Ile Ala Met Thr Gln Thr Pro Leu Ser Leu Ser
            20                  25                  30

Val Gly Pro Gly Glu Thr Ala Ser Ile Thr Cys Lys Ala Ser Gln Ser
        35                  40                  45

Leu Leu His Ser Asn Gly Asn Thr Tyr Leu Phe Trp Phe Arg Gln Lys
    50                  55                  60

Pro Gly Gln Ser Pro Gln Arg Leu Ile Tyr Leu Val Ser Asn Arg Asp
65                  70                  75                  80

Pro Gly Val Pro Asp Arg Phe Ser Gly Ser Gly Ser Gly Thr Asp Phe
                85                  90                  95

Thr Leu Thr Ile Ser Arg Val Glu Ala Asp Asp Ala Gly Ile Tyr Tyr
            100                 105                 110

Cys Gly Gln Ala Thr Gln Thr Pro Pro Thr Phe Gly Ala Gly Thr Lys
        115                 120                 125

Leu Asp Leu Lys Arg
    130

<210> SEQ ID NO 149
<211> LENGTH: 133
<212> TYPE: PRT
<213> ORGANISM: Canis lupus

<400> SEQUENCE: 149

Met Arg Phe Pro Ser Gln Leu Leu Gly Leu Leu Met Leu Trp Ile Pro
1               5                   10                  15

Gly Ser Ser Gly Asp Ile Val Met Ala Gln Thr Pro Leu Ser Leu Ser
            20                  25                  30

Val Ser Pro Gly Glu Pro Ala Ser Ile Ser Cys Lys Ala Ser Gln Ser
        35                  40                  45

Leu Leu His Ser Asp Gly Arg Thr Cys Leu Ser Trp Phe Arg Gln Lys
    50                  55                  60

Ser Gly Gln Ser Pro Gln Arg Leu Ile Tyr Glu Val Ser Asn Arg Asp
65                  70                  75                  80

Thr Gly Val Pro Asp Arg Phe Ser Gly Ser Gly Ser Gly Thr Asp Phe
                85                  90                  95

Thr Leu Arg Ile Ser Arg Val Glu Ala Asp Asp Thr Gly Ile Tyr Tyr
            100                 105                 110

Cys Gly Gln Thr Val Gln Phe Pro Leu Thr Phe Gly Gln Gly Thr Lys
        115                 120                 125

Leu Glu Ile Lys Arg
    130

<210> SEQ ID NO 150
<211> LENGTH: 68

<212> TYPE: PRT
<213> ORGANISM: Canis lupus

<400> SEQUENCE: 150

Gly Gln Ser Pro Gln Arg Leu Ile Tyr Lys Val Ser Asn Arg Asp Pro
1               5                   10                  15

Gly Val Pro Asp Arg Phe Ser Gly Ser Gly Thr Asp Phe Thr
            20                  25                  30

Leu Arg Ile Ser Arg Val Glu Pro Glu Asp Val Gly Val Tyr Tyr Cys
        35                  40                  45

Gly Gln Gly Thr Leu Asn Pro Trp Thr Phe Gly Ala Gly Thr Lys Val
    50                  55                  60

Glu Leu Lys Arg
65

<210> SEQ ID NO 151
<211> LENGTH: 63
<212> TYPE: PRT
<213> ORGANISM: Canis lupus

<400> SEQUENCE: 151

Met Arg Phe Pro Ser Gln Leu Leu Gly Leu Leu Met Leu Trp Ile Pro
1               5                   10                  15

Gly Ser Ser Gly Asp Val Val Met Thr Gln Thr Pro Leu Ser Leu Ser
            20                  25                  30

Val Ser Pro Gly Glu Thr Ala Ser Ile Ser Cys Arg Ala Ser Gln Ser
        35                  40                  45

Leu Leu His Ser Asn Gly Asn Thr Phe Leu Phe Trp Phe Arg Gln
    50                  55                  60

<210> SEQ ID NO 152
<211> LENGTH: 133
<212> TYPE: PRT
<213> ORGANISM: Canis lupus

<400> SEQUENCE: 152

Met Arg Phe Pro Ser Gln Leu Leu Gly Leu Leu Met Leu Trp Ile Pro
1               5                   10                  15

Gly Ser Gly Gly Asp Ile Val Met Thr Gln Thr Pro Ser Leu Ser
            20                  25                  30

Val Ser Pro Arg Glu Pro Ala Ser Ile Ser Cys Lys Ala Ser Gln Ser
        35                  40                  45

Leu Leu Arg Ser Asn Gly Asn Thr Tyr Leu Tyr Trp Phe Arg Gln Lys
    50                  55                  60

Pro Gly Gln Ser Pro Glu Gly Leu Ile Tyr Arg Val Ser Asn Arg Phe
65                  70                  75                  80

Thr Gly Val Ser Asp Arg Phe Ser Gly Ser Gly Ser Gly Thr Asp Phe
            85                  90                  95

Thr Leu Arg Ile Ser Thr Val Glu Ala Asp Ala Gly Val Tyr Tyr
        100                 105                 110

Cys Gly Gln Ala Thr Gln Phe Pro Ser Thr Phe Ser Gln Gly Thr Lys
    115                 120                 125

Leu Glu Ile Lys Arg
    130

<210> SEQ ID NO 153
<211> LENGTH: 133
<212> TYPE: PRT

```
<213> ORGANISM: Canis lupus
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (125)..(125)
<223> OTHER INFORMATION: Any amino acid
<220> FEATURE:
<221> NAME/KEY: MOD_RES
<222> LOCATION: (129)..(129)
<223> OTHER INFORMATION: Any amino acid

<400> SEQUENCE: 153

Met Arg Phe Pro Ser Gln Leu Leu Gly Leu Leu Met Leu Trp Ile Pro
1               5                   10                  15

Gly Ser Xaa Gly Asp Ile Val Leu Thr Gln Thr Pro Leu Ser Leu Ser
            20                  25                  30

Val Ser Pro Gly Glu Pro Ala Ser Ile Ser Cys Lys Ala Ser Gln Ser
        35                  40                  45

Leu Leu His Ser Asn Gly Ile Thr Tyr Leu Asn Trp Tyr Arg Gln Arg
    50                  55                  60

Pro Gly Gln Ser Pro Gln Xaa Leu Ile Tyr Lys Val Ser Asn Arg Asp
65                  70                  75                  80

Thr Gly Val Pro Asp Arg Phe Ser Gly Ser Gly Ser Gly Thr Asp Phe
                85                  90                  95

Thr Leu Arg Xaa Ser Lys Val Glu Ala Asp Asp Thr Gly Ile Tyr Tyr
            100                 105                 110

Cys Gly Gln Asp Thr Gln Phe Pro Leu Thr Leu Gly Xaa Gly Thr His
        115                 120                 125

Xaa Glu Ile Lys Arg
    130

<210> SEQ ID NO 154
<211> LENGTH: 132
<212> TYPE: PRT
<213> ORGANISM: Canis lupus

<400> SEQUENCE: 154

Met Arg Phe Pro Ser Gln Leu Leu Gly Leu Leu Met Leu Trp Ile Pro
1               5                   10                  15

Gly Ser Thr Gly Asp Ile Val Met Thr Gln Thr Pro Leu Ser Leu Ser
            20                  25                  30

Val Ser Pro Gly Glu Pro Ala Ser Ile Tyr Cys Lys Ala Ser Gln Ser
        35                  40                  45

Leu Leu His Ser Asn Gly Lys Thr Phe Leu Tyr Trp Phe Arg Gln Lys
    50                  55                  60

Pro Gly Gln Ser Pro Gln Arg Leu Ile Tyr Arg Val Ser Asn Arg Asp
65                  70                  75                  80

Pro Gly Val Pro Asp Arg Phe Ser Gly Ser Gly Ser Gly Thr Asp Phe
                85                  90                  95

Thr Leu Arg Ile Ser Arg Val Glu Ala Asp Asp Ala Gly Ile Tyr Tyr
            100                 105                 110
```

```
Cys Gly Gln Gly Ile Gln Asp Pro Thr Phe Gly Gln Gly Thr Lys Val
        115                 120                 125

Glu Ile Lys Arg
    130

<210> SEQ ID NO 155
<211> LENGTH: 133
<212> TYPE: PRT
<213> ORGANISM: Canis lupus

<400> SEQUENCE: 155

Met Arg Phe Pro Ser Gln Leu Leu Gly Leu Leu Met Leu Trp Ile Pro
1               5                   10                  15

Gly Ser Gly Gly Asp Ile Val Met Thr Gln Thr Pro Pro Ser Leu Ser
            20                  25                  30

Val Ser Pro Arg Glu Ala Ala Ser Ile Ser Cys Lys Ala Ser Gln Ser
        35                  40                  45

Leu Leu Lys Ser Asn Gly Asn Thr Tyr Phe Tyr Trp Phe Arg Gln Lys
    50                  55                  60

Pro Gly Gln Val Ser Glu Gly Leu Ile Tyr Lys Val Ser Ser Arg Phe
65                  70                  75                  80

Thr Gly Val Ser Asp Arg Phe Ser Gly Ser Gly Ser Gly Thr Asp Phe
                85                  90                  95

Thr Leu Arg Ile Ser Arg Val Glu Ala Asp Asp Ala Gly Val Tyr Phe
            100                 105                 110

Cys Gly Gln Ala Leu Gln Phe Pro Tyr Thr Phe Ser Gln Gly Thr Lys
        115                 120                 125

Leu Asp Ile Lys Arg
    130

<210> SEQ ID NO 156
<211> LENGTH: 133
<212> TYPE: PRT
<213> ORGANISM: Canis lupus

<400> SEQUENCE: 156

Met Arg Phe Pro Ser Gln Leu Leu Gly Leu Leu Met Leu Trp Ile Pro
1               5                   10                  15

Glu Ser Gly Gly Asp Val Val Leu Thr Gln Thr Pro Pro Ser Leu Ser
            20                  25                  30

Leu Ser Pro Gly Glu Thr Ala Ser Ile Ser Cys Lys Ala Ser Arg Ser
        35                  40                  45

Leu Leu Asn Ser Asp Gly Ser Thr Tyr Leu Asp Trp Tyr Leu Gln Lys
    50                  55                  60

Pro Gly Gln Ser Pro Arg Leu Leu Ile Tyr Leu Val Ser Asn Arg Phe
65                  70                  75                  80

Ser Gly Val Ser Asp Arg Phe Ser Gly Ser Gly Ser Gly Thr Asp Phe
                85                  90                  95

Thr Leu Thr Ile Ser Arg Val Glu Ala Asp Asp Ala Gly Val Tyr Tyr
            100                 105                 110

Cys Gly Gln Gly Ser Arg Val Pro Leu Thr Phe Gly Gln Gly Thr Lys
        115                 120                 125

Val Glu Ile Lys Arg
    130

<210> SEQ ID NO 157
```

```
<211> LENGTH: 133
<212> TYPE: PRT
<213> ORGANISM: Canis lupus

<400> SEQUENCE: 157

Met Arg Phe Pro Ser Gln Leu Leu Gly Leu Leu Met Leu Trp Ile Pro
1               5                   10                  15

Gly Ser Ser Gly Asp Ile Val Met Thr Gln Thr Pro Leu Ser Leu Ser
                20                  25                  30

Val Ser Pro Gly Glu Thr Ala Ser Ile Ser Cys Arg Ala Ser Gln Ser
            35                  40                  45

Leu Leu His Arg Asn Gly Ile Thr Tyr Leu Ser Trp Phe Arg Gln Arg
        50                  55                  60

Pro Gly Gln Ser Pro Gln Arg Leu Ile Asn Leu Val Ser Asn Arg Asp
65                  70                  75                  80

Pro Gly Val Pro Asp Arg Phe Ser Gly Ser Gly Ser Gly Thr Asp Phe
                85                  90                  95

Thr Leu Arg Ile Ser Arg Val Glu Ala Asp Asp Val Gly Val Tyr Tyr
            100                 105                 110

Cys Gly His Gly Leu Gln Thr Pro Tyr Thr Phe Gly Gln Gly Thr Ser
        115                 120                 125

Leu Glu Ile Glu Arg
    130

<210> SEQ ID NO 158
<211> LENGTH: 133
<212> TYPE: PRT
<213> ORGANISM: Canis lupus

<400> SEQUENCE: 158

Met Arg Phe Pro Ser Gln Leu Leu Gly Leu Leu Val Leu Trp Ile Pro
1               5                   10                  15

Gly Ser Ser Gly Asp Ile Val Met Thr Gln Thr Pro Leu Ser Leu Ser
                20                  25                  30

Val Ser Pro Gly Glu Thr Val Ser Ile Ser Cys Arg Ala Ser Gln Ser
            35                  40                  45

Leu Leu Tyr Ser Asp Gly Asn Ile Tyr Leu Phe Trp Phe Arg Arg Lys
        50                  55                  60

Pro Gly Gln Ser Pro Gln His Leu Ile Asn Leu Val Ser Asn Arg Asp
65                  70                  75                  80

Pro Gly Val Pro Asp Arg Phe Ser Gly Ser Gly Ser Gly Thr Asp Phe
                85                  90                  95

Thr Leu Arg Ile Ser Arg Val Glu Ala Asp Asp Ala Gly Val Tyr Tyr
            100                 105                 110

Cys Gly Gln Gly Thr Gln Pro Pro Tyr Thr Phe Ser Gly Gly Thr Lys
        115                 120                 125

Val Glu Ile Lys Arg
    130

<210> SEQ ID NO 159
<211> LENGTH: 133
<212> TYPE: PRT
<213> ORGANISM: Canis lupus

<400> SEQUENCE: 159

Met Arg Phe Pro Ser Gln Leu Leu Gly Leu Leu Met Leu Trp Ile Pro
1               5                   10                  15
```

```
Glu Ser Gly Gly Asp Val Val Leu Thr Gln Thr Pro Pro Ser Leu Ser
            20                  25                  30

Leu Ser Pro Gly Glu Thr Ala Ser Ile Ser Cys Lys Ala Ser Arg Ser
        35                  40                  45

Leu Leu Asn Ser Asp Gly Ser Thr Tyr Leu Asp Trp Tyr Leu Gln Lys
    50                  55                  60

Pro Gly Gln Ser Pro Arg Leu Leu Ile Tyr Leu Val Ser Asn Arg Phe
65                  70                  75                  80

Ser Gly Val Ser Asp Arg Phe Ser Gly Ser Gly Ser Gly Thr Asp Phe
                85                  90                  95

Thr Leu Thr Ile Ser Arg Val Glu Ala Asp Asp Ala Gly Val Tyr Tyr
            100                 105                 110

Cys Gly Gln Gly Ser Arg Val Pro Leu Thr Phe Gly Gln Gly Thr Lys
            115                 120                 125

Val Glu Ile Lys Arg
        130

<210> SEQ ID NO 160
<211> LENGTH: 133
<212> TYPE: PRT
<213> ORGANISM: Canis lupus

<400> SEQUENCE: 160

Met Arg Phe Pro Ser Gln Leu Leu Gly Leu Leu Met Leu Trp Ile Pro
1               5                   10                  15

Gly Ser Ser Gly Asp Ile Val Met Ala Gln Thr Pro Leu Ser Leu Ser
            20                  25                  30

Val Ser Pro Gly Glu Thr Ala Ser Ile Ser Cys Arg Ala Ser Gln Ser
        35                  40                  45

Leu Leu His Ser Asn Gly Ile Thr Tyr Leu Phe Trp Tyr Arg Gln Lys
    50                  55                  60

Pro Gly Gln Ser Pro Gln Arg Leu Ile Ser Met Val Phe Asn Arg Asp
65                  70                  75                  80

Pro Gly Val Pro Asp Arg Phe Gly Ser Gly Ser Gly Thr Asp Phe
                85                  90                  95

Thr Leu Arg Ile Ser Arg Val Glu Ala Asp Asp Ala Gly Leu Tyr Phe
            100                 105                 110

Cys Gly His Gly Thr Gln Ile Pro Tyr Ser Phe Ser Gln Gly Thr Lys
            115                 120                 125

Leu Glu Ile Lys Arg
        130

<210> SEQ ID NO 161
<211> LENGTH: 133
<212> TYPE: PRT
<213> ORGANISM: Canis lupus

<400> SEQUENCE: 161

Met Arg Phe Pro Ser Gln Leu Leu Gly Leu Leu Met Leu Trp Ile Pro
1               5                   10                  15

Gly Ser Ser Gly Asp Ile Val Met Thr Gln Thr Pro Leu Ser Leu Ser
            20                  25                  30

Ile Ser Pro Gly Glu Pro Ala Ser Ile Ser Cys Lys Ala Ser Gln Ser
        35                  40                  45

Leu Leu His Ser Gly Gly Asp Thr Tyr Leu Asn Trp Phe Arg Gln Arg
    50                  55                  60
```

-continued

Pro Gly Gln Ser Pro Gln Leu Leu Ile Asn Arg Val Ser Ser Arg Lys
65                  70                  75                  80

Lys Gly Val Pro Asp Arg Phe Ser Gly Ser Gly Ser Gly Thr Glu Phe
                85                  90                  95

Thr Leu Arg Ile Ser Arg Val Glu Ala Asp Asp Ala Gly Ile Tyr Phe
                100                 105                 110

Cys Gly Gln Gly Thr Gln Phe Pro Tyr Thr Phe Ser Gln Gly Thr Lys
            115                 120                 125

Leu Glu Ile Lys Arg
    130

<210> SEQ ID NO 162
<211> LENGTH: 133
<212> TYPE: PRT
<213> ORGANISM: Canis lupus

<400> SEQUENCE: 162

Met Arg Phe Pro Ser Gln Leu Leu Gly Leu Leu Met Leu Trp Ile Pro
1               5                   10                  15

Gly Ser Gly Gly Asp Ile Val Met Thr Gln Thr Pro Pro Ser Leu Ser
                20                  25                  30

Val Ser Pro Gly Glu Pro Ala Ser Met Ser Cys Lys Ala Ser Gln Ser
            35                  40                  45

Leu Leu His Ser Asn Gly Asn Thr Tyr Leu Tyr Trp Phe Arg Gln Lys
    50                  55                  60

Pro Gly Gln Ser Pro Glu Ala Leu Ile Tyr Lys Val Ser Asn Arg Phe
65                  70                  75                  80

Thr Gly Val Ser Asp Arg Phe Ser Gly Ser Gly Ser Gly Thr Asp Phe
                85                  90                  95

Thr Leu Arg Ile Asn Arg Val Glu Ala Asp Asp Val Gly Val Tyr Tyr
                100                 105                 110

Cys Gly Gln Gly Ile Gln Ile Pro Tyr Thr Phe Ser Gly Gly Thr Lys
            115                 120                 125

Leu Glu Ile Lys Arg
    130

<210> SEQ ID NO 163
<211> LENGTH: 133
<212> TYPE: PRT
<213> ORGANISM: Canis lupus

<400> SEQUENCE: 163

Met Arg Phe Pro Ser Gln Leu Leu Gly Leu Leu Met Leu Trp Ile Pro
1               5                   10                  15

Gly Ser Thr Gly Glu Ile Val Leu Thr Gln Thr Pro Leu Ser Leu Ser
                20                  25                  30

Val Ser Pro Gly Glu Ser Ala Ser Ile Ser Cys Lys Ala Ser Gln Ser
            35                  40                  45

Leu Leu Tyr Ser Asn Gly Asn Thr Tyr Leu Tyr Trp Phe Arg Gln Lys
    50                  55                  60

Ala Gly Gln Ser Pro Gln Arg Val Ile Tyr Arg Val Ser Asn Arg Asp
65                  70                  75                  80

Pro Gly Val Pro Asp Arg Phe Ser Gly Ser Gly Ser Gly Thr Asp Phe
                85                  90                  95

Thr Leu Arg Ile Ser Ser Val Glu Asn Asp Asp Ala Gly Val Tyr Tyr
                100                 105                 110

```
Cys Gly Gln Gly Ser Glu Asp Pro Pro Thr Phe Gly Ala Gly Thr Lys
        115                 120                 125

Val Glu Leu Lys Arg
    130

<210> SEQ ID NO 164
<211> LENGTH: 133
<212> TYPE: PRT
<213> ORGANISM: Canis lupus
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (102)..(102)
<223> OTHER INFORMATION: Any amino acid

<400> SEQUENCE: 164

Met Arg Phe Pro Ser Gln Leu Leu Gly Leu Leu Thr Leu Trp Ile Pro
1               5                   10                  15

Gly Ser Thr Gly Asp Ile Val Met Thr Gln Thr Pro Leu Ser Leu Ser
            20                  25                  30

Val Ser Pro Gly Glu Pro Ala Ser Ile Ser Cys Lys Ala Ser Gln Ser
        35                  40                  45

Leu Leu His Ser Asn Gly Asn Thr Tyr Leu Tyr Trp Phe Arg Gln Lys
    50                  55                  60

Pro Gly Gln Ser Pro Gln Arg Leu Ile Tyr Lys Val Ser Asn Arg Asp
65                  70                  75                  80

Pro Gly Val Pro Xaa Arg Phe Ser Gly Ser Gly Ser Gly Thr Asp Phe
                85                  90                  95

Thr Leu Arg Val Ser Xaa Val Glu Ala Asp Asp Ala Gly Val Tyr Tyr
            100                 105                 110

Cys Gly Gln Gly Val Gln Asp Pro Phe Thr Phe Gly Gln Gly Thr Lys
        115                 120                 125

Leu Glu Ile Lys Arg
    130

<210> SEQ ID NO 165
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Phe Trp Val Arg Gln Ala Thr Gly Lys Gly Leu Glu Trp Val
        35                  40                  45

Ser Thr Ile Ser Asp Gly Gly Ser Tyr Thr Tyr Tyr Thr Asp Asn Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Gly Asp Thr Ala Val Tyr Tyr Cys
                85                  90                  95

Ala Arg Asp Trp Ser Asp Ser Glu Gly Phe Ala Tyr Trp Gly Gln Gly
```

Thr Leu Val Thr Val Ser Ser
        115

<210> SEQ ID NO 166
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Arg Ile Asp Pro Tyr Gly Gly Gly Thr Lys His Asn Glu Lys Phe
    50                  55                  60

Lys Arg Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gly Tyr Asp Tyr Tyr Phe Asp Val Trp Gly Gln Gly Thr
            100                 105                 110

Thr Val Thr Val Ser Ser
        115

<210> SEQ ID NO 167
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Ile Tyr Trp Val Arg Gln Ala Pro Gly Gln Gly Leu Glu Trp Met
        35                  40                  45

Gly Arg Ile Asp Pro Ala Asn Gly Asn Thr Ile Tyr Ala Ser Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Tyr Tyr Ala Tyr Trp Gly Gln Gly Thr Thr Val Thr
            100                 105                 110

Val Ser Ser
        115

<210> SEQ ID NO 168
<211> LENGTH: 115
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Tyr Trp Val Arg Gln Ala Pro Gly Gln Gly Leu Glu Trp Met
        35                  40                  45

Gly Arg Ile Asp Pro Ala Asn Gly Asn Thr Ile Tyr Ala Ser Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Gly Tyr Tyr Ala Tyr Trp Gly Gln Gly Thr Thr Val Thr
            100                 105                 110

Val Ser Ser
        115

<210> SEQ ID NO 169
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn His
            20                  25                  30

Tyr Met Tyr Trp Val Arg Gln Ala Pro Gly Lys Gly Leu Glu Trp Val
        35                  40                  45

Gly Ser Ile Ser Asp Gly Gly Ala Tyr Thr Phe Tyr Pro Asp Thr Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Glu Glu Ser Ala Asn Asn Gly Phe Ala Phe Trp Gly Gln Gly
            100                 105                 110

Thr Leu Val Thr Val Ser Ser
        115

<210> SEQ ID NO 170
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Thr Leu Lys Glu Ser Gly Pro Val Leu Val Lys Pro Thr Glu
1               5                   10                  15

```
Thr Leu Thr Leu Thr Cys Thr Val Ser Gly Phe Ser Leu Thr Gly Tyr
            20                  25                  30

Asn Ile Asn Trp Ile Arg Gln Pro Gly Lys Ala Leu Glu Trp Leu
        35                  40                  45

Ala Met Ile Trp Gly Tyr Gly Asp Thr Asp Tyr Asn Ser Ala Leu Lys
50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp His Tyr Gly Gly Asn Asp Trp Tyr Phe Asp Val Trp Gly Gln
            100                 105                 110

Gly Thr Thr Val Thr Val Ser Ser
        115                 120
```

<210> SEQ ID NO 171
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val Gln Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110

Arg
```

<210> SEQ ID NO 172
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
Asp Ile Gln Met Ile Gln Ser Pro Ser Phe Leu Ser Ala Ser Val Gly
1               5                   10                  15

Asp Arg Val Ser Ile Ile Cys Arg Ala Ser Glu Asn Ile Tyr Ser Phe
            20                  25                  30

Leu Ala Trp Tyr Leu Gln Lys Pro Gly Lys Ser Pro Lys Leu Phe Leu
        35                  40                  45

Tyr Asn Ala Asn Thr Leu Ala Glu Gly Val Ser Ser Arg Phe Ser Gly
50                  55                  60
```

-continued

Arg Gly Ser Gly Thr Asp Phe Thr Leu Thr Ile Ser Leu Lys Pro
65                  70                  75                  80

Glu Asp Phe Ala Ala Tyr Tyr Cys Gln His His Phe Gly Thr Pro Phe
                85                  90                  95

Thr Phe Gly Gln Gly Thr Lys Leu Glu Ile Lys Arg
                100                 105

<210> SEQ ID NO 173
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Ile Val Met Thr Gln Thr Pro Leu Ser Leu Pro Val Thr Pro Gly
1               5                   10                  15

Glu Pro Ala Ser Ile Ser Cys Lys Ser Thr Lys Ser Leu Leu Asn Gly
                20                  25                  30

Asp Gly Phe Thr Tyr Leu Asp Trp Tyr Leu Gln Lys Pro Gly Gln Ser
            35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Glu Ser
                85                  90                  95

Asn Tyr Leu Phe Thr Phe Gly Gln Gly Thr Lys Leu Glu Ile Lys Arg
                100                 105                 110

<210> SEQ ID NO 174
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Asp Ile Val Met Thr Gln Thr Pro Leu Ser Leu Pro Val Thr Pro Gly
1               5                   10                  15

Glu Pro Ala Ser Ile Ser Cys Lys Ser Thr Lys Ser Leu Leu Asn Gly
                20                  25                  30

Asp Gly Phe Thr Tyr Leu Asp Trp Tyr Leu Gln Lys Pro Gly Gln Ser
            35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Glu Ser
                85                  90                  95

Asn Tyr Leu Phe Thr Phe Gly Gln Gly Thr Lys Leu Glu Ile Lys Arg
                100                 105                 110

<210> SEQ ID NO 175
<211> LENGTH: 113
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 175

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ala His Val Pro Phe Thr Phe Gly Gln Gly Thr Lys Leu Glu Ile Lys
            100                 105                 110

Arg
```

<210> SEQ ID NO 176
<211> LENGTH: 108
<212> TYPE: PRT
<213> ORGANISM: Canis lupus

<400> SEQUENCE: 176

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Lys Thr Leu Pro Arg
                85                  90                  95

Thr Phe Gly Gln Gly Thr Lys Leu Glu Ile Lys Arg
            100                 105
```

<210> SEQ ID NO 177
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Glu Val Gln Leu Glu Glu Ser Gly Gly Asp Leu Val Lys Pro Gly Gly
1               5                   10                  15

Ser Leu Arg Leu Ser Cys Val Ala Ser Gly Phe Thr Phe Ser Asn His
            20                  25                  30

Tyr Met Tyr Trp Val Arg Gln Ser Pro Gly Lys Gly Leu Gln Trp Val
        35                  40                  45

Ala Ser Ile Ser Asp Gly Gly Ala Tyr Thr Phe Tyr Pro Asp Thr Val
    50                  55                  60
```

-continued

Lys Gly Arg Phe Thr Ile Ser Arg Asp Asn Ala Lys Asn Thr Leu Phe
65                  70                  75                  80

Leu Gln Met Asn Ser Leu Arg Ala Glu Asp Thr Ala Val Tyr Phe Cys
                85                  90                  95

Val Lys Glu Glu Ser Ala Asn Asn Gly Phe Ala Phe Trp Gly Gln Gly
            100                 105                 110

Thr Leu Val Thr Val Ser Ser
        115

<210> SEQ ID NO 178
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Val Gln Leu Glu Glu Ser Gly Gly Asp Leu Val Lys Pro Gly Gly
1               5                   10                  15

Ser Leu Arg Leu Ser Cys Val Ala Ser Gly Phe Ser Ile Gly Ser Tyr
            20                  25                  30

Gly Met Ser Trp Val Arg Gln Ser Pro Gly Lys Gly Leu Gln Trp Val
        35                  40                  45

Ala Trp Ile Lys Tyr Asp Gly Ser Arg Thr Phe Tyr Ala Asp Ala Val
    50                  55                  60

Lys Gly Arg Phe Thr Ile Ser Arg Asp Asn Ala Lys Asn Thr Leu Phe
65                  70                  75                  80

Leu Gln Met Asn Ser Leu Arg Ala Glu Asp Thr Ala Val Tyr Phe Cys
                85                  90                  95

Val Lys Gly Pro Asn Ser Ser Trp Leu Pro Ser Thr Tyr Phe Ala Ser
            100                 105                 110

Trp Gly Gln Gly Thr Leu Val Thr Val Ser Ser
        115                 120

<210> SEQ ID NO 179
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val His Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Phe Trp Ile Arg Gln Ser Pro Gly Lys Gly Leu Glu Trp Val
        35                  40                  45

Ala Thr Ile Ser Asp Gly Gly Ser Tyr Thr Tyr Tyr Thr Asp Asn Val
    50                  55                  60

Lys Gly Arg Phe Thr Ile Ser Arg Asp Asn Ala Asn Asn Leu Tyr
65                  70                  75                  80

Leu Gln Met Asn Ser Leu Lys Ala Glu Asp Thr Ala Val Tyr Tyr Cys
                85                  90                  95

Ala Lys Asp Trp Ser Asp Ser Glu Gly Phe Ala Tyr Trp Gly Gln Gly
            100                 105                 110

Thr Leu Val Thr Val Ser Ser
        115

<210> SEQ ID NO 180
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val His Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Phe Trp Val Arg His Ser Pro Gly Lys Gly Leu Glu Trp Val
        35                  40                  45

Ala Thr Ile Ser Asp Gly Gly Ser Tyr Thr Tyr Tyr Thr Asp Asn Val
    50                  55                  60

Lys Gly Arg Phe Thr Ile Ser Arg Asp Asn Ala Asn Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Ser Asp Ser Glu Gly Phe Ala Tyr Trp Gly Gln Gly
            100                 105                 110

Thr Leu Val Thr Val Ser Ser
        115

<210> SEQ ID NO 181
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Asp Ile Val Met Thr Gln Thr Pro Pro Ser Leu Ser Val Ser Pro Arg
1               5                   10                  15

Glu Pro Ala Ser Ile Ser Cys Arg Ser Ser Gln Ser Ile Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Thr Gly Val Tyr Tyr Cys Phe Gln Gly
                85                  90                  95

Ser His Val Pro Phe Thr Phe Gly Ala Gly Thr Lys Val Glu Leu Lys
            100                 105                 110

Arg

<210> SEQ ID NO 182
<211> LENGTH: 118
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 182

Glu Val Gln Leu Val Gln Ser Ala Ala Glu Val Lys Lys Pro Gly Ala
1               5                   10                  15

Ser Val Lys Val Ser Cys Lys Ala Ser Gly Tyr Ile Phe Ile Asn Tyr
            20                  25                  30

Trp Met His Trp Val Gln Gln Ala Pro Gly Ala Gly Leu Glu Trp Met
        35                  40                  45

Gly Arg Ile Asp Pro Tyr Gly Gly Thr Lys His Asn Glu Lys Phe
    50                  55                  60

Lys Arg Arg Val Thr Leu Thr Ala Asp Lys Ser Thr Ser Thr Val Tyr
65                  70                  75                  80

Met Glu Leu Ser Asn Leu Arg Thr Glu Asp Thr Ala Val Tyr Tyr Cys
                85                  90                  95

Thr Arg Ser Gly Tyr Asp Tyr Tyr Phe Asp Val Trp Gly Gln Gly Thr
            100                 105                 110

Leu Val Thr Val Ser Ser
        115

<210> SEQ ID NO 183
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 183

Asp Ile Gln Met Thr Gln Thr Pro Leu Ser Leu Ser Ala Ser Pro Gly
1               5                   10                  15

Glu Ser Ala Ser Ile Ser Cys Arg Ala Ser Glu Asn Ile Tyr Ser Phe
            20                  25                  30

Leu Ala Trp His Arg Gln Lys Pro Gly Gln Ser Pro Gln Leu Leu Ile
        35                  40                  45

Tyr Asn Ala Asn Thr Leu Ala Glu Gly Val Pro Ser Arg Phe Ser Gly
    50                  55                  60

Ser Gly Ser Gly Thr Gln Phe Thr Leu Arg Ile Ser Arg Val Glu Asp
65                  70                  75                  80

Glu Asp Ala Gly Leu Tyr Tyr Cys Gln His His Phe Gly Thr Pro Phe
                85                  90                  95

Thr Phe Gly Gln Gly Thr Lys Leu Glu Ile Lys Arg
            100                 105

<210> SEQ ID NO 184
<211> LENGTH: 115
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 184

Glu Val Gln Leu Val Gln Ser Ala Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Tyr Trp Val Lys Gln Ala Pro Gly Ala Gly Leu Glu Trp Ile

```
                35                  40                  45
Gly Arg Ile Asp Pro Ala Asn Gly Asn Thr Ile Tyr Ala Ser Lys Phe
 50                  55                  60

Gln Gly Lys Ala Ser Ile Thr Ala Asp Thr Ser Thr Asn Thr Ala Tyr
 65                  70                  75                  80

Met Glu Leu Ser Asn Leu Arg Thr Glu Asp Thr Ala Val Tyr Tyr Cys
                85                  90                  95

Ala Gly Tyr Gly Tyr Tyr Ala Tyr Trp Gly Gln Gly Thr Leu Val Thr
                100                 105                 110

Val Ser Ser
        115

<210> SEQ ID NO 185
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Val Gln Ser Ala Ala Glu Val Lys Lys Pro Gly Ala
 1               5                  10                  15

Ser Val Lys Val Ser Cys Lys Ala Ser Gly Tyr Ile Phe Ile Asp Thr
                20                  25                  30

Tyr Ile Tyr Trp Val Lys Gln Ala Pro Gly Ala Gly Leu Glu Trp Met
                35                  40                  45

Gly Arg Ile Asp Pro Ala Asn Gly Asn Thr Ile Tyr Ala Ser Lys Phe
 50                  55                  60

Gln Gly Arg Val Thr Leu Thr Ala Asp Thr Ser Thr Asn Thr Val Tyr
 65                  70                  75                  80

Met Glu Leu Ser Asn Leu Arg Thr Glu Asp Thr Ala Val Tyr Tyr Cys
                85                  90                  95

Ala Gly Tyr Gly Tyr Tyr Ala Tyr Trp Gly Gln Gly Thr Leu Val Thr
                100                 105                 110

Val Ser Ser
        115

<210> SEQ ID NO 186
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Leu Val Leu Thr Gln Thr Pro Arg Ser Leu Ser Val Ser Pro Gly
 1               5                  10                  15

Glu Thr Ala Ser Ile Ser Cys Lys Ser Thr Lys Ser Leu Leu Asn Gly
                20                  25                  30

Asp Gly Phe Thr Tyr Leu Asp Trp Tyr Arg Gln Lys Pro Gly Gln Ser
                35                  40                  45

Pro Gln Leu Leu Ile Tyr Leu Val Ser Asn Arg Phe Ser Gly Val Pro
 50                  55                  60

Asp Arg Phe Ser Gly Ser Gly Ser Gly Thr Asp Phe Thr Leu Arg Ile
 65                  70                  75                  80

Ser Arg Val Glu Ala Asp Asp Thr Gly Leu Tyr Tyr Cys Phe Glu Ser
```

85                  90                  95

Asn Tyr Leu Phe Thr Phe Ser Gln Gly Thr Asn Leu Glu Met Lys Arg
            100                 105                 110

<210> SEQ ID NO 187
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Glu Val Gln Leu Val Glu Ser Gly Gly Asp Leu Met Lys Pro Gly Gly
1               5                   10                  15

Ser Leu Arg Leu Ser Cys Val Ala Ser Gly Phe Thr Phe Ser Asn His
            20                  25                  30

Tyr Met Tyr Trp Val Arg Gln Ala Pro Gly Lys Gly Leu Glu Trp Val
        35                  40                  45

Ala Ser Ile Ser Asp Gly Gly Ala Tyr Thr Phe Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Thr Glu Asp Thr Gly Arg Val Leu Tyr
                85                  90                  95

Cys Thr Gly Glu Glu Ser Ala Asn Asn Gly Phe Ala Phe Trp Gly His
            100                 105                 110

Gly Thr Leu Val Thr Val Ser Ser
        115                 120

<210> SEQ ID NO 188
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asp Val Leu Met Thr Gln Ala Pro Pro Ser Leu Ser Val Ser Pro Arg
1               5                   10                  15

Glu Pro Ala Ser Ile Ser Cys Arg Ser Ser Gln Ser Ile Leu His Ser
            20                  25                  30

Asn Gly Asn Thr Tyr Leu Glu Trp Tyr Arg Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Leu Gly Val Tyr Tyr Cys Phe Gln Gly
                85                  90                  95

Ala His Val Pro Phe Thr Phe Gly Gln Gly Thr Lys Leu Glu Ile Lys
            100                 105                 110

Arg

<210> SEQ ID NO 189
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Glu Glu Ser Gly Gly Asp Leu Val Lys Pro Gly Gly
1               5                   10                  15

Ser Leu Arg Leu Ser Cys Val Ala Ser Gly Phe Thr Phe Ser Asn His
            20                  25                  30

Tyr Met Tyr Trp Val Arg Gln Ser Pro Gly Lys Gly Leu Glu Trp Val
        35                  40                  45

Ala Ser Ile Ser Asp Gly Gly Ala Tyr Thr Phe Tyr Pro Asp Thr Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Lys Lys Glu Asp Thr Ala Val Tyr Tyr Cys
                85                  90                  95

Thr Arg Glu Glu Ser Ala Asn Asn Gly Phe Ala Phe Trp Gly Gln Gly
            100                 105                 110

Thr Leu Val Thr Val Ser Ser
        115

<210> SEQ ID NO 190
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Glu Val Gln Leu Glu Glu Ser Gly Gly Asp Leu Val Lys Pro Gly Gly
1               5                   10                  15

Ser Leu Arg Leu Ser Cys Val Ala Ser Gly Phe Thr Phe Ser Asn His
            20                  25                  30

Tyr Met Tyr Trp Val Arg Gln Ser Pro Gly Lys Gly Leu Glu Trp Val
        35                  40                  45

Ala Ser Ile Ser Asp Gly Gly Ala Tyr Thr Phe Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Lys Glu Asp Thr Ala Val Tyr Tyr Cys
                85                  90                  95

Thr Lys Glu Glu Ser Ala Asn Asn Gly Phe Ala Phe Trp Gly Gln Gly
            100                 105                 110

Thr Leu Val Thr Val Ser Ser
        115

<210> SEQ ID NO 191
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Ile Gln Met Thr Gln Thr Pro Leu Ser Leu Ser Ala Ser Pro Gly
1               5                   10                  15

```
Glu Ser Ala Ser Ile Thr Cys Arg Ala Ser Gln Asp Ile Thr Asn Tyr
                20                  25                  30

Leu Asn Trp Tyr Arg Gln Lys Pro Gly Gln Ser Val Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Arg Ile Ser Arg Val Glu Asp
65                  70                  75                  80

Glu Asp Ala Gly Leu Tyr Phe Cys Gln Gln Gly Lys Thr Leu Pro Arg
                85                  90                  95

Thr Phe Gly Gln Gly Thr Lys Leu Glu Ile Lys Arg
            100                 105
```

<210> SEQ ID NO 192
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 192

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Thr Gly Tyr
                20                  25                  30

Asn Ile Asn Trp Ile Arg Gln Arg Pro Asp Arg Gly Leu Glu Trp Met
            35                  40                  45

Gly Met Ile Trp Gly Tyr Gly Asp Thr Asp Tyr Asn Ser Ala Leu Lys
50                  55                  60

Ser Arg Ile Ser Ile Thr Lys Asp Asn Thr Lys Ser Gln Leu Phe Leu
65                  70                  75                  80

Gln Leu Thr Ser Thr Thr Thr Glu Asp Thr Ala Val Tyr Tyr Cys Ala
                85                  90                  95

Arg Asp His Tyr Gly Gly Asn Asp Trp Tyr Phe Asp Val Trp Gly Gln
            100                 105                 110

Gly Thr Leu Val Thr Val Ser Ser
            115                 120
```

<210> SEQ ID NO 193
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 193

```
Asp Ile Gln Met Thr Gln Thr Pro Leu Ser Leu Ser Ala Ser Pro Gly
1               5                   10                  15

Glu Ser Ala Ser Ile Ser Cys Arg Ala Ser Gln Asp Ile Thr Asn Tyr
                20                  25                  30

Leu Asn Trp Tyr Arg Gln Lys Pro Gly Gln Ser Pro Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Arg Ile Ser Arg Val Glu Asp
65                  70                  75                  80
```

Glu Asp Ala Gly Leu Tyr Phe Cys Gln Gln Gly Lys Thr Leu Pro Arg
                85                  90                  95

Thr Phe Gly Gln Gly Thr Lys Leu Glu Ile Lys Arg
            100                 105

<210> SEQ ID NO 194
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Glu Ala Glu Asp Leu Gly Val Tyr Tyr Cys Phe Gln Gly Ser
                85                  90                  95

His Val Pro Phe Thr Phe Gly Ser Gly Thr Lys Leu Glu Ile Lys Arg
            100                 105                 110

Asn Asp Ala Gln Pro Ala Val Tyr Leu Phe Gln Pro Ser Pro Asp Gln
        115                 120                 125

Leu His Thr Gly Ser Ala Ser Val Val Cys Leu Leu Asn Ser Phe Tyr
    130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Lys Asp Ser Thr Tyr
                165                 170                 175

Ser Leu Ser Ser Thr Leu Thr Met Ser Ser Thr Glu Tyr Leu Ser His
            180                 185                 190

Glu Leu Tyr Ser Cys Gly Ile Thr His Lys Ser Leu Pro Ser Thr Leu
        195                 200                 205

Ile Lys Ser Phe Gln Arg Ser Glu Cys Gln Arg Val Asp
    210                 215                 220

<210> SEQ ID NO 195
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val His Leu Val Glu Ser Gly Gly Gly Leu Val Lys Pro Gly Gly
1               5                   10                  15

Phe Leu Ile Leu Ser Cys Ala Ala Ser Gly Phe Thr Phe Ser Asp Tyr
            20                  25                  30

Tyr Met Phe Trp Ile Arg Gln Thr Pro Gly Lys Arg Leu Glu Trp Val
        35                  40                  45

```
Ala Thr Ile Ser Asp Gly Gly Ser Tyr Thr Tyr Tyr Thr Asp Asn Val
 50              55                  60

Lys Gly Arg Phe Thr Ile Ser Arg Asp Asn Val Lys Asn Asn Leu Tyr
 65              70                  75                  80

Leu Gln Met Ser His Leu Lys Ser Ala Asp Thr Ala Met Tyr Tyr Cys
                 85                  90                  95

Ala Arg Asp Trp Ser Asp Ser Glu Gly Phe Ala Tyr Trp Gly Gln Gly
                100                 105                 110

Thr Leu Val Thr Val Ser Ala Ala Ser Thr Thr Ala Pro Ser Val Phe
                115                 120                 125

Pro Leu Ala Pro Ser Cys Gly Ser Thr Ser Gly Ser Thr Val Ala Leu
130                 135                 140

Ala Cys Leu Val Ser Gly Tyr Phe Pro Glu Pro Val Thr Val Ser Trp
145                 150                 155                 160

Asn Ser Gly Ser Leu Thr Ser Gly Val His Thr Phe Pro Ser Val Leu
                165                 170                 175

Gln Ser Ser Gly Leu His Ser Leu Ser Ser Met Val Thr Val Pro Ser
                180                 185                 190

Ser Arg Trp Pro Ser Glu Thr Phe Thr Cys Asn Val Val His Pro Ala
                195                 200                 205

Ser Asn Thr Lys Val Asp Lys Pro Val Phe Asn Glu Cys Arg Cys Thr
210                 215                 220

Asp Thr Pro Pro Cys Pro Val Pro Glu Pro Leu Gly Gly Pro Ser Val
225                 230                 235                 240

Leu Ile Phe Pro Pro Lys Pro Lys Asp Ile Leu Arg Ile Thr Arg Thr
                245                 250                 255

Pro Glu Val Thr Cys Val Val Leu Asp Leu Gly Arg Glu Asp Pro Glu
                260                 265                 270

Val Gln Ile Ser Trp Phe Val Asp Gly Lys Glu Val His Thr Ala Lys
                275                 280                 285

Thr Gln Ser Arg Glu Gln Gln Phe Asn Gly Thr Tyr Arg Val Val Ser
                290                 295                 300

Val Leu Pro Ile Glu His Gln Asp Trp Leu Thr Gly Lys Glu Phe Lys
305                 310                 315                 320

Cys Arg Val Asn His Ile Asp Leu Pro Ser Pro Ile Glu Arg Thr Ile
                325                 330                 335

Ser Lys Ala Arg Gly Arg Ala His Lys Pro Ser Val Tyr Val Leu Pro
                340                 345                 350

Pro Ser Pro Lys Glu Leu Ser Ser Ser Asp Thr Val Ser Ile Thr Cys
                355                 360                 365

Leu Ile Lys Asp Phe Tyr Pro Pro Asp Ile Asp Val Glu Trp Gln Ser
370                 375                 380

Asn Gly Gln Gln Glu Pro Glu Arg Lys His Arg Met Thr Pro Pro Gln
385                 390                 395                 400

Leu Asp Glu Asp Gly Ser Tyr Phe Leu Tyr Ser Lys Leu Ser Val Asp
                405                 410                 415

Lys Ser Arg Trp Gln Gln Gly Asp Pro Phe Thr Cys Ala Val Met His
                420                 425                 430

Glu Thr Leu Gln Asn His Tyr Thr Asp Leu Ser Leu Ser His Ser Pro
                435                 440                 445

Gly Lys
450
```

```
<210> SEQ ID NO 196
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Ile Gln Met Thr Gln Ser Pro Ala Ser Leu Ser Ala Ser Val Gly
1               5                   10                  15

Glu Thr Val Thr Val Thr Cys Arg Ala Ser Glu Asn Ile Tyr Ser Phe
            20                  25                  30

Leu Ala Trp His Gln Gln Lys Gln Gly Lys Ser Pro Gln Leu Leu Val
        35                  40                  45

Tyr Asn Ala Asn Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Phe Gly Thr Pro Phe
                85                  90                  95

Thr Phe Gly Ser Gly Thr Lys Leu Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215

<210> SEQ ID NO 197
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Arg Ile Asp Pro Tyr Gly Gly Gly Thr Lys His Asn Glu Lys Phe
    50                  55                  60

Lys Arg Lys Ala Thr Val Thr Ala Asp Lys Ser Ser Ser Thr Ala Tyr
65                  70                  75                  80

Ile Leu Leu Ser Ser Leu Thr Ser Glu Asp Ser Ala Val Tyr Tyr Cys
```

```
                85                  90                  95
Thr Arg Ser Gly Tyr Asp Tyr Tyr Phe Asp Val Trp Gly Thr Gly Thr
            100                 105                 110

Thr Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu His Ser Leu Ser Ser Met Val Thr Val Pro Ser Ser
            180                 185                 190

Arg Trp Pro Ser Glu Thr Phe Thr Cys Asn Val Val His Pro Ala Ser
        195                 200                 205

Asn Thr Lys Val Asp Lys Pro Val Phe Asn Glu Cys Arg Cys Thr Asp
    210                 215                 220

Thr Pro Pro Cys Pro Val Pro Glu Pro Leu Gly Gly Pro Ser Val Leu
225                 230                 235                 240

Ile Phe Pro Pro Lys Pro Lys Asp Ile Leu Arg Ile Thr Arg Thr Pro
                245                 250                 255

Glu Val Thr Cys Val Val Leu Asp Leu Gly Arg Glu Asp Pro Glu Val
            260                 265                 270

Gln Ile Ser Trp Phe Val Asp Gly Lys Glu Val His Thr Ala Lys Thr
        275                 280                 285

Gln Ser Arg Glu Gln Gln Phe Asn Gly Thr Tyr Arg Val Val Ser Val
    290                 295                 300

Leu Pro Ile Glu His Gln Asp Trp Leu Thr Gly Lys Glu Phe Lys Cys
305                 310                 315                 320

Arg Val Asn His Ile Asp Leu Pro Ser Pro Ile Glu Arg Thr Ile Ser
                325                 330                 335

Lys Ala Arg Gly Arg Ala His Lys Pro Ser Val Tyr Val Leu Pro Pro
            340                 345                 350

Ser Pro Lys Glu Leu Ser Ser Ser Asp Thr Val Ser Ile Thr Cys Leu
        355                 360                 365

Ile Lys Asp Phe Tyr Pro Pro Asp Ile Asp Val Glu Trp Gln Ser Asn
    370                 375                 380

Gly Gln Gln Glu Pro Glu Arg Lys His Arg Met Thr Pro Gln Leu
385                 390                 395                 400

Asp Glu Asp Gly Ser Tyr Phe Leu Tyr Ser Lys Leu Ser Val Asp Lys
                405                 410                 415

Ser Arg Trp Gln Gln Gly Asp Pro Phe Thr Cys Ala Val Met His Glu
            420                 425                 430

Thr Leu Gln Asn His Tyr Thr Asp Leu Ser Leu Ser His Ser Pro Gly
        435                 440                 445

Val

<210> SEQ ID NO 198
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 198

Asp Val Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Gly
            20                  25                  30

Asp Gly Phe Thr Tyr Leu Asp Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Glu Ser
                85                  90                  95

Asn Tyr Leu Phe Thr Phe Gly Ser Gly Thr Lys Leu Glu Met Lys Arg
            100                 105                 110

Asn Asp Ala Gln Pro Ala Val Tyr Leu Phe Gln Pro Ser Pro Asp Gln
        115                 120                 125

Leu His Thr Gly Ser Ala Ser Val Val Cys Leu Leu Asn Ser Phe Tyr
    130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Lys Asp Ser Thr Tyr
                165                 170                 175

Ser Leu Ser Ser Thr Leu Thr Met Ser Ser Thr Glu Tyr Leu Ser His
            180                 185                 190

Glu Leu Tyr Ser Cys Glu Ile Thr His Lys Ser Leu Pro Ser Thr Leu
        195                 200                 205

Ile Lys Ser Phe Gln Arg Ser Glu Cys Gln Arg Val Asp
    210                 215                 220

<210> SEQ ID NO 199
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile Tyr Trp Val Lys Gln Arg Pro Glu Gln Gly Leu Glu Trp Ile
        35                  40                  45

Gly Arg Ile Asp Pro Ala Asn Gly Asn Thr Ile Tyr Ala Ser Lys Phe
    50                  55                  60

Gln Gly Lys Ala Ser Ile Thr Ala Asp Thr Ser Ser Asn Thr Ala Tyr
65                  70                  75                  80

Met Gln Leu Ser Ser Leu Thr Ser Gly Asp Thr Ala Val Tyr Tyr Cys
                85                  90                  95

Ala Gly Tyr Gly Tyr Tyr Ala Tyr Trp Gly Gln Gly Thr Thr Leu Thr
            100                 105                 110

Val Ser Ser Ala Ser Thr Thr Ala Pro Ser Val Phe Pro Leu Ala Pro
        115                 120                 125

Ser Cys Gly Ser Thr Ser Gly Ser Thr Val Ala Leu Ala Cys Leu Val
130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu His Ser Leu Ser Ser Met Val Thr Val Pro Ser Ser Arg Trp Pro
                180                 185                 190

Ser Glu Thr Phe Thr Cys Asn Val His Pro Ala Ser Asn Thr Lys
                195                 200                 205

Val Asp Lys Pro Val Phe Asn Glu Cys Arg Cys Thr Asp Thr Pro Pro
210                 215                 220

Cys Pro Val Pro Glu Pro Leu Gly Gly Pro Ser Val Leu Ile Phe Pro
225                 230                 235                 240

Pro Lys Pro Lys Asp Ile Leu Arg Ile Thr Arg Thr Pro Glu Val Thr
                245                 250                 255

Cys Val Val Leu Asp Leu Gly Arg Glu Asp Pro Glu Val Gln Ile Ser
                260                 265                 270

Trp Phe Val Asp Gly Lys Glu Val His Thr Ala Lys Thr Gln Ser Arg
                275                 280                 285

Glu Gln Gln Phe Asn Gly Thr Tyr Arg Val Val Ser Val Leu Pro Ile
290                 295                 300

Glu His Gln Asp Trp Leu Thr Gly Lys Glu Phe Lys Cys Arg Val Asn
305                 310                 315                 320

His Ile Asp Leu Pro Ser Pro Ile Glu Arg Thr Ile Ser Lys Ala Arg
                325                 330                 335

Gly Arg Ala His Lys Pro Ser Val Tyr Val Leu Pro Pro Ser Pro Lys
                340                 345                 350

Glu Leu Ser Ser Ser Asp Thr Val Ser Ile Thr Cys Leu Ile Lys Asp
                355                 360                 365

Phe Tyr Pro Pro Asp Ile Asp Val Glu Trp Gln Ser Asn Gly Gln Gln
370                 375                 380

Glu Pro Glu Arg Lys His Arg Met Thr Pro Pro Gln Leu Asp Glu Asp
385                 390                 395                 400

Gly Ser Tyr Phe Leu Tyr Ser Lys Leu Ser Val Asp Lys Ser Arg Trp
                405                 410                 415

Gln Gln Gly Asp Pro Phe Thr Cys Ala Val Met His Glu Thr Leu Gln
                420                 425                 430

Asn His Tyr Thr Asp Leu Ser Leu Ser His Ser Pro Gly Lys
                435                 440                 445

<210> SEQ ID NO 200
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
                20                  25                  30

Asn Gly Asn Thr Tyr Leu Glu Trp Tyr Leu Gln Lys Pro Gly Gln Ser
                35                  40                  45

-continued

Pro Asn Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ala His Val Pro Phe Thr Phe Gly Ser Gly Thr Lys Leu Glu Ile Lys
                100                 105                 110

Arg Asn Asp Ala Gln Pro Ala Val Tyr Leu Phe Gln Pro Ser Pro Asp
            115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Lys Asp Ser Thr
                165                 170                 175

Tyr Ser Leu Ser Ser Thr Leu Thr Met Ser Ser Thr Glu Tyr Leu Ser
                180                 185                 190

His Glu Leu Tyr Ser Cys Glu Ile Thr His Lys Ser Leu Pro Ser Thr
            195                 200                 205

Leu Ile Lys Ser Phe Gln Arg Ser Glu Cys Gln Arg Val Asp
    210                 215                 220

<210> SEQ ID NO 201
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Val Glu Ser Gly Gly Gly Ala Val Lys Pro Gly Gly
1               5                   10                  15

Ser Leu Thr Leu Ser Cys Ala Ala Ser Gly Phe Thr Phe Ser Asn His
                20                  25                  30

Tyr Met Tyr Trp Val Arg Gln Thr Pro Glu Lys Arg Leu Glu Trp Val
            35                  40                  45

Ala Ser Ile Ser Asp Gly Gly Ala Tyr Thr Phe Tyr Pro Asp Thr Val
    50                  55                  60

Lys Gly Arg Phe Thr Ile Ser Arg Asp Asn Val Asn Asn Asn Leu Tyr
65                  70                  75                  80

Leu Gln Met Arg His Leu Lys Ser Glu Asp Thr Ala Met Tyr Tyr Cys
                85                  90                  95

Thr Arg Glu Glu Ser Ala Asn Asn Gly Phe Ala Phe Trp Gly Gln Gly
                100                 105                 110

Thr Leu Val Thr Val Ser Ala Ala Ser Thr Thr Ala Pro Ser Val Phe
            115                 120                 125

Pro Leu Ala Pro Ser Cys Gly Ser Thr Ser Gly Ser Thr Val Ala Leu
    130                 135                 140

Ala Cys Leu Val Ser Gly Tyr Phe Pro Glu Pro Val Thr Val Ser Trp
145                 150                 155                 160

Asn Ser Gly Ser Leu Thr Ser Gly Val His Thr Phe Pro Ser Val Leu
                165                 170                 175

Gln Ser Ser Gly Leu His Ser Leu Ser Ser Met Val Thr Val Pro Ser

```
            180                 185                 190
Ser Arg Trp Pro Ser Glu Thr Phe Thr Cys Asn Val Val His Pro Ala
        195                 200                 205
Ser Asn Thr Lys Val Asp Lys Pro Val Phe Asn Glu Cys Arg Cys Thr
    210                 215                 220
Asp Thr Pro Pro Cys Pro Val Pro Glu Pro Leu Gly Gly Pro Ser Val
225                 230                 235                 240
Leu Ile Phe Pro Pro Lys Pro Lys Asp Ile Leu Arg Ile Thr Arg Thr
                245                 250                 255
Pro Glu Val Thr Cys Val Val Leu Asp Leu Gly Arg Glu Asp Pro Glu
            260                 265                 270
Val Gln Ile Ser Trp Phe Val Asp Gly Lys Glu Val His Thr Ala Lys
        275                 280                 285
Thr Gln Ser Arg Glu Gln Gln Phe Asn Gly Thr Tyr Arg Val Val Ser
    290                 295                 300
Val Leu Pro Ile Glu His Gln Asp Trp Leu Thr Gly Lys Glu Phe Lys
305                 310                 315                 320
Cys Arg Val Asn His Ile Asp Leu Pro Ser Pro Ile Glu Arg Thr Ile
                325                 330                 335
Ser Lys Ala Arg Gly Arg Ala His Lys Pro Ser Val Tyr Val Leu Pro
            340                 345                 350
Pro Ser Pro Lys Glu Leu Ser Ser Asp Thr Val Ser Ile Thr Cys
        355                 360                 365
Leu Ile Lys Asp Phe Tyr Pro Pro Asp Ile Asp Val Glu Trp Gln Ser
    370                 375                 380
Asn Gly Gln Gln Glu Pro Glu Arg Lys His Arg Met Thr Pro Pro Gln
385                 390                 395                 400
Leu Asp Glu Asp Gly Ser Tyr Phe Leu Tyr Ser Lys Leu Ser Val Asp
                405                 410                 415
Lys Ser Arg Trp Gln Gln Gly Asp Pro Phe Thr Cys Ala Val Met His
            420                 425                 430
Glu Thr Leu Gln Asn His Tyr Thr Asp Leu Ser Leu Ser His Ser Pro
        435                 440                 445
Gly Val
    450

<210> SEQ ID NO 202
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asp Ile Gln Met Thr Gln Thr Thr Ser Ser Leu Ser Ala Ser Leu Gly
1               5                   10                  15
Asp Arg Val Thr Ile Thr Cys Arg Ala Ser Gln Asp Ile Thr Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Tyr Ser Leu Thr Ile Ser Asn Leu Asp Gln
65                  70                  75                  80
```

```
Glu Asp Ile Ala Thr Tyr Phe Cys Gln Gln Gly Lys Thr Leu Pro Arg
                85                  90                  95

Thr Phe Gly Gly Gly Thr Lys Leu Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215
```

<210> SEQ ID NO 203
<211> LENGTH: 451
<212> TYPE: PRT
<213> ORGANISM: Canis lupus

<400> SEQUENCE: 203

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Asn Ile Asn Trp Val Arg Gln Pro Pro Gly Lys Gly Leu Glu Trp Leu
        35                  40                  45

Gly Met Ile Trp Gly Tyr Gly Asp Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp His Tyr Gly Gly Asn Asp Trp Tyr Phe Asp Val Trp Gly Thr
            100                 105                 110

Gly Thr Thr Val Thr Val Ser Ser Ala Ser Thr Thr Ala Pro Ser Val
        115                 120                 125

Phe Pro Leu Ala Pro Ser Cys Gly Ser Thr Ser Gly Ser Thr Val Ala
    130                 135                 140

Leu Ala Cys Leu Val Ser Gly Tyr Phe Pro Glu Pro Val Thr Val Ser
145                 150                 155                 160

Trp Asn Ser Gly Ser Leu Thr Ser Gly Val His Thr Phe Pro Ser Val
                165                 170                 175

Leu Gln Ser Ser Gly Leu His Ser Leu Ser Ser Met Val Thr Val Pro
            180                 185                 190

Ser Ser Arg Trp Pro Ser Glu Thr Phe Thr Cys Asn Val Val His Pro
        195                 200                 205

Ala Ser Asn Thr Lys Val Asp Lys Pro Val Phe Asn Glu Cys Arg Cys
    210                 215                 220

Thr Asp Thr Pro Pro Cys Pro Val Pro Glu Pro Leu Gly Gly Pro Ser
225                 230                 235                 240
```

Val Leu Ile Phe Pro Lys Pro Lys Asp Ile Leu Arg Ile Thr Arg
            245                 250                 255

Thr Pro Glu Val Thr Cys Val Val Leu Asp Leu Gly Arg Glu Asp Pro
                260                 265                 270

Glu Val Gln Ile Ser Trp Phe Val Asp Gly Lys Glu Val His Thr Ala
            275                 280                 285

Lys Thr Gln Ser Arg Glu Gln Gln Phe Asn Gly Thr Tyr Arg Val Val
        290                 295                 300

Ser Val Leu Pro Ile Glu His Gln Asp Trp Leu Thr Gly Lys Glu Phe
305                 310                 315                 320

Lys Cys Arg Val Asn His Ile Asp Leu Pro Ser Pro Ile Glu Arg Thr
                325                 330                 335

Ile Ser Lys Ala Arg Gly Arg Ala His Lys Pro Ser Val Tyr Val Leu
            340                 345                 350

Pro Pro Ser Pro Lys Glu Leu Ser Ser Ser Asp Thr Val Ser Ile Thr
        355                 360                 365

Cys Leu Ile Lys Asp Phe Tyr Pro Pro Asp Ile Asp Val Glu Trp Gln
        370                 375                 380

Ser Asn Gly Gln Gln Glu Pro Glu Arg Lys His Arg Met Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Gln Gly Asp Pro Phe Thr Cys Ala Val Met
                420                 425                 430

His Glu Thr Leu Gln Asn His Tyr Thr Asp Leu Ser Leu Ser His Ser
            435                 440                 445

Pro Gly Lys
    450

<210> SEQ ID NO 204
<211> LENGTH: 155
<212> TYPE: PRT
<213> ORGANISM: Canis lupus

<400> SEQUENCE: 204

Leu Trp Ile Ser Gly Gly Ser Ala Leu Gly Thr Pro Thr Met Ala Trp
1               5                   10                  15

Thr His Leu Leu Leu Pro Val Leu Thr Leu Cys Thr Gly Ser Val Ala
                20                  25                  30

Ser Ser Val Leu Thr Gln Pro Pro Ser Val Ser Val Ser Leu Gly Gln
            35                  40                  45

Thr Ala Thr Ile Ser Cys Ser Gly Glu Ser Leu Ser Lys Tyr Tyr Ala
        50                  55                  60

Gln Trp Phe Gln Gln Lys Ala Gly Gln Val Pro Val Leu Val Ile Tyr
65                  70                  75                  80

Lys Asp Thr Glu Arg Pro Ser Gly Ile Pro Asp Arg Phe Ser Gly Ser
                85                  90                  95

Ser Ser Gly Asn Thr His Thr Leu Thr Ile Ser Arg Ala Arg Ala Glu
            100                 105                 110

Asp Glu Ala Asp Tyr Tyr Cys Glu Ser Glu Val Ser Thr Gly Thr Tyr
        115                 120                 125

Cys Val Arg Arg Arg His Pro Ser Asn Arg Pro Arg Ser Ala Gln Gly
    130                 135                 140

Leu Pro Leu Gly His Thr Leu Pro Ala Leu Leu

<210> SEQ ID NO 205
<211> LENGTH: 106
<212> TYPE: PRT
<213> ORGANISM: Canis lupus

<400> SEQUENCE: 205

Leu Cys Ser Ala Val Gly Pro Pro Lys Thr Glu Ser Val Met Thr Ser
1               5                   10                  15

Thr Met Gly Trp Ser Pro Leu Leu Thr Leu Leu Ala His Cys Thr
            20                  25                  30

Gly Ser Trp Ala Gln Ser Val Leu Thr Gln Pro Ala Ser Val Ser Gly
            35                  40                  45

Ser Leu Gly Gln Arg Val Thr Ile Pro Cys Thr Gly Ser Ser Ser Asn
    50                  55                  60

Ile Asp Arg Tyr Asn Val Ala Trp Phe Gln Gln Leu Pro Gly Thr Gly
65                  70                  75                  80

Pro Lys Pro Ser Ser Ile Val Leu Leu Thr Asp Pro Gln Gly Ser Leu
                85                  90                  95

Ile Asp Ser Leu Ala Pro Ser Gln Ala Ala
            100                 105

<210> SEQ ID NO 206
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Glu Val Gln Leu Glu Glu Ser Gly Gly Asp Leu Val Lys Pro Gly Gly
1               5                   10                  15

Ser Leu Arg Leu Ser Cys Val Ala Ser Gly Phe Thr Phe Ser Asn His
            20                  25                  30

Tyr Met Tyr Trp Val Arg Gln Ser Pro Gly Lys Gly Leu Glu Trp Val
            35                  40                  45

Ala Ser Ile Ser Asp Gly Gly Ala Tyr Thr Phe Tyr Pro Asp Thr Val
    50                  55                  60

Lys Gly Arg Phe Thr Ile Ser Arg Asp Asn Ala Lys Asn Asn Leu Tyr
65                  70                  75                  80

Leu Gln Met Asn Ser Leu Lys Ala Glu Asp Thr Ala Val Tyr Tyr Cys
                85                  90                  95

Thr Arg Glu Glu Ser Ala Asn Asn Gly Phe Ala Phe Trp Gly Gln Gly
            100                 105                 110

Thr Leu Val Thr Val Ser Ser
        115

<210> SEQ ID NO 207
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Val Gln Leu Glu Glu Ser Gly Gly Asp Leu Val Lys Pro Gly Gly
1               5                   10                  15

```
Ser Leu Arg Leu Ser Cys Val Ala Ser Gly Phe Thr Phe Ser Asn His
         20                  25                  30

Tyr Met Tyr Trp Val Arg Gln Ser Pro Gly Lys Gly Leu Glu Trp Val
         35                  40                  45

Ala Ser Ile Ser Asp Gly Gly Ala Tyr Thr Phe Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Lys Glu Glu Ser Ala Asn Asn Gly Phe Ala Phe Trp Gly Gln Gly
             100                 105                 110

Thr Leu Val Thr Val Ser Ser
         115

<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 208

His His His His His His
 1               5

<210> SEQ ID NO 209
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Ser Ser Gly
 1

<210> SEQ ID NO 210
<211> LENGTH: 69
<212> TYPE: PRT
<213> ORGANISM: Canis lupus

<400> SEQUENCE: 210

Pro Gly Gln Ser Pro Gln Arg Leu Ile Asn Phe Val Ser Asn Arg Asp
 1               5                  10                  15

Pro Gly Val Pro Asp Arg Phe Ser Gly Ser Gly Ser Gly Thr Asp Phe
             20                  25                  30

Thr Leu Arg Ile Ser Arg Val Glu Ala Asp Asp Ala Gly Ile Tyr Tyr
             35                  40                  45

Cys Gly Gln Gly Leu Leu Ala Pro Pro Thr Phe Gly Gln Gly Thr Lys
 50                  55                  60

Val Glu Ile Arg Arg
 65
```

ANTI-NGF ANTIBODIES AND THEIR USE

CROSS-REFERENCE TO RELATED APPLICATIONS

This is the U.S. national stage entry of International Patent Application No. PCT/US2011/048518, filed on Aug. 19, 2011, which claims priority to U.S. Provisional Patent Application No. 61/375,193, filed on Aug. 19, 2010, the contents of all of which are herein fully incorporated by reference.

TECHNICAL FIELD

The disclosure relates to anti-NGF antibodies and polynucleotides encoding the same, and use of such antibodies and/or polynucleotides in the treatment and/or prevention of pain, including but not limited to post-surgical pain, rheumatoid arthritis pain, cancer pain, and osteoarthritis pain.

BACKGROUND

Nerve growth factor (NGF) is a secreted protein that was discovered over 50 years ago as a molecule that promotes the survival and differentiation of sensory and sympathetic neurons. (See Levi-Montalcini, Science 187: 113 (1975), for a review). The crystal structure of NGF and NGF in complex with the tyrosinekinase A (TrkA) receptor has been determined (McDonald et al., Nature 354: 411 (1991); Wiesmann et al., Nature 401: 184-188 (1999)).

The role of NGF in the development and survival of both peripheral and central neurons has been well characterized. NGF has been shown to be a critical survival and maintenance factor in the development of peripheral sympathetic and embryonic sensory neurons and of basal forebrain cholinergic neurons (see, e.g., Smeyne et al., Nature 368: 246-9 (1994); and Crowley et al., Cell, 76:1001-11 (1994)). It has been shown to inhibit amyloidogenesis that leads to Alzheimer's disease (Calissano et al., Cell Death and Differentiation, 17: 1126-1133 (2010)). NGF up-regulates expression of neuropeptides in sensory neurons (Lindsay et al., Nature, 337:362-364 (1989)) and its activity is mediated through two different membrane-bound receptors, the TrkA receptor and the p75 common neurotrophin receptor (Chao et al., Science, 232:518-521 (1986); Huang et al., Annu. Rev. Neurosci., 24:677-736 (2001); Bibel et al., Genes Dev., 14:2919-2937 (2000)).

NGF is produced by a number of cell types including mast cells (Leon, et al., Proc. Natl. Acad. Sci., 91: 3739-3743 (1994)), B-lymphocytes (Torcia, et al., Cell, 85: 345-356 (1996), keratinocytes (Di Marco, et al., J. Biol. Chem., 268: 22838-22846)), smooth muscle cells (Ueyama, et al., J. Hypertens., 11: 1061-1065 (1993)), fibroblasts (Lindholm, et al., Eur. J. Neurosci., 2: 795-801 (1990)), bronchial epithelial cells (Kassel, et al., Clin, Exp. Allergy, 31:1432-40 (2001)), renal mesangial cells (Steiner, et al., Am. J. Physiol., 261:F792-798 (1991)) and skeletal muscle myotubes (Schwartz, et al., J. Photochem. Photobiol., B66: 195-200 (2002)). In addition, NGF receptors have been found on a variety of cell types outside of the nervous system.

NGF has been implicated in processes outside of the nervous system, e.g., NGF has been shown to enhance vascular permeability (Otten, et al., Eur J. Pharmacol., 106: 199-201 (1984)), enhance T- and B-cell immune responses (Otten, et al., Proc. Natl. Acad. Sci., USA 86: 10059-10063 (1989)), induce lymphocyte differentiation and mast cell proliferation and cause the release of soluble biological signals from mast cells (Matsuda, et al., Proc. Natl. Acad. Sci., 85: 6508-6512 (1988); Pearce, et al., J. Physiol., 372:379-393 (1986); Bischoff, et al., Blood, 79: 2662-2669 (1992); Horigome, et al., J. Biol. Chem., 268: 14881-14887 (1993)).

Both local and systemic administrations of NGF have been shown to elicit hyperalgesia and allodynia (Lewin, G. R. et al., Eur. J. Neurosci. 6: 1903-1912 (1994)). Intravenous infusion of NGF in humans produces a whole body myalgia while local administration evokes injection site hyperalgesia and allodynia in addition to the systemic effects (Apfel, S. C. et al., Neurology, 51: 695-702 (1998)). Furthermore, in certain forms of cancer, excess NGF facilitates the growth and infiltration of nerve fibers with induction of cancer pain (Zhu, Z. et al., J. Clin. Oncol., 17: 241-228 (1999)). Although exogenously added NGF has been shown to be capable of having all of these effects, it is important to note that it has only rarely been shown that endogenous NGF is important in any of these processes in vivo (Torcia, et al., Cell, 85(3): 345-56 (1996)).

An elevated level of NGF has been implicated in certain inflammatory conditions in humans and animals, e.g., systemic lupus erythematosus (Bracci-Laudiero, et al., Neuroreport, 4: 563-565 (1993)), multiple sclerosis (Bracci-Laudiero, et al., Neurosci. Lett., 147:9-12 (1992)), psoriasis (Raychaudhuri, et al., Acta Derm. l'enereol., 78: 84-86 (1998)), arthritis (Falcim, et al., Ann. Rheum. Dis., 55: 745-748 (1996)), interstitial cystitis (Okragly, et al., J. Urology, 161: 438-441 (1999)) and asthma (Braun, et al., Eur. J. Immunol., 28:3240-3251 (1998)). The synovium of patients affected by rheumatoid arthritis expresses high levels of NGF while in non-inflamed synovium NGF has been reported to be undetectable (Aloe, et al., Arch. Rheum., 35:351-355 (1992)). Similar results were seen in rats with experimentally induced rheumatoid arthritis (Aloe, et al., Clin. Exp. Rheumatol., 10: 203-204 (1992)). Elevated levels of NGF have been reported in transgenic arthritic mice along with an increase in the number of mast cells (Aloe, et al., Int. J. Tissue Reactions-Exp. Clin. Aspects, 15: 139-143 (1993)). Additionally, elevated levels of expression of canine NGF has been shown in lame dogs (Isola, M., Ferrari, V., Stabile, F., Bernardini, D., Canner, P., Busetto, R. Nerve growth factor concentrations in the synovial fluid from healthy dogs and dogs with secondary osteoarthritis. Vet. Comp. Orthop. Traumatol. 4: 279 (2011)). PCT Publication No. WO 02/096458 discloses use of anti-NGF antibodies of certain properties in treating various NGF related disorders such as inflammatory condition (e.g., rheumatoid arthritis). It has been reported that a purified anti-NGF antibody injected into arthritic transgenic mice carrying the human tumor necrosis factor (TNF) gene caused reduction in the number of mast cells, as well as a decrease in histamine and substance P levels within the synovium of arthritis mice (Aloe et al., Rheumatol. Int., 14: 249-252 (1995)). It has been shown that exogenous administration of a NGF antibody reduced the enhanced level of TNF occurring in arthritic mice (Manni et al., Rheumatol. Int., 18: 97-102 (1998)).

Increased expression of NGF and high affinity NGF receptor (TrkA) was observed in human osteoarthritis chondrocytes (Iannone et al., Rheumatology, 41: 1413-1418 (2002)). Rodent anti-NGF antagonist antibodies have been reported (Hongo et al., Hybridoma, 19(3):215-227 (2000); Ruberti et al., Cell. Molec. Neurobiol., 13(5): 559-568 (1993)). However, when rodent antibodies are used therapeutically in non-rodent subjects, an anti-murine antibody response develops in significant numbers of treated subjects.

The involvement of NGF in chronic pain has led to considerable interest in therapeutic approaches based on inhibiting the effects of NGF (Saragovi, et al., *Trends Pharmacol Sci.* 21: 93-98 (2000)). For example, a soluble form of the TrkA receptor was used to block the activity of NGF, which was shown to significantly reduce the formation of neuromas, responsible for neuropathic pain, without damaging the cell bodies of the lesioned neurons (Kryger, et al., *J. Hand Surg. (Am.)*, 26: 635-644 (2001)).

Certain anti-NGF antibodies have been described (PCT Publication Nos. WO 2001/78698, WO 2001/64247, WO 2002/096458, WO 2004/032870, WO 2005/061540, WO 2006/131951, WO 2006/110883; U.S. Publication Nos. US 20050074821, US 20080033157, US 20080182978 and US 20090041717; and U.S. Pat. No. 7,449,616). In animal models of neuropathic pain (e.g., nerve trunk or spinal nerve ligation) systemic injection of neutralizing antibodies to NGF prevents both allodynia and hyperalgesia (Ramer et al., *Eur. J. Neurosci.*, 11: 837-846 (1999); Ro et al., *Pain,* 79: 265-274 (1999)). Furthermore, treatment with a neutralizing anti-NGF antibody produces significant pain reduction in a murine cancer pain model (Sevcik et al., *Pain,* 115: 128-141 (2005)). Thus, there is a serious need for anti-NGF antagonist antibodies for humans and animals.

SUMMARY OF THE INVENTION

The present disclosure provides a novel family of binding proteins, CDR grafted antibodies, mammalized (such as bovanized, camelized, caninized, equinized, felinized, humanized etc.) antibodies, and fragments thereof, capable of binding and neutralizing NGF. The disclosure provides a therapeutic means with which to inhibit NGF and provides compositions and methods for treating disease associated with increased levels of NGF, particularly inflammatory disorders.

In one aspect, the present disclosure provides a binding protein, or fragment thereof, comprising hypervariable region sequences wholly or substantially identical to sequences from an antibody from a donor species; and constant region sequences wholly or substantially identical to sequences of antibodies from a target species, wherein the donor and target species are different. The binding protein may for example specifically bind NGF and have a heavy chain having a heavy chain variable region and a light chain having a light chain variable region.

In another aspect, the present disclosure provides a binding protein that specifically binds NGF and which has a heavy chain having a heavy chain variable region and a light chain having a light chain variable region, wherein the heavy chain variable region comprises an amino acid sequence having at least 90% identity with a sequence selected from the group consisting of SEQ ID NO: 2, SEQ ID NO: 6, SEQ ID NO: 10, SEQ ID NO:14, SEQ ID NO: 18, SEQ ID NO: 22, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 165, SEQ ID NO: 166, SEQ ID NO: 167, SEQ ID NO: 168, SEQ ID NO: 169, SEQ ID NO: 170, SEQ ID NO: 177, SEQ ID NO: 179, SEQ ID NO: 180, SEQ ID NO: 182, SEQ ID NO: 184, SEQ ID NO: 185, SEQ ID NO: 187, SEQ ID NO: 189, SEQ ID NO: 190, SEQ ID NO: 192, SEQ ID NO: 195, SEQ ID NO: 197, SEQ ID NO: 199, SEQ ID NO: 201, SEQ ID NO: 203, SEQ ID NO: 206, SEQ ID NO: 207, or an antigen-binding or an immunologically functional immunoglobulin fragment thereof.

In another aspect, the present disclosure provides a binding protein that specifically binds NGF and which has a heavy chain having a heavy chain variable region and a light chain having a light chain variable region, wherein the light chain variable region comprises an amino acid sequence having at least 90% identity with a sequence selected from the group consisting of SEQ ID NO: 4, SEQ ID NO: 8, SEQ ID NO: 12, SEQ ID NO: 16, SEQ ID NO: 20, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, and SEQ ID NO: 44, SEQ ID NO: 171, SEQ ID NO: 172, SEQ ID NO: 173, SEQ ID NO: 174, SEQ ID NO: 175, SEQ ID NO: 176, SEQ ID NO: 181, SEQ ID NO: 183, SEQ ID NO: 186, SEQ ID NO: 188, SEQ ID NO: 191, SEQ ID NO: 193, SEQ ID NO: 194, SEQ ID NO: 196, SEQ ID NO: 198, SEQ ID NO: 200, SEQ ID NO: 202, or an antigen-binding or an immunologically functional immunoglobulin fragment thereof.

A binding protein of the present disclosure may comprise at least one CDR comprising an amino acid sequence selected from: a) heavy chain CDRs consisting of SEQ ID NO: 55, 56, 57, 61, 62, 63, 67, 68, 69, 73, 74, 75, 79, 80, 81, and modified CDR amino acid sequences having a sequence identity of at least 50% to one of said sequences; and b) light chain CDRs consisting of SEQ ID NO: 58, 59, 60, 64, 65, 66, 70, 71, 72, 76, 77, 78, 82, 83, 84, and modified CDR amino acid sequences having a sequence identity of at least 50% to one of said sequences. Alternatively, the binding protein of the present disclosure may comprise at least one CDR comprising an amino acid sequence selected from: a) heavy chain CDRs consisting of SEQ ID NO: 55, 56, 57, 61, 62, 63, 67, 68, 69, 73, 74, 75, 79, 80, 81, and modified CDR amino acid sequences having a sequence identity of at least 70% to one of said sequences; and b) light chain CDRs consisting of SEQ ID NO: 58, 59, 60, 64, 65, 66, 70, 71, 72, 76, 77, 78, 82, 83, 84, and modified CDR amino acid sequences having a sequence identity of at least 70% to one of said sequences. The binding protein of the present disclosure may comprise at least one CDR comprising an amino acid sequence selected from: a) heavy chain CDRs consisting of SEQ ID NO: 55, 56, 57, 61, 62, 63, 67, 68, 69, 73, 74, 75, 79, 80, 81, and modified CDR amino acid sequences having a sequence identity of at least 80% to one of said sequences; and b) light chain CDRs consisting of SEQ ID NO: 58, 59, 60, 64, 65, 66, 70, 71, 72, 76, 77, 78, 82, 83, 84, and modified CDR amino acid sequences having a sequence identity of at least 80% to one of said sequences. binding protein of the present disclosure may comprise at least one CDR comprising an amino acid sequence selected from: a) heavy chain CDRs consisting of SEQ ID NO: 55, 56, 57, 61, 62, 63, 67, 68, 69, 73, 74, 75, 79, 80, 81, and modified CDR amino acid sequences having a sequence identity of at least 90% to one of said sequences; and b) light chain CDRs consisting of SEQ ID NO: 58, 59, 60, 64, 65, 66, 70, 71, 72, 76, 77, 78, 82, 83, 84, and modified CDR amino acid sequences having a sequence identity of at least 90% to one of said sequences.

A binding protein of the present disclosure may comprise a heavy chain human immunoglobulin constant domain selected from the group consisting of IgM constant domain, IgG4 constant domain, IgG1 constant domain, IgE constant domain, IgG2 constant domain, IgG3 constant domain, and IgA constant domain. A binding proteins of the present disclosure may alternatively comprise a heavy chain canine immunoglobulin constant domain selected from the group consisting of IgM constant domain, IgG4 constant domain, IgG1 constant domain, IgE constant domain, IgG2 constant domain, IgG3 constant domain, and IgA constant domain. A binding protein of the present disclosure may alternatively comprise a heavy chain feline immunoglobulin constant domain. A binding protein of the present disclosure may alternatively comprise a heavy chain equine immunoglobulin constant domain. A binding protein of the present disclosure may further comprise a constant region having an amino acid sequence selected from the group consisting of SEQ ID NO:52 and SEQ ID NO:54.

Any of the above binding proteins may be selected from the group consisting of; an immunoglobulin molecule, disulfide linked Fv, monoclonal antibody, scFv, chimeric antibody, single domain antibody, CDR-grafted antibody, diabody, humanized antibody, caninized mAb, canine mAb, feline mAb, felinized mAb, equine mAb, equinized mAb, a multispecific antibody, a Fab, a dual specific antibody, a DVD-Ig, a Fab', a bispecific antibody, a F(ab')2, and a Fv.

Any of the above binding proteins may be capable of modulating a biological function of NGF, or neutralizing NGF.

Any of the above binding proteins may be capable of neutralizing NGF with a potency ($IC_{50}$) of at least about 10 nM, at least about 5 nM, at least about 1 nM, at least about 0.5 nM, at least about 0.1 nM, at least about 0.05 nM, at least about 0.01 nM, or at least about 0.001 nM, as measured in the TF-1 cell proliferation assay or the pERK and Pathhunter assays.

Any of the above binding proteins may have an on rate constant ($K_{on}$) for NGF of: at least about $10^2 M^{-1} s^{-1}$, at least about $10^3 M^{-1} s^{-1}$, at least about $10^4 M^{-1} s^{-1}$, at least about $10^5 M^{-1} s^{-1}$, or at least about $10^6 M^{-1} s^{-1}$, or at least about $10^7 M^{-1} s^{-1}$, as measured by surface plasmon resonance.

Any of the above binding proteins may have an off rate constant ($K_{off}$) for NGF selected from the group consisting of: at most about $10^{-3} s^{-1}$, at most about $10^{-4} s^{-1}$, at most about $10^{-5} s^{-1}$, at most about $10^{-6} s^{-1}$, and at most about $10^{-7} s^{-1}$, as measured by surface plasmon resonance.

Any of the above binding proteins may have a dissociation constant ($K_D$) for NGF selected from the group consisting of: at most about $10^{-7}$ M, at most about $10^{-8}$ M, at most about $10^{-9}$ M, at most about $10^{-10}$ M, at most about $10^{-11}$ M at most about $10^{-12}$ M, at most about $10^{-13}$ M and at most about $10^{-14}$ M. The dissociation constant ($K_D$) may be, for example, about $1 \times 10^{-9}$ M, about $1 \times 10^{-10}$ M, about $3.14 \times 10^{-10}$ M, about $1 \times 10^{-11}$ M, about $2.37 \times 10^{-11}$ M, about $1 \times 10^{-12}$ M, about $1 \times 10^{-13}$ M, and about $3.3 \times 10^{-14}$ M.

Any of the above binding proteins may further comprise an agent selected from the group consisting of; an immunoadhension molecule, an imaging agent, a therapeutic agent, and a cytotoxic agent. The agent may be, for example, an imaging agent selected from the group consisting of a radiolabel, an enzyme, a fluorescent label, a luminescent label, a bioluminescent label, a magnetic label, and biotin. The imaging agent may be a radiolabel selected from the group consisting of: 3H, 14C, 35S, 90Y, 99Tc, 111In, 125I, 131I, 177Lu, 166Ho, and 153Sm. Alternatively, the agent may be a therapeutic or cytotoxic agent, such as, for example, an anti-metabolite, an alkylating agent, an antibiotic, a growth factor, a cytokine, an anti-angiogenic agent, an anti-mitotic agent, an anthracycline, toxin, and an apoptotic agent.

Any of the binding proteins may possess a murine, canine, feline, human or equine glycosylation pattern.

Any of the binding proteins may be a crystallized binding protein. The crystallized binding protein may be a carrier-free pharmaceutical controlled release crystallized binding protein.

In another aspect, the present disclosure provides an isolated nucleic acid encoding any of the above binding proteins. The isolated nucleic acid may comprise RNA or DNA.

In another aspect, the present disclosure provides an isolated nucleic acid comprising or complementary to a nucleic acid sequence that encodes a binding protein that specifically binds NGF having a heavy chain having a heavy chain variable region and a light chain having a light chain variable region, wherein the heavy chain variable region is encoded by a nucleotide sequence having at least 90% sequence identity with a sequence selected from the group consisting of SEQ ID NOS: 1, 5, 9, 13, 17, and 21.

In another aspect, the present disclosure provides an isolated nucleic acid comprising or complementary to a nucleic acid sequence that encodes a binding protein that specifically binds NGF having a heavy chain having a heavy chain variable region and a light chain having a light chain variable region, wherein the light chain variable region is encoded by a nucleotide sequence having at least 90% sequence identity with a sequence selected from the group consisting of SEQ ID NOS: 3, 7, 11, 15, 19 and 23.

In another aspect, the present disclosure provides a recombinant vector comprising an isolated nucleic acid encoding a binding protein that specifically binds NGF as described herein. A recombinant vector according to the present disclosure may comprise pcDNA, pTT, pTT3, pEF-BOS, pBV, pJV or pBJ. Also provided is a host cell comprising such a recombinant vector. The host cell may be for example a eukaryotic cell, or a prokaryotic cell. The host cell may be a protist cell; an animal cell such as but not limited to a mammalian cell, avian cell; an insect cell, such as but not limited to an insect Sf9 cell; a plant cell; or a fungal cell. The host cell may be for example an *E. coli* cell. The host cell may be a CHO cell, or a COS cell. Also provided is an isolated cell line that produces a binding protein that specifically binds NGF as described herein.

In another aspect, the present disclosure provides a pharmaceutical or diagnostic composition comprising a binding protein that specifically binds NGF as described herein, and a pharmaceutically acceptable carrier, diluent or excipient. A pharmaceutical composition may comprise a therapeutically effective amount of the NGF binding protein.

In another aspect, the present disclosure provides a composition for the release of a binding protein, the composition comprising: (a) a composition comprising a binding protein that specifically binds NGF as described herein, and a pharmaceutically acceptable carrier, excipient or diluent, and (b) at least one polymeric carrier.

In another aspect, the present disclosure provides a method for reducing NGF activity in a subject (for example, a dog, cat, horse, ferret, etc.) suffering from a disorder in which NGF activity is detrimental, comprising administering to the subject a therapeutically effective amount of a binding protein that specifically binds NGF as described herein.

In another aspect, the present disclosure provides a method for making anti-NGF antibodies comprising: (a) production of murine monoclonal antibodies; (b) screening hybridoma supernatants; (c) grafting of donor CDRs into target frameworks; and (d) introducing backmutations in the framework region of the target antibodies, wherein the anti-NGF antibodies comprise hypervariable region sequences wholly or substantially identical to sequences from an antibody from the donor species and constant region sequences wholly or substantially identical to sequences of an antibody from the target species, wherein the donor and the target species are different. In the method, the donor may be, for example, a mouse and the target a non-murine mammal, such as but not limited to a bovine, canine, equine, or feline mammal, or a camel goat, human or sheep.

In another aspect, the present disclosure provides a method for detecting the presence or amount of NGF in a sample, comprising: providing a reagent comprising any of the above binding proteins that specifically bind NGF; combining the binding protein with the sample for a time and under conditions sufficient for the binding protein to bind to any NGF in the sample; and determining the presence or amount of NGF in the sample based on specific binding of the binding protein to NGF. In the method, the binding protein may be immobilized or may be capable of being immobilized on a solid support. In the method, the binding protein may be coupled to a detectable label, such as, for example, an imaging agent such as but not limited to a radiolabel, an enzyme, a fluorescent label, a luminescent label, a bioluminescent label, a magnetic label, and biotin. The imaging agent may be for example a radiolabel selected from the group consisting of: 3H, 14C, 35S, 90Y, 99Tc, 111In, 125I, 131I, 177Lu, 166Ho, and 153Sm.

In another aspect, the present disclosure provides an immunoassay device for detecting the presence or amount of NGF in a sample, the device comprising any of the above binding proteins that specifically bind NGF, immobilized on a solid support.

In another aspect, the present disclosure provides a kit for detecting the presence or amount of NGF in a sample, the kit comprising: an immunoregamet comprising any of the above binding proteins that specifically bind NGF, and instructions for determining the presence or amount of NGF in the sample based on specific binding of the immunoreagent to NGF. In the kit, the binding protein may be immobilized on a solid support.

In still yet another aspect, the present disclosure relates to an antibody or antigen binding fragment thereof comprising:

a heavy chain variable region comprises an amino acid sequence having at least 90% identity with a sequence selected from the group consisting of SEQ ID NO: 2, SEQ ID NO: 6, SEQ ID NO: 10, SEQ ID NO: 14, SEQ ID NO: 18, SEQ ID NO: 22, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 165, SEQ ID NO: 166, SEQ ID NO: 167, SEQ ID NO: 168, SEQ ID NO: 169, SEQ ID NO: 170, SEQ ID NO: 177, SEQ ID NO: 179, SEQ ID NO: 180, SEQ ID NO: 182, SEQ ID NO: 184, SEQ ID NO: 185, SEQ ID NO: 187, SEQ ID NO: 189, SEQ ID NO: 190, SEQ ID NO: 192, SEQ ID NO: 195, SEQ ID NO: 197, SEQ ID NO: 199, SEQ ID NO: 201, SEQ ID NO: 203, SEQ ID NO: 206, SEQ ID NO: 207, or an antigen-binding or an immunologically functional immunoglobulin fragment thereof; and a light chain variable region comprises an amino acid sequence having at least 90% identity with a sequence selected from the group consisting of SEQ ID NO: 4, SEQ ID NO: 8, SEQ ID NO: 12, SEQ ID NO: 16, SEQ ID NO: 20, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, and SEQ ID NO: 44, SEQ ID NO: 171, SEQ ID NO: 172, SEQ ID NO: 173, SEQ ID NO: 174, SEQ ID NO: 175, SEQ ID NO: 176, SEQ ID NO: 181, SEQ ID NO: 183, SEQ ID NO: 186, SEQ ID NO: 188, SEQ ID NO: 191, SEQ ID NO: 193, SEQ ID NO: 194, SEQ ID NO: 196, SEQ ID NO: 198, SEQ ID NO: 200, SEQ ID NO: 202, or an antigen-binding or an immunologically functional immunoglobulin fragment thereof.

More specifically, the above-described antibody may comprise at least one CDR comprising an amino acid sequence selected from: a) heavy chain CDRs consisting of SEQ ID NO: 55, 56, 57, 61, 62, 63, 67, 68, 69, 73, 74, 75, 79, 80, 81, and modified CDR amino acid sequences having a sequence identity of at least 50% to one of said sequences; and b) light chain CDRs consisting of SEQ ID NO: 58, 59, 60, 64, 65, 66, 70, 71, 72, 76, 77, 78, 82, 83, 84, and modified CDR amino acid sequences having a sequence identity of at least 50% to one of said sequences. Alternatively, the above-described antibody may comprise at least one CDR comprising an amino acid sequence selected from: a) heavy chain CDRs consisting of SEQ ID NO: 55, 56, 57, 61, 62, 63, 67, 68, 69, 73, 74, 75, 79, 80, 81, and modified CDR amino acid sequences having a sequence identity of at least 70% to one of said sequences; and b) light chain CDRs consisting of SEQ ID NO: 58, 59, 60, 64, 65, 66, 70, 71, 72, 76, 77, 78, 82, 83, 84, and modified CDR amino acid sequences having a sequence identity of at least 70% to one of said sequences. Alternatively, the above-described antibody may comprise at least one CDR comprising an amino acid sequence selected from: a) heavy chain CDRs consisting of SEQ ID NO: 55, 56, 57, 61, 62, 63, 67, 68, 69, 73, 74, 75, 79, 80, 81, and modified CDR amino acid sequences having a sequence identity of at least 80% to one of said sequences; and b) light chain CDRs consisting of SEQ ID NO: 58, 59, 60, 64, 65, 66, 70, 71, 72, 76, 77, 78, 82, 83, 84, and modified CDR amino acid sequences having a sequence identity of at least 80% to one of said sequences. Alternatively, the above-described antibody may comprise at least one CDR comprising an amino acid sequence selected from: a) heavy chain CDRs consisting of SEQ ID NO: 55, 56, 57, 61, 62, 63, 67, 68, 69, 73, 74, 75, 79, 80, 81, and modified CDR amino acid sequences having a sequence identity of at least 90% to one of said sequences; and b) light chain CDRs consisting of SEQ ID NO: 58, 59, 60, 64, 65, 66, 70, 71, 72, 76, 77, 78, 82, 83, 84, and modified CDR amino acid sequences having a sequence identity of at least 90% to one of said sequences.

The above-described antibody may comprise a heavy chain human immunoglobulin constant domain selected from the group consisting of IgM constant domain, IgG4 constant domain, IgG1 constant domain, IgE constant domain, IgG2 constant domain, IgG3 constant domain, and IgA constant domain. More specifically, the antibody may comprise a heavy chain canine immunoglobulin constant domain selected from the group consisting of IgM constant domain, IgG4 constant domain, IgG1 constant domain, IgE constant domain, IgG2 constant domain, IgG3 constant domain, and IgA constant domain. Alternatively, the antibody comprises a heavy chain feline immunoglobulin constant domain. Still further alternatively, the antibody comprises a heavy chain equine immunoglobulin constant domain. Moreover, the above-described antibody may comprise a constant region having an amino acid sequence selected from the group consisting of SEQ ID NO:52 and SEQ ID NO:54. Still further, the above-described antibody is selected from the group consisting of: an immunoglobulin molecule, disulfide linked Fv, monoclonal antibody, scFv, chimeric antibody, single domain antibody, CDR-grafted antibody, diabody, humanized antibody, caninized mAb, canine mAb, feline mAb, felinized mAb, equine mAb, equinized mAb, a multispecific antibody, a Fab, a dual specific antibody, a DVD-Ig, a Fab', a bispecific antibody, a F(ab')$_2$, and a Fv.

In another aspect, the above-identified antibody is capable of modulating a biological function of NGF.

In still yet another aspect, the present disclosure relates to an isolated nucleic acid encoding the above-described antibody.

In another aspect, the present invention relates to an antibody or antigen binding fragment thereof having a heavy chain variable region that comprises an amino acid sequence having at least 90% identity with a sequence of SEQ ID NO:37 and a light chain variable region that comprises an amino acid sequence having at least 90% identity with a sequence of SEQ ID NO:38. The above-described antibody may comprise a heavy chain human immunoglobulin constant domain selected from the group consisting of IgM constant domain, IgG4 constant domain, IgG1 constant domain, IgE constant domain, IgG2 constant domain, IgG3 constant domain, and IgA constant domain. More specifically, the antibody may comprise a heavy chain canine immunoglobulin constant domain selected from the group consisting of IgM constant domain, IgG4 constant domain, IgG1 constant domain, IgE constant domain, IgG2 constant domain, IgG3 constant domain, and IgA constant domain. Alternatively, the antibody comprises a heavy chain feline immunoglobulin constant domain. Still further alternatively, the antibody comprises a heavy chain equine immunoglobulin constant domain. Moreover, the above-described antibody may comprise a constant region having an amino acid sequence selected from the group consisting of SEQ ID NO:52 and SEQ ID NO:54. Still further, the above-described antibody is selected from the group consisting of: an immunoglobulin molecule, disulfide linked Fv, monoclonal antibody, scFv, CDR-grafted antibody, diabody, humanized antibody, caninized mAb, canine mAb, feline mAb, felinized mAb, equine mAb, equinized mAb, a multispecific antibody, a Fab, a dual specific antibody, a DVD-Ig, a Fab', a bispecific antibody, a F(ab')$_2$, and a Fv.

In another aspect, the above-identified antibody is capable of modulating a biological function of NGF.

In still yet another aspect, the present disclosure relates to an isolated nucleic acid encoding the above-described antibody.

In another aspect, the present invention relates to an antibody or antigen binding fragment thereof having a heavy chain variable region comprises an amino acid sequence having at least 90% identity with a sequence of SEQ ID NO: 192 and the light chain variable region comprises an amino acid sequence having at least 90% identity with a sequence of SEQ ID NO: 193. The above-described antibody may comprise a heavy chain human immunoglobulin constant domain selected from the group consisting of IgM constant domain, IgG4 constant domain, IgG1 constant domain, IgE constant domain, IgG2 constant domain, IgG3 constant domain, and IgA constant domain. More specifically, the antibody may comprise a heavy chain canine immunoglobulin constant domain selected from the group consisting of IgM constant domain, IgG4 constant domain, IgG1 constant domain, IgE constant domain, IgG2 constant domain, IgG3 constant domain, and IgA constant domain. Alternatively, the antibody comprises a heavy chain feline immunoglobulin constant domain. Still further alternatively, the antibody comprises a heavy chain equine immunoglobulin constant domain. Moreover, the above-described antibody may comprise a constant region having an amino acid sequence selected from the group consisting of SEQ ID NO: 52 and SEQ ID NO: 54. Still further, the above-described antibody is selected from the group consisting of: an immunoglobulin molecule, disulfide linked Fv, monoclonal antibody, scFv, chimeric antibody, single domain antibody, CDR-grafted antibody, diabody, humanized antibody, caninized mAb, canine mAb, feline mAb, felinized mAb, equine mAb, equinized mAb, a multispecific antibody, a Fab, a dual specific antibody, a DVD-Ig, a Fab', a bispecific antibody, a F(ab')$_2$, and a Fv.

In another aspect, the above-identified antibody is capable of modulating a biological function of NGF.

In still yet another aspect, the present disclosure relates to an isolated nucleic acid encoding the above-described antibody.

In still yet another aspect, the present disclosure relates to a pharmaceutical or diagnostic composition comprising at least one of the above-described antibodies, and a pharmaceutically acceptable carrier, diluent or excipient. More specifically, the pharmaceutical or diagnostic composition may comprise a therapeutically effective amount of at least one of the above-described antibodies. In addition, the pharmaceutical or diagnostic composition may comprise at least one preservative. Examples of at least one preservative that may be used is methylparaben, propylparaben, benzyl alcohol, chlorobutanol or benzalkonium chloride.

The pharmaceutical composition can have a pH of greater than about 7.0. Alternatively, the pharmaceutical composition can have a pH of between about 6.8 and about 8.2. Alternatively, the pharmaceutical composition can have a pH of between about 7.2 and about 7.8. Still further alternatively, the pH of the pharmaceutical composition can be between about 7.4 and about 7.6. Still further alternatively, the pH of the pharmaceutical composition can be about 6.8, 6.9, 7.0, 7.1, 7.2, 7.3, 7.4, 7.5, 7.6, 7.7, 7.8, 7.9, 8.0, 8.1 or 8.2.

The pharmaceutical composition of the present disclosure may have a half-life of from about 8.0 days to about 15.0 days when dosed intravenously or subcutaneously. Alternatively, the pharmaceutical composition of the present invention may have a half-life of from about 10.0 days to about 13.0 days. Still further alternatively, the pharmaceutical composition of the present invention may have a half-life of about 8.0 days, about 8.5 days, about 9.0 days, about 9.5 days, about 10.0 days, about 10.5 days, about 11.0 days, about 11.5 days, about 12.0 days, about 12.5 days, about 13.0 days, about 13.5 days, about 14.0 days, about 14.5 days or about 15.0 days.

In another aspect, the present disclosure relates to a method for reducing NGF activity in a subject suffering from a disorder in which NGF activity is detrimental, comprising administering to the subject a therapeutically effective amount of an antibody of antigen binding fragment thereof of at least one of the above-described antibodies or antigen-binding fragments thereof.

BRIEF DESCRIPTION OF FIGURES

FIG. 1 illustrates PR-1254972 VH nucleotide sequence (SEQ ID NO: 1) of mouse anti-NGF antibody.

FIG. 2 illustrates PR-1254972 VH amino acid sequence (SEQ ID NO: 2) of mouse anti-NGF antibody.

FIG. 3 illustrates PR-1254972 VL nucleotide sequence (SEQ ID NO: 3) of mouse anti-NGF antibody.

FIG. 4 illustrates PR-1254972 VL amino acid (SEQ ID NO: 4) of mouse anti-NGF antibody.

FIG. 5 illustrates PR-1254973 VH nucleotide sequence (SEQ ID NO: 5) of mouse anti-NGF antibody.

FIG. 6 illustrates PR-1254973 VH amino acid (SEQ ID NO: 6) of mouse anti-NGF antibody.

FIG. 7 illustrates PR-1254973 VL nucleotide sequence (SEQ ID NO: 7) of mouse anti-NGF antibody.

FIG. 8 illustrates PR-1254973 VL amino acid (SEQ ID NO: 8) of mouse anti-NGF antibody.

FIG. 9 illustrates PR-1254977 VH nucleotide sequence (SEQ ID NO: 9) of mouse anti-NGF antibody.

FIG. 10 illustrates PR-1254977 VH amino acid (SEQ ID NO: 10) of mouse anti-NGF antibody.

FIG. 11 illustrates PR-1254977 VL nucleotide sequence (SEQ ID NO: 11) of mouse anti-NGF antibody.

FIG. 12 illustrates PR-1254977 VL amino acid (SEQ ID NO: 12) of mouse anti-NGF antibody.

FIG. 13 illustrates PR-1254980 VH nucleotide sequence (SEQ ID NO: 13) of mouse anti-NGF antibody.

FIG. 14 illustrates PR-1254980 VH amino acid (SEQ ID NO: 14) of mouse anti-NGF antibody.

FIG. 15 illustrates PR-1254980 VL nucleotide sequence (SEQ ID NO: 15) of mouse anti-NGF antibody.

FIG. 16 illustrates PR-1254980 VL amino acid (SEQ ID NO: 16) of mouse anti-NGF antibody.

FIG. 17 illustrates PR-1254981 VH nucleotide sequence (SEQ ID NO: 17) of mouse anti-NGF antibody.

FIG. 18 illustrates PR-1254981 VH amino acid (SEQ ID NO: 18) of mouse anti-NGF antibody.

FIG. 19 illustrates PR-1254981 VL nucleotide sequence (SEQ ID NO: 19) of mouse anti-NGF antibody.

FIG. 20 illustrates PR-1254981 VL amino acid (SEQ ID NO: 20) of mouse anti-NGF antibody.

FIG. 21 illustrates PR-1254982 VH nucleotide sequence (SEQ ID NO: 21) of mouse anti-NGF antibody.

FIG. 22 illustrates PR-1254982 VH amino acid (SEQ ID NO: 22) of mouse anti-NGF antibody.

FIG. 23 illustrates PR-1254982 VL nucleotide sequence (SEQ ID NO: 23) of mouse anti-NGF antibody.

FIG. 24 illustrates PR-1254982 VL amino acid (SEQ ID NO: 24) of mouse anti-NGF antibody.

FIG. 25 illustrates mouse anti-NGF mAb caninized by CDR grafting onto canine Ig frameworks (CDRs are underlined), SEQ ID NO: 25 (72.1 VH amino acid).

FIG. 26 illustrates mouse anti-NGF mAb caninized by CDR grafting onto canine Ig frameworks (CDRs are underlined), SEQ ID NO: 26 (72.1 VL amino acid).

FIG. 27 illustrates mouse anti-NGF mAb caninized by CDR grafting onto canine Ig frameworks (CDRs are underlined) SEQ ID NO: 27 (73.1 VH amino acid).

FIG. 28 illustrates mouse anti-NGF mAb caninized by CDR grafting onto canine Ig frameworks (CDRs are underlined) SEQ ID NO: 28 (73.1 VL amino acid).

FIG. 29 illustrates mouse anti-NGF mAb caninized by CDR grafting onto canine Ig frameworks (CDRs are underlined), SEQ ID NO: 29 (77.1 VH amino acid).

FIG. 30 illustrates mouse anti-NGF mAb caninized by CDR grafting onto canine Ig frameworks (CDRs are underlined), SEQ ID NO: 30 (77.1 VL amino acid).

FIG. 31A illustrates mouse anti-NGF mAb caninized by CDR grafting onto canine Ig frameworks (CDRs are underlined), SEQ ID NO: 31 (81.1 VH amino acid).

FIG. 31B illustrates mouse anti-NGF mAb caninized by CDR grafting onto canine Ig frameworks (CDRs are underlined), SEQ ID NO: 177 (81.1B VH amino acid).

FIG. 32 illustrates mouse anti-NGF mAb caninized by CDR grafting onto canine Ig frameworks (CDRs are underlined), SEQ ID NO: 32 (81.1 VL amino acid).

FIG. 33 illustrates mouse anti-NGF mAb caninized by CDR grafting onto canine Ig frameworks (CDRs are underlined), SEQ ID NO: 33 (82.1 VH amino acid)

FIG. 34 illustrates mouse anti-NGF mAb caninized by CDR grafting onto canine Ig frameworks (CDRs are underlined), SEQ ID NO: 34 (82.1 VL amino acid).

FIG. 35 illustrates caninized anti-NGF antibodies containing back mutation residues (backmutation residues shown in bold), SEQ ID NO: 35 (72.2 VH amino acid).

FIG. 36A illustrates caninized anti-NGF antibodies containing back mutation residues (backmutation residues shown in bold), SEQ ID NO: 36 (72.2 VL amino acid).

FIG. 36B illustrates caninized anti-NGF antibodies containing back mutation residues (backmutation residues shown in bold), SEQ ID NO: 179 (72.3 VH amino acid).

FIG. 36C illustrates caninized anti-NGF antibodies containing back mutation residues (backmutation residues shown in bold), SEQ ID NO: 180 (72.4 VH amino acid).

FIG. 36D illustrates caninized anti-NGF antibodies containing back mutation residues (backmutation residues shown in bold), SEQ ID NO: 181 (72.4 VL amino acid).

FIG. 37 illustrates caninized anti-NGF antibodies containing back mutation residues (backmutation residues shown in bold), SEQ ID NO: 37 (73.2 VH amino acid).

FIG. 38A illustrates caninized anti-NGF antibodies containing back mutation residues (backmutation residues shown in bold), SEQ ID NO: 38 (73.2 VL amino acid).

FIG. 38B illustrates caninized anti-NGF antibodies containing back mutation residues (backmutation residues shown in bold), SEQ ID NO: 182 (73.4 VH amino acid).

FIG. 38C illustrates caninized anti-NGF antibodies containing back mutation residues (backmutation residues shown in bold), SEQ ID NO: 183 (73.4 VL amino acid).

FIG. 39 illustrates caninized anti-NGF antibodies containing back mutation residues (backmutation residues shown in bold), SEQ ID NO: 39 (77.2 VH amino acid).

FIG. 40A illustrates caninized anti-NGF antibodies containing back mutation residues (backmutation residues shown in bold), SEQ ID NO: 40 (77.2 VL amino acid).

FIG. 40B illustrates caninized anti-NGF antibodies containing back mutation residues (backmutation residues shown in bold), SEQ ID NO: 184 (77.3 VH amino acid).

FIG. 40C illustrates caninized anti-NGF antibodies containing back mutation residues (backmutation residues shown in bold), SEQ ID NO: 185 (77.4 VH amino acid).

FIG. 40D illustrates caninized anti-NGF antibodies containing back mutation residues (backmutation residues shown in bold), SEQ ID NO: 186 (77.4 VL amino acid).

FIG. 41 illustrates caninized anti-NGF antibodies containing back mutation residues (backmutation residues shown in bold), SEQ ID NO: 41 (81.2 VH amino acid).

FIG. 42A illustrates caninized anti-NGF antibodies containing back mutation residues (backmutation residues shown in bold), SEQ ID NO: 42 (81.2 VL amino acid).

FIG. 42B illustrates caninized anti-NGF antibodies containing back mutation residues (backmutation residues shown in bold), SEQ ID NO: 187 (81.4 VH amino acid).

FIG. 42C illustrates caninized anti-NGF antibodies containing back mutation residues (backmutation residues shown in bold), SEQ ID NO: 188 (81.4 VL amino acid).

FIG. 42D illustrates caninized anti-NGF antibodies containing back mutation residues (backmutation residues shown in bold), SEQ ID NO: 189 (81.2B VH amino acid).

FIG. 42E illustrates caninized anti-NGF antibodies containing back mutation residues (backmutation residues shown in bold), SEQ ID NO: 190 (81.4B VH amino acid).

FIG. 42F illustrates caninized anti-NGF antibodies containing back mutation residues (backmutation residues shown in bold, SEQ ID NO:206 (81.5B VH amino acid).

FIG. 42G illustrates caninized anti-NGF antibodies containing back mutation residues (backmutation residues shown in bold, SEQ ID NO:207 (81.6B VH amino acid).

FIG. 43 illustrates caninized anti-NGF antibodies containing back mutation residues (backmutation residues shown in bold), SEQ ID NO: 43 (82.2 VH amino acid).

FIG. 44A illustrates caninized anti-NGF antibodies containing back mutation residues (backmutation residues shown in bold), SEQ ID NO: 44 (82.2 VL amino acid).

FIG. 44B illustrates caninized anti-NGF antibodies containing back mutation residues (backmutation residues shown in bold), SEQ ID NO: 191 (82.3 VL amino acid).

FIG. 44C illustrates caninized anti-NGF antibodies containing back mutation residues (backmutation residues shown in bold), SEQ ID NO: 192 (82.4 VH amino acid).

FIG. 44D illustrates caninized anti-NGF antibodies containing back mutation residues (backmutation residues shown in bold), SEQ ID NO: 193 (82.4 VL amino acid).

FIG. 45 illustrates primer sequence to clone canine NGF, SEQ ID NO: 45 (NGF-Dog-S primer).

FIG. 46 illustrates primer sequence to clone canine NGF, SEQ ID NO: 46 (NGF-Dog-AS primer).

FIG. 47 illustrates primer sequence to clone canine NGF, SEQ ID NO: 47 (NGF-d-Ec-S primer).

FIG. 48 illustrates primer sequence to clone canine NGF, SEQ ID NO: 48 (NGF-d-Ec-AS primer).

FIG. 49 illustrates canine NGF C-terminal 6H is (SEQ ID NO: 208) fusion nucleotide sequence, SEQ ID NO: 49.

FIG. 50 illustrates canine NGF C-terminal 6-His (SEQ ID NO: 208) amino acid sequence, SEQ ID NO: 50.

FIG. 51 illustrates canine IgG constant region nucleotide sequence, SEQ ID NO: 51.

FIG. 52 illustrates canine IgG constant region amino acid sequence, SEQ ID NO: 52.

FIG. 53 illustrates canine kappa constant region nucleotide sequence, SEQ ID NO: 53

FIG. 54 illustrates canine kappa constant region amino acid sequence, SEQ ID NO: 54.

FIG. 55 illustrates complementarity determining region, SEQ ID NO: 55 (72.1 VH amino acid; CDR1).

FIG. 56 illustrates complementarity determining region, SEQ ID NO: 56 (72.1 VH amino acid; CDR2).

FIG. 57 illustrates complementarity determining region, SEQ ID NO: 57 (72.1 VH amino acid; CDR3).

FIG. 58 illustrates complementarity determining region, SEQ ID NO: 58 (72.1 VL amino acid; CDR1).

FIG. 59 illustrates complementarity determining region, SEQ ID NO: 59 (72.1 VL amino acid; CDR2).

FIG. 60 illustrates complementarity determining region, SEQ ID NO: 60 (72.1 VL amino acid; CDR3).

FIG. 61 illustrates complementarity determining region, SEQ ID NO: 61 (73.1 VH amino acid; CDR1).

FIG. 62 illustrates complementarity determining region, SEQ ID NO: 62 (73.1 VH amino acid; CDR2).

FIG. 63 illustrates complementarity determining region, SEQ ID NO: 63 (73.1 VH amino acid; CDR3).

FIG. 64 illustrates complementarity determining region, SEQ ID NO: 64 (73.1 VL amino acid; CDR1).

FIG. 65 illustrates complementarity determining region, SEQ ID NO: 65 (73.1 VL amino acid; CDR2).

FIG. 66 illustrates complementarity determining region, SEQ ID NO: 66 (73.1 VL amino acid; CDR3).

FIG. 67 illustrates complementarity determining region, SEQ ID NO: 67 (77.1 VH amino acid; CDR1).

FIG. 68 illustrates complementarity determining region, SEQ ID NO: 68 (77.1 VH amino acid; CDR2).

FIG. 69 illustrates complementarity determining region, SEQ ID NO: 69 (77.1 VH amino acid; CDR3).

FIG. 70 illustrates complementarity determining region, SEQ ID NO: 70 (77.1 VL amino acid; CDR1).

FIG. 71 illustrates complementarity determining region, SEQ ID NO: 71 (77.1 VL amino acid; CDR2).

FIG. 72 illustrates complementarity determining region, SEQ ID NO: 72 (77.1 VL amino acid; CDR3).

FIG. 73 illustrates complementarity determining region, SEQ ID NO: 73 (81.1 VH amino acid; CDR1).

FIG. 74 illustrates complementarity determining region, SEQ ID NO: 74 (81.1 VH amino acid; CDR2).

FIG. 75 illustrates complementarity determining region, SEQ ID NO: 75 (81.1 VH amino acid; CDR3).

FIG. 76 illustrates complementarity determining region, SEQ ID NO: 76 (81.1 VL amino acid; CDR1).

FIG. 77 illustrates complementarity determining region, SEQ ID NO: 77 (81.1 VL amino acid; CDR2).

FIG. 78 illustrates complementarity determining region, SEQ ID NO: 78 (81.1 VL amino acid; CDR3).

FIG. 79 illustrates complementarity determining region, SEQ ID NO: 79 (82.1 VH amino acid; CDR1).

FIG. 80 illustrates complementarity determining region, SEQ ID NO: 80 (82.1 VH amino acid; CDR2).

FIG. 81 illustrates complementarity determining region, SEQ ID NO: 81 (82.1 VH amino acid; CDR3).

FIG. 82 illustrates complementarity determining region, SEQ ID NO: 82 (82.1 VL amino acid; CDR1).

FIG. 83 illustrates complementarity determining region, SEQ ID NO: 83 (82.1 VL amino acid; CDR2).

FIG. 84 illustrates complementarity determining region, SEQ ID NO: 84 (82.1 VL amino acid; CDR3).

FIG. 85 illustrates the sequence of human NGF (SEQ ID NO: 85).

FIG. 86 illustrates the sequences shown in Table 14 illustrating SEQ ID NOs 178, 86-88 from canine heavy chain variable domain sequence derived from canine PBMC.

FIG. 86A illustrates the sequences shown in Table 14 illustrating SEQ ID NOs 89-93 from canine heavy chain variable domain sequences derived from canine PBMC.

FIG. 86B illustrates the sequences shown in Table 14 illustrating SEQ ID NOs 94-98 from canine heavy chain variable domain sequences derived from canine PBMC.

FIG. 86C illustrates the sequences shown in Table 14 illustrating SEQ ID NOs 99-102 from canine heavy chain variable domain sequences derived from canine PBMC.

FIG. 86D illustrates the sequences shown in Table 14 illustrating SEQ ID NOs 103-107 from canine variable domain sequences derived from canine PBMC.

FIG. 86E illustrates the sequences shown in Table 14 illustrating SEQ ID NOs 108-109 from canine heavy variable domain sequences derived from canine PBMC.

FIG. 87 illustrates the sequences shown in Table 15 illustrating SEQ ID NOs 110, 111, 204, 112 from canine lambda light chain variable domain sequences derived from canine PBMC RNA.

FIG. 87A illustrates the sequences shown in Table 15 illustrating SEQ ID NOs 113-117 from canine lambda light chain variable domain sequences derived from canine PBMC RNA.

FIG. 87B illustrates the sequences shown in Table 15 illustrating SEQ ID NOs 118-122 from canine lambda light chain variable domain sequences derived from canine PBMC RNA.

FIG. 87C illustrates the sequences shown in Table 15 illustrating SEQ ID NOs 123-126 from canine lambda light chain variable domain sequences derived from canine PBMC RNA.

FIG. 88 illustrates the sequences shown in Table 16 illustrating SEQ ID NOs 127-131 from canine kappa light chain variable domain sequences derived from canine PBMC RNA.

FIG. 88A illustrates the sequences shown in Table 16 illustrating SEQ ID NOs 132-136 from canine kappa light chain variable domain sequences derived from canine PBMC RNA.

FIG. 88B illustrates the sequences shown in Table 16 illustrating SEQ ID NOs 137-141 from canine kappa light chain variable domain sequences derived from canine PBMC RNA.

FIG. 88C illustrates the sequences shown in Table 16 illustrating SEQ ID NOs 142-146 from canine kappa light chain variable domain sequences derived from canine PBMC RNA.

FIG. 88D illustrates the sequences shown in Table 16 illustrating SEQ ID NOs 147-151 from canine kappa light chain variable domain sequences derived from canine PBMC RNA.

FIG. 88E illustrates the sequences shown in Table 16 illustrating SEQ ID NOs 152-156 from canine kappa light chain variable domain sequences derived from canine PBMC RNA.

FIG. 88F illustrates the sequences shown in Table 16 illustrating SEQ ID NOs 157-161 from canine kappa light chain variable domain sequences derived from canine PBMC RNA.

FIG. 88G illustrates the sequences shown in Table 16 illustrating SEQ ID NOs 162-164 from canine kappa light chain variable domain sequences derived from canine PBMC RNA.

FIG. 89 illustrates the sequences shown in Table 17 illustrating SEQ ID NOs 165-168 from mouse anti-NGF CDRs grafted onto Human Ig Frameworks (CDR-grafted Anti-NGF); CDRs underlined.

FIG. 89A illustrates the sequences shown in Table 17 illustrating SEQ ID NOs 169-173 from mouse anti-NGF CDRs grafted onto Human Ig Frameworks (CDR-grafted Anti-NGF); CDRs underlined.

FIG. 89B illustrates the sequences shown in Table 17 illustrating SEQ ID NOs 174-176 from mouse anti-NGF CDRs grafted onto Human Ig Frameworks (CDR-grafted Anti-NGF); CDRs underlined.

FIG. 90 illustrates the sequences shown in Table 18 illustrating SEQ ID NOs 194-196 from Mouse/Canine Chimeric Antibody sequences.

FIG. 90A illustrates the sequences shown in Table 18 illustrating SEQ ID NOs 197-199 from Mouse/Canine Chimeric Antibody sequences.

FIG. 90B illustrates the sequences shown in Table 18 illustrating SEQ ID NOs 200-202 from Mouse/Canine Chimeric Antibody sequences.

FIG. 90C illustrates the sequences shown in Table 18 illustrating SEQ ID NOs 203 from Mouse/Canine Chimeric Antibody sequences.

DETAILED DESCRIPTION OF THE DISCLOSURE

The disclosure describes NGF binding proteins, particularly anti-NGF antibodies, or antigen-binding portions thereof, that bind NGF. Various aspects of the disclosure relate to antibodies and antibody fragments, and pharmaceutical compositions thereof, as well as nucleic acids, recombinant expression vectors and host cells for making such antibodies and fragments. Methods of using the antibodies of the disclosure to detect human and canine NGF, to inhibit human and canine NGF activity, either in vitro or in vivo; and to regulate gene expression are also encompassed by the disclosure.

Unless otherwise defined herein, scientific and technical terms used in connection with the present disclosure shall have the meanings that are commonly understood by those of ordinary skill in the art. The meaning and scope of the terms should be clear, however, in the event of any latent ambiguiy, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present disclosure are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present disclosure may be more readily understood, select terms and phrases as used herein are defined below.

A. DEFINITIONS

The terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. The term "acceptor" encompasses an antibody amino acid or nucleic acid sequence providing or encoding the constant region(s). The term also encompasses the antibody amino acid or nucleic acid sequence providing or encoding one or more of the framework regions and the constant region(s). For example, the term "acceptor" may refer to a human antibody amino acid or nucleic acid sequence that provides or encodes at least 80%, at least 85%, at least 90%, at least 95%, at least 98%, or 100% of the amino acid sequences of one or more of the framework regions. Such an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

The term "agonist" refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, NGF polypeptides or polypeptides, nucleic acids, carbohydrates, or any other molecules that bind to NGF.

The term "antagonist" or "inhibitor" refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of NGF. Antagonists and inhibitors of NGF may include, but are not limited to, proteins, nucleic acids, carbohydrates, or any other molecules, which bind to NGF.

The term "antibody" broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting examples are discussed herein below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions may be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules may be of any type (e.g., IgG, IgE, IgM, IgD, IgA and IgY), class (e.g., IgG 1, IgG2, IgG 3, IgG4, IgA1 and IgA2) or subclass.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. In one aspect the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The term "antibody construct" refers to a polypeptide comprising one or more the antigen binding portions linked to a linker polypeptide or an immunoglobulin constant domain. Linker polypeptides comprise two or more amino acid residues joined by peptide bonds and are used to link one or more antigen binding portions. Such linker polypeptides are well known in the art (Holliger, et al., *Proc. Natl. Acad. Sci.*, 90: 6444-6448 (1993); Poljak, et al., *Structure* 2: 1121-1123 (1994)). An immunoglobulin constant domain refers to a heavy or light chain constant domain. Human IgG heavy chain and light chain constant domain amino acid sequences are known in the art; canine, equine, and feline are rarer.

The term "antibody fragments" or "antigen-binding moiety" comprises a portion of a full length antibody, generally the antigen binding or variable domain thereof. Examples of antibody fragments include Fab, Fab', F(ab)$_2$, Fv, sFv fragments, diabodies, linear antibodies, single-chain antibody molecules.

The term "antigen-binding portion" of an antibody (or simply "antibody portion") refers to one or more fragments of an antibody that retain the ability to specifically bind to an antigen (e.g., NGF). It has been shown that the antigen-binding function of an antibody may be performed by fragments of a full-length antibody. These may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature,* 341: 544-546 (1989); PCT publication WO 90/05144), which comprises a single variable domain; and (vi) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain Fv (scFv) (Bird et al., *Science,* 242: 423-426 (1988); and Huston et al., *Proc. Natl. Acad. Sci.,* 85: 5879-5883 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (Holliger, et al., *Proc. Natl. Acad. Sci.,* 90: 6444-6448 (1993); Poljak, et al., *Structure* 2: 1121-1123 (1994)). Such antibody binding portions are known in the art (Kontermann and Dubel eds., Antibody Engineering (2001) Springer-Verlag. New York. 790 pp. (ISBN 3-540-41354-5).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al., *Human Antibodies and Hybridomas,* 6: 93-101 (1995)) and use of a cysteine residue, a marker peptide and a C-terminal polyhistidine tag to make bivalent and biotinylated scFv molecules (Kipriyanov, et al., *Mol. Immunol.*, 31: 1047-1058 (1994)). Antibody portions, such as Fab and F(ab')$_2$ fragments, may be prepared from whole antibodies using conventional techniques, such as papain or pepsin digestion, respectively, of whole antibodies. Moreover, antibodies, antibody portions and immunoadhesion molecules may be obtained using standard recombinant DNA techniques, as described herein.

The term "anti-NGF antibody" refers to an antibody which is able to bind to nerve growth factor (NGF) and inhibit NGF biological activity and/or downstream pathway(s) mediated by NGF signaling. An anti-NGF antibody encompasses antibodies that block, antagonize, suppress or reduce (including significantly) NGF biological activity, including downstream pathways mediated by NGF signaling, such as receptor binding and/or elicitation of a cellular response to NGF. Anti-NGF antibodies encompass those that neutralize NGF biological activity, bind NGF and prevent NGF dimerization and/or binding to an NGF receptor (such as p75 and/or trkA), and/or bind NGF and prevent trkA receptor dimerization and/or trkA autophosphorylation. Examples of anti-NGF antibodies are provided herein.

The term "binding protein" refers to a natural or synthetic polypeptide that specifically binds to any portion of a target such as an antigen. The term "binding protein" encompasses antibodies as described herein, including an isolated antibody, antigen-binding portion thereof, or immunologically functional fragment thereof The term "canine antibody" refers to a naturally-occurring or recombinantly produced immunoglobulin composed of amino acid sequences representative of natural antibodies isolated from canines of various breeds. Canine antibodies are antibodies having variable and constant regions derived from canine germline immunoglobulin sequences. The canine antibodies of the disclosure may include amino acid residues not encoded by canine germline immunoglobulin sequences (e.g., mutations introduced by random or site-specific mutagenesis in vitro or by somatic mutation in vivo), for example in the CDRs and in particular CDR3. However, the term "canine antibody" is not intended to include antibodies in which CDR sequences derived from the germline of another mammalian species, such as a mouse, have been grafted onto canine framework sequences.

The term "caninization" is defined as a method for transferring non-canine antigen-binding amino acids from a donor antibody to a canine antibody acceptor framework to generate protein therapeutic treatments useful in dogs.

The term "caninized antibody" refers to antibodies which comprise heavy and light chain variable region sequences from a non-canine species (e.g., a mouse) but in which at least a portion of the VH and/or VL sequence has been altered to be more "canine-like", i.e., more similar to canine germline variable sequences. One type of caninized antibody is a CDR-grafted antibody, in which non-canine CDR sequences are introduced into canine VH and VL sequences to replace the corresponding canine CDR sequences.

Caninized forms of non-canine antibodies provided herein are canine antibodies that contain sequence derived from a non-canine antibody. For the most part, caninized antibodies are canine antibody sequences ("acceptor" or "recipient" antibody) in which hypervariable region residues of the recipient are replaced by hypervariable region residues from a non-canine species ("donor" antibody) such as mouse, rat, rabbit, cat, goat, chicken, bovine, horse, llama, camel, dromedaries, sharks, non-human primates, human, humanized, recombinant sequence, or an engineered sequence having the desired properties. In some instances, framework region (FR) residues of the canine antibody are replaced by corresponding non-canine FR residues. Furthermore, caninized antibodies may include residues that are not found in the recipient antibody or in the donor antibody. These modifications are made to further refine antibody performance. The caninized antibody may also comprise at least a portion of an immunoglobulin constant region (Fc) of a canine antibody. Strategies for caninization of antibodies include, but are not limited to, the strategies disclosed in WO 2003/060080.

The caninized antibody is an antibody or a variant, derivative, analog or fragment thereof which immunospecifically binds to an antigen of interest and which comprises a framework (FR) region having substantially the amino acid sequence of a canine antibody and a complementary determining region (CDR) having substantially the amino acid sequence of a non-canine antibody. A caninized antibody comprises substantially all of at least one, and typically two, variable domains (Fab, Fab', F(ab')$_2$, FabC, Fv) in which all or substantially all of the CDR regions correspond to those of a non-canine immunoglobulin (i.e., donor antibody) and all or substantially all of the framework regions are those of a canine immunoglobulin consensus sequence. A caninized antibody also comprises at least a portion of an immunoglobulin constant region (Fc), typically that of a canine immunoglobulin. A canine or caninized antibody may contain both the light chain as well as at least the variable domain of a heavy chain. The antibody also may include the CH1, hinge, CH$_2$, CH$_3$, and CH4 regions of the heavy chain. A caninized antibody may only contain a caninized light chain, or may only contain a caninized heavy chain. An exemplary caninized antibody contains a caninized variable domain of a light chain and a caninized variable domain of a heavy chain.

The term "canonical" residue refers to a residue in a CDR or framework that defines a particular canonical CDR structure as defined by Chothia et al. (*J. Mol. Biol.*, 196:901-907 (1987); Chothia et al., *J. Mol. Biol.*, 227:799 (1992). According to Chothia et al., critical portions of the CDRs of many antibodies have nearly identical peptide backbone conformations despite great diversity at the level of amino acid sequence. Each canonical structure specifies primarily a set of peptide backbone torsion angles for a contiguous segment of amino acid residues forming a loop.

The term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain methods described herein use Kabat or Chothia defined CDRs.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "chimeric antibody" refers to antibodies which comprise heavy and light chain variable region sequences from one species and constant region sequences from another species, such as antibodies having murine heavy and light chain variable regions linked to human, canine, equine, or feline constant regions. Chimeric antibodies comprise a portion of the heavy and/or light chain that is identical to or homologous with corresponding sequences from antibodies derived from a particular species or belonging to a particular antibody class or subclass, while the remainder of the chain(s) is identical to or homologous with corresponding sequences in antibodies from another species or belonging to another antibody class or subclass, as well as fragments of such antibodies, exhibiting the desired biological activity (See e.g., U.S. Pat. No. 4,816,567; and Morrison et al., Proc. Natl. Acad. Sci. USA 81:6851-6855 (1984)).

The terms "crystal" and "crystallized" refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is short to allow pairing between the two domains on the same chain, the domains are forced to pair with the complementary domains of another chain and create two antigen-binding sites.

The terms "donor" and "donor antibody" refer to an antibody providing one or more CDRs. A donor antibody may be an antibody from a species different from the antibody from which the framework regions are obtained or derived. In the context of a humanized antibody, the term "donor antibody" refers to a non-human antibody providing one or more CDRs. In the context of a caninized antibody, the term "donor antibody" refers to a non-canine antibody providing one or more CDRs. In the context of a felinized antibody, the term "donor antibody" refers to a non-feline antibody providing one or more CDRs. In the context of a equinized antibody, the term "donor antibody" refers to a non-equine antibody providing one or more CDRs.

The term "epitope" includes any polypeptide determinant capable of specific binding to an immunoglobulin or T-cell receptor. Epitope determinants may include chemically active surface groupings of molecules such as amino acids, sugar side chains, phosphoryl, or sulfonyl, and may have specific three dimensional structural characteristics, and/or specific charge characteristics. An epitope is a region of an antigen that is bound by an antibody. An antibody is said to specifically bind an antigen when it preferentially recognizes its target antigen in a complex mixture of proteins and/or macromolecules.

The term "equine antibody" refers to a naturally-occurring or recombinantly produced immunoglobulin composed of amino acid sequences representative of natural antibodies isolated from equines of various breeds. Equine antibodies are antibodies having variable and constant regions derived from equine germline immunoglobulin sequences. The equine antibodies of the disclosure may include amino acid residues not encoded by equine germline immunoglobulin sequences (e.g., mutations introduced by random or site-specific mutagenesis in vitro or by somatic mutation in vivo), for example in the CDRs and in particular CDR3. However, the term "equine antibody" is not intended to include antibodies in which CDR sequences derived from the germline of another mammalian species, such as a mouse, have been grafted onto equine framework sequences.

The term "equinization" is defined as a method for transferring non-equine antigen-binding amino acids from a donor antibody to an equine antibody acceptor framework to generate protein therapeutic treatments useful in horses.

The term "equinized antibody" refers to antibodies which comprise heavy and light chain variable region sequences from a non-equine species (e.g., a mouse) but in which at least a portion of the VH and/or VL sequence has been altered to be more "equine-like", i.e., more similar to equine germline variable sequences. One type of equinized antibody is a CDR-grafted antibody, in which non-equine CDR sequences are introduced into equine VH and VL sequences to replace the corresponding equine CDR sequences.

Equinized forms of non-equine antibodies provided herein are equine antibodies that contain sequence derived from a non-equine antibody. For the most part, equinized antibodies are equine antibody sequences ("acceptor" or "recipient" antibody) in which hypervariable region residues of the recipient are replaced by hypervariable region residues from a non-equine species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the equine antibody are replaced by corresponding non-equine FR residues. Furthermore, equinized antibodies may include residues that are not found in the recipient antibody or in the donor antibody.

These modifications are made to further refine antibody performance. The equinized antibody may also comprise at least a portion of an immunoglobulin constant region (Fc) of an equine antibody.

The equinized antibody is an antibody or a variant, derivative, analog or fragment thereof which immunospecifically binds to an antigen of interest and which comprises a framework (FR) region having substantially the amino acid sequence of a equine antibody and a complementary determining region (CDR) having substantially the amino acid sequence of a non-equine antibody. An equinized antibody comprises substantially all of at least one, and typically two, variable domains (Fab, Fab', F(ab')2, FabC, Fv) in which all or substantially all of the CDR regions correspond to those of a non-equine immunoglobulin (i.e., donor antibody) and all or substantially all of the framework regions are those of an equine immunoglobulin consensus sequence. An equinized antibody also comprises at least a portion of an immunoglobulin constant region (Fc), typically that of an equine immunoglobulin. An equine or equinized antibody for example may contain both the light chain as well as at least the variable domain of a heavy chain. The antibody also may include the CH1, hinge, CH2, CH3, and CH4 regions of the heavy chain. An equinized antibody may only contain an equinized light chain, or an equinized heavy chain. An exemplary equinized antibody contains an equinized variable domain of a light chain an equinized variable domain of a heavy chain. Equine isotypes include, for example, IgGa, IgGb, IgGc, IgG(T), IgM, IgA The term "Fab" refers to antibody fragments. Papain digestion of antibodies produces two identical antigen-binding fragments, called "Fab" fragments, each with a single antigen-binding site, and a residual "Fc" fragment, whose name reflects its ability to readily crystallize. Pepsin treatment yields a binding cross-linking antigen. The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "feline antibody" refers to a naturally-occurring or recombinantly produced immunoglobulin composed of amino acid sequences representative of natural antibodies isolated from felines of various breeds. Feline antibodies are antibodies having variable and constant regions derived from feline germline immunoglobulin sequences. The feline antibodies of the disclosure may include amino acid residues not encoded by feline germline immunoglobulin sequences (e.g., mutations introduced by random or site-specific mutagenesis in vitro or by somatic mutation in vivo), for example in the CDRs and in particular CDR3. However, the term "feline antibody" is not intended to include antibodies in which CDR sequences derived from the germline of another mammalian species, such as a mouse, have been grafted onto feline framework sequences.

The term "felinization" is defined as a method for transferring non-feline antigen-binding amino acids from a donor antibody to a feline antibody acceptor framework to generate protein therapeutic treatments useful in cats.

The term "felinized antibody" refers to antibodies which comprise heavy and light chain variable region sequences from a non-feline species (e.g., a mouse) but in which at least a portion of the VH and/or VL sequence has been altered to be more "feline-like", i.e., more similar to feline germline variable sequences. One type of felinized antibody is a CDR-grafted antibody, in which non-feline CDR sequences are introduced into feline VH and VL sequences to replace the corresponding feline CDR sequences.

Felinized forms of non-feline antibodies provided herein are feline antibodies that contain sequence derived from a non-feline antibody. For the most part, felinized antibodies are feline antibody sequences ("acceptor" or "recipient" antibody) in which hypervariable region residues of the recipient are replaced by hypervariable region residues from a non-feline species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the feline antibody are replaced by corresponding non-feline FR residues. Furthermore, felinized antibodies may include residues that are not found in the recipient antibody or in the donor antibody. These modifications are made to further refine antibody performance. The felinized antibody may also comprise at least a portion of an immunoglobulin constant region (Fc) of a feline antibody.

The felinized antibody is an antibody or a variant, derivative, analog or fragment thereof which immunospecifically binds to an antigen of interest and which comprises a framework (FR) region having substantially the amino acid sequence of a feline antibody and a complementary determining region (CDR) having substantially the amino acid sequence of a non-feline antibody. A felinized antibody comprises substantially all of at least one, and typically two, variable domains (Fab, Fab', F(ab')2, FabC, Fv) in which all or substantially all of the CDR regions correspond to those of a non-feline immunoglobulin (i.e., donor antibody) and all or substantially all of the framework regions are those of a feline immunoglobulin consensus sequence. A felinized antibody also comprises at least a portion of an immunoglobulin constant region (Fc), typically that of a feline immunoglobulin. A feline or felinized antibody may contain both the light chain as well as at least the variable domain of a heavy chain. The antibody also may include the CH1, hinge, CH2, CH3, and CH4 regions of the heavy chain. A felinized antibody may only contain a felinized light chain or a felinized heavy chain. An exemplary felinized antibody only contains a felinized variable domain of a light chain and a felinized variable domain of a heavy chain.

The term "framework" or "framework sequence" refers to the remaining sequences of a variable region minus the CDRs. Because the exact definition of a CDR sequence may be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. An FR represents one of the four sub-regions, and FRs represents two or more of the four sub-regions constituting a framework region. Human heavy chain and light chain acceptor sequences are known in the art. Canine heavy chain and light chain acceptor sequences are also known (patent application publication WO03/060080 and U.S. Pat. No. 7,261,890B2).

The term "germline antibody gene" or "gene fragment" refers to an immunoglobulin sequence encoded by non-lymphoid cells that have not undergone the maturation process that leads to genetic rearrangement and mutation for expression of a particular immunoglobulin (Shapiro et al., Crit. Rev. Immunol. 22(3): 183-200 (2002); Marchalonis et al., Adv Exp Med. Biol. 484:13-30 (2001)). One of the advantages provided by the binding proteins of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

The term "Fv" refers to the minimum antibody fragment that contains a complete antigen-recognition and binding site. This region consists of a dimer of one heavy chain and one light chain variable domain.

The term "human antibody" refers to antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" is not intended to include antibodies in which CDR sequences derived from the germline of another mammalian species, such as a mouse, have been grafted onto human framework sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which non-human CDR sequences are introduced into human VH and VL sequences to replace the corresponding human CDR sequences.

The humanized antibody is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. A humanized antibody comprises substantially all, or at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. A humanized antibody also comprises at least a portion of an immunoglobulin constant region (Fc), typically that of a human immunoglobulin. A humanized or caninized antibody may contain both the light chain as well as at least the variable domain of a heavy chain. The antibody also may include the CH1, hinge, CH2, CH3, and CH4 regions of the heavy chain. Alternatively, a humanized antibody may only contain a humanized light chain, or a humanized heavy chain. An exemplary humanized antibody contains a humanized variable domain of a light chain and a humanized variable domain of a heavy chain.

The bovanized, camelized, caninized, equinized, felinized, or humanized antibody may be selected from any class of immunoglobulins, including IgM, IgG, IgD, IgA and IgE, and any isotype, including without limitation IgG 1, IgG2, IgG3 and IgG4. The bovanized, camelized, caninized, equinized, felinized, or humanized antibody may comprise sequences from more than one class or isotype, and particular constant domains may be selected to optimize desired effector functions using techniques well-known in the art.

The framework and CDR regions of a bovanized, camelized, caninized, equinized, felinized, or humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. Such mutations, however, will not be extensive. Usually, at least 50%, at least 60%, at least 70%, at least 80%, at least 90% and at least 95% of the bovanized, camelized, caninized, equinized, felinized, or humanized antibody residues will correspond to those of the parental FR and CDR sequences. The term "consensus framework" refers to the framework region in the consensus immunoglobulin sequence. The term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either may be included in the consensus sequence.

The term "hypervariable region" refers to the amino acid residues of an antibody which are responsible for antigen-binding. The hypervariable region comprises amino acid residues from a "complementarity determining region" or "CDR" in the light chain variable domain and in the heavy chain variable domain as defined by Kabat et al., 5th Ed. Public Health Service, National Institutes of Health, Bethesda, Md. (1991) and/or as defined by (Chothia and Lesk, Mol. Biol. 196:901-917 (1987) and/or as defined as "AbM loops" by Martin, et al., Proc. Natl. Acad. Sci. USA, 86:9268-9272 (1989) and/or as defined by Lefranc et al., Nucleic Acids Res, 27:209-212 (1999) in the international ImMunoGeneTics information systems database. "Framework" or "FR" residues are those variable domain residues other than the hypervariable region residues as herein defined.

The term "identity" refers to a relationship between the sequences of two or more polypeptide molecules or two or more nucleic acid molecules, as determined by comparing their sequences thereof, wherein "identity" refers more specifically to the degree of sequence relatedness between nucleic acid molecules or polypeptides, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms") The term "similarity" is used to refer to a related concept with respect to the relationship of two or more nucleic acid molecules or two or more polypeptide molecules. In contrast to "identity," "similarity" refers to a measure of relatedness, which includes both identical matches and conservative substitution matches. For example, for two polypeptide sequences that have 50/100 identical amino acids, and the remainder are all non-conservative substitutions, then the percent identity and similarity would both be 50%. With respect to the same two sequences, if 25 more positions had conservative substitutions, then the percent identity remains 50%, while percent similarity would be 75% (75/100). Identity and similarity of related nucleic acids and polypeptides may be readily calculated by methods well known and readily available in the art, including but are not limited to, those described in COMPUTATIONAL MOLECULAR BIOLOGY, (Lesk, A. M., ed.), 1988, Oxford University Press, New York; BIOCOMPUTING: INFORMATICS AND GENOME PROJECTS, (Smith, D. W., ed.), 1993, Academic Press, New York; COMPUTER ANALYSIS OF SEQUENCE DATA, Part 1, (Griffin, A. M., and Griffin, H. G., eds.), 1994, Humana Press, New Jersey; von Heinje, G., SEQUENCE ANALYSIS IN MOLECULAR BIOLOGY, 1987, Academic Press; SEQUENCE ANALYSIS PRIMER, (Gribskov, M. and Devereux, J., eds.), 1991, M. Stockton Press, New York; Carillo et al., 1988, SIAM J. Applied Math., 48:1073; and Durbin et al., 1998, BIOLOGICAL SEQUENCE ANALYSIS, Cambridge University Press.

Preferred methods to determine identity are designed to provide the highest match between the compared sequences, and are well described in readily publicly available computer programs. Preferred such computerized methods for determining identity between two sequences include, but are not limited to, the GCG program package, including GAP (Devereux et al., 1984, Nucl. Acid. Res., 12:387; Genetics Computer Group, University of Wisconsin, Madison, Wis.), BLASTP, BLASTN, and FASTA (Altschul et al., 1990, J. Mol. Biol., 215:403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990, supra). The well-known Smith Waterman algorithm may also be used to determine identity.

The terms "individual," "patient," and "subject" are used interchangeably herein, to refer to mammals, including, but not limited to, humans, murines, simians, felines, canines, equines, bovines, porcines, ovines, caprines, mammalian farm and agricultural animals, mammalian sport animals, and mammalian pets. Exemplary subjects companion animals, such as a dog, cat or horse.

An "isolated antibody" refers to an antibody that is substantially free of other antibodies having different antigenic specificities (e.g., an isolated antibody that specifically binds NGF is substantially free of antibodies that specifically bind antigens other than NGF). An isolated antibody that specifically binds NGF may, however, have cross-reactivity to other antigens, such as NGF molecules from other species. Moreover, an isolated antibody may be substantially free of other cellular material and/or chemicals.

The terms "isolated polynucleotide" and "isolated nucleic acid" as used interchangeably herein refer to a polynucleotide of genomic, cDNA, or synthetic origin or some combination thereof, which by virtue of its origin is not associated with all or a portion of a polynucleotide in which the isolated polynucleotide is found in nature, or is linked to a another polynucleotide to which it is not linked in nature, or is not found in nature within a larger sequence.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "$K_d$" refers to the dissociation constant of a particular antibody-antigen interaction as is known in the art.

The term "$K_{on}$" is refers to the on rate constant for association of an antibody to the antigen to form the antibody/antigen complex as is known in the art.

The term "$K_{off}$" refers to the off rate constant for dissociation of an antibody from the antibody/antigen complex as is known in the art.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al., Ann. NY Acad, Sci., 190:382-391 (1971); and Kabat et al., Sequences of Proteins of Immunological Interest, Fifth Edition, U.S. Department of Health and Human Services, NIH Publication No. 91-3242 (1991)). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "key residue" refers to certain residues within the variable region that have more impact on the binding specificity and/or affinity of an antibody, in particular a mammalized antibody such as humanized, caninized, equinized or felinized antibody. A key residue includes, but is not limited to, one or more of the following: a residue that is adjacent to a CDR, a potential glycosylation site (may be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "labeled binding protein" refers to a protein with a label incorporated that provides for the identification of the binding protein. In one aspect, the label is a detectable marker, e.g., incorporation of a radiolabeled amino acid or attachment to a polypeptide of biotinyl moieties that may be detected by marked avidin (e.g., streptavidin containing a fluorescent marker or enzymatic activity that may be detected by optical or colorimetric methods). Examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{166}Ho$, $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "mammalization" refers to a method for transferring donor antigen-binding information to a mammalian antibody acceptor to generate useful therapeutic treatments. More specifically, the invention provides methods for felinization, equinization and caninization of antibodies.

The term "mammalized antibody" refers to antibodies which comprise heavy and light chain variable region sequences from a mammal species (e.g., a mouse) but in which at least a portion of the VH and/or VL sequence has been altered to be more like "mammal of interest," see for example, humanized, caninized, equinized or felinized antibodies defined herein. Such mammalized antibodies include, but are not limited to, bovanized, camelized, caninized, equinized, felinized, or humanized antibodies.

The terms "modulate" and "regulate" are used interchangeably and refer to a change or an alteration in the activity of a molecule of interest (e.g., the biological activity of NGF). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

The term "modulator" is a compound capable of changing or altering an activity or function of a molecule of interest (e.g., the biological activity of NGF). For example, a modulator may cause an increase or decrease in the magnitude of a certain activity or function of a molecule compared to the magnitude of the activity or function observed in the absence of the modulator. A modulator may be an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

The term "monoclonal antibody" refers to an antibody that is derived from a single clone, including any eukaryotic, prokaryotic, or phage clone; and not the method by which it is produced and is not limited to antibodies produced through hybridoma technology.

The term "multivalent binding protein" is used in this specification to denote a binding protein comprising two or more antigen binding sites. The multivalent binding protein is engineered to have the three or more antigen binding sites, and is generally not a naturally occurring antibody. The term "multispecific binding protein" refers to a binding protein capable of binding two or more related or unrelated targets. Dual variable domain (DVD) binding proteins are binding proteins that comprise two or more antigen binding sites and are tetravalent or multivalent binding proteins. Such DVDs may be monospecific, i.e capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. patent application Ser. No. 11/507,050 and incorporated herein by reference.

One aspect of the disclosure pertains to a DVD binding protein comprising binding proteins capable of binding NGF. In another aspect, the DVD binding protein is capable of binding NGF and a second target.

The terms "nerve growth factor" and "NGF" refer to nerve growth factor and variants thereof that retain at least part of the biological activity of NGF. NGF includes all mammalian species of native sequence NGF, including murine, rat, human, rabbit, canine, feline, equine, or bovine.

TABLE 1

Sequence of NGF

| Protein | Sequence Identifier |
| --- | --- |
| Canine NGF C-terminal 6-His | SEQ ID NO: 50 |
| Human NGF | SEQ ID NO: 85 |

The term "NGF receptor" refers to a polypeptide that is bound by or activated by NGF. NGF receptors include the TrkA receptor and the p75 receptor of any mammalian species, including, but are not limited to, human, canine, feline, equine, primate, or bovine.

The terms "NGF-related disease" and "NGF-related disorder" encompass any disease or disorder in which the activity of NGF in a subject suffering from the disease or disorder has been shown to be or is suspected of being either responsible for the pathophysiology of the disease or disorder, or a factor that contributes to a worsening of the disease or disorder, which may occur as a result of increased levels of NGF or increased sensitivity of the subject to NGF. Accordingly, an NGF-related disease or NGF-related disorder is a disease or disorder in which reduction of NGF activity is expected to alleviate the symptoms and/or progression of the disease or disorder. Such diseases and disorders may be evidenced, for example, by an increase in the concentration of NGF in a biological fluid of a subject suffering from the disorder (e.g., an increase in the concentration of NGF in serum, plasma, synovial fluid, etc. of the subject), which may be detected, for example, using an anti-NGF antibody as described above. Non-limiting examples of diseases and disorders that may be treated with the antibodies of the disclosure include those diseases and disorders discussed in the section below pertaining to pharmaceutical compositions of the antibodies of the disclosure, and encompass acute pain resulting for example from surgery or other trauma, and chronic pain.

The term "neutralizing" refers to neutralization of biological activity of a NGF when a binding protein specifically binds NGF. A neutralizing binding protein is a neutralizing antibody, whose binding to NGF results in inhibition of a biological activity of NGF. The neutralizing binding protein binds NGF and reduces a biologically activity of NGF by at least about 20%, 40%, 60%, 80%, 85% or more Inhibition of a biological activity of NGF by a neutralizing binding protein may be assessed by measuring one or more indicators of NGF biological activity well known in the art, including cell proliferation, cell morphology changes, cell signaling, or any detectable cellular response resulting from binding of NGF to the TrkA receptor.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and may also include additional components whose presence is advantageous, for example, leader sequences and fusion partner sequences.

The term "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The term "polynucleotide" means a polymeric form of two or more nucleotides, either ribonucleotides or deoxynucleotides or a modified form of either type of nucleotide. The term includes single and double stranded forms of DNA. The term "isolated polynucleotide" shall mean a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "polypeptide" refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "prophylactically effective amount" refers to an amount effective, at dosages and for periods of time necessary, to achieve the desired prophylactic result.

The term "recombinant host cell" (or simply "host cell") is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell". In one aspect, host cells include prokaryotic and eukaryotic cells selected from any of the Kingdoms of life. Eukaryotic cells include protist, fungal, plant and animal cells. In another aspect host cells include, but are not limited to, the prokaryotic cell line *E. Coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

The term "recombinant antibody" refers to all species of antibodies or immunoglobulins that are prepared, expressed, created or isolated by recombinant means, such as antibodies expressed using a recombinant expression vector transfected into a host cell, antibodies isolated from a recombinant, combinatorial human antibody library (Hoogenboom, *TIB Tech.*, 15: 62-70 (1997); Azzazy et al., *Clin. Biochem.*, 35: 425-445 (2002); Gavilondo et al., *BioTechniques*, 29: 128-145 (2002); Hoogenboom et al., *Immunology Today*, 21: 371-378 (2000)), antibodies isolated from an animal (e.g., a mouse) that is transgenic for human immunoglobulin genes (see e.g., Taylor, L. D., et al. (1992) Nucl. Acids Res. 20:6287-6295; Kellermann et al., *Current Opinion in Biotechnology*, 13: 593-597 (2002); Little et al., *Immunology Today*, 21: 364-370 (2000)) or antibodies prepared, expressed, created or isolated by any other means that involves splicing of immunoglobulin gene sequences to other DNA sequences. Such recombinant antibodies have variable and constant regions derived from species-specific germline immunoglobulin sequences. Such recombinant antibodies may be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to species-specific germline VH and VL sequences, may not naturally exist within the antibody germline repertoire in vivo.

The term "recovering" refers to the process of rendering a chemical species such as a polypeptide substantially free of naturally associated components by isolation, e.g., using protein purification techniques well known in the art.

The term "sample" is used in its broadest sense. A "biological sample" includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

The term "single-chainFv" or "scFv" refers to antibody fragments comprising the VH and VL domains of antibody, wherein these domains are present in a single polypeptide chain. Generally, the Fv polypeptide further comprises a polypeptide linker between the VH and VL domains which enables the sFv to form the desired structure for antigen binding. For a review of scFv, see Pluckthun in The Pharmacology of Monoclonal Antibodies, vol. 113, Rosenburg and Moore eds. Springer-Verlag, New York, pp. 269-315 (1994).

The terms "specific binding" or "specifically binding" in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "substantially" in the context of a CDR refers to a CDR having an amino acid sequence at least 80%, at least 85%, at least 90%, at least 95%, at least 98% or at least 99% identical to the amino acid sequence of a non-human antibody CDR.

The term "surface plasmon resonance" refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions (Jönsson, et al. *Ann. Biol. Clin.* 51: 19-26 (1993); Jönsson, et al., *Biotechniques* 11: 620-627 (1991); Johnsson, et al., *J. Mol. Recognit.* 8:125-131 (1995); and Johnnson, B., et al., *Anal. Biochem.*, 198: 268-277 (1991)).

The term "therapeutically effective amount" refers to an amount effective, at dosages and for periods of time necessary, to achieve the desired therapeutic result. A therapeutically effective amount may be the amount and/or duration of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects.

The term "transformation" refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "transgenic organism" refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors are capable of directing the expression of genes to which they are operatively linked Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "Vernier zone" refers to a subset of framework residues that may adjust CDR structure and fine-tune the fit to antigen as described by Foote and Winter (1992, *J. Mol. Biol.* 224:487-499, which is incorporated herein by reference). Vernier zone residues form a layer underlying the CDRs and may impact on the structure of CDRs and the affinity of the antibody.

B. ANTI NGF BINDING PROTEINS

The present disclosure provides a novel family of binding proteins, murine antibodies, CDR grafted antibodies, mammalized (bovanized, camelized, caninized, equinized, felinized, or humanized) antibodies, and fragments thereof, capable of binding and modulating the biological activity or function of NGF, including the capability of neutralizing NGF. The disclosure thus also provides a therapeutic means with which to inhibit NGF and provides compositions and methods for treating disease associated with increased levels of NGF, particularly a disease, condition or disorder where increased levels of NGF, as compared to NGF levels observed in comparable normal subjects, is detrimental.

Binding proteins of the present disclosure may be made by any of a number of techniques known in the art and as described herein, including culturing a host cell described herein in culture medium under conditions sufficient to produce a binding protein capable of binding NGF.

Monoclonal antibodies may be prepared using a wide variety of techniques known in the art including the use of hybridoma, recombinant, and phage display technologies, or a combination thereof. For example, monoclonal antibodies may be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981).

Methods for producing and screening for specific antibodies using hybridoma technology are well known in the art. Such methods include, for example, culturing a hybridoma cell secreting an antibody of the disclosure wherein the hybridoma is generated by fusing splenocytes isolated from a mouse immunized with an antigen of the disclosure with myeloma cells and then screening the hybridomas resulting from the fusion for hybridoma clones that secrete an antibody able to bind a polypeptide of the disclosure. Briefly, or example, mice may be immunized with an NGF antigen. The NGF antigen may be administered, with or without an adjuvant, to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. If a polypeptide is being administered, the immunization schedule will involve two or more administrations of the polypeptide, spread out over several weeks.

After immunization of an animal with an NGF antigen, antibodies and/or antibody-producing cells may be obtained from the animal. An anti-NGF antibody-containing serum may be obtained from the animal by bleeding or sacrificing the animal. The serum may be used as it is obtained from the animal, an immunoglobulin fraction may be obtained from the serum, or the anti-NGF antibodies may be purified from the serum. Serum or immunoglobulins obtained in this manner are polyclonal, thus having a heterogeneous array of properties.

Once an immune response is detected, e.g., antibodies specific for the antigen NGF are detected in the mouse serum, the mouse spleen may be harvested and splenocytes isolated. The splenocytes are then fused by well-known techniques to any suitable myeloma cells, such as, for example, cells from cell line SP20 available from the ATCC. Hybridomas may be selected and cloned by limited dilution. The hybridoma clones may then be assayed by methods known in the art for cells that secrete antibodies capable of binding NGF. Ascites fluid, which generally contains high levels of antibodies, may be generated by immunizing mice with positive hybridoma clones.

Antibody-producing immortalized hybridomas may be prepared from the immunized animal. After immunization, the animal may be sacrificed and the splenic B cells fused to immortalized myeloma cells as is well known in the art (Harlow et al., supra). Alternatively, the myeloma cells may be from a non-secretory cell line and do not secrete immunoglobulin polypeptides. After fusion and antibiotic selection, the hybridomas may be screened using NGF, or a portion thereof, or a cell expressing NGF. Initial screening may be performed, for example, using an enzyme-linked immunoassay (ELISA) or a radioimmunoassay (RIA). An example of ELISA screening is provided in WO 00/37504.

Anti-NGF antibody-producing hybridomas may be selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

An exemplary animal system for preparing hybridomas is the mouse. Hybridoma production in the mouse is very well established, and immunization protocols and techniques for isolation of immunized splenocytes for fusion are well known. Fusion partners (e.g., murine myeloma cells) and fusion procedures are also known. Alternatively, the hybridomas may be produced in a non-human, non-mouse species such as a rat, sheep, pig, goat, cattle or horse. Alternatively, human hybridomas may be produced, in which a human non-secretory myeloma is fused with a human cell expressing an anti-NGF antibody.

Antibody fragments that recognize specific epitopes may be generated by known techniques. For example, Fab and F(ab')2 fragments of the disclosure may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

Recombinant antibodies may be generated from single, isolated lymphocytes using a procedure referred to in the art as the selected lymphocyte antibody method (SLAM), as described in U.S. Pat. No. 5,627,052, PCT Publication WO 92/02551 and Babcock et al., Proc. Natl. Acad. Sci., 93: 7843-7848 (1996). In this method, single cells secreting antibodies of interest, e.g., lymphocytes derived from any one of the immunized animals described in Section 1, are screened using an antigen-specific hemolytic plaque assay, wherein the antigen NGF, or a fragment thereof, is coupled to sheep red blood cells using a linker, such as biotin, and used to identify single cells that secrete antibodies with specificity for NGF. Following identification of antibody-secreting cells of interest, heavy- and light-chain variable region cDNAs may be rescued from the cells by reverse transcriptase-PCR and these variable regions may then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, may then undergo further analysis and selection in vitro, for example by panning the transfected cells to isolate cells expressing antibodies to NGF. The amplified immunoglobulin sequences further may be manipulated in vitro, such as by in vitro affinity maturation methods such as those described in PCT Publication WO 97/29131 and PCT Publication WO 00/56772.

Antibodies may be produced by immunizing a non-human animal comprising some or all of the human immunoglobulin loci with an NGF antigen. For example, human monoclonal antibodies directed against NGF may be generated using transgenic mice carrying parts of the human immune system rather than the mouse system, referred to in the literature and herein as "HuMab" mice, contain a human immunoglobulin gene minilocus that encodes unrearranged human heavy (μ and γ) and κ light chain immunoglobulin sequences, together with targeted mutations that inactivate the endogenous μ and κ chain loci (Lonberg et al., 1994, Nature 368:856-859). These mice exhibit reduced expression of mouse IgM or κ and in response to immunization, and the introduced human heavy chain and light chain transgenes undergo class switching and somatic mutation to generate high affinity human IgG κ monoclonal antibodies. The preparation of HuMab mice is well described in the literature. (See, e.g., Lonberg et al., 1994, Nature 368:856-859; Lonberg, 1994, Handbook of Exp. Pharmacology 113: 49-101; Taylor et al., 1994, International Immunology 6:579-591; Lonberg & Huszar, 1995, Intern. Rev. Immunol. 13:65-93; and Harding & Lonberg, 1995, Ann. N.Y. Acad. Sci. 764:536-546). Alternatively, other known mouse strains such as the HCo7, HCo12, and KM transgenic mice strains may be used to generate human anti-NGF antibodies. Another suitable, though non-limiting example of a transgenic mouse is the XENOMOUSE® transgenic mouse, which is an engineered mouse strain that comprises large fragments of the human immunoglobulin loci and is deficient in mouse antibody production. See, e.g., Green et al. *Nature Genetics,* 7:13-21 (1994); and U.S. Pat. Nos. 5,916,771, 5,939,598, 5,985,615, 5,998,209, 6,075,181, 6,091,001, 6,114,598 and 6,130,364; WO 91/10741, WO 94/02602, WO 96/34096, WO 96/33735, WO 98/16654, WO 98/24893, WO 98/50433, WO 99/45031, WO 99/53049, WO 00 09560, and WO 00/037504. The XENOMOUSE® transgenic mouse produces an adult-like human repertoire of fully human antibodies, and generates antigen-specific human Mabs. The XENOMOUSE® transgenic mouse contains approximately 80% of the human antibody repertoire through introduction of megabase sized, germline configuration YAC fragments of the human heavy chain loci and light chain loci (Mendez et al., *Nature Genetics* 15:146-156 (1997), Green et al., *J. Exp. Med.,* 188: 483-495 (1998)).

In vitro methods also may be used to make the antibodies of the disclosure, wherein an antibody library is screened to identify an antibody having the desired binding specificity. Methods for such screening of recombinant antibody libraries are well known in the art and include methods described in, for example, U.S. Pat. No. 5,223,409; PCT Publication Nos. WO 92/18619; WO 91/17271; WO 92/20791; WO 92/15679; WO 93/01288; WO 92/01047; WO 92/09690; Fuchs et al. *Bio/Technology,* 9:1370-1372 (1991); Hay et al., *Hum Antibod Hybridomas,* 3: 81-85 (1992); Huse et al., *Science,* 246: 1275-1281 (1989); McCafferty et al., *Nature,* 348: 552-554 (1990); Griffiths et al., *EMBO J.,* 12: 725-734 (1993); Hawkins et al., *J Mol Biol.,* 226: 889-896 (1992); Clackson et al., *Nature,* 352: 624-628 (1991); Gram et al., *PNAS,* 89: 3576-3580 (1992); Garrad et al., *Bio/Technology,* 9:1373-1377 (1991); Hoogenboom et al., *Nuc Acid Res,* 19: 4133-4137 (1991); and Barbas et al., *PNAS,* 88: 7978-7982 (1991), US patent application publication 20030186374, and PCT Publication No. WO 97/29131.

The recombinant antibody library may be from a subject immunized with NGF, or a portion of NGF. Alternatively, the recombinant antibody library may be from a naïve subject that has not been immunized with NGF, such as a canine antibody library from a canine subject that has not been immunized with canine NGF. Antibodies of the disclosure are selected by screening the recombinant antibody library with the peptide comprising canine NGF to thereby select those antibodies that recognize NGF. Methods for conducting such screening and selection are well known in the art, such as described in the references in the preceding paragraph. To select antibodies of the disclosure having particular binding affinities for hNGF, such as those that dissociate from canine NGF with a particular $k_{off}$ rate constant, the art-known method of surface plasmon resonance may be used to select antibodies having the desired $k_{off}$ rate constant. To select antibodies of the disclosure having a particular neutralizing activity for hNGF, such as those with a particular an $IC_{50}$, standard methods known in the art for assessing the inhibition of hNGF activity may be used.

For example, the antibodies of the present disclosure may also be generated using various phage display methods known in the art. In phage display methods, functional antibody domains are displayed on the surface of phage particles which carry the polynucleotide sequences encoding them. In a particular aspect, such phage may be utilized to display antigen-binding domains expressed from a repertoire or combinatorial antibody library (e.g., canine, human or murine). Phage expressing an antigen binding domain that binds the antigen of interest may be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that may be used to make the antibodies of the present disclosure include those disclosed in Brinkman et al., *J. Immunol. Methods,* 182: 41-50 (1995); Ames et al., *J. Immunol. Methods,* 184: 177-186 (1995); Kettleborough et al., *Eur. J. Immunol.,* 24:952-958 (1994); Persic et al., *Gene,* 187: 9-18 (1997); Burton et al., *Advances in Immunology,* 57: 191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780, 225; 5,658,727; 5,733,743 and 5,969,108.

As described in the above references, after phage selection, the antibody coding regions from the phage may be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments may also be employed using methods known in the art such as those disclosed in PCT publication WO 92/22324; Mullinax et al., *BioTechniques,* 12(6):864-869 (1992); and Sawai et al., AJRI 34:26-34 (1995); and Better et al., *Science,* 240:1041-1043 (1988) (said references incorporated by reference in their entireties). Examples of techniques which may be used to produce single-chain Fvs and antibodies include those described in U.S. Pat. Nos. 4,946,778 and 5,258, 498; Huston et al., *Methods in Enzymology,* 203:46-88 (1991); Shu et al., *PNAS,* 90:7995-7999 (1993); and Skerra et al., *Science,* 240:1038-1040 (1988).

Alternatives to screening of recombinant antibody libraries by phage display are known and include other methodologies for screening large combinatorial libraries which may be applied to the identification of dual specificity antibodies of the disclosure. One type of alternative expression system is one in which the recombinant antibody library is expressed as RNA-protein fusions, as described in PCT Publication No. WO 98/31700, and in Roberts et al., *Proc. Natl. Acad. Sci.,* 94:12297-12302 (1997). In this system, a covalent fusion is created between a mRNA and the peptide or protein that it encodes by in vitro translation of synthetic mRNAs that carry puromycin, a peptidyl acceptor antibiotic, at their 3' end. Thus, a specific mRNA may be enriched from a complex mixture of mRNAs (e.g., a combinatorial library) based on the properties of the encoded peptide or protein, e.g., antibody, or portion thereof, such as binding of the antibody, or portion thereof, to the dual specificity antigen.

Nucleic acid sequences encoding antibodies, or portions thereof, recovered from screening of such libraries may be expressed by recombinant means as described above (e.g., in mammalian host cells) and, moreover, may be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present disclosure may also be generated or affinity matured using yeast display methods known in the art. In yeast display methods, genetic methods are used to tether antibody domains to the yeast cell wall and display them on the surface of yeast. In particular, such yeast may be utilized to display antigen-binding domains expressed from a repertoire or combinatorial antibody library (e.g., human or murine). Examples of yeast display methods that may be used to make the antibodies of the present disclosure include those disclosed Wittrup, et al. U.S. Pat. No. 6,699,658 incorporated herein by reference.

The antibodies or antigen binding fragments described herein may also be produced by genetic engineering. For example, the technology for expression of both heavy and light chain genes in *E. coli* is the subject of the PCT patent applications: publication number WO 901443, WO901443, and WO 9014424 and in Huse et al., 1989 Science 246: 1275-81. The present disclosure thus also encompasses the isolated nucleic acids encoding any of the binding proteins described herein, as well as a recombinant vector comprising such a nucleic acid molecule, and a host cell comprising such a recombinant vector.

A vector is a nucleic acid molecule, which may be a construct, capable of transporting another nucleic acid to which it has been linked. A vector may include any preferred or required operational elements. Preferred vectors are those for which the restriction sites have been described and which contain the operational elements needed for transcription of the nucleic acid sequence. Such operational elements include for example at least one suitable promoter, at least one operator, at least one leader sequence, at least one terminator codon, and any other DNA sequences necessary or preferred for appropriate transcription and subsequent translation of the nucleic acid sequence. Such vectors contain at least one origin of replication recognized by the host organism along with at least one selectable marker and at least one promoter sequence capable of initiating transcription of the nucleic acid sequence. A vector may be a plasmid into which additional DNA segments may be ligated. A vector may be a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as a plasmid is the most commonly used form of vector. However, the present disclosure is intended to include such other forms of expression vectors, such as viral vectors (e.g., replication defective retroviruses, adenoviruses and adeno-associated viruses), which serve equivalent functions. By way of example and not limitation, suitable vectors include pcDNA, pTT (Durocher et al., Nucleic Acids Research, Vol 30, No. 2 (2002)); pTT3 (pTT with additional multiple cloning site, pEFBOS (Mizushima et al., Nucleic acids Research, Vol 18, No. 17 (1990)), pBV, pJV, pBJ, or pHybE (patent publication no.: US 2009/0239259 A1).

Sequences that are operably linked are in a relationship permitting them to function in their intended manner. A control sequence operably linked to a coding sequence is ligated in such a way that expression of the coding sequence is achieved under conditions compatible with the control sequences. Operably linked sequences include both expression control sequences that are contiguous with the gene of interest and expression control sequences that act in trans or at a distance to control the gene of interest. Expression control sequences are polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, such control sequences generally include promoters and transcription termination sequence. Control sequences may include components whose presence is essential for expression and processing, and may also include additional components whose presence is advantageous, for example, leader sequences and fusion partner sequences.

A host cell may be transformed with a vector that introduces exogenous DNA into a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, calcium-phosphate precipitation, DEAE-dextran transfection, particle bombardment and the like. Transformed cells include stably transformed cells in which the inserted DNA is capable of replication either as an autonomously replicating plasmid or as part of the host chromosome, and cells which transiently express the inserted DNA or RNA for limited periods of time.

Host organisms such as host cells are cultured under conditions appropriate for amplification of the vector and expression of the protein, as well known in the art. Expressed recombinant proteins may be detected by any of a number of methods also well known in the art.

Suitable host organisms include for example a prokaryotic or eukaryotic cell system. A eukaryotic cell may be a protist cell, animal cell, plant cell or fungal cell. A eukaryotic cell is for example an animal cell which may be a mammalian cell, avian cell, or an insect cell such as an insect Sf9 cell. Cells from established and readily available may be used, such as but not limited to HeLa, MRC-5 or CV-1. The host cell may be an *E. coli* cell, or a yeast cell such as but not limited to *Saccharomyces cerevisiae*. Mammalian host cells for expressing the recombinant antibodies of the disclosure also include Chinese Hamster Ovary (CHO cells) (including dhfr-CHO cells, described in Urlaub et al., *Proc. Natl. Acad. Sci.*, 77: 4216-4220 (1980), used with a DHFR selectable marker, e.g., as described in Kaufman et al., *Mol. Biol.*, 159: 601-621 (1982)), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells, or by secretion of the antibody into the culture medium in which the host cells are grown. Antibodies may be recovered from the culture medium using standard protein purification methods.

Host cells may also be used to produce functional antibody fragments, such as Fab fragments or scFv molecules. It will be understood that variations on the above procedure are within the scope of the present disclosure. For example, it may be desirable to transfect a host cell with DNA encoding functional fragments of either the light chain and/or the heavy chain of an antibody of this disclosure. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure and the other heavy and light chain are specific for an antigen other than the antigens of interest by crosslinking an antibody of the disclosure to a second antibody by standard chemical cross-linking methods.

In a system for recombinant expression of an antibody, or antigen-binding portion thereof, of the disclosure, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the disclosure provides a method of synthesizing a recombinant antibody of the disclosure by culturing a host cell of the disclosure in a suitable culture medium until a recombinant antibody of the disclosure is synthesized. The method may further comprise isolating the recombinant antibody from the culture medium.

The present disclosure thus provides anti NGF binding proteins that are specific for and substantially neutralize NGF polypeptides, including active human NGF. Also provided are antibody heavy and light chain amino acid sequences which are substantially specific for and substantially neutralize NGF polypeptides when they are bound to them. This specificity enables the anti-human NGF human antibodies, and human monoclonal antibodies with like specificity, to be effective immunotherapy for NGF associated diseases.

The present disclosure encompasses anti NGF binding proteins comprising at least one of the amino acid sequences selected from the group consisting of: SEQ ID NO: 2, SEQ ID NO: 6, SEQ ID NO: 10, SEQ ID NO: 14, SEQ ID NO: 18, SEQ ID NO: 22, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 165, SEQ ID NO: 166, SEQ ID NO: 167, SEQ ID NO: 168, SEQ ID NO: 169, SEQ ID NO: 170, SEQ ID NO: 177, SEQ ID NO: 179, SEQ ID NO: 180, SEQ ID NO: 182, SEQ ID NO: 184, SEQ ID NO: 185, SEQ ID NO: 187, SEQ ID NO: 189, SEQ ID NO: 190, SEQ ID NO: 192, SEQ ID NO: 195, SEQ ID NO: 197, SEQ ID NO: 199, SEQ ID NO: 201, SEQ ID NO: 203, SEQ ID NO: 206, SEQ ID NO: 207 and SEQ ID NO: 4, SEQ ID NO: 8, SEQ ID NO: 12, SEQ ID NO: 16, SEQ ID NO: 20, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, and SEQ ID NO: 44, SEQ ID NO: 171, SEQ ID NO: 172, SEQ ID NO: 173, SEQ ID NO: 174, SEQ ID NO: 175, SEQ ID NO: 176, SEQ ID NO: 181, SEQ ID NO: 183, SEQ ID NO: 186, SEQ ID NO: 188, SEQ ID NO: 191, SEQ ID NO: 193, SEQ ID NO: 194, SEQ ID NO: 196, SEQ ID NO:198, SEQ ID NO: 200, SEQ ID NO: 202, and which binds an NGF polypeptide epitope with substantially high affinity as described herein and has the capacity to substantially modulate, including substantially reduce, NGF polypeptide activity.

Examples of such binding proteins include binding proteins comprising a variable heavy chain polypeptide comprising an amino acid sequence selected from the group consisting of SEQ ID NO:2, SEQ ID NO: 6, SEQ ID NO: 10, SEQ ID NO: 14, SEQ ID NO: 18, SEQ ID NO: 22, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 165, SEQ ID NO: 166, SEQ ID NO: 167, SEQ ID NO: 168, SEQ ID NO: 169, SEQ ID NO: 170, SEQ ID NO: 177, SEQ ID NO: 179, SEQ ID NO: 180, SEQ ID NO: 182, SEQ ID NO: 184, SEQ ID NO: 185, SEQ ID NO: 187, SEQ ID NO: 189, SEQ ID NO: 190, SEQ ID NO: 192, SEQ ID NO: 195, SEQ ID NO: 197, SEQ ID NO: 199, SEQ ID NO: 201, SEQ ID NO: 203, SEQ ID NO: 206 and SEQ ID NO: 207; and a variable light chain polypeptide comprising an amino acid sequence selected from the group consisting of SEQ ID NO: 4, SEQ ID NO: 8, SEQ ID NO: 12, SEQ ID NO: 16, SEQ ID NO: 20, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, and SEQ ID NO: 44, SEQ ID NO: 171, SEQ ID NO: 172, SEQ ID NO: 173, SEQ ID NO: 174, SEQ ID NO: 175, SEQ ID NO: 176, SEQ ID NO: 181, SEQ ID NO: 183, SEQ ID NO: 186, SEQ ID NO: 188, SEQ ID NO: 191, SEQ ID NO: 193, SEQ ID NO: 194, SEQ ID NO: 196, SEQ ID NO: 198, SEQ ID NO: 200 and SEQ ID NO: 202.

Exemplary pairings of a variable heavy chain polypeptide and a variable light chain polypeptide are represented by the following pairings: SEQ ID NO: 2 and SEQ ID NO: 4; SEQ ID NO: 6 and SEQ ID NO: 8; SEQ ID NO: 10 and SEQ ID NO: 12; SEQ ID NO: 14 and SEQ ID NO: 16; SEQ ID NO: 18 and SEQ ID NO: 20; SEQ ID NO: 22 and SEQ ID NO: 24; SEQ ID NO: 25 and SEQ ID NO: 26; SEQ ID NO: 27 and SEQ ID NO: 28; SEQ ID NO: 29 and SEQ ID NO: 30; SEQ ID NO: 31 and SEQ ID NO: 32; SEQ ID NO: 177 and SEQ ID NO: 32; SEQ ID NO: 33 and SEQ ID NO: 34, SEQ ID NO: 35 and SEQ ID NO:36; SEQ ID NO: 37 and SEQ ID NO: 38; SEQ ID NO: 39 and SEQ ID NO: 40; SEQ ID NO: 41 and SEQ ID NO: 42; SEQ ID NO: 43 and SEQ ID NO: 44; SEQ ID NO: 180 and SEQ ID NO: 181, SEQ ID NO: 182 and SEQ ID NO: 183; SEQ ID NO: 185 and SEQ ID NO: 186; SEQ ID NO: 187 and SEQ ID NO: 188; and SEQ ID NO: 192 and SEQ ID NO: 193.

Also encompassed in the disclosure are binding proteins that specifically bind NGF as described herein and comprise a heavy chain variable region having at least 90%, at least 91%, at least 92%, at least 93%, at least 94%, at least 95%, at least 96%, at least 97%, at least 98%, or at least 99% identity with any of SEQ ID NO: 2, SEQ ID NO: 6, SEQ ID NO: 10, SEQ ID NO: 14, SEQ ID NO: 18, SEQ ID NO: 22, SEQ ID NO: 25, SEQ ID NO:27, SEQ ID NO: 29, SEQ ID NO:31, SEQ ID NO:33, SEQ ID NO:35, SEQ ID NO: 37, SEQ ID NO: 39, SEQ ID NO: 41, SEQ ID NO: 43, SEQ ID NO: 165, SEQ ID NO: 166, SEQ ID NO: 167, SEQ ID NO: 168, SEQ ID NO: 169, SEQ ID NO: 170, SEQ ID NO: 177, SEQ ID NO: 179, SEQ ID NO: 180, SEQ ID NO: 182, SEQ ID NO: 184, SEQ ID NO: 185, SEQ ID NO: 187, SEQ ID NO: 189, SEQ ID NO: 190, SEQ ID NO: 192, SEQ ID NO: 195, SEQ ID NO: 197, SEQ ID NO: 199, SEQ ID NO: 201, SEQ ID NO: 203, SEQ ID NO: 206, SEQ ID NO: 207. Also encompassed are binding proteins that specifically bind NGF as described herein and comprise a light chain variable region having at least 90%, at least 91%, at least 92%, at least 93%, at least 94%, at least 95%, at least 96%, at least 97%, at least 98%, or at least 99% identity with any of SEQ ID NO: 4, SEQ ID NO: 8, SEQ ID NO: 12, SEQ ID NO: 16, SEQ ID NO: 20, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, and SEQ ID NO: 44, SEQ ID NO: 171, SEQ ID NO: 172, SEQ ID NO: 173, SEQ ID NO: 174, SEQ ID NO: 175, SEQ ID NO: 176, SEQ ID NO: 181, SEQ ID NO: 183, SEQ ID NO: 186, SEQ ID NO: 188, SEQ ID NO: 191, SEQ ID NO: 193, SEQ ID NO: 194, SEQ ID NO: 196, SEQ ID NO: 198, SEQ ID NO: 200, SEQ ID NO: 202.

Exemplary binding proteins that specifically bind NGF as described herein preferably comprise a heavy chain variable region and a light chain variable region as follows:

a heavy chain variable region comprising an amino acid sequence having at least 90% identity with SEQ ID NO: 2, or an antigen-binding or an immunologically functional immunoglobulin fragment thereof, and the light chain variable region comprising an amino acid sequence having at least 90% identity with SEQ ID NO: 4 or an antigen-binding or an immunologically functional immunoglobulin fragment thereof;

a heavy chain variable region comprising an amino acid sequence having at least 90% identity with SEQ ID NO: 6 or an antigen-binding or an immunologically functional immunoglobulin fragment thereof, and a light chain variable region comprising an amino acid sequence having at least 90% identity with SEQ ID NO: 8 or an antigen-binding or an immunologically functional immunoglobulin fragment thereof;

a heavy chain variable region comprising an amino acid sequence having at least 90% identity with SEQ ID NO: 10 or an antigen-binding or an immunologically functional immunoglobulin fragment thereof, and a light chain variable region comprising an amino acid sequence having at least 90% identity with SEQ ID NO: 12 or an antigen-binding or an immunologically functional immunoglobulin fragment thereof;

a heavy chain variable region comprising an amino acid sequence having at least 90% identity with SEQ ID NO: 14 or an antigen-binding or an immunologically functional immunoglobulin fragment thereof, and a light chain variable region comprising an amino acid sequence having at least 90% identity with SEQ ID NO: 16 or an antigen-binding or an immunologically functional immunoglobulin fragment thereof;

a heavy chain variable region comprising an amino acid sequence having at least 90% identity with SEQ ID NO: 18 or an antigen-binding or an immunologically functional immunoglobulin fragment thereof, and a light chain variable region comprising an amino acid sequence having at least 90% identity with SEQ ID NO: 20 or an antigen-binding or an immunologically functional immunoglobulin fragment thereof;

a heavy chain variable region comprising an amino acid sequence having at least 90% identity with SEQ ID NO: 22 or an antigen-binding or an immunologically functional immunoglobulin fragment thereof, and a light chain variable region comprising an amino acid sequence having at least 90% identity with SEQ ID NO: 24 or an antigen-binding or an immunologically functional immunoglobulin fragment thereof;

a heavy chain variable region comprising an amino acid sequence having at least 90% identity with SEQ ID NO: 25 or an antigen-binding or an immunologically functional immunoglobulin fragment thereof, and a light chain variable region comprising an amino acid sequence having at least 90% identity with SEQ ID NO: 26 or an antigen-binding or an immunologically functional immunoglobulin fragment thereof;

a heavy chain variable region comprising an amino acid sequence having at least 90% identity with SEQ ID NO: 27 or an antigen-binding or an immunologically functional immunoglobulin fragment thereof, and a light chain variable region comprising an amino acid sequence having at least 90% identity with SEQ ID NO: 28 or an antigen-binding or an immunologically functional immunoglobulin fragment thereof;

a heavy chain variable region comprising an amino acid sequence having at least 90% identity with SEQ ID NO: 29 or an antigen-binding or an immunologically functional immunoglobulin fragment thereof, and a light chain variable region comprising an amino acid sequence having at least 90% identity with SEQ ID NO: 30 or an antigen-binding or an immunologically functional immunoglobulin fragment thereof;

a heavy chain variable region comprising an amino acid sequence having at least 90% identity with SEQ ID NO: 31 or an antigen-binding or an immunologically functional immunoglobulin fragment thereof, and a light chain variable region comprising an amino acid sequence having at least 90% identity with SEQ ID NO: 32 or an antigen-binding or an immunologically functional immunoglobulin fragment thereof;

a heavy chain variable region comprising an amino acid sequence having at least 90% identity with SEQ ID NO: 177 or an antigen-binding or an immunologically functional immunoglobulin fragment thereof, and a light chain variable region comprising an amino acid sequence having at least 90% identity with SEQ ID NO: 32 or an antigen-binding or an immunologically functional immunoglobulin fragment thereof;

a heavy chain variable region comprising an amino acid sequence having at least 90% identity with SEQ ID NO: 33 or an antigen-binding or an immunologically functional immunoglobulin fragment thereof, and a light chain variable region comprising an amino acid sequence having at least 90% identity with SEQ ID NO: 34 or an antigen-binding or an immunologically functional immunoglobulin fragment thereof;

a heavy chain variable region comprising an amino acid sequence having at least 90% identity with SEQ ID NO: 35 or an antigen-binding or an immunologically functional immunoglobulin fragment thereof, and a light chain variable region comprising an amino acid sequence having at least 90% identity with SEQ ID NO: 36 or an antigen-binding or an immunologically functional immunoglobulin fragment thereof;

a heavy chain variable region comprising an amino acid sequence having at least 90% identity with SEQ ID NO: 37 or an antigen-binding or an immunologically functional immunoglobulin fragment thereof, and a light chain variable region comprising an amino acid sequence having at least 90% identity with SEQ ID NO: 38 or an antigen-binding or an immunologically functional immunoglobulin fragment thereof;

a heavy chain variable region comprising an amino acid sequence having at least 90% identity with SEQ ID NO: 39 or an antigen-binding or an immunologically functional immunoglobulin fragment thereof, and a light chain variable region comprising an amino acid sequence having at least 90% identity with SEQ ID NO: 40 or an antigen-binding or an immunologically functional immunoglobulin fragment thereof;

a heavy chain variable region comprising an amino acid sequence having at least 90% identity with SEQ ID NO: 41 or an antigen-binding or an immunologically functional immunoglobulin fragment thereof, and a light chain variable region comprising an amino acid sequence having at least 90% identity with SEQ ID NO: 42 or an antigen-binding or an immunologically functional immunoglobulin fragment thereof;

a heavy chain variable region comprising an amino acid sequence having at least 90% identity with SEQ ID NO: 43 or an antigen-binding or an immunologically functional immunoglobulin fragment thereof, and a light chain variable region comprising an amino acid sequence having at least 90% identity with SEQ ID NO: 44 or an antigen-binding or an immunologically functional immunoglobulin fragment thereof;

a heavy chain variable region comprising an amino acid sequence having at least 90% identity with SEQ ID NO: 180 or an antigen-binding or an immunologically functional immunoglobulin fragment thereof, and a light chain variable region comprising an amino acid sequence having at least 90% identity with SEQ ID NO: 181 or an antigen-binding or an immunologically functional immunoglobulin fragment thereof;

a heavy chain variable region comprising an amino acid sequence having at least 90% identity with SEQ ID NO: 182 or an antigen-binding or an immunologically functional immunoglobulin fragment thereof, and a light chain variable region comprising an amino acid sequence having at least 90% identity with SEQ ID NO: 183 or an antigen-binding or an immunologically functional immunoglobulin fragment thereof;

a heavy chain variable region comprising an amino acid sequence having at least 90% identity with SEQ ID NO: 185 or an antigen-binding or an immunologically functional immunoglobulin fragment thereof, and a light chain variable region comprising an amino acid sequence having at least 90% identity with SEQ ID NO: 186 or an antigen-binding or an immunologically functional immunoglobulin fragment thereof;

a heavy chain variable region comprising an amino acid sequence having at least 90% identity with SEQ ID NO: 187 or an antigen-binding or an immunologically functional immunoglobulin fragment thereof, and a light chain variable region comprising an amino acid sequence having at least 90% identity with SEQ ID NO: 188 or an antigen-binding or an immunologically functional immunoglobulin fragment thereof;

a heavy chain variable region comprising an amino acid sequence having at least 90% identity with SEQ ID NO: 189 or an antigen-binding or an immunologically functional immunoglobulin fragment thereof, and a light chain variable region comprising an amino acid sequence having at least 90% identity with SEQ ID NO: 42 or an antigen-binding or an immunologically functional immunoglobulin fragment thereof;

a heavy chain variable region comprising an amino acid sequence having at least 90% identity with SEQ ID NO: 190 or an antigen-binding or an immunologically functional immunoglobulin fragment thereof, and a light chain variable region comprising an amino acid sequence having at least 90% identity with SEQ ID NO: 188 or an antigen-binding or an immunologically functional immunoglobulin fragment thereof;

a heavy chain variable region comprising an amino acid sequence having at least 90% identity with SEQ ID NO: 206 or an antigen-binding or an immunologically functional immunoglobulin fragment thereof, and a light chain variable region comprising an amino acid sequence having at least 90% identity with SEQ ID NO: 42 or an antigen-binding or an immunologically functional immunoglobulin fragment thereof;

a heavy chain variable region comprising an amino acid sequence having at least 90% identity with SEQ ID NO: 207 or an antigen-binding or an immunologically functional immunoglobulin fragment thereof, and a light chain variable region comprising an amino acid sequence having at least 90% identity with SEQ ID NO: 188 or an antigen-binding or an immunologically functional immunoglobulin fragment thereof; and a heavy chain variable region comprising an amino acid sequence having at least 90% identity with SEQ ID NO: 192 or an antigen-binding or an immunologically functional immunoglobulin fragment thereof, and a light chain variable region comprising an amino acid sequence having at least 90% identity with SEQ ID NO: 193 or an antigen-binding or an immunologically functional immunoglobulin fragment thereof.

Exemplary binding proteins as disclosed herein may include at least one CDR comprising an amino acid sequence selected from: a) heavy chain CDRs consisting of SEQ ID NOS: 55, 56, 57, 61, 62, 63, 67, 68, 69, 73, 74, 75, 79, 80, 81; or modified CDR amino acid sequences having a sequence identity of at least 50%, at least 60%, at least 70%, at least 80%, or at least 90% to one of said sequences; b) light chain CDRs consisting of SEQ ID NOS: 58, 59, 60, 64, 65, 66, 70, 71, 72, 76, 77, 78, 82, 83, 84; or modified CDR amino acid sequences having a sequence identity of at least 50% %, at least 60%, at least 70%, at least 80%, or at least 90% to one of said sequences.

It should be understood that variations are contemplated in any of the nucleic acid and amino acid sequences described herein. Such variations include those that will result in a nucleic acid sequence that is capable of directing production of analogs of the corresponding NGF binding proteins. It will be understood that due to the degeneracy of the genetic code, many substitutions of nucleotides may be made that will lead to a DNA sequence that remains capable of directing production of the corresponding protein or its analogs. All such variant DNA sequences that are functionally equivalent to any of the sequences described herein, are encompassed by the present disclosure.

A variant of any of the binding proteins described herein means a protein (or polypeptide) that differs from a given protein (e.g., an anti-NGF antibody) in amino acid sequence by the addition (e.g., insertion), deletion, or conservative substitution of amino acids, but that retains the biological activity of the given protein. A conservative substitution of an amino acid, i.e., replacing an amino acid with a different amino acid of similar properties (e.g., hydrophilicity and degree and distribution of charged regions) is recognized in the art as typically involving a minor change. These minor changes may be identified, in part, by considering the hydropathic index of amino acids, as understood in the art (see, e.g., Kyte et al., J. Mol. Biol. 157: 105-132 (1982)). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids also may be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101, which is incorporated herein by reference). Substitution of amino acids having similar hydrophilicity values may result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also may be used to describe a polypeptide or fragment thereof that has been differentially processed, such as by proteolysis, phosphorylation, or other post-translational modification, yet retains its biological activity or antigen reactivity, e.g., the ability to bind to NGF. Use of "variant" herein is intended to encompass fragments of a variant unless otherwise contradicted by context.

The binding proteins described herein encompass an immunoglobulin molecule, disulfide linked Fv, scFv, monoclonal antibody, murine antibody, chimeric antibody, single domain antibody, CDR-grafted antibody, diabody, mammalized (bovanized, camelized, caninized, equinized, felinized, or humanized) antibody, a canine antibody, feline antibody, equine antibody, murine antibody, multispecific antibody, Fab, dual specific antibody, DVD, Fab', bispecific antibody, F(ab')2, or Fv including a single chain Fv fragment.

A binding protein may comprise a particular heavy chain constant region, such as an IgG1, IgG2, IgG3, IgG4, IgA, IgE, IgM or IgD constant region. An exemplary binding protein includes an IgG1 heavy chain constant region or an IgG4 heavy chain constant region. Furthermore, the antibody may comprise a light chain constant region, such as a kappa light chain constant region or a lambda light chain constant region. An exemplary binding protein comprises a kappa light chain constant region.

Replacements of amino acid residues in the Fc portion to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. At least one amino acid residue may be replaced in the constant region of the antibody, for example the Fc region of the antibody, such that effector functions of the antibody are altered.

Binding proteins according to the present disclosure may comprise a heavy chain immunoglobulin constant domain such as, for example, a human or canine or equine or feline IgM constant domain, a human or canine or equine or feline IgG4 constant domain, a human or canine or equine or feline IgG1 constant domain, a human or canine or equine or feline IgE constant domain, a human or canine or equine or feline IgG2 constant domain, a human or canine or equine or feline IgG3 constant domain, and a human or canine or equine or feline IgA constant domain. A binding protein as described herein may comprise a light chain immunoglobulin constant domain such as but not limited to any of human, canine, equine or feline, kappa or lambda constant domains, or any of canine, equine or feline kappa or lambda equivalent constant domains. An exemplary such binding protein has a constant region having an amino acid sequence of SEQ ID NO: 52 or SEQ ID NO: 54.

Binding proteins as described herein may also encompass an NGF anti-idiotype antibody relative to at least one NGF binding protein of the present disclosure. The anti-idiotype antibody includes any protein or peptide containing molecule that comprises at least a portion of an immunoglobulin molecule such as, but not limited to, at least one complementarity determining region (CDR) of a heavy or light chain or a ligand binding portion thereof, a heavy chain or light chain variable region, a heavy chain or light chain constant region, a framework region, or; any portion thereof, which may be incorporated into a binding protein of the present disclosure.

The binding proteins of the disclosure are capable of binding to human and canine NGF with high specificity, and additionally are capable of modulating the biological activity or function of NGF in an organism or a subject, including substantially neutralizing human and canine NGF. Also encompassed by the present disclosure are isolated murine monoclonal antibodies, or antigen-binding portions thereof, that bind to NGF with a substantially high affinity, have a slow off rate and/or have a substantially high neutralizing capacity. An exemplary binding protein as disclosed herein is capable of neutralizing NGF with a potency ($IC_{50}$) of at least about 10 nM, at least about 5 nM, at least about 1 nM, at least about 0.5 nM, at least about 0.1 nM, at least about 0.05 nM, at least about 0.01 nM, or at least about 0.001 nM, as measured in the TF-1 cell proliferation assay or the pERK and Pathhunter assays. Binding proteins as described herein may have an on rate constant ($K_{on}$) to NGF of at least about $10^2 M^{-1}s^{-1}$; at least about $10^3 M^{-1}s^{-1}$; at least about $10^4 M^{-1}s^{-1}$; at least about $10^5 M^{-1}s^{-1}$; at least about $10^6 M^{-1}s^{-1}$; or at least about $10^7 M^{-1}s^{-1}$ as measured by surface plasmon resonance. Binding proteins as described herein may have an off rate constant ($K_{off}$) to NGF of at most about $10^{-3}s^{-1}$; at most about $10^{-4}s^{-1}$; at most about $10^{-5}s^{-1}$; at most about $10^{-6}s^{-1}$ or at most about $10^{-7}s^{-1}$, as measured by surface plasmon resonance. Binding proteins as described herein may have a dissociation constant ($K_D$) to NGF of at most about $10^{-7}$ M; at most about $10^{-8}$ M; at most about $10^{-9}$ M; at most about $10^{-10}$ M; at most about $10^{-11}$ M; at most about $10^{-12}$ M; at most about $10^{-13}$ M, or at most about $10^{-14}$ M. For example, a binding protein as described herein may have a dissociation constant ($K_D$) of about $1 \times 10^{-9}$ M, about $1 \times 10^{-10}$ M, about $3.14 \times 10^{-10}$ M, about $1 \times 10^{-11}$ M, about $2.37 \times 10^{-11}$ M, about $1 \times 10^{-12}$ M, about $1 \times 10^{-13}$ M, or about $3.3 \times 10^{-14}$ M.

Binding proteins as described herein including an isolated antibody, or antigen-binding portion thereof, or immunologically functional fragment thereof, may bind NGF and dissociate from NGF with a $k_{off}$ rate constant of about $0.1s^{-1}$ or less, as determined by surface plasmon resonance, or may inhibit NGF activity with an $IC_{50}$ of about $1 \times 10^{-6}$ M or less. Alternatively, the antibody, or an antigen-binding portion thereof, may dissociate from NGF with a $k_{off}$ rate constant of about $1 \times 10^{-2} s^{-1}$ or less, as determined by surface plasmon resonance, or may inhibit NGF activity with an $IC_{50}$ of about $1 \times 10^{-7}$ M or less. Alternatively, the antibody, or an antigen-binding portion thereof, may dissociate from NGF with a $k_{off}$ rate constant of about $1 \times 10^{-3} s^{-1}$ or less, as determined by surface plasmon resonance, or may inhibit NGF with an $IC_{50}$ of about $1 \times 10^{-8}$ M or less. Alternatively, the antibody, or an antigen-binding portion thereof, may dissociate from NGF with a $k_{off}$ rate constant of about $1 \times 10^{-4} s^{-1}$ or less, as determined by surface plasmon resonance, or may inhibit NGF activity with an $IC_{50}$ of about $1 \times 10^{-9}$ M or less. Alternatively, the antibody, or an antigen-binding portion thereof, may dissociate from NGF with a $k_{off}$ rate constant of about $1 \times 10^{-5} s^{-1}$ or less, as determined by surface plasmon resonance, or may inhibit NGF activity with an $IC_{50}$ of about $1 \times 10^{-10}$ M or less. Alternatively, the antibody, or an antigen-binding portion thereof, may dissociate from NGF with a $k_{off}$ rate constant of about $1 \times 10^{-5} s^{-1}$ or less, as determined by surface plasmon resonance, or may inhibit NGF activity with an $IC_{50}$ of about $1 \times 10^{-11}$ M or less.

A binding protein as described herein may bind canine NGF, wherein the antibody, or antigen-binding portion thereof, may dissociate from canine NGF with a $k_{off}$ rate constant of about $0.1s^{-1}$ or less, as determined by surface plasmon resonance, or may inhibit canine NGF activity with an $IC_{50}$ of about $1 \times 10^{-6}$ M or less. Alternatively, the antibody, or an antigen-binding portion thereof, may dissociate from canine NGF with a $k_{off}$ rate constant of about $1 \times 10^{-2} s^{-1}$ or less, as determined by surface plasmon resonance, or may inhibit canine NGF activity with an $IC_{50}$ of about $1 \times 10^{-7}$ M or less. Alternatively, the antibody, or an antigen-binding portion thereof, may dissociate from canine NGF with a $k_{off}$ rate constant of about $1 \times 10^{-3} s^{-1}$ or less, as determined by surface plasmon resonance, or may inhibit canine NGF with an $IC_{50}$ of about $1 \times 10^{-8}$ M or less. Alternatively, the antibody, or an antigen-binding portion thereof, may dissociate from canine NGF with a $k_{off}$ rate constant of about $1 \times 10^{-4} s^{-1}$ or less, as determined by surface plasmon resonance, or may inhibit canine NGF activity with an $IC_{50}$ of about $1 \times 10^{-9}$ M or less. Alternatively, the antibody, or an antigen-binding portion thereof, may dissociate from canine NGF with a $k_{off}$ rate constant of about $1 \times 10^{-5} s^{-1}$ or less, as determined by surface plasmon resonance, or may inhibit canine NGF activity with an $IC_{50}$ of about $1 \times 10^{-10}$ M or less. Alternatively, the antibody, or an antigen-binding portion thereof, may dissociate from canine NGF with a $k_{off}$ rate constant of about $1 \times 10^{-5} s^{-1}$ or less, as determined by surface plasmon resonance, or may inhibit canine NGF activity with an $IC_{50}$ of about $1 \times 10^{-11}$ M or less.

The binding proteins of the disclosure further encompass binding proteins coupled to an immunoadhesion molecule, imaging agent, therapeutic agent, or cytotoxic agent. Non-limiting examples of suitable imaging agents include an enzyme, fluorescent label, luminescent label, bioluminescent label, magnetic label, biotin or a radiolabel including, but not limited to, 3H, 14C, 35S, 90Y, 99Tc, 111In, 125I, 131I, 177Lu, 166Ho, and 153Sm. The therapeutic or cytotoxic agent may be an anti-metabolite, alkylating agent, antibiotic, growth factor, cytokine, anti-angiogenic agent, anti-mitotic agent, anthracycline, toxin, or apoptotic agent. Also provided herein is a labeled binding protein wherein an antibody or antibody portion of the disclosure is derivatized or linked to another functional molecule (e.g., another peptide or protein). For example, a labeled binding protein of the disclosure may be derived by functionally linking an antibody or antibody portion of the disclosed binding protein (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that may mediate associate of the antibody or antibody portion with another molecule (such as a streptavidin core region or a polyhistidine tag).

Useful detectable agents with which an antibody or antibody portion of the disclosure may be derivatized, may include fluorescent compounds. Exemplary fluorescent detectable agents include, for example, fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, addition of hydrogen peroxide and diaminobenzidine leads to a colored reaction product, which is detectable. An antibody may also be derivatized with biotin, and detected through indirect measurement of avidin or streptavidin binding.

The binding proteins described herein may be in crystallized form. Crystallized binding proteins according to the present disclosure may be produced according to methods known in the art, as disclosed for example in WO 02072636. Preferably the crystallized binding protein retains biological activity after crystallization. The binding proteins may thus be provided as crystals of whole anti-NGF antibodies or portions or fragments thereof as disclosed herein. Such crystals may be used to prepare formulations and compositions incorporating anti NGF binding proteins, including diagnostic and therapeutic compositions. An exemplary such crystallized binding protein is a carrier-free, controlled release crystallized binding protein. An exemplary crystallized binding protein demonstrates a greater half-life in vivo than the soluble counterpart of the binding protein.

Anti NGF binding proteins as described herein may be glycosylated. The glycosylation may demonstrate, for example, a bovine, camel, canine, murine, equine, feline, or human glycosylation pattern. Glycosylated binding proteins as described herein include the antibody or antigen-binding portion coupled to one or more carbohydrate residues. Nascent in vivo protein production may undergo further processing, known as post-translational modification. Sugar (glycosyl) residues may be added enzymatically, a process known as glycosylation. The resulting proteins bearing covalently linked oligosaccharide side chains are known as glycosylated proteins or glycoproteins. Protein glycosylation depends on the amino acid sequence of the protein of interest, as well as the host cell in which the protein is expressed. Different organisms may produce different glycosylation enzymes (eg., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the disclosure may include, but are not limited to, glucose, galactose, mannose, fucose, n-acetylglucosamine and sialic acid. The glycosylated binding protein comprises glycosyl residues such that the glycosylation pattern is human, murine, canine, feline, bovine or equine.

It is known to those skilled in the art that differing protein glycosylation may result in differing protein characteristics. For instance, the efficacy of a therapeutic protein produced in a microorganism host, such as yeast, and glycosylated utilizing the host endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, such as a glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art, a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent applications 20040018590 and 20020137134).

Further, it will be appreciated by those skilled in the art that a protein of interest may be expressed using a library of host cells genetically engineered to express various glycosylation enzymes such that member host cells of the library produce the protein of interest with variant glycosylation patterns. A practitioner may then select and isolate the protein of interest with particular novel glycosylation patterns. The protein having a particularly selected novel glycosylation pattern exhibits improved or altered biological properties.

Anti NGF Chimeric Antibodies

A chimeric antibody is a molecule in which different portions of the antibody are derived from different animal species, such as antibodies having a variable region derived from a murine monoclonal antibody and a non-murine immunoglobulin constant region. Methods for producing chimeric antibodies are known in the art, see e.g., Morrison, Science, 229: 1202 (1985); Oi et al., BioTechniques, 4: 214 (1986); Gillies et al., J. Immunol. Methods, 125: 191-202 (1989); U.S. Pat. Nos. 5,807,715; 4,816,567; and 4,816,397. In addition, techniques developed for the production of "chimeric antibodies" (Morrison et al., Proc. Natl. Acad. Sci. 81: 851-855 (1984); Neuberger et al., Nature, 312:604-608 (1984); Takeda et al., Nature, 314: 452-454 (1985)) by splicing genes from a mouse antibody molecule of appropriate antigen specificity together with genes from a human antibody molecule of appropriate biological activity may be used.

Anti NGF CDR Grafted Antibodies

CDR-grafted antibodies of the disclosure may comprise heavy and light chain variable region sequences from a non-murine antibody wherein one or more of the CDR regions of $V_H$ and/or $V_L$ are replaced with CDR sequences of the murine antibodies of the disclosure. A framework sequence from any non-murine antibody may serve as the template for CDR grafting. However, straight chain replacement onto such a framework often leads to some loss of binding affinity to the antigen. The more homologous a non-murine antibody is to the original murine antibody, the less likely the possibility that combining the murine CDRs with the non-murine framework will introduce distortions in the CDRs that could reduce affinity.

A non-murine variable framework that is chosen to replace the murine variable framework apart from the CDRs may have at least 50%, at least 60%, at least 70%, at least 80% or at least 90% sequence identity with the murine antibody variable region framework. The non-murine variable framework, apart from the CDRs, that is chosen to replace the murine variable framework, apart from the CDRs, may be a bovine, camel, canine, equine, feline or human variable framework. For example, the non-murine variable framework that is chosen to replace the murine variable framework, apart from the CDRs, is a canine variable framework and has at least 50%, at least 60%, at least 70%, at least 80%, at least 90%, at least 91%, at least 92%, at least 93%, at least 94%, at least 95%, at least 96%, at least 97%, at least 98% or at least 99% sequence identity with the murine antibody variable region framework.

Methods for producing CDR-grafted antibodies are known in the art (see EP 239,400; PCT publication WO 91/09967; U.S. Pat. Nos. 5,225,539; 5,530,101; and 5,585,089), and include veneering or resurfacing (EP 592,106; EP 519,596; Padlan, Molecular Immunology 28(4/5): 489-498 (1991); Studnicka et al., Protein Engineering, 7(6):805-814 (1994); Roguska et al., PNAS, 91:969-973 (1994)), and chain shuffling (U.S. Pat. No. 5,565,352).

Anti NGF Humanized Antibodies

The process of modifying a monoclonal antibody from an animal to render it less immunogenic for therapeutic administration to humans (humanization) has been aggressively pursued and has been described in a number of publicatons (Antibody Engineering: A practical Guide. Carl A. K. Borrebaeck ed. W.H. Freeman and Company, 1992; and references cited above). Humanized antibodies are antibody molecules from non-human species antibody that binds the desired antigen having one or more complementarity determining regions (CDRs) from the non-human species and framework regions from a human immunoglobulin molecule. Known human Ig sequences are disclosed in a variety of websites which are available on the Internet (such as the NCBI website, Antibody Resource, and known to those skilled in the art as well as in Kabat et al., Sequences of Proteins of Immunological Interest, U.S. Dept. Health (1983), which is incorporated herein by reference. Additional sequences are shown in Table 1A below. Such imported sequences may be used to reduce immunogenicity or reduce, enhance or modify binding, affinity, on-rate, off-rate, avidity, specificity, half-life, or any other suitable characteristic of the antibody, as known in the art.

TABLE 1A

Mouse Anti-NGF mAb CDRs Grafted onto Human Ig Frameworks (CDR-Grafted Anti-NGF Abs (This Table 1A is identical to Table 17 in the Examples)

| Name | Sequence (CDRs are underlined) |
|---|---|
| HU72 VH (CDR GRAFT VH3-13/JH5) | EVQLVESGGGLVQPGGSLRLSCAASGFTFS<u>DYYM</u> FWVRQATGKGLEWVS<u>TISDGGSYTYYTDNVKGRF</u> TISRENAKNSLYLQMNSLRAGDTAVYYCAR<u>DWSD SEGFAY</u>WGQGTLVTVSS (SEQ ID NO: 165) |
| Hu73 VH (CDR GRAFT VH1-18/JH6) | QVQLVQSGAEVKKPGASVKVSCKASGYTFT<u>NYWM HW</u>VRQAPGQGLEWMG<u>RIDPYGGGTKHNEKFKR</u>RV TMTTDTSTSTAYMELRSLRSDDTAVYYCAR<u>SGYD YYFDV</u>WGQGTTVTVSS (SEQ ID NO: 166) |
| HU77 VH (CDR GRAFT VH1-69/JH6) | QVQLVQSGAEVKKPGSSVKVSCKASGFNIK<u>DTYI YW</u>VRQAPGQGLEWMG<u>RIDPANGNTIYASKFQ</u>GRV TITADKSTSTAYMELSSLRSEDTAVYYCAR<u>YGYY AY</u>WGQGTTVTVSS (SEQ ID NO: 167) |
| HU80 VH (CDR GRAFT VH1-18/JH6) | QVQLVQSGAEVKKPGASVKVSCKASGFNIK<u>DTYI YW</u>VRQAPGQGLEWMG<u>RIDPANGNTIYASKFQ</u>GRV TMTTDTSTSTAYMELRSLRSDDTAVYYCAR<u>YGYY AY</u>WGQGTTVTVSS (SEQ ID NO: 168) |
| HU81 VH (CDR GRAFT VH3-15/JH1) | EVQLVESGGGLVKPGGSLRLSCAASGFTFS<u>NHYM YW</u>VRQAPGKGLEWVG<u>SISDGGAYTFYPDTVKGRF</u> TISRDDSKNTLYLQMNSLKTEDTAVYYCTT<u>EESA NNGPAF</u>WGQGTLVTVSS (SEQ ID NO: 169) |
| HU82 VH (CDR GRAFT VH2-26/JH6) | QVTLKESGPVLVKPTETLTLTCTVSGFSLT<u>GYNI NW</u>IRQPPGKALEWLA<u>MIWGYGDTDYNSALKS</u>RLT ISKDTSKSQVVLTMTNMDPVDTATYYCARD<u>HYGG NDWYFDV</u>WGQGTTVTVSS (SEQ ID NO: 170) |
| HU72 VL (CDR GRAFT O1/JK2) | DIVMTQTPLSLPVTPGEPASISC<u>RSSQSIVQSNG NTYLE</u>WYLQKPGQSPQLLIY<u>KVSNRFS</u>GVPDRFS GSGSGTDFTLKISRVEAEDVGVYYC<u>FQGSHVPFT</u> FGQGTKLEIKR (SEQ ID NO: 171) |
| HU73 VL (CDR GRAFT L22/JK2) | DIQMIQSPSFLSASVGDRVSIIC<u>RASENIYSFLA</u> WYLQKPGKSPKLFLY<u>NANTLAE</u>GVSSRFSGRGSG TDFTLTIISLKPEDFAAYYC<u>QHHFGTPFT</u>FGQGT KLEIKR (SEQ ID NO: 172) |
| HU77 VL (CDR GRAFT O1/JK2) | DIVMTQTPLSLPVTPGEPASISC<u>KSTKSLLNGDG FTYLD</u>WYLQKPGQSPQLLIY<u>LVSNRFS</u>GVPDRFS GSGSGTDFTLKISRVEAEDVGVYYC<u>FESNYLFT</u> FGQGTKLEIKR (SEQ ID NO: 173) |
| HU80 VL (CDR GRAFT O1/JK2) | DIVMTQTPLSLPVTPGEPASISC<u>KSTKSLLNGDG FTYLD</u>WYLQKPGQSPQLLIY<u>LVSNRFS</u>GVPDRFS GSGSGTDFTLKISRVEAEDVGVYYC<u>FESNYLFT</u> FGQGTKLEIKR (SEQ ID NO: 174) |
| HU81 VL (CDR GRAFT O1/JK2) | DIVMTQTPLSLPVTPGEPASISC<u>RSSQSILHSNG NTYLE</u>WYLQKPGQSPQLLIY<u>RVSNRFS</u>GVPDRFS GSGSGTDFTLKISRVEAEDVGVYYC<u>FQGAHVPFT</u> FGQGTKLEIKR (SEQ ID NO: 175) |

TABLE 1A-continued

Mouse Anti-NGF mAb CDRs Grafted onto Human Ig Frameworks (CDR-Grafted Anti-NGF Abs (This Table 1A is identical to Table 17 in the Examples)

| Name | Sequence (CDRs are underlined) |
|---|---|
| HU82 VL (CDR GRAFT O8/JK2) | DIQMTQSPSSLSASVGDRVTITC<u>RASQDITNYLN</u> WYQQKPGKAPKLLIY<u>YTSRLHS</u>GVPSRFSGSGSG TDFTFTISSLQPEDIATYYC<u>QQGKTLPRT</u>FGQGT KLEIKR (SEQ ID NO: 176) |

Framework residues in the human framework regions may be substituted with the corresponding residue from the CDR donor antibody to alter or improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues may be selected and combined from the consensus and import sequences so that the desired antibody characteristic, such as increased affinity for the target antigen(s), is achieved. In general, the CDR residues are directly and most substantially involved in influencing antigen binding. Antibodies may be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567.

Anti NGF Caninized Antibodies

The process of modifying a monoclonal antibody from an animal to render it less immunogenic for therapeutic administration to canines (caninization) has been described in U.S. Pat. No. 7,261,890 B2 2007). The amino acid sequence of canine IgG1 is provided in GenBank (AF354264). Determination of the amino acid sequence of the variable regions of both a canine IgM and a canine IgA heavy chain (Wasserman et al., *Biochem.*, 16, 3160 (1977), determination of the amino acid sequence of the κ light chain from a canine IgA (Wasserman et al., *Immunochem.*, 15, 303 (1978)), complete amino-acid sequence of a canine μ chain was disclosed (McCumber et al., *Mol. Immunol.*, 16, 565 (1979)), a single canine IgG-Aγ chain cDNA and four canine IgG-Aγ chain protein sequences were disclosed (Tang et al., *Vet. Immunology Immunopathology*, 80, 259 (2001)). It describes PCR amplification of a canine spleen cDNA library with a degenerate oligonucleotide primer designed from the conserved regions of human, mouse, pig, and bovine IgGs. Canine immunoglobulin variable domains, caninized antibodies, and methods for making and using them are disclosed in US Patent Application No. 2004/0181039 and U.S. Pat. Nos. 7,261,890; 6,504,013; 5,852,183; 5,5225,539.

Table 2 below is a list of amino acid sequences of VH and VL regions of selected caninized anti-NGF antibodies of the disclosure.

TABLE 2

| SEQ ID NO: | Region |
|---|---|
| 25 | 72.1 VH |
| 26 | 72.1 VL |
| 27 | 73.1 VH |
| 28 | 73.1 VL |
| 29 | 77.1 VH |
| 30 | 77.1 VL |
| 31 | 81.1 VH |
| 32 | 81.1 VL |
| 33 | 82.1 VH |
| 34 | 82.1 VL |
| 35 | 72.2 VH |
| 36 | 72.2 VL |
| 37 | 73.2 VH |
| 38 | 73.2 VL |
| 39 | 77.2 VH |
| 40 | 77.2 VL |
| 41 | 81.2 VH |
| 42 | 81.2 VL |
| 43 | 82.2 VH |
| 44 | 82.2 VL |
| 177 | 81.1B VH |
| 179 | 72.3 VH |
| 180 | 72.4 VH |
| 181 | 72.4 VL |
| 182 | 73.4 VH |
| 183 | 73.4 VL |
| 184 | 77.3 VH |
| 185 | 77.4 VH |
| 186 | 77.4 VL |
| 187 | 81.4 VH |
| 188 | 81.4 VL |
| 189 | 81.2B VH |
| 190 | 81.4B VH |
| 191 | 82.3 VL |
| 192 | 82.4 VH |
| 193 | 82.4 VL |
| 206 | 81.5B VH |
| 207 | 81.6B VH |

C. USES OF ANTI-NGF ANTIBODIES

Binding proteins as described herein may be used in a method for detecting the presence of NGF in a sample in vivo or in vitro (e.g., in a biological sample, such as serum, plasma, tissue, biopsy). The in vitro method may be used for example to diagnose a disease or disorder, e.g., an NGF-associated disorder. The method includes (i) contacting the sample or a control sample with the anti-NGF antibody or fragment thereof as described herein; and (ii) detecting formation of a complex between the anti-NGF antibody or fragment thereof, and the sample or the control sample, wherein a statistically significant change in the formation of the complex in the sample relative to the control sample is indicative of the presence of the NGF in the sample.

Binding proteins as described herein may be used in a method for detecting the presence of NGF in vivo (e.g., in vivo imaging in a subject). The method may be used to diagnose a disorder, e.g., an NGF-associated disorder. The method includes: (i) administering the anti-NGF antibody or fragment thereof as described herein to a subject or a control subject under conditions that allow binding of the antibody or fragment to NGF; and (ii) detecting formation of a complex between the antibody or fragment and NGF, wherein a statistically significant change in the formation of the complex in the subject relative to the control subject is indicative of the presence of NGF.

Given the ability to bind to NGF, the anti-NGF antibodies, or portions thereof, or combinations thereof, as described herein may be used as immunoreagent(s) to detect NGF (e.g., in a biological sample, such as serum or plasma), in a conventional immunoassay, such as an enzyme linked immunosorbent assays (ELISA), a radioimmunoassay (RIA) or tissue immunohistochemistry. A method for detecting NGF in a biological sample involves contacting a biological sample with an antibody, or antibody portion, of the disclosure and detecting either the antibody (or antibody portion) bound to NGF or unbound antibody (or antibody portion), to thereby detect NGF in the biological sample. The binding protein may be directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

NGF may alternatively be assayed in biological fluids by a competition immunoassay utilizing recombinant NGF standards labeled with a detectable substance and an unlabeled anti-NGF antibody. In this assay, the biological sample, the labeled recombinant NGF standards and the anti-NGF antibody are combined and the amount of labeled rNGF standard bound to the unlabeled antibody is determined. The amount of NGF in the biological sample is inversely proportional to the amount of labeled rNGF standard bound to the anti-NGF antibody. Similarly, NGF may also be assayed in biological fluids by a competition immunoassay utilizing rNGF standards labeled with a detectable substance and an unlabeled anti-NGF antibody.

The disclosure thus also contemplates immunoassay reagents, devices and kits including one or more of the presently disclosed binding proteins for detecting the presence or amount of NGF in a sample. It is contemplated for example that an immunoreagent comprising one or more of the presently disclosed binding proteins may be provided in the form of a kit with one or more containers such as vials or bottles, with each container containing a separate reagent such as an anti-NGF binding protein, or a cocktail of anti-NGF binding proteins, detection reagents and washing reagents employed in the assay. The immunoreagent(s) may be advantageously provided in a device in which the immunoreagents(s) is immobilized on a solid support, such as but not limited to a cuvette, tube, microtiter plates or wells, strips, chips or beads. The kit may comprise at least one container for conducting the assay, and/or a buffer, such as an assay buffer or a wash buffer, either one of which may be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The kit may contain instructions for determining the presence or amount of NGF in the sample based on specific binding of the immunoreagent to NGF, in paper form or computer-readable form, such as a disk, CD, DVD, or the like, and/or may be made available online.

The binding proteins in the kit may be labeled with a detectable label such as those described above including a fluorophore, a radioactive moiety, an enzyme, a biotin/avidin label, a chromophore, a chemiluminescent label, or the like; or the kit may include reagents for carrying out detectable labeling. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme cofactors, enzyme substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like. Instructions:

It will be appreciated that the antibodies and antibody portions of the disclosure are capable of substantially neutralizing NGF activity both in vitro and in vivo. Accordingly, such antibodies and antibody portions of the disclosure can also be used to substantially inhibit NGF activity, e.g., in a cell culture containing NGF, in mammalian subjects having NGF with which an antibody of the disclosure cross-reacts. The disclosure thus provides a method for inhibiting NGF activity comprising contacting NGF with an antibody or antibody portion of the disclosure such that NGF activity is substantially inhibited. For example, in a cell culture containing, or suspected of containing NGF, an antibody or antibody portion of the disclosure can be added to the culture medium to inhibit NGF activity in the culture.

Accordingly, the disclosure also provides a method for inhibiting NGF activity comprising contacting NGF with a binding protein such that NGF activity is substantially inhibited. In another aspect, the disclosure provides a method for inhibiting NGF activity in a subject suffering from a disorder in which NGF activity is detrimental, comprising administering to the subject a binding protein disclosed above such that NGF activity in the subject is substantially inhibited and treatment is achieved.

The disclosure also provides a method for reducing NGF activity in a subject, such as a subject suffering from a disease or disorder in which NGF activity is detrimental. The disclosure provides methods for reducing NGF activity in a subject suffering from such a disease or disorder, which method comprises administering to the subject an antibody or antibody portion of the disclosure such that NGF activity in the subject is reduced. The subject can be a mammal expressing an NGF to which an antibody of the disclosure is capable of binding. Still further the subject can be a mammal into which NGF has been introduced (e.g., by administration of NGF or by expression of an NGF transgene). An antibody of the disclosure can be administered to a subject in need thereof for therapeutic purposes.

An antibody of the disclosure can be administered for veterinary purposes to a non-human mammal expressing an NGF with which the antibody is capable of binding. For example, an antibody of the disclosure can be administered for veterinary purposes to a non-human mammal such as a dog, horse, cat, or livestock (beef and dairy cattle, swine, sheep, goats, poultry, etc.) expressing an NGF with which the antibody is capable of binding.

In another aspect, the disclosure provides a method of treating (e.g., curing, suppressing, ameliorating, delaying or preventing or decreasing the risk of the onset, recurrence or relapse of) or preventing an NGF associated disorder, in a subject. The method includes: administering to the subject a disclosed NGF binding protein (particularly an antagonist), e.g., an anti-NGF antibody or fragment thereof as described herein, in an amount sufficient to treat or prevent the NGF associated disorder. The NGF antagonist, e.g., the anti-NGF antibody or fragment thereof, can be administered to the subject, alone or in combination with other therapeutic modalities as described herein.

An antibody of the disclosure can be administered to a non-human mammal expressing an NGF with which the antibody is capable of binding as an animal model of human disease. Such animal models may be useful for evaluating the therapeutic efficacy of antibodies of the disclosure (e.g., testing of dosages and time courses of administration).

In another aspect, the antibodies and binding proteins of the disclosure are useful for treating NGF-related diseases and disorders including or involving acute or chronic pain. Non-limiting examples of NGF-related diseases and disorders include general inflammation, surgical and post-surgical pain including pain from amputation, dental pain, pain from trauma, fracture pain, pain from abscess, neuropathic pain, hyperalgesia and allodynia, neuropathic pain, postherpetic neuralgia, diabetes including, but not limited to, diabetic neuropathy pain, stroke, thalamic pain syndrome, gout joint pain, osteoarthritis or rheumatoid arthritis pain, rheumatic diseases, lupus, psoriasis, sciatica, pain associated with musculoskeletal diseases including, but not limited to, chronic low back pain, fibromyalgia, sprains, pains associated with sickle cell crises, general headache, migraine, cluster headache, tension headache, trigeminal neuralgia, dysmenorrhea, endometriosis, ovarian cysts, visceral pain, prostatitis, cystitis, interstitial cystitis, erythromelalgia or pain caused by pancreatitis or kidney stones, general gastrointestinal disorders including, but not limited to, colitis, gastric ulceration and duodenal ulcers, gastroesophageal reflux, dyspepsia, inflammatory bowel disorders, irritable bowel syndrome, inflammatory bladder disorders, incisional pain, pain from burns and/or wounds, ankylosing spondilitis, periarticular pathologies, cancer pain including, but not limited to, pain from bone metastases and pain from cancer treatment, and pain from HIV or AIDS. Other examples of NGF-related diseases and conditions include malignant melanoma, Sjogren's syndrome, rhinitis, bronchial disorders, and asthma, such as uncontrolled asthma with severe airway hyper-responsiveness, intractable cough; and pain from skin diseases or disorders with an inflammatory component such as, but not limited to, sunburn, allergic skin reactions, dermatitis, pruritis, and vitiligo.

The disclosure also provides a method of treating a subject suffering from a disorder in which NGF is detrimental comprising administering a binding protein before, concurrent, or after the administration of a second agent. In another aspect, the additional therapeutic agent that can be coadministered and/or coformulated with one or more NGF antagonists, (e.g., anti-NGF antibodies or fragments thereof,) include, but are not limited to, TNF antagonists; a soluble fragment of a TNF receptor; ENBREL®; TNF enzyme antagonists; TNF converting enzyme (TACE) inhibitors; muscarinic receptor antagonists; TGF-beta antagonists; interferon gamma; perfenidone; chemotherapeutic agents, methotrexate; leflunomide; sirolimus (rapamycin) or an analog thereof, CCI-779; COX2 or cPLA2 inhibitors; NSAIDs; immunomodulators; p38 inhibitors; TPL-2, MK-2 and NFκB inhibitors; budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; anti-IL-6 antibodies; growth factors; elastase inhibitors; pyridinylimidazole compounds; antibodies or agonists of TNF, CGRP, substance P, bradykinin, MMP-2, MMP-9, MMP-13, LT, IL-1α, IL-1β, IL-2, IL-3, IL-4, IL-5, IL-6, IL-7, IL-8, IL-9, IL-10, IL-11, IL-12, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, EMAP-II, GM-CSF, FGF, or PDGF; antibodies of CD2, CD3, CD4, CD8, CD25, CD28, CD30, CD40, CD45, CD69, CD90 or their ligands; FK506; rapamycin; mycophenolate mofetil; ibuprofen; prednisolone; phosphodiesterase inhibitors; adensosine agonists; antithrombotic agents; complement inhibitors; adrenergic agents; IRAK, NIK, IKK, p38, or MAP kinase inhibitors; IL-1P converting enzyme inhibitors; α converting enzyme inhibitors; T-cell signaling inhibitors; metalloproteinase inhibitors; 6-mercaptopurines; angiotensin converting enzyme inhibitors; soluble cytokine receptors; soluble p55 TNF receptor; soluble p75 TNF receptor; sIL-1RI; sIL-1RII; sIL-6R; anti-inflammatory cytokines; IL-4; IL-10; IL-11; and TGFβ.

D. PHARMACEUTICAL COMPOSITIONS

The antibodies and antibody-portions of the disclosure can be incorporated into pharmaceutical compositions suitable for administration to a subject. Typically, the pharmaceutical composition comprises at least one antibody or antibody portion of the disclosure and a pharmaceutically acceptable carrier. Such compositions can be used for example in a method for treating a mammal for a disease or disorder involving increased levels of NGF by administering to the mammal an effective amount of the composition. A pharmaceutical composition may include a therapeutically effective amount of the antibody or antibody portion. The pharmaceutical compositions as described herein may be used for diagnosing, detecting, or monitoring a disorder or one or more symptoms thereof; preventing, treating, managing, or ameliorating a disorder or one or more symptoms thereof; and/or research. As used herein, the phrase "increased levels of NGF" refers to a level of NGF in a subject, such as a mammal, that is greater or higher than an established or predetermined baseline level of NGF such as, for example, a level previously established for said subject or averaged from a group of subjects.

A pharmaceutical composition may comprise, for example, a binding protein and a pharmaceutically acceptable carrier, excipient or diluent. For example, pharmaceutical compositions may comprise a therapeutically effective amount of one or more of the binding proteins as disclosed herein, together with a pharmaceutically acceptable diluent, carrier, solubilizer, emulsifier, preservative and/or adjuvant. The pharmaceutical composition may contain one or more various formulation materials for modifying, maintaining or preserving the composition or properties of the composition, for example, the color, consistency, isotonicity, odor, osmolarity, pH, sterility, stability, viscosity and other properties of the composition. Such formulation materials are generally well known and many suitable formulation materials are described for example in REMINGTON'S PHARMACEUTICAL SCIENCES, 18$^{th}$ Ed. (A. R. Gennaro, ed.) 1990, Mack Publishing Company. Non-limiting examples of suitable formulation materials include amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. In addition, the pharmaceutical composition can also contain one or more preservatives. Examples of suitable preservatives that can be used include, but are not limited to, methylparaben, propylparaben, benzyl alcohol, chlorobutanol, and benzalkonium chloride. Optimal pharmaceutical formulations can be readily determined by one skilled in the art depending upon, for example, the intended route of administration, delivery format and desired dosage.

The pharmaceutical composition may comprise at least one additional therapeutic agent for treating a disorder in which NGF activity is detrimental. The additional agent can be, for example, a therapeutic agent, imaging agent, cytotoxic agent, angiogenesis inhibitors, kinase inhibitors, co-stimulation molecule blockers, adhesion molecule blockers, anti-cytokine antibody or functional fragment thereof, methotrexate, cyclosporine, rapamycin, FK506, detectable label or reporter, TNF antagonist, anti-rheumatic, muscle relaxant, narcotic, non-steroid anti-inflammatory drug (NSAID), analgesic, anesthetic, sedative, local anesthetic, neuromuscular blocker, antimicrobial, antipsoriatic, corticosteriod, anabolic steroid, erythropoietin, immunoglobulin, immunosuppressive, growth hormone, hormone replacement drug, radiopharmaceutical, antidepressant, antipsychotic, stimulant, asthma medication, beta agonist, inhaled steroid, oral steroid, epinephrine or analog, cytokine, or a cytokine antagonist.

The pharmaceutical composition of the present disclosure may have a pH greater than about 7.0 or between about 7.0 and about 8.0. Alternatively, the pharmaceutical composition may have a pH of between about 7.2 to about 7.8. Still further alternatively, the pH of the pharmaceutical composition may be between about 7.4 to about 7.6. Still further alternatively, the pH of the pharmaceutical composition may be about 7.0, 7.1, 7.2, 7.3, 7.4, 7.5, 7.6 7.7, 7.8, 7.9 or 8.0. With respect to the pharmaceutical compositions of the present disclosure, there is an increase in degradation, an increase in fragmentation or an increase in degradation and an increase in fragmentation at a pH of 6.0 or less. This finding was surprising as many pharmaceutical compositions comprising humanized antibodies exhibit an increase in degradation, an increase fragmentation or an increase in degradation and an increase in fragmentation at a pH lower than 5.0 and again at a pH higher than about 6.0. Accordingly, most pharmaceutical compositions containing humanized antibodies are stable at a pH between about 5.0 to about 6.0.

A composition for the release of a binding protein may comprise, for example, a formulation including an amount of a crystallized binding protein, crystallized antibody construct or crystallized antibody conjugate as disclosed above. The composition may further comprise an additional ingredient, such as carrier, excipient or diluent, and at least one polymeric carrier. The polymeric carrier can comprise one or more polymers selected from the following: poly(acrylic acid), poly(cyanoacrylates), poly(amino acids), poly(anhydrides), poly(depsipeptide), poly(esters), poly(lactic acid), poly(lactic-co-glycolic acid) or PLGA, poly(b-hydroxybutyrate), poly(caprolactone), poly(dioxanone); poly(ethylene glycol), poly((hydroxypropyl) methacrylamide, poly [(organo)phosphazene], poly(ortho esters), poly(vinyl alcohol), poly(vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. The additional ingredient may be, for example, albumin, sucrose, trehalose, lactitol, gelatin, hydroxypropyl-β-cyclodextrin, methoxypolyethylene glycol and polyethylene glycol.

The polymeric carrier may be capable of affecting the release of the binding protein from the composition as described further herein below. Polymeric materials can be used in the formulation of pharmaceutical compositions comprising the disclosed binding proteins to achieve controlled or sustained release of the disclosed binding proteins (*Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger et al., *J. Macromol. Sci. Rev. Macromol. Chem.*, 23:61 (1983); Levy et al., *Science*, 228: 190 (1985); During et al., *Ann. Neurol.*, 25: 351 (1989); Howard et al., *J. Neurosurg.*, 7 1:105 (1989); U.S. Pat. Nos. 5,679,377; 5,916,597; 5,912,015; 5,989,463; 5,128,326; PCT Publication Nos. WO 99/15154; and WO 99/20253). Examples of polymers used in sustained release formulations include, but are not limited to, poly(2-hydroxy ethyl methacrylate), poly (methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (Science, 249:1527-1533 (1990)). Any technique known to one of skill in the art can be used to produce sustained release formulations comprising one or more therapeutic agents of the disclosure (U.S. Pat. No. 4,526, 938; PCT publication Nos. WO 91/05548 and WO 96/20698; Ning et al., *Radiotherapy & Oncology*, 39: 179-189 (1996), Song et al., *PDA Journal of Pharmaceutical Science &Technology*, 50: 372-397 (1995); Cleek et al., *Pro. Int'l. Symp. Control. Rel. Bioact. Mater.*, 24: 853-854 (1997); and Lam et al., *Proc. Int'l. Symp. Control Rel. Bioact. Mater.*, 24: 759-760 (1997)).

The binding proteins of the present disclosure can be administered by a variety of methods known in the art. For example, the binding proteins of the present disclosure may be administered by subcutaneous injection, intravenous injection or infusion. Administration can be systemic or local. As will be appreciated by the skilled artisan, the route and/or mode of administration may vary depending upon the desired results. The active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art. See, e.g., *Sustained and Controlled Release Drug Delivery Systems*, J. R. Robinson, ed., Marcel Dekker, Inc., New York, 1978.

For example, such pharmaceutical compositions may be administered to a subject by parenteral, intradermal, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. Methods of administering a prophylactic or therapeutic agent of the disclosure also include, but are not limited to, epidural administration, intratumoral administration, and mucosal administration (e.g., intranasal and oral routes). In addition, pulmonary administration can be employed, e.g., by use of an inhaler or nebulizer, and formulation with an aerosolizing agent (U.S. Pat. Nos. 6,019,968; 5,985,320; 5,985,309; 5,934, 272; 5,874,064; 5,855,913; 5,290, 540; and 4,880, 078; and PCT Publication Nos. WO 92/19244, WO 97/32572, WO 97/44013, WO 98/31346, and WO 99/66903). The antibodies and antibody portions described herein can be administered for example using Alkermes AIR® pulmonary drug delivery technology (Alkermes, Inc., Cambridge, Mass.). The prophylactic or therapeutic agents may be administered by any convenient route, and may be administered together with other biologically active agents.

Various delivery systems are known and can be used to administer one or more disclosed binding proteinsor the combination of one or more disclosed binding proteins and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu et al., *J. Biol. Chem.*, 262: 4429-4432 (1987)), construction of a nucleic acid as part of a retroviral or other vector, etc. It may be desirable to administer the disclosed binding proteins locally to the area in need of treatment, which may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. An effective amount of one or more disclosed binding proteins can be administered locally to the affected area to a subject to prevent, treat, manage, and/or ameliorate a disorder or a symptom thereof. Alternatively, an effective amount of one or more of the disclosed binding proteins is administered locally to the affected area in combination with an effective amount of one or more therapies (e.g., one or more prophylactic or therapeutic agents) other than disclosed binding proteins of a subject to prevent, treat, manage, and/or ameliorate a disorder or one or more symptoms thereof.

The disclosed binding proteins can be delivered in a controlled release or sustained release system such as, for example, an infusion pump device operable to achieve controlled or sustained release of the disclosed binding proteins (see Langer, supra; Sefton, *CRC Crit. Ref. Biomed. Eng.* 14:20 (1987); Buchwald et al., *Surgery,* 88: 507 (1980); Saudek et al., *N. Engl. J. Med.,* 321: 574 (1989)).

When a composition as described herein comprises a nucleic acid encoding a binding protein as described herein as a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (Joliot et al., *Proc. Natl. Acad. Sci.,* 88: 1864-1868 (1991)). Alternatively, a nucleic acid can be introduced intracellularly and incorporated within host cell DNA for expression by homologous recombination.

A pharmaceutical composition of the disclosure is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. For example, a composition may be formulated in accordance with routine procedures as a pharmaceutical composition adapted for intravenous, subcutaneous, intramuscular, oral, intranasal, or topical administration to human beings and companion animals. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the disclosure are to be administered topically, the compositions can be formulated in the form of an ointment, cream, transdermal patch, lotion, gel, shampoo, spray, aerosol, solution, emulsion, or other form well-known to one of skill in the art (*Remington's Pharmaceutical Sciences and Introduction to Pharmaceutical Dosage Forms,* 19th ed., Mack Pub. Co., Easton, Pa. (1995)). For non-sprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in combination with a solid or liquid inert carrier, is packaged in a mixture with a pressurized volatile (e.g., a gaseous propellant, such as Freon) or in a squeeze bottle. Moisturizers or humectants can also be added to pharmaceutical compositions and dosage forms if desired. Examples of such additional ingredients are well-known in the art.

The pharmaceutical composition of the present disclosure can have a half-life of from about 8 days to about 15 days when dosed intravenously or subcutaneously. Alternatively, the pharmaceutical composition of the present invention can have a half-life of from about 10 days to about 13 days. Still further alternatively, the pharmaceutical composition of the present invention can have a half-life of about 8 days, such as about 8.5 days, about 9 days, such as about 9.5 days, about 10 days, such as about 10.5 days, about 11 days, such as about 11.5 days, about 12 days, about 12.5 days, about 13 days, such as about 13.5 days, about 14 days, such as about 14.5 days, or about 15 days.

If the method of the disclosure comprises intranasal administration of a composition, the composition can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the disclosure comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the disclosure may comprise pulmonary administration, e.g., by use of an inhaler or nebulizer, of a composition formulated with an aerosolizing agent (U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903). For example, an antibody of the disclosure, combination therapy, and/or composition of the disclosure may be administered using Alkermes AIR® pulmonary drug delivery technology (Alkermes, Inc., Cambridge, Mass.).

The method of the disclosure may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the disclosure may additionally comprise administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the disclosure encompass administration of compositions formulated as neutral or salt forms. Pharmaceutically acceptable salts include those formed with anions, such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The ingredients of the disclosed compositions may be supplied either separately or mixed together in unit dosage form, for example, as a dry lyophilized powder or a substantially water-free concentrate in a hermetically sealed container such as an ampoule or sachette which may indicate the quantity of active agent. Where the mode of administration is infusion, the disclosed compositions can be dispensed with an infusion solution containing sterile pharmaceutical grade solution such as water or saline. Where the mode of administration is by injection, an ampoule of sterile solution such as water or saline can be provided so that the ingredients may be mixed prior to administration.

In particular, the disclosure also provides that one or more of disclosed binding proteins or pharmaceutical compositions thereof is packaged in a hermetically sealed container such as an ampoule or sachette which may indicate the quantity of the agent. One or more of the disclosed binding proteins or pharmaceutical compositions thereof may be supplied as a dry sterilized lyophilized powder or substantially water-free concentrate in a hermetically sealed container and can be reconstituted (e.g., with water or saline) to the appropriate concentration for administration to a subject. One or more of the disclosed binding proteins or pharmaceutical compositions thereof may be supplied as a dry sterile lyophilized powder in a hermetically sealed container at a unit dosage of at least about 0.5 mg, 1 mg, 2 mg, 4 mg, 5 mg, 10 mg, 15 mg, 25 mg, 35 mg, 45 mg, 50 mg, 75 mg, or 100 mg. The lyophilized disclosed binding proteins or pharmaceutical compositions thereof may be stored at any suitable temperature, such as, for example, between about 2° C. and about 8° C. and may be stored in its original container. The disclosed binding proteins or pharmaceutical compositions thereof may be administered within about 1 week, within about 5 days, within about 72 hours, within about 48 hours, within about 24 hours, within about 12 hours, within about 6 hours, within about 5 hours, within about 3 hours, or within about 1 hour after being reconstituted. Alternatively, one or more of the disclosed binding proteins or pharmaceutical compositions thereof may be supplied in liquid form in a hermetically sealed container which may indicate the quantity and concentration of the agent. The liquid form of the administered composition may be supplied in a hermetically sealed container at concentrations of at least about 0.01 mg/mL, at least about 0.05 mg/mL, at least about 0.1 mg/mL, at least about 0.2 mg/mL, at least about 0.25 mg/ml, at least about 0.5 mg/ml, at least about 1 mg/ml, at least about 2.5 mg/ml, at least about 5 mg/ml, at least about 8 mg/ml, at least about 10 mg/ml, at least about 15 mg/kg, at least about 25 mg/ml, at least about 50 mg/ml, at least about 75 mg/ml, or at least about 100 mg/ml. The liquid form may be stored at any suitable temperature such as between about 2° C. and about 8° C. and may be stored in its original container.

The binding proteins of the disclosure can be incorporated into a pharmaceutical composition suitable for parenteral administration. In one aspect, binding proteins are prepared as an injectable solution containing between about 0.1 and about 250 mg/ml antibody. The injectable solution can be composed of either a liquid or lyophilized dosage form in a flint or amber vial, ampoule or pre-filled syringe. The buffer can be any suitable buffer such as L-histidine or a phosphate buffer saline at a concentration of about 1-50 mM, or about 5-10 mM Other suitable buffers include, but are not limited to, sodium succinate, sodium citrate, sodium phosphate and potassium phosphate. Buffers may be used to modify the toxicity of the pharmaceutical composition. For example, sodium chloride can be used to modify the toxicity of the binding protein solution at a concentration of from about 0.1 and about 300 mM, such as about 150 mM saline to modify the toxicity of a liquid dosage form. Cryoprotectants, such as sucrose, can be included in a lyophilized dosage form at a concentration of about 0.1 to about 10% or from about 0.5 to about 1.0% may be used. Other suitable cryoprotectants include, but are not limited to, trehalose and lactose. Bulking agents, such as mannitol, can be included in a lyophilized dosage form at a concentration of about 1 to about 10%, or from about 2 to about 4%. Stabilizers, such as L-Methionine, can be used in both liquid and lyophilized dosage forms at a concentration of about 1 to about 50 mM, or about 5 to about 10 mM). Other suitable bulking agents include, but are not limited to, glycine and arginine. Surfactants, such as polysorbate-80, can be included in both liquid and lyophilized dosage forms at a concentration of about 0.001 to about 0.05% or about 0.005 to about 0.01%. Additional surfactants include, but are not limited to, polysorbate 20 and BRIJ surfactants.

An exemplary pharmaceutical formulation or composition of the present disclosure may be a liquid pharmaceutical composition having a pH between about 7.4 to about 8.0. The liquid pharmaceutical composition comprises about 5 mg/ml to about 50 mg/ml of an antibody comprising a heavy chain variable region comprising an amino acid sequence having a sequence of SEQ ID NO: 37 and a light chain variable region comprising an amino acid sequence comprising a sequence of SEQ ID NO: 38. The liquid pharmaceutical composition further comprises at least one buffer (such as, phosphate buffer saline, tris or histidine). The molarity of buffer that can be used can be from about 1 mM to about 60 mM. Optionally, said pharmaceutical composition or formulation can also contain at least one preservative, such as, methylparaben, propylparaben, benzyl alcohol, chlorobutanol or benzalkonium chloride. The amount of preservative that can be used can be from about 0.01 percent by volume to about 5.0% by volume depending on the preservative used.

Another exemplary pharmaceutical formulation or composition of the present disclosure may be a liquid pharmaceutical composition comprising a pH between about 7.4 to about 8.0. The liquid pharmaceutical composition comprises about 5 mg/ml to about 50 mg/ml of an antibody comprising a heavy chain variable region comprising an amino acid sequence having a sequence of SEQ ID NO: 192 and a light chain variable region comprising an amino acid sequence comprising a sequence of SEQ ID NO: 193. The liquid pharmaceutical composition further comprises at least one buffer (such as, phosphate buffer saline, tris or histidine). The molarity of buffer that can be used can be from about 1 mM to about 60 mM. Optionally, said pharmaceutical composition or formulation can also contain at least one preservative, such as, methylparaben, propylparaben, benzyl alcohol, chlorobutanol or benzalkonium chloride. The amount of preservative that can be used can be from about 0.01 percent by volume to about 5.0% by volume depending on the preservative used.

The compositions of this disclosure may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form of the disclosed composition may depend on the intended mode of administration and therapeutic application. The disclosed compositions may be in the form of injectable or infusible solutions, such as compositions similar to those used for passive immunization of humans with other antibodies. The mode of administration may be parenteral (e.g., intravenous, subcutaneous, intraperitoneal, intramuscular). The disclosed binding proteins may be administered by intravenous infusion or injection, or by intramuscular or subcutaneous injection.

Therapeutic compositions typically must be sterile and stable under the conditions of manufacture and storage. The composition can be formulated as a solution, microemulsion, dispersion, liposome, or other suitable ordered structure such as those suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Dispersions may be prepared by incorporating the active compound into a sterile vehicle that contains a basic dispersion medium and the required other ingredients from those enumerated above. In the case of sterile, lyophilized powders for the preparation of sterile injectable solutions, the methods of preparation include, but are not limited to, vacuum drying and spray-drying that yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption such as, for example, monostearate salts and gelatin.

An antibody or antibody portion of the disclosure may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the disclosure by other than parenteral administration, it may be necessary to coat the compound with, or co-administer the compound with, a material to prevent its inactivation.

The disclosed binding proteins may be co-administered with other active compounds which may also be incorporated into the disclosed compositions. An antibody or antibody portion of the disclosure may be coformulated with and/or coadministered with one or more additional therapeutic agents that are useful for treating disorders in which NGF activity is detrimental. For example, an anti-NGF antibody or antibody portion of the disclosure may be coformulated and/or coadministered with one or more additional antibodies that bind other targets (e.g., antibodies that bind other cytokines or that bind cell surface molecules). Furthermore, one or more disclosed binding proteins may be used in combination with two or more of the foregoing therapeutic agents. Such combination therapies may, for example, enable the use of lower dosages of the administered therapeutic agents, thus avoiding possible toxicities or complications associated with the various monotherapies.

An antibody to NGF or fragment thereof may be formulated with a vehicle that extends the half-life of the binding protein. Suitable vehicles known in the art include, but are not limited to, the Fc domain, polyethylene glycol, and dextran. Such vehicles are described, e.g., in U.S. application Ser. No. 09/428,082 and published PCT Application No. WO 99/25044.

Isolated nucleic acid sequences comprising nucleotide sequences encoding disclosed binding proteins or another prophylactic or therapeutic agent of the disclosure may be administered to treat, prevent, manage, or ameliorate a disorder or one or more symptoms thereof by way of gene therapy. Gene therapy refers to therapy performed by the administration to a subject of an expressed or expressible nucleic acid, wherein the nucleic acids produce their encoded antibody or prophylactic or therapeutic agent of the disclosure that mediates a prophylactic or therapeutic effect.

Any of the methods for gene therapy available in the art can be used according to the present disclosure. For general reviews of the methods of gene therapy, see Goldspiel et al., *Clinical Pharmacy*, 12: 488-505 (1993); Wu et al., *Biotherapy*, 3: 87-95 (1991); Tolstoshev, *Ann. Rev. Phamacol. Toxicol.*, 32: 573-596 (1993); Mulligan, *Science*, 260: 926-932 (1993); and Morgan et al., *Ann. Rev. Biochem.*, 62: 191-217 (1993); TIBTECH, 11(5):155-215 (1993). Methods commonly known in the art of recombinant DNA technology which can be used are described in, for example, Ausubel et al. (eds.), *Current Protocols in Molecular Biology*, John Wiley & Sons, NY (1993); and Kriegler, *Gene Transfer and Expression*, A Laboratory Manual, Stockton Press, NY (1990). Detailed descriptions of various methods of gene therapy are disclosed in US20050042664A1.

Antibodies of the disclosure, or antigen binding portions thereof, can be used alone or in combination to treat NGF related diseases. It should be understood that the antibodies of the disclosure or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present disclosure. The additional agent also can be an agent that imparts a beneficial attribute to the therapeutic composition e.g., an agent which affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the present disclosure and at least one additional agent selected from the lists below. The combination can also include more than one additional agent, e.g., two or three additional agents if the combination is such that the formed composition can perform its intended function.

Combinations include non-steroidal anti-inflammatory drug(s) also referred to as NSAIDS which include drugs like ibuprofen. Other combinations are corticosteroids including prednisolone; the well known side-effects of steroid use can be reduced or even eliminated by tapering the steroid dose required when treating patients in combination with the anti-NGF antibodies of this disclosure. Non-limiting examples of therapeutic agents for rheumatoid arthritis or pain with which an antibody, or antibody portion, of the disclosure can be combined include the following: cytokine suppressive anti-inflammatory drug(s) (CSAIDs); antibodies to or antagonists of cytokines or growth factors, for example, TNF, LT, IL-1, IL-2, IL-3, IL-4, IL-5, IL-6, IL-7, IL-8, IL-15, IL-16, IL-18, IL-21, interferons, EMAP-II, GM-CSF, FGF, and PDGF. Antibodies of the disclosure, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Combinations of therapeutic agents may interfere at different points in the autoimmune and subsequent inflammatory cascade; examples include TNF antagonists like chimeric, humanized or human TNF antibodies, D2E7, (PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNFα converting enzyme (TACE) inhibitors; similarly other IL-1 inhibitors (Interleukin-1-converting enzyme inhibitors, IL-1RA etc.) may be effective for the same reason. Other combinations include Interleukin 11.

The antibodies of the disclosure, or antigen binding portions thereof, may also be combined with agents, such as methotrexate, 6-MP, azathioprine sulphasalazine, mesalazine, olsalazine chloroquinine/hydroxychloroquine, pencilamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as α or IL-1 (e.g. IRAK, NIK, IKK, p38 or MAP kinase inhibitors), IL-1β converting enzyme inhibitors, α converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, and Mesopram. Other combinations include methotrexate or leflunomide and in moderate or severe rheumatoid arthritis cases, cyclosporine. The antibodies of the disclosure, or antigen binding portions thereof, may also be combined with agents, such as cancer chemotherapeutics, antimicrobials, anti-inflammatories, and anthelmintics used in animals.

The NSAID may be any non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and slindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam. Another class of NSAID has been described which selectively inhibit cyclooxygenase 2. Cox-2 inhibitors have been described (U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311). Certain exemplary COX-2 inhibitors include celecoxib (SC-58635), rofecoxib, DUP-697, flosulide (CGP-28238), meloxicam, 6-methoxy-2 naphthylacetic acid (6-MNA), MK-966, nabumetone (prodrug for 6-MNA), nimesulide, NS-398, SC-5766, SC-58215, T-614; or combinations thereof.

The NGF antagonist and/or an additional therapeutic agent, such as NSAID, can be administered to a subject via any suitable route. For example, they can be administered together or separately, and/or simultaneously and/or sequentially, orally, intravenously, sublingually, subcutaneously, intraarterially, intramuscularly, rectally, intraspinally, intrathoracically, intraperitoneally, intraventricularly, sublingually, transdermally or by inhalation. Administration can be systemic, e.g., intravenous, or localized. The nerve growth factor antagonist and the additional therapeutic agent may be present together with one or more pharmaceutically acceptable carriers or excipients, or they may be present in separate compositions. In another aspect, the invention provides a synergistic composition of an NGF antagonist and an NSAID.

The pharmaceutical compositions of the disclosure may include a "therapeutically effective amount" or a "prophylactically effective amount" of an antibody or antibody portion of the disclosure. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the disclosure is about 0.001 to about 20 mg/kg or about 0.001 to about 10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the disclosure described herein are obvious and may be made using suitable equivalents without departing from the scope of the disclosure or the embodiments disclosed herein. Having now described the present disclosure in detail, the same will be more clearly understood by reference to the following examples, which are included for purposes of illustration only and are not intended to be limiting of the disclosure.

E. EXAMPLES

The following examples are provided for exemplary guidance to make and use the disclosed binding proteins and pharmaceutical compositions thereof according to the inventive subject matter. However, it should be recognized that numerous modifications may be made without departing from the inventive concept presented herein.

Example 1

Immunization of Mice with NGF

To generate mouse anti-NGF mAbs, female A/J mice were immunized subcutaneously with 25 µg of human β NGF (R&D Systems catalog #256-GF/CF) in CFA. Animals were boosted every three weeks with 25 µg human β NGF in IFA. Four days prior to fusion, the mice were boosted with 10 µg of human β NGF in sterile saline intravenously. Spleen cells from the immunized mouse were fused with SP2/0-Ag14 myeloma cells at a 5:1 ratio spleen to SP2/0 cells, using standard techniques. Seven to ten days post fusion, when macroscopic colonies were observed, supernatants were tested in a capture ELISA format for binding to biotinylated human or rat β NGF. ELISA-positive wells were expanded to 24 well plates and tested for binding to biotinylated rat β NGF. Supernatants from hybridoma cell lines testing positive for both human and rat NGF were evaluated in a bioassay format. Cell lines of interest were cloned by limiting dilution to isolate an NGF-specific mouse monoclonal antibody.

Example 2

Screening Hybridoma Supernatants to Identify Secreted Anti-NGF MAbs

A. Indirect Binding ELISA

To determine if anti-NGF mAbs were present in hybridoma supernatants, ELISA plates were coated with goat anti-murine IgG Fc (Jackson ImmunoResearch, cat #115-005-164) and incubated overnight at 4° C. The plates were washed three times with wash buffer. The plates were blocked with 200 µl of 2% milk and incubated for 1 hour at room temperature. The plates were washed as above. Hybridoma supernatants were diluted 5-fold, 25-fold, 125-fold and 1625-fold with PBS and then added to the plate wells and incubated for 1 hour at room temperature. The positive control was crude sera (diluted 1:500 with PBS) isolated from a β NGF immunized mouse and the negative control was hybridoma supernatant derived from a mouse immunized with an antigen other than NGF. The plates were washed and then 50 μl of biotinylated human or rat β NGF at 50 ng/ml was added and incubated for 1 hour at room temperature. The plates were washed. Streptavidin-HRP (Thermo, cat #21126) conjugate was diluted at 10,000 and added to the plates. The plates were incubated for 30 minutes at room temperature. The plates were washed and then TMB substrate (Invitrogen, catalog #00-2023) was added. The reaction was stopped using 2N $H_2SO_4$ (VWR, catalog #BDH3500-1). The absorbance at 450 nm was read on a Spectromax 2E plate reader (Molecular Devices); these absorbance readings are shown in Tables 1 and 2. The numerical value indicates binding of mouse anti-NGF antibodies to biotinylated human or rat β NGF. This data indicates that several hybridoma supernatants contained anti-NGF antibodies.

TABLE 3

Biotinylated Human NGF Indirect Binding ELISA data

| Supernatant dilution (fold) | 30F11 | 23F1 | 22E1 | 3C3 | 16B9 | 17G6 | 23H2 | 25E5 | 29E6 | 7H1 | 19C1 | 30A1 |
|---|---|---|---|---|---|---|---|---|---|---|---|---|
| 5 | 1.066 | 1.143 | 1.288 | 1.137 | 0.821 | 1.122 | 0.913 | 1.299 | 1.196 | 1.155 | 0.936 | 1.090 |
| 25 | 1.005 | 1.171 | 1.255 | 1.108 | 0.644 | 0.529 | 1.254 | 1.127 | 1.159 | 0.555 | 0.926 |
| 125 | 0.873 | 0.979 | 0.772 | 0.948 | 0.340 | 1.017 | 0.191 | 0.988 | 0.889 | 1.002 | 0.234 | 0.507 |
| 625 | 0.436 | 0.696 | 0.296 | 0.571 | 0.107 | 0.713 | 0.085 | 0.512 | 0.426 | 0.673 | 0.100 | 0.223 |

| Supernatant dilution (fold) | 29A7 | 27A5 | 26D5 | 26H12 | 23D7 | 22A9 | 22G3 | 21D4 | 3E9 | 3F9 | 2G11 | 1D6 |
|---|---|---|---|---|---|---|---|---|---|---|---|---|
| 5 | 1.198 | 1.116 | 0.954 | 0.943 | 1.087 | 0.707 | 0.662 | 1.154 | 1.167 | 0.974 | 1.038 | 0.545 |
| 25 | 1.092 | 0.887 | 0.903 | 0.794 | 1.060 | 0.549 | 0.498 | 1.042 | 0.996 | 0.694 | 0.992 | 0.457 |
| 125 | 0.762 | 0.395 | 0.823 | 0.381 | 0.857 | 0.348 | 0.240 | 0.899 | 0.655 | 0.323 | 0.819 | 0.164 |
| 625 | 0.293 | 0.174 | 0.542 | 0.135 | 0.489 | 0.168 | 0.126 | 0.543 | 0.298 | 0.145 | 0.486 | 0.066 |

| Supernatant dilution (fold) | 4B6 | 8E4 | 9E2 | 9H2 | 20B10 | 14G6 | 12H12 | 11D1 |
|---|---|---|---|---|---|---|---|---|
| 5 | 1.252 | 1.294 | 1.126 | 1.167 | 1.098 | 1.274 | 1.222 | 0.642 |
| 25 | 1.131 | 1.076 | 1.085 | 0.915 | 0.997 | 1.206 | 1.083 | 0.497 |
| 125 | 0.768 | 0.595 | 0.938 | 0.395 | 0.576 | 0.956 | 0.741 | 0.275 |
| 625 | 0.341 | 0.250 | 0.605 | 0.171 | 0.143 | 0.598 | 0.363 | 0.117 |

| Supernatant dilution (fold) | Positive control | 4E2 | 12D6 | 1D10 | 2D8 | 3F7 | 4F11 | 4H2 | 5D8 | 5G9 | 6B2 | 6F10 |
|---|---|---|---|---|---|---|---|---|---|---|---|---|
| 3 | 1.018 | 1.078 | 0.985 | 1.105 | 1.046 | 1.282 | 1.192 | 1.013 | 0.790 | 1.052 | 1.231 | 1.096 |
| 15 | 0.981 | 0.991 | 0.844 | 0.963 | 0.868 | 1.166 | 1.016 | 0.800 | 0.654 | 0.919 | 0.939 | 1.045 |
| 75 | 1.020 | 0.705 | 0.501 | 0.655 | 0.436 | 1.049 | 0.702 | 0.447 | 0.420 | 0.534 | 0.505 | 0.999 |

| Supernatant dilution (fold) | Negative 6H2 | 7C10 | 7G1 | 8G9 | 10A12 | 10B6 | 11A9 | 12A5 | 12F6 | 13E3 | 14A9 | Negative control |
|---|---|---|---|---|---|---|---|---|---|---|---|---|
| 3 | 1.322 | 0.745 | 0.233 | 0.849 | 0.192 | 1.135 | 0.056 | 0.725 | 1.003 | 1.003 | 1.107 | 0.054 |
| 15 | 1.221 | 0.378 | 0.106 | 0.548 | 0.089 | 1.088 | 0.051 | 0.401 | 0.944 | 0.881 | 1.082 | 0.053 |
| 75 | 0.791 | 0.151 | 0.066 | 0.220 | 0.060 | 0.872 | 0.050 | 0.183 | 0.681 | 0.463 | 0.951 | 0.051 |

TABLE 4

Biotinylated Rat NGF Indirect Binding ELISA data

| Supernatant dilution (fold) | 30F11 | 23F1 | 22E1 | 3C3 | 16B9 | 17G6 | 23H2 | 25E5 | 29E6 | 7H1 | 19C1 | 30A1 |
|---|---|---|---|---|---|---|---|---|---|---|---|---|
| 5 | 0.694 | 0.764 | 1.054 | 0.698 | 0.443 | 0.749 | 0.670 | 1.091 | 0.677 | 0.733 | 0.660 | 0.690 |
| 25 | 0.734 | 0.767 | 0.936 | 0.729 | 0.350 | 0.758 | 0.412 | 1.099 | 0.655 | 0.664 | 0.462 | 0.681 |
| 125 | 0.603 | 0.737 | 0.557 | 0.628 | 0.218 | 0.751 | 0.176 | 0.803 | 0.523 | 0.603 | 0.197 | 0.445 |
| 625 | 0.361 | 0.528 | 0.229 | 0.520 | 0.094 | 0.567 | 0.083 | 0.396 | 0.261 | 0.401 | 0.088 | 0.180 |

| Supernatant dilution (fold) | 29A7 | 27A5 | 26D5 | 26H12 | 23D7 | 22A9 | 22G3 | 21D4 | 3E9 | 3F9 | 2G11 | 1D6 |
|---|---|---|---|---|---|---|---|---|---|---|---|---|
| 5 | 0.967 | 0.610 | 0.611 | 0.538 | 0.684 | 0.508 | 0.521 | 0.787 | 1.098 | 0.633 | 0.705 | 0.327 |
| 25 | 0.907 | 0.514 | 0.571 | 0.368 | 0.775 | 0.417 | 0.384 | 0.760 | 0.945 | 0.502 | 0.669 | 0.278 |
| 125 | 0.441 | 0.236 | 0.516 | 0.169 | 0.654 | 0.240 | 0.209 | 0.671 | 0.530 | 0.264 | 0.588 | 0.132 |
| 625 | 0.224 | 0.113 | 0.413 | 0.082 | 0.396 | 0.117 | 0.107 | 0.453 | 0.219 | 0.117 | 0.353 | 0.063 |

TABLE 4-continued

Biotinylated Rat NGF Indirect Binding ELISA data

| Supernatant dilution (fold) | 4B6 | 8E4 | 9E2 | 9H2 | 20B10 | 14G6 | 12H12 | 11D1 |
|---|---|---|---|---|---|---|---|---|
| 5 | 0.607 | 0.685 | 0.632 | 0.453 | 0.472 | 0.755 | 0.676 | 0.122 |
| 25 | 0.508 | 0.518 | 0.559 | 0.310 | 0.431 | 0.739 | 0.571 | 0.095 |
| 125 | 0.438 | 0.317 | 0.529 | 0.157 | 0.261 | 0.665 | 0.357 | 0.076 |
| 625 | 0.234 | 0.150 | 0.382 | 0.085 | 0.108 | 0.424 | 0.173 | 0.060 |

| Supernatant dilution (fold) | Positive control | 4E2 | 12D6 | 1D10 | 2D8 | 3F7 | 4F11 | 4H2 | 5D8 | 5G9 | 6B2 | 6F10 |
|---|---|---|---|---|---|---|---|---|---|---|---|---|
| 3 | 0.773 | 0.777 | 0.459 | 1.023 | 0.590 | 1.097 | 0.952 | 0.945 | 0.565 | 0.952 | 1.122 | 0.937 |
| 15 | 0.736 | 0.651 | 0.379 | 0.877 | 0.599 | 1.125 | 0.690 | 0.684 | 0.467 | 0.767 | 0.876 | 1.005 |
| 75 | 0.760 | 0.471 | 0.210 | 0.548 | 0.323 | 1.044 | 0.576 | 0.348 | 0.294 | 0.406 | 0.453 | 0.849 |

| Supernatant dilution (fold) | 6H2 | 7C10 | 7G1 | 8G9 | 10A12 | 10B6 | 11A9 | 12A5 | 12F6 | 13E3 | 14A9 | Negative control |
|---|---|---|---|---|---|---|---|---|---|---|---|---|
| 3 | 1.108 | 0.541 | 0.197 | 0.681 | 0.145 | 0.440 | 0.058 | 0.521 | 0.904 | 0.786 | 0.845 | 0.055 |
| 15 | 0.860 | 0.275 | 0.093 | 0.396 | 0.077 | 0.784 | 0.052 | 0.334 | 0.810 | 0.737 | 0.777 | 0.053 |
| 75 | 0.603 | 0.115 | 0.061 | 0.155 | 0.060 | 0.727 | 0.051 | 0.153 | 0.565 | 0.413 | 0.582 | 0.052 |

B. TrkA Binding ELISA

To determine if anti-NGF mAbs in hybridoma supernatants blocked NGF from binding to the TrkA receptor, ELISA plates were coated with goat anti-human IgG Fc (Jackson ImmunoResearch, cat #109-005-008) at 2 µg/ml in PBS and incubated over night at 4° C. The plates were washed three times with PBS/Tween. The plates were blocked with 200 µl/well of 2% milk in PBS for 1 hour at room temperature. The plates were washed three times as above. Rat TrkA/Fc chimera (R&D Systems, catalog #1056-TK) was added at 1 µg/ml (50 µl/well) in PBS/0.1% BSA and then incubated for 1 hour at room temperature. Biotinylated human NGF was titered and pre-incubated with anti-NGF antibody supernatants diluted 1-fold, 5-fold, and 25-fold, or purified anti-NGF mAbs diluted to 0.08, 0.4, 2, or 10 µg/ml for 1 hour at room temperature on a plate shaker. The negative control was unrelated conditioned supernatant. The positive control was sera from a mouse immunized with NGF. The plates were washed and then 50 µl of each biotinylated NGF/Ab mix was added to the appropriate wells. The plates were incubated for 1 hour at room temperature. The plates were washed. 50 µl of streptavidin-HRP (Thermo, cat #21126) was added at 10,000 dilution. The plates were incubated for 30 min at room temperature. The plates were washed. 50 µl of TMB (Invitrogen, cat #00-2023) was added and the reaction was stopped using 2N $H_2SO_4$ (VWR, cat #BDH3500-1). The absorbance at 450 nm was read on a Spectromax 2E plate reader (Molecular Devices), and the absorbance readings are shown in Table 5. The numerical value indicates binding of biotinylated human β NGF to rat TrkA/Fc chimera. This data indicates that several hybridoma supernatants contained anti-NGF receptor-blocking antibodies.

TABLE 5

Rat TrkA Inhibition Binding ELISA Data for Anti-NGF Hybridoma Supernatants

| Supernatant dilution (fold) | Negative control | Positive control | 30F11 | 23F1 | 22E1 | 3C3 | 16B9 | 17G6 | 23H2 | 25E5 | 29E6 | 7H1 |
|---|---|---|---|---|---|---|---|---|---|---|---|---|
| 1 | 0.465 | 0.050 | 0.158 | 0.108 | 0.357 | 0.146 | 0.142 | 0.091 | 0.379 | 0.304 | 0.291 | 0.217 |
| 5 | 0.456 | 0.055 | 0.210 | 0.140 | 0.429 | 0.195 | 0.249 | 0.123 | 0.622 | 0.354 | 0.600 | 0.419 |
| 25 | 0.462 | 0.102 | 0.331 | 0.276 | 0.558 | 0.345 | 0.409 | 0.210 | 0.418 | 0.505 | 0.881 | 0.758 |

| Supernatant dilution (fold) | 19C1 | 30A1 | 29A7 | 27A5 | 26D5 | 26H12 | 23D7 | 22A9 | 22G3 | 21D4 | 3E9 | 3F9 |
|---|---|---|---|---|---|---|---|---|---|---|---|---|
| 1 | 0.285 | 0.148 | 0.427 | 0.444 | 0.063 | 0.344 | 0.131 | 0.322 | 0.150 | 0.133 | 0.328 | 0.186 |
| 5 | 0.567 | 0.281 | 0.462 | 0.800 | 0.076 | 0.621 | 0.212 | 0.362 | 0.211 | 0.242 | 0.416 | 0.295 |
| 25 | 0.686 | 0.464 | 0.502 | 0.680 | 0.101 | 0.665 | 0.393 | 0.453 | 0.337 | 0.404 | 0.682 | 0.498 |

| Supernatant dilution (fold) | Neg | Pos | 2G11 | 1D6 | 4B6 | 8E4 | 9E2 | 9H2 |
|---|---|---|---|---|---|---|---|---|
| 1 | 0.372 | 0.052 | 0.138 | 0.226 | 0.169 | 0.273 | 0.103 | 0.380 |
| 5 | 0.336 | 0.073 | 0.205 | 0.281 | 0.287 | 0.669 | 0.125 | 0.604 |
| 25 | 0.318 | 0.228 | 0.328 | 0.343 | 0.424 | 0.693 | 0.151 | 0.521 |

TABLE 5-continued

Rat TrkA Inhibition Binding ELISA Data for Anti-NGF Hybridoma Supernatants

| Supernatant dilution (fold) | 20B10 | 14G6 | 12H12 | 11D1 | 19A12 | 2B12 | PBS | PBS |
|---|---|---|---|---|---|---|---|---|
| 1 | 0.166 | 0.113 | 0.060 | 0.101 | 0.100 | 0.065 | 0.295 | 0.315 |
| 5 | 0.200 | 0.192 | 0.099 | 0.152 | 0.170 | 0.070 | 0.334 | 0.297 |
| 25 | 0.289 | 0.334 | 0.190 | 0.264 | 0.295 | 0.095 | 0.306 | 0.289 |

| Supernatant dilution (fold) | −ve contrl | +ve contrl | +ve contrl | +ve contrl | 13E3 | 14A9 | 4E2 | 12D6 | 1D10 | 2D8 | 3F7 | 4F11 |
|---|---|---|---|---|---|---|---|---|---|---|---|---|
| 1 | 0.386 | 0.112 | 0.145 | 0.104 | 0.400 | 0.121 | 0.283 | 0.145 | 0.248 | 0.359 | 0.056 | 0.286 |
| 5 | 0.388 | 0.164 | 0.234 | 0.140 | 0.383 | 0.208 | 0.290 | 0.211 | 0.312 | 0.588 | 0.083 | 0.356 |
| 25 | 0.386 | 0.308 | 0.488 | 0.216 | 0.497 | 0.376 | 0.334 | 0.364 | 0.447 | 0.497 | 0.149 | 0.541 |

| Supernatant dilution (fold) | 4H2 | 5D8 | 5G9 | 6B2 | 6F10 | 6H2 | 7C10 | 8G9 | 10B6 | 12A5 | 12F6 | PBS |
|---|---|---|---|---|---|---|---|---|---|---|---|---|
| 1 | 0.396 | 0.363 | 0.344 | 0.096 | 0.206 | 0.400 | 0.230 | 0.409 | 0.329 | 0.306 | 0.172 | 0.436 |
| 5 | 0.457 | 0.398 | 0.387 | 0.215 | 0.212 | 0.523 | 0.489 | 0.473 | 0.364 | 0.328 | 0.227 | 0.351 |
| 25 | 0.606 | 0.504 | 0.473 | 0.451 | 0.242 | 0.738 | 0.487 | 0.413 | 0.399 | 0.406 | 0.324 | 0.338 |

C. SureFire Cellular Phospho-ERK (pERK) Assay

To determine if anti-NGF mAbs in hybridoma supernatants blocked downstream signaling as a result of blocking NGF from binding to TrkA, Neuroscreen-1 cells (Thermo Fisher Scientific) were grown on collagen I-coated flasks in RPMI medium supplemented with 10% horse serum, 5% FBS, 100 units/ml penicillin/streptomycin, 2 mM L-glutamine, and 10 mM HEPES at 37° C. in a humidified atmosphere at 95% air and 5% $CO_2$. For the ERK phosphorylation assay, $5 \times 10^4$ cells were seeded in each well of a 96-well plate coated with collagen I (Becton Dickinson). Cells were then serum starved for 24 hours before stimulation. 130 pM human β NGF (R&D Systems catalog #256-GF/CF) was mixed into diluted hybridoma supernatants (to achieve a final supernatant dilution (fold) of 10-fold, 100-fold, 500-fold or 1,000-fold) and mixtures were pre-incubated for 15 min at 37° C. before being added to the cells. Each diluted hybridoma supernatant was tested in quadruplicate. After 5 min of stimulation, the medium was removed and replaced with SureFire™ AlphaScreen cell lysis (PerkinElmer). Cell lysates were then processed according to the manufacturer's instructions and fluorescence signals quantified using an EnVision plate reader (PerkinElmer); the fluorescence data is summarized in Table 6. The numerical value indicates ERK phosphorylation due to TrkA signaling in the presence of human β NGF and is expressed as the percentage of signal vs. maximum signal. The maximum signal is defined as 100% response from cells showing ERK phosphorylation in the presence of only β NGF (no hybridoma supernatant). This data indicates that several hybridoma supernatants contained neutralizing anti-NGF antibodies.

TABLE 6

SureFire pERK Assay Data Generated with Anti-NGF mAb Hybridoma Supernatants

| Supernatant dilution (fold) | 23F1 | | | | 17G6 | | | | 30F11 | | | | 3C3 | | | |
|---|---|---|---|---|---|---|---|---|---|---|---|---|---|---|---|---|
| 100 | 5 | 2 | 4 | 2 | 2 | 0 | 1 | 1 | 5 | 2 | 2 | 0 | 5 | 2 | 5 | 3 |
| 1000 | 5 | 3 | 4 | 3 | 2 | 2 | 2 | 1 | 4 | 2 | 4 | 3 | 6 | 3 | 5 | 4 |
| 5000 | 8 | 7 | 8 | 8 | 13 | 7 | 15 | 8 | 30 | 26 | 28 | 25 | 24 | 25 | 22 | 23 |
| 10000 | 35 | 33 | 32 | 32 | 44 | 25 | 43 | 23 | 65 | 45 | 56 | 42 | 57 | 52 | 68 | 62 |

| Supernatant dilution (fold) | 2B12 | | | | 21D4 | | | | 4B6 | | | | 22G3 | | | |
|---|---|---|---|---|---|---|---|---|---|---|---|---|---|---|---|---|
| 100 | 0 | 0 | −1 | 0 | 4 | 3 | 5 | 2 | 5 | 4 | 1 | 0 | 13 | 7 | 7 | 2 |
| 1000 | 0 | 0 | 0 | 0 | 5 | 3 | 5 | 3 | 1 | 0 | 2 | 1 | 3 | 2 | 4 | 2 |
| 5000 | 18 | 16 | 21 | 17 | 11 | 7 | 12 | 8 | 8 | 8 | 7 | 8 | 23 | 18 | 25 | 20 |
| 10000 | 51 | 43 | 49 | 41 | 38 | 23 | 37 | 23 | 30 | 34 | 30 | 35 | 51 | 45 | 47 | 43 |

| Supernatant dilution (fold) | 2G11 | | | | 14G6 | | | | 16B9 | | | | 19A12 | | | |
|---|---|---|---|---|---|---|---|---|---|---|---|---|---|---|---|---|
| 100 | 5 | 2 | 6 | 3 | 4 | 3 | 0 | −1 | 3 | 3 | 3 | 2 | 2 | 1 | 2 | 1 |
| 1000 | 6 | 3 | 6 | 3 | −1 | 0 | 0 | 0 | 65 | 57 | 70 | 60 | 3 | 2 | 3 | 2 |
| 5000 | 14 | 8 | 14 | 8 | 7 | 7 | 8 | 7 | 72 | 63 | 73 | 62 | 47 | 36 | 46 | 32 |
| 10000 | 44 | 30 | 74 | 48 | 38 | 36 | 36 | 36 | 76 | 62 | 77 | 62 | 69 | 55 | 81 | 65 |

TABLE 6-continued

SureFire pERK Assay Data Generated with Anti-NGF mAb Hybridoma Supernatants

| Supernatant dilution (fold) | 30A1 | | | | 26D5 | | | | 23D7 | | | | 23H2 | | | |
|---|---|---|---|---|---|---|---|---|---|---|---|---|---|---|---|---|
| 100 | 0 | 0 | 1 | 0 | 0 | 0 | 0 | 0 | 2 | 2 | −1 | 0 | 47 | 41 | 44 | 44 |
| 1000 | 1 | 2 | 2 | 2 | 1 | 1 | 1 | 1 | 1 | 0 | 1 | 1 | 86 | 80 | 79 | 82 |
| 5000 | 40 | 41 | 42 | 40 | 37 | 30 | 35 | 30 | 59 | 48 | 56 | 54 | 85 | 80 | 85 | 83 |
| 10000 | 62 | 67 | 63 | 64 | 64 | 52 | 80 | 71 | 74 | 63 | 70 | 60 | 85 | 84 | 82 | 84 |

| Supernatant dilution (fold) | 9E2 | | | | 20B10 | | | | 12H12 | | | | 11D1 | | | |
|---|---|---|---|---|---|---|---|---|---|---|---|---|---|---|---|---|
| 100 | 3 | 3 | 3 | 4 | 2 | 1 | 1 | 1 | 3 | 3 | 3 | 2 | 69 | 75 | 70 | 78 |
| 1000 | 5 | 7 | 5 | 8 | 1 | 1 | 1 | 0 | 30 | 30 | 30 | 32 | 71 | 84 | 72 | 85 |
| 5000 | 37 | 57 | 36 | 55 | 20 | 28 | 19 | 29 | 62 | 64 | 60 | 61 | 76 | 78 | 80 | 76 |
| 10000 | 55 | 69 | 56 | 67 | 55 | 71 | 73 | 84 | 69 | 78 | 76 | 77 | 89 | 95 | 102 | 101 |

D. PathHunter Assay

To determine if anti-NGF mAbs in hybridoma supernatants blocked downstream signaling as a result of blocking NGF from binding to TrkA, the PathHunter U2OS stable cell line stably expressing the NGF receptor TrkA and the co-activator protein SHC1 fused to complementing fragments of β-galactosidase was purchased from DiscoveRx. Cells were grown in MEM media supplemented with 10% FBS, 100 units/ml penicillin/streptomycin, 2 mM L-glutamine, 500 μg/ml Geneticin G418, and 250 μg/ml Hygromycin at 37° C. in a humidified atmosphere at 95% air and 5% $CO_2$. Sixteen hours before the assay, $2 \times 10^4$ cells were seeded in each well of a 96-well half-volume black plate in 40 μl of MEM media supplemented with 0.5% horse serum. 440 pM human β NGF (R and D Systems catalog #256-GF/CF) was mixed into diluted hybridoma supernatants (to achieve a final supernatant dilution of 10-fold, 100-fold, 500-fold or 1,000-fold) and mixtures were pre-incubated for 15 min at 37° C. before being added to the cells. Cell plates were incubated for 5 min at room temperature before stimulation with 10 μl per well of NGF/antibody mixture. After 3 hours of cell induction at room temperature, 25 μl of PathHunter detection reagent was added to each well according to the manufacturer's instructions. The chemiluminescent signal was detected 1 hour later using a TopCount plate reader (PerkinElmer); the chemiluminescence signal data is shown in Table 7. The numerical value indicates β-galactosidase generation due to TrkA signaling in the presence of human β NGF and is expressed as the percentage of signal vs. maximum signal. The maximum signal is defined as 100% response from cells showing in the presence of β-galactosidase generation in the presence of only β NGF (no hybridoma supernatant). This data indicates that several hybridoma supernatants contained neutralizing anti-NGF antibodies.

TABLE 7

PathHunter Data Generated with Hybridoma Supernatants

| Supernatant dilution (fold) | 30F11 | | 23F1 | | 3C3 | | 16B9 | | 17G6 | | 19A12 | |
|---|---|---|---|---|---|---|---|---|---|---|---|---|
| 100 | 21 | 22 | 5 | 5 | 16 | 29 | 19 | 24 | 10 | 14 | 25 | 28 |
| 1000 | 42 | 37 | 23 | 13 | 40 | 46 | 117 | 114 | 23 | 24 | 21 | 30 |
| 5000 | 97 | 99 | 69 | 70 | 71 | 81 | 120 | 127 | 100 | 115 | 93 | 92 |
| 10000 | 94 | 93 | 92 | 91 | 78 | 84 | 114 | 129 | 115 | 120 | 89 | 98 |

| Supernatant dilution (fold) | 2B12 | | 30A1 | | 26D5 | | 23D7 | | 23H2 | | 22G3 | |
|---|---|---|---|---|---|---|---|---|---|---|---|---|
| 100 | 89 | 90 | 21 | 24 | 83 | 84 | 31 | 28 | 142 | 176 | 16 | 16 |
| 1000 | 64 | 70 | 50 | 57 | 49 | 51 | 54 | 53 | 88 | 134 | 20 | 23 |
| 5000 | 128 | 127 | 126 | 139 | 92 | 96 | 112 | 131 | 117 | 120 | 89 | 99 |
| 10000 | 128 | 133 | 133 | 129 | 95 | 84 | 124 | 148 | 111 | 136 | 86 | 101 |

| Supernatant dilution (fold) | 21D4 | | 2G11 | | 4B6 | | 9E2 | | 20B10 | |
|---|---|---|---|---|---|---|---|---|---|---|
| 100 | 9 | 10 | 22 | 22 | 24 | 31 | 102 | 104 | 6 | 5 |
| 1000 | 16 | 17 | 29 | 27 | 46 | 49 | 77 | 91 | 0 | 4 |
| 5000 | 107 | 100 | 66 | 72 | 88 | 94 | 137 | 152 | 25 | 31 |
| 10000 | 108 | 112 | 66 | 72 | 102 | 109 | 137 | 143 | 52 | 58 |

TABLE 7-continued

PathHunter Data Generated with Hybridoma Supernatants

| Supernatant dilution (fold) | 14G6 | | 12H12 | | 11D1 | | 26H12 | | Unrelated hybridoma | |
|---|---|---|---|---|---|---|---|---|---|---|
| 100 | 18 | 17 | 26 | 23 | 117 | 101 | 106 | 119 | 156 | 185 |
| 1000 | 27 | 27 | 46 | 56 | 127 | 118 | 124 | 115 | 136 | 144 |
| 5000 | 105 | 83 | 145 | 137 | 109 | 99 | 137 | 166 | 126 | 132 |
| 10000 | 113 | 109 | 122 | 145 | 91 | 98 | 151 | 167 | 138 | 137 |

Example 3

Hybridoma Sub-Cloning

Hybridoma cell lines were subcloned using standard limiting dilution techniques. Cells were diluted to a concentration of 50, 5, or 0.5 cells/mL. 200 uL of the diluted cell suspensions were plated into 96 well tissue culture plates. The plates were incubated at 37° C. with 5% $CO_2$ and ~90% relative humidity. The growth was visually checked at day 7 for macroscopic colonies. Supernatants from wells were screened for antibody production when colony growth was visible. Table 8 shows the subclone identification nomenclature and monikers. This data indicates that several anti-NGF antibodies could be isolated from a clonal population of cells.

TABLE 8

Hybridoma Subclone Identification and Monikers

| Hybridoma Supernatant Name | Subcloned Hybridoma Name | Moniker | Lot # |
|---|---|---|---|
| 14G6 | ML129-14G6.3H3 | PR-1254970 | 1734671 |
| 2G11 | ML129-2G11.3B1 | PR-1254971 | 1734673 |
| 20B10 | ML129-20B10.3F4 | PR-1254972 | 1734675 |
| 2B12 | ML129-2B12.5G9 | PR-1254973 | 1734676 |
| 17G6 | ML129-17G6.3E7 | PR-1254974 | 1734677 |
| 21D4 | ML129-21D4.4A11 | PR-1254977 | 1734678 |
| 4B6 | ML129-4B6.4H3 | PR-1254978 | 1734679 |
| 22G3 | ML129-22G3.3F3 | PR-1254979 | 1734680 |
| 23F1 | ML129-23F1.4G3 | PR-1254980 | 1734681 |
| 14A9 | ML130-14A9.5B12 | PR-1254981 | 1734682 |
| 3F7 | ML130-3F7.4A8 | PR-1254982 | 1734683 |

Example 4

Scale Up and Purification of Monoclonal Antibodies

Subcloned hybridoma cell lines were expanded into Hybridoma SFM (Invitrogen catalog #12045) with 5% Low IgG Fetal bovine serum (Invitrogen catalog #16250-078). Supernatants were harvested, centrifuged and filtered to remove cellular debris, and concentrated. Antibodies were mixed with Pierce binding buffer A (Thermo, catalog #21001) in a 1 ratio. The antibodies were loaded onto a recombinant Protein A sepharose (GE Healthcare, catalog #17-1279-04) chromatography column, eluted using Pierce elution buffer (Thermo, catalog #21004), neutralized using 2M Tris pH 7.5, and then dialyzed into PBS. This work allowed the isolation of anti-NGF mAbs for characterization studies.

Example 5

Cloning of Canine NGF

The coding region of canine NGF was amplified from canine universal cDNA (Biochain Institute, catalog #4734565) using primers of SEQ ID NO: 45 and SEQ ID NO: 46 or primers of SEQ ID NO: 47 and SEQ ID NO: 48 and cloned into a mammalian or bacterial expression vector, respectively. The PCR reactions were set up as recommended by the manufacturer (Novagen, KOD Hot Start Master Mix, catalog #71842-3). The mammalian clone was made as a C-terminal 6-His fusion protein (SEQ ID NO: 208) by ligating the PCR product with pTT6 vector (Abbott) at the KpnI/XbaI restriction sites. The bacterial clone was made with the pro-NGF sequence using the mammalian clone as a template and ligated with pET15B (Novagen) at the NdeI/XhoI restriction sites. The DNA sequence and amino acid sequence of the canine NGF isolated are listed as SEQ ID NO: 49 and SEQ ID NO: 50, respectively. This work allowed expression of canine NGF protein for purification.

Example 6

Expression of Canine NGF

The canine NGF clone in the bacterial expression vector was grown at 37° C. in overnight express auto inducing Terrific Broth (Novagen) in Rosetta2 (DE3) *E. coli* host (EMD Biosciences) in 2 L non-baffled flasks. The cells were centrifuged down and the cell paste was resuspended in 100 mL of lysis buffer (25 mM Tris, 300 mM NaCl, 10% glycerol, 0.1% Triton X 100 pH 8.0) with lysonase and sonicated for 2 min on ice. The sample was centrifuged at 15000 RPM and the pellet was solubilized in 50 mL of 25 mM Tris, 6 M GdHCl pH 8.0. The sample was centrifuged at 15000 rpm for 30 min and the supernatant was loaded on to a 10 ml IMAC resin.

A. IMAC Chromatography

A 10 ml GE-Ni FF column was prepared. Buffer A: 25 mM Tris, 6 M GdHCl pH 8.0, Buffer B: A+500 mM Imidazole. The resin was equilibrated and loaded with recirculation to allow for complete binding (~10 passes) overnight at 4° C. The column was washed with Buffer A. Batch elution was carried out with 40 ml Buffer A, followed by 30 ml Buffer A. 5 ml fractions were collected and pooled.

B. Refolding by Rapid Dilution

The pooled fraction was reduced by adding 50 mM DTT, and EDTA was added to 10 mM, and incubated for 1 h at RT. The sample was acidified by adding 6M HCl to pH 4.0 and dialyzed into 6M GdHCl pH 5.0 to remove excess DTT. Refolding was performed by diluting the reduced/acidified sample in 1 L of 100 mM Tris, 1 M Arginine, 5 mM EDTA, 5 mM GSH, 1 mM GSSG (SEQ ID NO: 209) pH 9.5 for 4 h at 4° C. The refolded protein was dialyzed against 25 mM Tris, 200 mM NaCl, 10% Glycerol pH 8.0. Precipitation was cleared by filtration. The clarified sample was concentrated and diafiltered into 25 mM Tris, 200 mM NaCl, 10% Glycerol pH 8.0 using a 10K membrane.

C. Ni-IMAC

Refolded pro-NGF was loaded on a 5 ml Ni-IMAC. Buffer A: 25 mM Tris, 300 mM NaCl, 10% Glycerol pH 8.0. Buffer B: A+500 mM Imidazole. The column was washed with Buffer A. 8 ml fractions were collected. Elution was performed with a linear gradient 0-100% Buffer B. 5 ml fractions were collected. Samples of each fraction were mixed with non-reducing NuPage SLB (Invitrogen) and separated on a 4-12% NuPAGE Novex Bis-Tris Midi gel for analysis. Fractions containing protein were pooled and dialyzed against 20 mM Na Phosphate, 50 mM NaCl, 10% glycerol pH 7.4.

D. Trypsin Digestion

Pro-β NGF was mixed with trypsin in resuspension buffer and incubated on ice for 30 min. Immobilized inhibitor was added and incubated for 15 min and then filtered.

E. Sepharose Cation Exchange Chromatography

The sample was loaded on a 5 ml SP Sepharose high performance chromatography column (GE Healthcare). Buffer A: 20 mM Na Phosphate, 50 mM NaCl, 10% Glycerol pH 7.4, Buffer B: A+1 M NaCl. The column was washed with Buffer A. Elution was performed with linear gradient 0-100% Buffer B. 5 ml fractions were collected. The fractions were separated on a 4-12% Criterion XT Bis-Tris Midi gel for analysis. Fractions containing protein were pooled, dialyzed in PBS pH 7.4, and concentrated.

This work resulted in the production of several milligrams of purified canine NGF for characterization studies and for studies of anti-NGF canine antibodies.

Example 7

Characterization of Subloned and Purified Hybridoma Antibodies

A. Canine NGF Direct Binding ELISA

To determine if purified mouse anti-NGF mAbs bind to canine β NGF, ELISA plates were coated with 50 μl/well of canine NGF (Abbott Laboratories) at 1 μg/ml in PBS and incubated over night at 4° C. The plates were washed three times with PBS+Tween buffer. The plates were blocked with 200 μl/well of 2% milk in PBS for 1 hour at room temperature. The plates were washed three times as above. Purified antibodies were diluted to 0.4, 2, or 10 μg/ml. 50 μl of each concentration of purified antibody was added to the plates. The plates were incubated for 1 hour at room temperature. The plates were washed. 50 μl of a 5000-fold diluted goat anti-mouse IgG Fc-HRP (Thermo, catalog #31439) was added. The plates were incubated for 1 hour at room temperature. 50 μl of TMB (Invitrogen, catalog #00-2023) was added and the reaction was stopped using 2N $H_2SO_4$ (VWR, catalog #BDH3500-1). The absorbance at 450 nm was read on a Spectromax 2E plate reader (Molecular Devices). The results are shown in Table 9, and the numerical value indicates binding of mouse anti-NGF antibodies to canine β NGF.

TABLE 9

Canine NGF Direct Binding ELISA Data Using Purified Anti-NGF mAbs

| μg/ml Mab | PR-1254970 | PR-1254971 | PR-1254972 | PR-1254973 | PR-1254974 | PR-1254977 | PR-1254978 | PR-1254979 | PR-1254980 | PR-1254981 | PR-1254982 |
|---|---|---|---|---|---|---|---|---|---|---|---|
| 10 | 0.530 | 0.497 | 0.154 | 0.905 | 0.552 | 0.552 | 0.579 | 0.683 | 0.491 | 0.610 | 0.208 |
| 2 | 0.342 | 0.324 | 0.091 | 0.836 | 0.383 | 0.414 | 0.458 | 0.566 | 0.334 | 0.458 | 0.142 |
| 0.4 | 0.176 | 0.165 | 0.071 | 0.769 | 0.209 | 0.223 | 0.253 | 0.313 | 0.168 | 0.229 | 0.095 |

B. TF-1 Cell Proliferation Potency Assay

TF-1 is a human erythroleukaemic cell line that expresses human TrkA and proliferates in response to recombinant β NGF. To determine if purified anti-NGF mAbs blocked NGF-induced proliferation, TF-1 cells (ATCC# CRL-2003) were maintained at 37° C. and 5% $CO_2$ in RPMI (Gibco, cat #11875-093) media containing recombinant human GM-CSF at 2 ng/mL (R&D Systems, cat #215-GM) and fetal bovine serum (FBS, Hyclone, cat #SH 30070.03). GM-CSF and FBS was removed 24 hours before the assay. On day one of the assay each anti-NGF mAb was titrated (concentrations ranging from 33.3 nM to 1.7 fM) and added to a fixed concentration of recombinant canine NGF (70 pM) and TF-1 cells ($2.5 \times 10^4$ cells/well) in RPMI+4% FBS for 72 hours. Cell proliferation was measured using Cell Titer-glo (Promega, cat #G7571). The $IC_{50}$ values of each anti-NGF mAb on canine NGF-induced TF-1 cell proliferation is shown in Table 10, and the data shows that in the presence of 70 pM canine NGF, most of the anti-NGF antibodies display sub-nM potencies, and some display potencies of less than 50 pM.

TABLE 10

Potency of Mouse Anti-NGF Antibodies on Canine NGF-Induced TF-1 Cell Proliferation

| Moniker | Lot | IC50 (nM) |
|---|---|---|
| PR-1254970 | 1734671 | 0.662 |
| PR-1254971 | 1734673 | 1.088 |
| PR-1254972 | 1734675 | 0.303 |
| PR-1254973 | 1734676 | 0.039 |
| PR-1254974 | 1734677 | 0.230 |
| PR-1254977 | 1734678 | 0.217 |
| PR-1254978 | 1734679 | 0.978 |
| PR-1254979 | 1734680 | 0.288 |
| PR-1254980 | 1734681 | 0.343 |
| PR-1254981 | 1734682 | 0.046 |
| PR-1254982 | 1734683 | 0.025 |

C. SureFire Cellular pERK and PathHunter Assays

To determine if purified mouse anti-NGF mAbs blocked canine NGF-induced cellular responses, purified antibodies were characterized by titration in the SureFire cellular pERK (using 128 pM canine β NGF in each test well) and PathHunter assays (using 441 pM canine NGF in each test well) as described in Example 2 Sections C and D. The $IC_{50}$ of each anti-NGF mAb on canine β NGF-induced cellular responses is summarized in Table 11, and the data shows that in the presence of 128 pM canine NGF all the anti-NGF antibodies display sub-nM potencies, and some display potencies of less than 50 pM (pERK assay). Also, in the presence of 441 pM canine NGF, all the anti-NGF antibodies display sub-nM potencies, and some display potencies of less than 150 pM (PathHunter assay).

TABLE 11

Summary of pERK and Path Hunter Assay Data for Purified Anti-NGF mAbs

| Antibody | SureFire pERK $IC_{50}$ (nM) | PathHunter $IC_{50}$ (nM) |
| --- | --- | --- |
| PR-1254970 | 0.02711 | 0.3346 |
| PR-1254971 | 0.04750 | 0.4986 |
| PR-1254972 | 0.2282 | 0.3133 |
| PR-1254973 | 0.01876 | 0.1428 |
| PR-1254974 | 0.01561 | 0.2464 |
| PR-1254977 | 0.01759 | 0.1810 |
| PR-1254978 | 0.02466 | 0.3559 |
| PR-1254979 | 0.01627 | 0.2414 |
| PR-1254980 | 0.01371 | 0.3812 |
| PR-1254981 | 0.02135 | 0.2794 |
| PR-1254982 | 0.005804 | 0.1505 | at 95% buffer B for 10 mins. The TOF acquisition parameters were: gas temperature at 350 C and OCT/RF at 750V. The mass range was from 600-3200 m/z and the rate specified was 1.03 spectra/s. Qualitative analysis software (Agilent) was used to deconvolute antibody molecular weights.

The antibodies were analyzed on Shimadzu LC-10AVP system (Shimadzu Scientific). The SEC column used was a Superdex-200 10/300L (GE Healthcare). The flow rate was 0.75 ml/min and UV280 was used to monitor peaks. The buffer used was $Na_2SO_4$+92 mM $NaPO_4$+5 mM $NaZ_3$, pH 7.0. The reagent antibody was injected in 10 μL (10 μg). The gel protein markers on SEC were from Bio-Rad (CN#151-1901). The MS and SEC results are summarized in Table 12. This data determined the hybridoma-derived antibodies were highly monomeric following purification. In addition, the molecular weights of the heavy and light chains comprising the hybridoma-derived antibodies were determined.

B. Antibody Isotype Determination

The isotype of the anti-NGF mAbs was determined using the Zymed Mouse MonoAb-ID Kit (Invitrogen catalog#90-6550 lot#1407589). The isotyping results are summarized in Table 12. This data indicates that murine IgG1/k, IgG2a/k, and IgG2b/k mouse antibodies are capable of binding and neutralizing NGF.

TABLE 12

Isotyping, Size Exclusion Chromatography, and Mass Spectrometry Analysis of Anti-NGF Antibodies

| Hybridoma Name | Moniker | Lot | Isotype | % Monomer | Molecular weight (Dal) Light Chain | Molecular weight (Dal) Heavy Chain |
| --- | --- | --- | --- | --- | --- | --- |
| ML129-14G6.3H3 | PR-1254970 | 1734671 | IgG1 Kappa | 96.9 | 24221.43 | 49479.67 |
| ML129-2G11.3B1 | PR-1254971 | 1734673 | IgG1 Kappa | 96.8 | 24156.26 | 49491.69 |
| ML129-20B10.3F4 | PR-1254972 | 1734675 | IgG2b Kappa | 99.0 | 24159.34 | 50329.24 |
| ML129-2B12.5G9 | PR-1254973 | 1734676 | IgG2b Kappa | 99.4 | 23539.38 | 51102.21 |
| ML129-17G6.3E7 | PR-1254974 | 1734677 | IgG1 Kappa | 98.8 | 24221.43 | 49479.45 |
| ML129-21D4.4A11 | PR-1254977 | 1734678 | IgG1 Kappa | 98.4 | 24221.46 | 49479.70 |
| ML129-4B6.4H3 | PR-1254978 | 1734679 | IgG1 Kappa | 96.7 | 24170.40 | 49533.92 |
| ML129-22G3.3F3 | PR-1254979 | 1734680 | IgG2a Kappa | 99.0 | 24221.42 | 50123.17 |
| ML129-23F1.4G3 | PR-1254980 | 1734681 | IgG1 Kappa | 99.5 | 24221.42 | 49493.95 |
| ML130-14A9.5B12 | PR-1254981 | 1734682 | IgG1 Kappa | 99.1 | 24180.28 | 50241.85 |
| ML130-3F7.4A8 | PR-1254982 | 1734683 | IgG1 Kappa | 99.4 | 23708.54 | 50289.13 |

Example 8

Characterization of Purified Anti-NGF Antibodies Following Hybridoma Subcloning

A. Mass Spectrophotometry (MS) and Size Exclusion Chromatography (SEC) Analysis on Anti-NGF Antibodies The mouse anti-NGF mAbs were reduced using 1M DTT and analyzed using HPLC/MS on a 6224 TOF mass spectrometer and a 1200 HPLC (Agilent technologies) using a Vydac C4, 1 MM×150 mm column (CN#214TP5115, the Nest Group) at a flow rate of 50 μl/min Buffer A: 99.9% HPLC water+0.1% FA+0.01% TFA and buffer B: 99.9% ACN+0.1% FA+0.01% TFA. The LC equilibrium and sample desalting was performed using 5% buffer B for 7 min. The separation gradient was performed using 30% to 50% Buffer B for 10 min and a washing step was performed Example 9

Binding Kinetics of Anti-NGF Antibodies

A biomolecular protein interaction analysis was used to evaluate the binding kinetics of the interaction between the purified anti-NGF hybridoma antibodies and recombinant canine β NGF. The antibodies were captured using a goat anti-mouse IgG FC (10000 RU) surface which was directly immobilized to a CM5 chip using an amine coupling procedure according to the manufacturer's instructions (Biacore). A sample size of 5 μl of antibody at a concentration of 1 μg/ml was captured at 10 μL/minute. Recombinant canine NGF was used as the antigen. Canine NGF was injected at 75 μl/min (concentration range: 5-0.039 nM) for mouse antibodies. The association rate was monitored for 3.3 minutes and the dissociation rate was monitored for 10 minutes. Aliquots of canine NGF were also simultaneously injected over a reference reaction CM surface to record any nonspecific binding background. The instrument sensitivity for on-rate is $1\times10^7$, such that any on-rate that is faster than $1\times10^7$ may not be accurately measured; the instrument sensitivity for off-rate is $1\times10^{-6}$, such that any off-rate that is slower than $1\times10^{-6}$ may not be accurately measured. Therefore, an on-rate that is faster than $1\times10^7$ is recorded as $>1\times10^7$ and an off-rate that is slower than $1\times10^{-6}$ is recorded as $<1\times10^{-6}$. The biomolecular protein interaction analysis results are summarized in Table 13. This data indicates that the isolated murine anti-NGF mAbs have fast on-rates (from greater than $7\times10^6$) and slow off-rates (from less than $1\times10^{-3}$). The overall KDs of the murine anti-NGF mAbs range from about 300 pM to 0.1 pM demonstrating efficient binding of the purified anti-NGF hybridoma antibodies to recombinant canine β NGF.

TABLE 13

Binding Kinetics of Anti-NGF mAbs to Canine NGF

| Antibody | | On rate (1/Ms) | Off rate (1/s) | Overall affinity (M) |
|---|---|---|---|---|
| PR-1254972 | Expt 1 | $>1 \times 10^7$ | $3.14 \times 10^{-3}$ | $<3.14 \times 10^{-10}$ |
| lot: 1734675 | Expt 2 | $>1 \times 10^7$ | $3.21 \times 10^{-3}$ | $<3.21 \times 10^{-10}$ |
|  | Average | $>1 \times 10^7$ | $3.18 \times 10^{-3}$ | $<3.18 \times 10^{-10}$ |
| PR-1254973 | Expt 1 | $>1 \times 10^7$ | $1.21 \times 10^{-4}$ | $<1.21 \times 10^{-11}$ |
| lot: 1734676 | Expt 2 | $>1 \times 10^7$ | $1.38 \times 10^{-4}$ | $<1.38 \times 10^{-11}$ |
|  | Average | $>1 \times 10^7$ | $1.30 \times 10^{-4}$ | $<1.30 \times 10^{-11}$ |
| PR-1254977 | Expt 1 | $>1 \times 10^7$ | $1.39 \times 10^{-4}$ | $<1.39 \times 10^{-11}$ |
| lot: 1734678 | Expt 2 | $>1 \times 10^7$ | $1.60 \times 10^{-4}$ | $<1.6 \times 10^{-11}$ |
|  | Average | $>1 \times 10^7$ | $1.50 \times 10^{-4}$ | $<1.5 \times 10^{-11}$ |
| PR-1254980 | Expt 1 | $>1 \times 10^7$ | $2.37 \times 10^{-4}$ | $<2.37 \times 10^{-11}$ |
| lot: 1734681 | Expt 2 | $>1 \times 10^7$ | $2.25 \times 10^{-4}$ | $<2.25 \times 10^{-11}$ |
|  | Average | $>1 \times 10^7$ | $2.31 \times 10^{-4}$ | $<2.31 \times 10^{-11}$ |
| PR-1254981 | Expt 1 | $8.67 \times 10^6$ | $1.27 \times 10^{-4}$ | $1.47 \times 10^{-11}$ |
| lot: 1734682 | Expt 2 | $7.48 \times 10^6$ | $1.40 \times 10^{-4}$ | $1.87 \times 10^{-11}$ |
|  | Average | $8.08 \times 10^6$ | $1.34 \times 10^{-4}$ | $1.67 \times 10^{-11}$ |
| PR-1254982 | Expt 1 | $>1 \times 10^7$ | $<1 \times 10^{-6}$ | $<1 \times 10^{-13}$ |
| lot: 1734683 | Expt 2 | $>1 \times 10^7$ | $<1 \times 10^{-6}$ | $<1 \times 10^{-13}$ |
|  | Average | $>1 \times 10^7$ | $<1e \times 10^{-6}$ | $<1 \times 10^{-13}$ |

Example 10

Method for Identifying Anti-NGF Antibody Sequences from Hybridomas by Cloning and Sequencing To identify the nucleotide and amino acid sequence of the six subcloned hybridoma mAbs shown in Table 13, the RNA from individual hybridoma cultures was extracted with Qiagen RNeasy kit (Qiagen, cat #74104). RNA was reverse-transcribed and cDNA antibody sequences amplified using the Qiagen One-Step RT-PCR kit (Qiagen, catalog #210212). Forward primers were degenerate and designed to anneal to the variable regions (heavy chain primers: 1HA, 1HB, 1HC, 1HD, 1HE, 1HF; and light chain primers: 1LA, 1LB, 1LC, 1LD, 1LE, 1LF, 1LG) (EMD4 Biosciences catalog #69896). Reverse primers were also degenerate and made to constant regions of gamma (heavy chains) and kappa (light chains). PCR products of approximately 400-450 base pairs were gel isolated and purified with Qiagen Gel Extraction kit (Qiagen, cat #28706).

Purified PCR products were cloned into TOPO TA cloning vectors (Invitrogen, cat #K4500-01SC). Each topoisomerase reaction mixture was used to transform TOP 10 chemically competent bacteria and plated on LB plates with 75 μg/ml Ampicillin and 60 μl 2% Bluo-Gal (Invitrogen, cat #15519-028). Isolated colonies were picked from the LB plate to inoculate 20 μl LB broth/100 μg/ml carbenicillin. One μl of this mini-culture was used in a PCR reaction with M13 forward and reverse primers to amplify the insert in the TOPO vector. PCR products were separated on 2% agarose gels; samples indicating an appropriately-sized insert in the vector were sequenced using an Applied Biosystems model 3730S DNA sequencer. DNA sequences derived from the identification of all murine mAb heavy and light chain variable domains were translated into protein sequence and are shown in FIG. 1 to FIG. 24.

Example 11

Homology Modeling of Murine Anti-NGF Antibodies

The sequences of the heavy and light chain variable regions of each anti-NGF antibody were imported into InsightII (Accelrys, San Diego, Calif.). Each sequence was used as a template for BLAST to find the Xray crystal structures from the Protein Data Bank (www.rcsb.org) which were closest in identity. One structure for each of the heavy and light chains was selected based both on percent identity and on matching the exact length of all CDR loops. The sequences of each template and each query sequence were aligned and standard homology modeling techniques used to construct homology models of each chain. The complex of both modeled chains was then minimized for 50 cycles of restrained (500 Kcal/Angstrom for all heavy atoms) conjugate gradient minimization using the CVFF forcefield in the DISCOVER program (Accelrys, San Diego, Calif.).

The likelihood that a given framework residue would impact the binding properties of the antibody depends on its proximity to the CDR residues. Therefore, using the model structures, residues that fell within 5 Å of any CDR atom were identified as most important and were recommended to be candidates for retention of the murine residue in the caninized antibody sequences. A change in nucleotide(s) in a mutant gene that restores the original sequence and hence the original phenotype is often referred to as a back mutation. Therefore, we refer to residues that are candidates for retention of the murine residue in the caninized antibody sequences as backmutations.

Example 12

Identification of Canine Heavy and Light Chain Antibody Sequences from Canine PBMCs To identify canine Ig heavy and lamda light chain antibody variable domain amino acid sequences, RNA was isolated from mongrel canine peripheral blood mononuclear cells (PBMCs) using an RNEasy kit (Qiagen #74104). Canine PBMC mRNA was reverse transcribed (RT) with SuperScript III reverse transcriptase (Invitrogen catalog #18080-093) and cDNAs were amplified using the 5' RACE System (Rapid Amplification of cDNA Ends) (Invitrogen #18374-058). RT and PCR primers (RK323, RK324, RK122, LG010, LG011, LG012) are described in patent publication number: U.S. Pat. No. 7,261,890 B2 entitled Methods for Using Canine Immunoglobulin Variable Domains and Caninized Antibodies). Primers RK323 and RK324 were used for canine IgG reverse transcription followed by nested PCR with RK326 and the Abridged Anchor Primer (AAP) (Invitrogen). LG011 was used for canine lambda light chain RT PCR, followed by nested PCR with LG010 and LG012 and AAP.

The resulting PCR products were separated by agarose gel electrophoresis. The 600 base pair (canine lambda and kappa light chains) and 800 base pair (canine Ig heavy chain) PCR products were purified from the agarose using a Gel Extraction kit (Qiagen #28706) and cloned into the TA site of the pCR2.1 TOPO vectors using the TOPO-TA Cloning system (Invitrogen #K4500-01SC). Transformed TOP10 bacteria were selected and plasmid DNA was isolated using Qiaprep Spin Mini-Prep Kit (Qiagen #27104). Plasmid DNA from 25 heavy chain, 38 kappa light chain and 23 lambda light chain colonies was sequenced to identify the nucleotide and corresponding amino acid sequences. Complete variable domain sequence data were obtained from 25 heavy chain, 38 kappa light chain and 19 lambda light chain clones. Variable domain sequence data including the leader peptide (when identified) are shown in Tables 14, 15 and 16. All derived heavy chain and light chain sequence are unique compared to those disclosed in patent publication number: U.S. Pat. No. 7,261,890 B2.

TABLE 14

Canine Heavy Chain Variable Domain Sequences Derived from Canine PBMC RNA

| Name | Sequence |
| --- | --- |
| Ca-1005 | EVQLEESGGDLVKPGGSLRLSCVASGFSIGSYGMSWVRQSPGK GLQWVAWIKYDGSRTFYADAVKGRFTISRDNAKNTLFLQMNSL RAEDTAVYFCVKGPNSSWLPSTYFASWGQGTLVTVSS (SEQ ID NO: 178) |
| Ca-2301 | EMQLVESGGDLVRPGGSLRLSCVASGFTFSTYGMTWVRQSPGK GLQWVATIGPGGRNTYYADAVKGRFTISRDDAENTLFLQMNSL RAEDTAVYYCAQAFDATYYTSFDCWGRGSLVAVSS (SEQ ID NO: 86) |
| Ca-2302 | MESVLSWVFLVALLQGIQGEIRLVESGGDLVKPGGSLRLSCVA SGFIFGNYDMSWVRQAPGKGLQWVAAVRYDGSSTYYSDAVKGR ITISRDDPGNTVYLQLDSLRAEDTATYYCVRGGYYSSSFYIGG AFGHWGPGTLITVSS (SEQ ID NO: 87) |
| Ca-2303 | MECVLGWVFLVAILRGVQGEVQLVESGGDLVKPGGSLRLSCVA SGFTFSDYYMSWIRQAPGKGLQWVADISDGGDTGYAGAVKGR FTVSRENVKNTLYLQMNDLRAEDTAIYYCTKAREMYGYRDFDS WGPGTLVTVSS (SEQ ID NO: 88) |
| Ca-2304 | MESVLGLVALLTILKGVQGEVQLVESGGDLVKPGGSLRLSCVA SGFTFSNYYMTWVRQAPGKGLEWVGYIHNGGTYTYYADAVKGR FTISRDDAKNTLYLEMNSLRAEDTAVYYCGKMIFDYWGQGTLV TVSS (SEQ ID NO: 89) |
| Ca-2305 | MESALSWVFLVTILKGVQGEVLLVESGGDLVKPGGSLRLSCLT SGFTFNTYDWGWVRQAPGKGLQWIAYIKKGGSDVRYADAVKGR FTISRDDAKNTLYLQMNSLRAEDTAVYYCARSAWDSFDYWGQG TLVTVSS (SEQ ID NO: 90) |
| Ca-2306 | MESVFCWVFLVAILKGVRGVQGEVQLVESGGDLVKPAGSLRLS CVASGFTFTDYSMNWVRQAPGKGLQWVATISNDGTSTDYTDAV KGRFTVSRDSARNTVYLQMTSLRADDTATYYCVSRHSYSLLAD YWGQGTLVTVSS (SEQ ID NO: 91) |
| Ca-2307 | MQMPWSLLCLLAAPLGVLSEVTLQESGPGLVKPSQTLSLTCAV SGGSVIRNYYWHWIRQRPGRGLEWMGCWSETTYYSPAFRGRIS ITIDAATDQFSLHLNSMTTDDTAVYYCARALYPTSSWYDGMDY WGHGASVVVSS (SEQ ID NO: 92) |
| Ca-2308 | EVQLVESGGDLVKPGGSLRLSCESSGFIFSQYAMNWVRQAPGK GLQWVAYIGGAGFITYHADDVKGRFTISRDNAKNTLYLQMNSL TINDTAVYYCVRSNSRIPDYWGQGTLVAVSS (SEQ ID NO: 93) |
| Ca-2309 | MESVFCWVFLVAILKGVQGEVQLVESGGDLVKPGGSLRLSCVA SGFTFSSVYMSWVRQAPGKGLQWVARITTDGTDTFYADAVKGR FTISRDNVKNMLYLEMNSLRAEDTAIYYCGDPWQPAYPDLWGQ GTMVTVSS (SEQ ID NO: 94) |

TABLE 14-continued

Canine Heavy Chain Variable Domain Sequences Derived from Canine PBMC RNA

| Name | Sequence |
| --- | --- |
| Ca-2310 | MESVLCWVFLVAILKGVQGEVHLVESGGDLVKPGGTLRLSCVA SGFTFSQYDMSWVRQSPGKGLQWVALSRYHGGGTYYADAVKGR FTISRDNAKNMLYLQMNSLRAEDTAVYYCVKEGSRWDLRGDYD YWGQGTLVTVSS (SEQ ID NO: 95) |
| Ca-2311 | MQMPWSLLCLLAAPLGVLSELTLQESGPGLVKPSQTLSLTCVV SGGSVTSSHYWNWIRQRPGRGLEWMGYWTGNVNYNPAFQGRIS IIGDAAKNQFSLHLSSMTTDDTAVYYCARCGIVAPGFLPIGDF DFWGQGTLVTVSS (SEQ ID NO: 96) |
| Ca-2312 | MESVFCWVFLVAILKGVQGEVQLVESGGDLVKPGGSLRLSCVA SGFSFSNYFMFWGRQAPGKGLQWVARIRSDGGSTYYADAVKGR FTISRDNARNTLYLQMNSLRAEDTATYYCAKADIIKLPEYRGQ GTLVTVSS (SEQ ID NO: 97) |
| Ca-2401 | ESVLGWIFLATILKGVQGEVQLVESGGDLVKPGGSLRLSCVGS GFTFSSSWMNWVRQAPGKGLQWIAEISGTGSSTNYADAVKGRF TISRDNDKNTLYLQMNSLRAEDTAMYYCARAAYYGNYRNDLDY WGQGTLVTVSS (SEQ ID NO: 98) |
| Ca-2402 | KPAGSLRLSCVASGFTFSSHSVTWVRQAPGKGLQFVAGITSGG NNRYYTDAVRGRPFTLSRDNAKNTVYLQMNSLRAEDTAMYFCAL GSYEWLSGEFDYWGQGTLVTVSS (SEQ ID NO: 99) |
| Ca-2403 | MESVFCWVFLVAILKGVQGEVQLVESGGDLVKPGGSLRLSCVA SGFTLNNYFMYWVRQAPGKGLQWVARLNSNGDSTFYADAVKGR FTISRDNAKNTLYLQMNSLRAEDTSMYYCAKDLIYGYTLWGQG TLVTVSS (SEQ ID NO: 100) |
| Ca-2404 | MASVLSWVFLVAIVKGVQGEVQLVESGGDLVKPGGSLRLSCVA SGFIFNKYEVYWVRQAPGKGLEWVARILESGNPTYYAEAVEGR FTISRDNAKNMAYLQMNSLRADDTAVYYCATPSVSSTVAIDYW GQGALVTVSS (SEQ ID NO: 101) |
| Ca-2405 | MQMPWSLLCLLATPLGVLSELTLQESGPGLVKPSQTLSLTCVV SRGSVTSDYYWNWIRQRPGRGLEWMGHWIGSTAYNPAFQGRIS ITADTAKNQLSLQLRSMTTEDTAVYFCARGSSWTPSGDSWGQG TLVTVSS (SEQ ID NO: 102) |
| Ca-2406 | MASVLKLGFSCRYCKKVSRVRCNXVESGGDLVKPGGSLRLSCV ASGFIFNKYEVYWVRQAPGKGLEWVARILESGNPTYYAEAVEG RFTISRDNAKNMAYLQMNSLRADDTAVYYCATPSVSSTVAIDY WGQGALVTVSS (SEQ ID NO: 103) |
| Ca-2407 | MDCSWRIFFLLALATGVHSEVQLVQSAAEVKKPGASVKVSCKT SGYTLTDYYIHWVQQAPGTGLHWMGWIDPEXGTTDYAQKFQGX VTLTTADTSTNTAYMELSGLRAEDTAVYYCARFPRSLDYGSFPF DYWGQGTLVTVSS (SEQ ID NO: 104) |
| Ca-2408 | MESVLCWVFLVAILKGVQGEVRLVESGGDLVKPGGSLRLSCVA SGFTFRNYGMSWVRQRPGKGLQWVAAIRSDGVTYYADDLKVRF TVSRDDARNTLYLQLNSLGAEDTAVYYCAKAPWGLYDAWGQGT LVTVSS (SEQ ID NO: 105) |
| Ca-2409 | MESVLSWVFLVAILQGVQGEVQVVESGGDLVKPAGSLRLSCVA SGYSISTYTMTWVRQVPGKGLQLVAGINGDGSSTYYTDAVKGR FTISRDNARNTVYLQMNSLRAEDTAMYYCLGEYSWFYYWGQGT LVTVSS (SEQ ID NO: 106) |
| Ca-2410 | MQMPWSLLCLLAAPLGVLSELTLQESGPRLVKPSQTLSLTCAV SGGSVTTTSYWSWIRQRPGRGLEWVGYWTGTTNYSPAFQGRIS ISADTAKNQFSLHLSSVTTEDTALYFCASKSASTSWYFSLFES WGQGTLVTVSS (SEQ ID NO: 107) |
| Ca-2411 | MESVLGLVFLLTILKGVQGEVQLVESGGDLVKPGGSLRLSCVA SGFTFSSYSMSWVRQAPGKGLQWVGYIDNGGTSTYYADAVKGR FTISRDNAKNTLYLQMNSLRAEDTAVYYCGRGSYGMEYWGHGT SLFVSS (SEQ ID NO: 108) |
| Ca-2412 | MESVLGLLFLVAILKGVQGEIQLVESGGDLLKPGGSLRLSCVA SGFTFSGSDMNWIRQAPGKGLQWVAHITHEGIGTSYVGSVKGR FTISRDNAKNTLYLQMNDLRAEDTAMYYCAYSPWNYYSFDSWG QGTLVTVSS (SEQ ID NO: 109) |

TABLE 15

Canine Lambda Light Chain Variable Domain Sequences Derived from Canine PBMC RNA

| Name | Sequence |
|---|---|
| Ca-1001 | MTSTMAWSPLLLTLLTHCTVSWAQTVLTQSPSVSAVLGRRVT ISCTGSDTNIGSHRDVQWYQLVPGKSPKTLIYGTDNRPSGIP VRFSGSKSGNSGTLTITGIQAEDEADYYCQSYDDDLSMNVFG GGTHLTVLG (SEQ ID NO: 110) |
| Ca-1002 | MDWVPFYILPFIFSTGFCALPVLTQPTNASASLEESVKLTCT LSSEHSNYIVRWYQQPGKAPRYLMYVRSDGSYKRGDGIPSR FSGSSSGADRYLTISNIKSEDEDDYYYCGADYTISGQYGSVF GGGTHLTVLG (SEQ ID NO: 111) |
| Ca-1003 | LWISGGSALGTPTMAWTHLLLPVLTLCTGSVASSVLTQPPSV SVSLGQTATISCSGESLSKYYAQWFQQKAGQVPVLVIYKDTE RPSGIPDRFSGSSSGNTHTLTISRARAEDEADYYCESEVSTG TYCVRRRHPSNRPRSAQGLPLGHTLPALL (SEQ ID NO: 204) |
| Ca-1006 | MTSTMAWSPLLLTLLTHCTGSWAQSVLTQPASLSGSLGQRVT ISCTGSSSNIGGYSVNWLQQLPGTGPRTIIYNNSNRPSGVPD RFSGSRSGTTATLTISGLQAEDEADYYCSTWDSNLRTIVFGG GTHLTVLG (SEQ ID NO: 112) |
| Ca-1007 | MTSTMDWSPLLLTLLAHCTGSWAQSVLTQPASVSGSLGQRVT ISCTGSTSNLGTYNVGWLQQVPGTGPRTVIYTNIYRPSGVPD RFSGSESGSTATLTISDLQAEDEAEYYCTAWDSSLNAYVFGS GTQLTVLG (SEQ ID NO: 113) |
| Ca-1008 | MTSNMAWCPFLLTLLAYCTGSWAQSVLTQPTSVSGSLGQRVT ISCSGSTNNIGIVGASWYQQLPGKAPKLLVYSDGDRPSGVPD RFSGSNSGNSDTLTITGLQAEDEADYYCQSFDTTLDAAVFGG GTHLTVLG (SEQ ID NO: 114) |
| Ca-1009 | MTSTMAWSPLLLTLLAHCTVSWAQAVLTQPPSVSAALGQRVT ISCTGSDTNIGSGYEVHWYRQVPGKSPAIIIYGNSNRPSGVP VRFSGSKSGSTATLTITGIEAEDEADYHCQSYDGNLDGGVFG GGTHLTVLG (SEQ ID NO: 115) |
| Ca-1010 | MTSTMGWFPLILTLLAHCAGSWAQSVLTQPASVSGSLGQRVT ISCTGSSPNVGYGDFVAWYQQVPGTSPRTLIYNTRSRPSGVP DRFSASRSGNTATLTISGLQAEDEADYYCSSYDNTLIGIVFG GGTHLTVLG (SEQ ID NO: 116) |
| Ca-1011 | MTSTMGWSPLLLTLLAHCTGSWAQSVLTQPASVSGSLGQRVT ITCTGSSSNIGRANVAWFQQVPGTGPRTVIYTSVKRPSGVPD RFSGSKSGSTATLTISGLQAEDEADYYCSSWDNSLDAGVFGG GTHLTVLG (SEQ ID NO: 117) |
| Ca-1012 | MTSTMGWFPLLLTLLAHSTGSWAQSVLTQPASVSGSLGQRVT ITCTGGTSNIGRGFVSWFQQVPGIGPKILIFDAYRRPSGVPD RFSGSRSGNTATLTISGLQAEDEADYYCAVYDSRLDVGVFGS GSQLTVLS (SEQ ID NO: 118) |
| Ca-1202 | MTSNMAWCPFLLTLLYCTGSWARSVLTQPASVSGSPGQKVT IYCSGTMSDIGVLGANWYQQLPGKAPKLLVDNDGDRPSGVPD RFSASKSGHSDTLTITGLQPEDEGDYYCQSFDSSLDAAIFGE GTHLTVLG (SEQ ID NO: 119) |
| Ca-1203 | SVASYVLTQSPSQNVTLRQAAHITCEGHNIGTKSVHWYQQKQ GQAPVLIIYDDKSRPSGIPERFSGANSGNTATLTISGALAED EADYYCLVWDSSAIWVFGEGTHLTVLG (SEQ ID NO: 120) |
| Ca-1204 | MTSTMAWSPLLLTLLAHFTGSWAQSVLTQPTSVSGSLGQRVT ISCTASSSNIDRDYVAWYQQLPGTRPRALIYANSNRPSGVPD RFSGSKSGSTATLTISGLQAEDEADYYCSTWDNSLTYVFGSG TQLTVLG (SEQ ID NO: 121) |
| Ca-1205 | SVASYVLTQVPSVSVNLGKTATITCEGDNVGEKYTHWYQQEY GQAPVLIIYEDSRRPSGIPERFSGSNSGNTATLTISGARAED ETDYYCQVWDDSGNVFGGGTHLTVLG (SEQ ID NO: 122) |
| Ca-1206 | MTSTMGWFPLILTLLAHCAGSWAQSVLTQPASVSGSLGQRVT ISCTGSDSNVGYGDSIAYGDSVAWYQQVPGTSPRTLIYDVTS RPSGVPDRFSGSRSGTTATLTISGLQAEDEADYYCSSFDKTL NGLIVGGGTHLTVLG (SEQ ID NO: 123) |
| Ca-1207 | MTSNMAWSPLLLTLLAYCTGSWAQSALTQPTSVSGSLGQRVS ISCSGGIHNIGSVGATWYQQLPGKAPKLLVSSDGDRPSGIPD RFSGSRSGNSVTLTITGLQAEDEAEYYCQSFDSTLGVHVVFG GGTHLTVLG (SEQ ID NO: 124) |
| Ca-1208 | LCSAVGPPKTESVMTSTMGWSPLLLTLLAHCTGSWAQSVLTQ PASVSGSLGQRVTIPCTGSSSNIDRYNVAWFQQLPGTGPKPS SIVLLTDPQGSLIDSLAPSQAA (SEQ ID NO: 205) |
| Ca-1209 | MTSTMAWFPLLLTLLAHYTGSWARSDLTQPASVSGSLGQRIT ISCTGSSSNIGRNYVGWYQQLPGRGPRTVVYGINSRPSGVPD RFSGSKSGSTVTLTISGLQAEDEADYYCSTWDDSLSVVVFGG GTHLTVLG (SEQ ID NO: 125) |
| Ca-1210 | MTSTMGWSPLLLTLTHWTGSWAQSVLSQPASMSGSLGLRITI CCTGKNSNINNSYVDWNQPLAGTGPRTVIHDDGDRPSGVPDQ FSGSKSGNTATLTISRLQAEDEADYNGASFETSFNAVFGGGT HVTVLG (SEQ ID NO: 126) |

TABLE 16

Canine Kappa Light Chain Variable Domain Sequences Derived from Canine PBMC RNA

| Name | Sequence |
|---|---|
| Ca Ka016-A1 | LSWLRQKPGHSPQRLIHQVSSRDPGVPDRFSGSGSGT DFTLTISRVEADDGGVYYCGQGSQSIPTFG QGTKVE IKR (SEQ. ID NO. 127) |
| Ca Ka016-A2 | MRFPSQLLGLLMLWIPGSAGDIVMTQTPLSLSVSPGE PASISCKASQSLLHSNGNTYLYWFRQKPGQSPQRLIY KVSNRDPGVPDRFSGSGSGTDFTLRISRVETDDAGVY YCGQVIQDPWTFGVGTKLELKR (SEQ. ID NO. 128) |
| Ca Ka016-A3 | MRFPSQLLGLLMLWIPGSSGDIVMTQTPLSLSVSPGE TASISCRASQTLLYSNGKNYLFWYRQKPGQSPQRLID LASNRDPGVPDRFSGSGSGTDFTLRISRVEADDAGVY YCGQGMEIPWTFGAGTKVELKR (SEQ. ID NO. 129) |
| Ca Ka016-A4 | MKFPSLLLGLLMLWIPGSTGEAVMTQTPLSLAVTPGE VATISCRASQSLLHSDGKSYLNWYLQKPGQTPRPLIY EASKRFSGVSDRFSGSGSGTDFTLKINRVEAEDVGVY YCQQSLHFPPTFGPGTKVELKR (SEQ. ID NO. 130) |
| Ca Ka016-A5 | PDRFSGSGSGTDFTLTISRVEADDAGIYYCGQATQTP PTFGAGTKLDLKR (SEQ. ID NO. 131) |
| Ca Ka016-A6 | MRFPSQLLGLLMLWIPGSSGDIVMTQTPLSLSVRPGE SASISCKASQSLLHSGGGTYLNWFRQRPGQSPQRLIY EVSKRDTGVPDRFSGSGSGTDFTLRITRVEADDTGIY YCGQNTQLPLTFGQGTKVEIKR (SEQ. ID NO. 132) |
| Ca Ka016-A7 | MRFPSQLLGLLMLWIPGSTGDIVMTQTPLSLSVSPGE PASISCKASQSLLHSNGNTYLFWLRQKPGQSPQRLIY RVSNRDPGVPDRFSGSGSGTDFTLRISRVEADDAGVY YCGQRVRSPWTFGAGTKVEVKR (SEQ. ID NO. 133) |
| Ca Ka016-A8 | MRFPSQLLGLLMLWIPGSAGDIVMTQTPLSLSVSPGE PASISCKASQSLLHSNGNTYLYWFRQKPGQSPQRLIY KVSNRDPGVPDRFSGSGSGTDFTLRISRVETDDAGVY YCGQVIQDPWTFGVGTKLELKR (SEQ. ID NO. 134) |
| Ca Ka016-A9 | MRFPSQLLGLLMLWIPGSSGDVVMAQTPLSLSVSPGE TASISCRASQSLLHSNGNTFLFWFRQKPGQSPQRLIN FLSNRDPGVPDRFSGSGSGTDFTLRINRVEADDAGLY YCGQGLQAPLTFGQGTKLEIKR (SEQ. ID NO. 135) |

TABLE 16-continued

Canine Kappa Light Chain Variable Domain Sequences Derived from Canine PBMC RNA

Ca Ka016-A10   MRFPSQLLGLLMLWIPGSNGDDVLTQTPLSLSVRPGE
               TVSILCKASESLLHSDGNTYLSWVRQKAGQSPQRLMY
               RVSDRDTGVPDRFSGSGSGTDFTLTISGVEADDAGIY
               YCGQATHYPLEFGQGTRVEIKR
               (SEQ. ID NO. 136)

Ca Ka016-A11   LMLWIPGSTGEIVLTQTPLSLSVSPGEPASISCKASQ
               SLLHPNGVTYLYWFRQKPGQSPQRLIYKVSNRDPGVP
               DRFSGSGSEIDFTLIISRVEADDGGIYYCGQGIQNPF
               TFGQGTKLEIKR (SEQ. ID NO. 137)

Ca Ka016-A12   MRFPSQLLGLLMLWIPGSIGDIVMTQTPLSLSVSPGE
               SASISCKASQSLLHSNGNTYLYWFRQKPGHSPQRLIH
               QVSSRDPGVPDRFSGSGSGTDFTLRISRVEADDAGLY
               YCGQGTQFPPTFGQGTKVEIKR
               (SEQ. ID NO. 138)

Ca Ka016-B1    MRFPSQLLGLLMLWIPGSIGDIVMTQTPLSLSVSPGE
               SASISCKASQSLLHSNGNTYLYWFRQKPGH SPQRLI
               HQVSSRDPGVPDRFSGSGSGTDFTLRISRVEADDAGL
               YYCGQGTQFPPTFGQGTKVEIKR
               (SEQ. ID NO. 139)

Ca Ka016-B2    MRFPSQLLGLLMLWIPGSSGDIVMTQTPLSLSVSPGE
               TASISCRASQSLLHSNGNTYSFWFRQKPGQSPQRLIN
               LVSSRGPGVPDRFSGSGSGTDFTLIISRVEADDAGVY
               YCGHGKEAPYTFSQGTKLEIKR
               (SEQ. ID NO. 140)

Ca Ka016-B3    MRFPSQLLGLLMLWIPGSVGDIVMTQSPMSLSVGPGE
               SASMSCKANQSLLYSDGITYLSWFLQRPGQSPQRLIY
               EVSKRDTGVPDRFIGSGAGTDFTLRIRVEADDAGVY
               YCGQALQFPLTFSQGAKLEIER
               (SEQ. ID NO. 141)

Ca Ka016-B4    MRFPSQLLGLLMLWIPGSSGDVVMTQTPLSLSVRPGE
               TASISCRASQSLLIISSGITKLFWYRQKPGQSPQRLV
               YWVSNRDPGVPDRFTGSGSGSTDFTLRISRLEADDAGI
               YYCGHAIGFPLTFGQGTKVEIKR
               (SEQ. ID NO. 142)

Ca Ka016-B5    MRFPSQLLGLLMLWIPGSSGDIVMTQTPLSLSVRPGE
               SASISCKASQSLLHSGGGTYLNWFRQRPGQSPQRLIY
               EVSKRDTGVPDRFSGSGSGTDFTLRITRVEADDTGIY
               YCGQNTQFPLTFGQGTKVEIKR
               (SEQ. ID NO. 143)

Ca Ka016-B6    MRFPSQLLGLLMLWIPGSSGGIVMTQTPLSLSVRPGE
               TASISCRASQSLLYSDGNTYLFWFRQKPGQSPQRLMY
               RVSDRDTGVPDRFSGSGSGTDFTLTISGVEADDAGIY
               YCGQATHYPLEFGQGTXVEIKR
               (SEQ. ID NO. 144)

Ca Ka016-B7    MRFPSQLLGLLMLWIPGSSGDIVMTQTPLSLSVRPGE
               SASISCKASQSLLHSGGGTYLNVVFRQRPGQSPQRLI
               YEVSKRDTGVPDRFIGSGAGTDFTLRISRVEADDAGV
               YYCGQGVQGPWTIGAGTKLELQR
               (SEQ. ID NO. 145)

Ca Ka016-B8    MRFPSQLLGLLMLWIPGSSGDIVMTQTPLSVSVSPGE
               TASISCKASQSLLSHDGNTYLHWFRQKPGQSPQRLIY
               KVSNRDTGVPDRFSGSGSGTDFTLKISRVEADDTGVY
               YCGQITQDPPTFGQGTKLEIKR
               (SEQ. ID NO. 146)

Ca Ka016-B9    MRFPSQLLGLLMLWIPGSSGDIVMTQTPLSLSVSPGE
               TASISCRASQSLLHSNGNTYLFWFRQKPGQSPQRLIN
               WVSNRDPGVPDRFGGSGSGTDFTLRISRVEADDAGIY
               YCGQGIQGPYTFSQGTKLEIKR
               (SEQ. ID NO. 147)

Ca Ka016-B10   MRFPSQFLGLLMLWIPGSSGDIAMTQTPLSLSVGPGE
               TASITCKASQSLLHSNGNTYLFWFRQKPGQSPQRLIY
               LVSNRDPGVPDRFSGSGSGTDFTLTISRVEADDAGIY
               YCGQATQTPPTFGAGTKLDLKR
               (SEQ. ID NO. 148)

Ca Ka016-B11   MRFPSQLLGLLMLWIPGSSGDIVMAQTPLSLSVSPGE
               PASISCKASQSLLHSDGRTCLSWFRQKGQSPQRLIY
               EVSNRDTGVPDRFSGSGSGTDFTLRISRVEADDTGIY
               YCGQTVQFPPLTFGQGTKLEIKR
               (SEQ. ID NO. 149)

Ca Ka016-B12   GQSPQRLIYKVSNRDPGVPDRFSGSGSGTDFTLRISR
               VEPEDVGVYYCGQGTLNPWTFGAGTKVELK R
               (SEQ. ID NO. 150)

Ca Ka017-1     MRFPSQLLGLLMLWIPGSSGDVVMTQTPLSLSVSPGE
               TASISCRASQSLLHSNGNTFLFWFRQ*PGQSPQRLIN
               FVSNRDPGVPDRFSGSGSGTDFTLRISRVEADDAGIY
               YCGQGLLAPPTFGQGTKVEIRR (SEQ. ID NOS
               151 and 210, respectively)
               NOTE: * INDICATES A STOP CODON Ca Ka017-2     MRFPSQLLGLLMLWIPGSGGDIVMTQTPPSLSVSPRE
               PASISCKASQSLLRSNGNTYLYWFRQKPGQSPEGLIY
               RVSNRFTGVSDRFSGSGSGTDFTLRISTVEADDAGVY
               YCGQATQFPSTFSQGTKLEIKR
               (SEQ. ID NO. 152)

Ca Ka017-3     MRFPSQLLGLLMLWIPGSXGDIVLTQTPLSLSVSPGE
               PASISCKASQSLLHSNGITYLNWYRQRPGQSPQXLIY
               KVSNRDTGVPDRFSGSGSGTDFTLRXSKVEADDTGIY
               YCGQDTQFPLTLGXGTHXEIKR
               (SEQ. ID NO. 153)

Ca Ka017-5     MRFPSQLLGLLMLWIPGSTGDIVMTQTPLSLSVSPGE
               PASIYCKASQSLLHSNGKTFLYWFRQKPGQS PQRLI
               YRVSNRDPGVPDRFSGSGSGTDFTLRISRVEADDAGI
               YYCGQGIQDPTFGQGTKVEIKR
               (SEQ. ID NO. 154)

Ca Ka017-6     MRFPSQLLGLLMLWIPGSGGDIVMTQTPPSLSVSPRE
               AASISCKASQSLLKSNGNTYFYWFRQKPG QVSEGLI
               YKVSSRFTGVSDRFSGSGSGTDFTLRISRVEADDAGV
               YFCGQALQFPYTFSQGTKLDIKR
               (SEQ. ID NO. 155)

Ca Ka017-10    MRFPSQLLGLLMLWIPESGGDVVLTQTPPSLSLSPGE
               TASISCKASRSLLNSDGSTYLDWYLQKPGQSPRLLIY
               LVSNRFSGVSDRFSGSGSGTDFTLTISRVEADDAGVY
               YCGQGSRVPLTFGQGTKVEIKR
               (SEQ. ID NO. 156)

Ca Ka017-11    MRFPSQLLGLLMLWIPGSSGDIVMTQTPLSLSVSPGE
               TASISCRASQSLLHRNGITYLSWFRQRPGQSP QRLI
               NLVSNRDPGVPDRFSGSGSGTDFTLRISRVEADDVGV
               YYCGHGLQTPYTFSQGTSLEIER
               (SEQ. ID NO. 157)

Ca Ka017-12    MRFPSQLLGLLVLWIPGSSGDIVMTQTPLSLSVSPGE
               TVSISCRASQSLLYSDGNIYLFWFRRKPGQSP QHLI
               NLVSNRDPGVPDRFSGSGSGTDFTLRISRVEADDAGV
               YYCGQGTQPPYTFSQGTKVEIKR
               (SEQ. ID NO. 158)

Ca Ka017-13    MRFPSQLLGLLMLWIPESGGDVVLTQTPPSLSLSPGE
               TASISCKASRSLLNSDGSTYLDWYLQKPGQS PRLLI
               YLVSNRFSGVSDRFSGSGSGTDFTLTISRVEADDAGV
               YYCGQGSRVPLTFGQGTKVEIKR
               (SEQ. ID NO. 159)

Ca Ka017-14    MRFPSQLLGLLMLWIPGSSGDIVMAQTPLSLSVSPGE
               TASISCRASQSLLHSNGITYLFWYRQKPGQS PQRLI
               SMVFNRDPGVPDRFGGSGSGTDFTLRISRVEADDAGL
               YFCGHGTQIPYSFSQGTKLEIKR
               (SEQ. ID NO. 160)

Ca Ka017-16    MRFPSQLLGLLMLWIPGSSGDIVMTQTPLSLSISPGE
               PASISCKASQSLLHSGGDTYLNWFRQRPGQS PQLLI
               NRVSSRKKGVPDRFSGSGSGTEFTLRISRVEADDAGI
               YFCGQGTQFPYTFSQGTKLEIKR
               (SEQ. ID NO. 161)

TABLE 16-continued

Canine Kappa Light Chain Variable Domain
Sequences Derived from Canine PBMC RNA

Ca Ka017-20   MRFPSQLLGLLMLWIPGSGGDIVMTQTPPSLSVSPGE
              PASMSCKASQSLLHSNGNTYLYWFRQKP GQSPEALI
              YKVSNRFTGVSDRFSGSGSGTDFTLRINRVEADDVGV
              YYCGQGIQIPYTFSQGTKLEIKR
              (SEQ. ID NO. 162)

Ca Ka017-23   MRFPSQLLGLLMLWIPGSTGEIVLTQTPLSLSVSPGE
              SASISCKASQSLLYSNGNTYLYWFRQKAGQSP QRVI
              YRVSNRDPGVPDRFSGSGSGTDFTLRISSVENDDAGV
              YYCGQGSEDPPTFGAGTKVELKR
              (SEQ. ID NO. 163)

Ca Ka017-24   MRFPSQLLGLLTLWIPGSTGDIVMTQTPLSLSVSPGE
              PASISCKASQSLLHSNGNTYLYWFRQKPGQS PQRLI
              YKVSNRDPGVPXRFSGSGSGTDFTLRVSXVEADDAGV
              YYCGQGVQDPFTFGQGTKLEIKR
              (SEQ. ID NO. 164)

Example 13

CDR-Grafting to Create Caninized Monoclonal Antibodies

To generate caninized antibody sequences from mouse anti-NGF antibodies, each murine variable heavy chain antibody gene sequence was separately aligned against 36 canine Ig germline variable heavy chain sequences using Vector NTI software. Eleven canine Ig germline variable heavy chain sequences were derived from U.S. Pat. No. 7,261,890 B2, (Methods for Using Canine Immunoglobulin Variable Domains and Caninized Antibodies), the contents of which are herein incorporated by reference, and 25 canine Ig germline variable heavy chain sequences were derived from Table 14 (Canine Heavy Chain Variable Domain Sequences Derived from Canine PBMC RNA). Each murine variable light chain gene sequence was separately aligned against 68 germline variable light chain sequences (derived from U.S. Pat. No. 7,261,890 B2) using Vector NTI software. Canine variable domain sequences having the highest overall homology to the original murine sequences were selected for each heavy chain and light chain sequence to provide the framework sequence. In silico construction of complete CDR grafted antibodies was accomplished by substitution of canine variable domain CDR sequences with murine CDR sequences (derived from the subcloned anti-NGF antibody hybridoma mAbs). To identify residues in each sequence, the first amino acid in each listed sequence was defined as 1, and all remaining residues numbered consecutively thereafter using Kabat numbering system.

The heavy chain CDR sequences from PR-1254972 were grafted in silico onto canine 894 as follows: (1) One N-linked glycosylation pattern (N-{P}-S/T) was found in these proposed constructs. (2) Six back-mutations (Q3H, V37I, Q46E, D73N, T77N, R83K) were introduced to make the 72.2 VH sequence. (3) One, two, three, four, five, or six of the back-mutations disclosed above could be introduced into 72.2 VH to maintain antibody affinity to NGF after caninization of mAb 72.2. (4) One, two, three, four, five, or six of these back-mutations may be substituted during subsequent affinity maturation of 72.2 VH. 72.3 VH was generated by introducing the back-mutations in 72.2 VH with the addition of H39Q back-mutation. 72.4 VH was generated by introducing back-mutations Q3H, H39Q, Q46E, D73N. The light chain CDR sequences from PR-1254972 were grafted in silico onto canine 1001 as follows: (1) No N-linked glycosylation pattern (N-{P}-S/T) was found in these proposed constructs. (2) Four back-mutations (I2V, V3L, Q45K, S59P) were introduced to make the 72.2 VL sequence. (3) One, two, three, or four of these back-mutations could be introduced into 72.2 VL to maintain antibody affinity to NGF after caninization of mAb 72.2. (4) One, two, three, or four of these back-mutations may be substituted during subsequent affinity maturation of 72.2 VL. 72.4 VL was generated by introducing back-mutations Q45K, and S59P.

The heavy chain CDR sequences from PR-1254973 were grafted in silico onto canine 894 as follows: (1) No N-linked glycosylation pattern (N-{P}-S/T) was found in these proposed constructs. (2) Eight back-mutations (T24A, M48I, V67A, L69V, T73K, N76S, V78A, A93T) were introduced to make the 73.2 VH sequence. (3) One, two, three, four, five, six, seven, or eight of these back-mutations could be introduced into 73.2 VH to maintain antibody affinity to NGF after caninization of mAb 73.2. (4) One, two, three, four, five, six, seven, or eight of these eight back-mutations may be substituted during subsequent affinity maturation of 73.2 VH. 73.4 VH was generated by introducing back-mutations T24A, T73K, A93T. The light chain CDR sequences from PR-1254973 were grafted in silico onto canine 1034 as follows: (1) No N-linked glycosylation pattern (N-{P}-S/T) was found in these proposed constructs. (2) Eight back-mutations (I1D, V3Q, S22T, F36H, R46L, I48V, D60S, D70Q) were introduced to make the 73.2 VL sequence. (3) One, two, three, four, five, six, seven or eight of these back-mutations could be introduced into 73.2 VL to maintain antibody affinity to NGF after caninization of mAb 73.2. (4) One, two, three, four, five, six, seven, or eight of these eight back-mutations may be substituted during subsequent affinity maturation of 73.2 VL. 73.4 VL was generated by introducing back-mutations I1D, V3Q, F36H, R46L, D60S, D70Q.

The heavy chain CDR sequences from PR-1254977 were grafted in silico onto canine 894 as follows: (1) No N-linked glycosylation pattern (N-{P}-S/T) was found in these proposed constructs. (2) Eight back-mutations (T24A, Q38K, M48I, R66K, V67A, T68S, L69I, V78A) were introduced to make the 77.2 VH sequence. (3) One, two, three, four, five, six, seven, or eight of these back-mutations could be introduced into 77.2 VH to maintain antibody affinity to NGF after caninization of mAb 77.2. (4) One, two, three, four, five, six, seven, or eight of these back-mutations may be substituted during subsequent affinity maturation of 77.2 VH. 77.3 VH was generated by introducing the back-mutations in 77.2 VH with the addition of R94G back-mutation. 77.4 VH was generated by introducing back-mutations T24A, Q38K, and R94G. The light chain CDR sequences from PR-1254977 were grafted in silico onto canine 997 as follows: (1) No N-linked glycosylation pattern (N-{P}-S/T) was found in these proposed constructs. (2) Four back-mutations (L2V, F36Y, R46L, S98G) were introduced to make the 77.2 VL sequence. (3) One, two, three, or four of these back-mutations could be introduced into 77.2 VL to maintain antibody affinity to NGF after caninization of mAb 77.2. (4) One, two, three, or four of these back-mutations may be substituted during subsequent affinity maturation of 77.2 VL. 77.4 VL was generated by introducing back-mutations F36Y and R46L.

The heavy chain CDR sequences from PR-1254981 were grafted in silico onto canine 876 as follows: (1) No N-linked glycosylation pattern (N-{P}-S/T) was found in these proposed constructs. (2) Six back-mutations (Q46E, G49A, T77N, R83K, L91Y, E93T) were introduced to make the 81.2 VH sequence. (3) One, two, three, four, five, or six of these back-mutations could be introduced into 81.2 VH to maintain antibody affinity to NGF after caninization of mAb 81.2. (4) One, two, three, four, five, or six of these six back-mutations may be substituted during subsequent affinity maturation of 81.2 VH. 81.4 VH was generated by introducing back-mutations Q46E, G49A, L91Y, and E93T.

The light chain CDR sequences from PR-1254981 were grafted in silico onto canine 1011 as follows: (1) No N-linked glycosylation pattern (N-{P}-S/T) was found in these proposed constructs. (2) Four back-mutations (V3L, A7T, F36Y, R46L) were introduced to make the 81.2 VL sequence. (3) One, two, three, or four of these back-mutations could be introduced into 81.2 VL to maintain antibody affinity to NGF after caninization of mAb 81.2. (4) One, two, three, or four of these back-mutations may be substituted during subsequent affinity maturation of 81.2 VL. 81.4 VL was generated by introducing back-mutations A7T, F36Y, and R46L.

Alternatively, the heavy chain CDR sequences from PR-1254981 were grafted in silico onto canine 1005 VH as follows: (1) No N-linked glycosylation pattern (N-{P}-S/T) was found in these proposed constructs. (2) Seven back-mutations (Q46E, T77N, F79Y, R83K, F91Y, V93T, K94R) were introduced to make the 81.5B VH sequence. (3) One, two, three, four, five, six, or seven of these back-mutations could be introduced into 81.5B VH to maintain antibody affinity to NGF after caninization of mAb 81.5B. (4) One, two, three, four, five, six, or seven of these seven back-mutations may be substituted during subsequent affinity maturation of 81.5B VH. 81.6B was generated by introducing back-mutations Q46E, F79Y, F91Y, and V93T. Variants 81.2B and 81.4B were generated by introducing A84K mutation to 81.5B and 81.6B, respectively.

The heavy chain CDR sequences from PR-1254982 were grafted in silico onto canine 892 as follows: (1) No N-linked glycosylation pattern (N-{P}-S/T) was found in these proposed constructs. (2) Twelve back-mutations (I3Q, I37V, M48L, I67L, T70S, A71K, G73N, N76S, H77Q, L78V, S79F, T93A) were introduced to make the 82.2 VH sequence. (3) One, two, three, four, five, six, seven, eight, nine, ten, eleven, or twelve of these back-mutations could be introduced into 82.2 VH to maintain antibody affinity to NGF after caninization of mAb 82.2. (4) One, two, three, four, five, six, seven, eight, nine, ten, eleven, or twelve of these back-mutations may be substituted during subsequent affinity maturation of 82.2 VH. 82.4 VH was generated by introducing back-mutations I3Q, A71K, H77Q, S79F, and T93A. The light chain CDR sequences from PR-1254982 were grafted in silico onto canine 1034 as follows: (1) No N-linked glycosylation pattern (N-{P}-S/T) was found in these proposed constructs. (2) Ten back-mutations (I1D, V3Q, S22T, F36Y, Q45K, R46L, D60S, F71Y, T72S, Y87F) were introduced to make the 82.2 VL sequence. (3) One, two, three, four, five, six, seven, eight, nine, or ten of these back-mutations could be introduced into 82.2 VL to maintain antibody affinity to NGF after caninization of mAb 82.2. (4) One, two, three, four, five, six, seven, eight, nine, or ten of these back-mutations may be substituted during subsequent affinity maturation of 82.2 VL. 82.3 VH was generated by introducing the back-mutations in 82.2 VH with the addition of P44V back-mutation. 82.4 VL was generated by introducing back-mutations I1D, V3Q, F36Y, Q45K, R46L, D60S, F71Y, and Y87F.

Example 14

Isoelectric Point of Canine Framework Amino Acids

The heavy chain framework amino acids (i.e. non-CDR amino acids) of the caninized IgG1 kappa antibodies yield a calculated isoelectric point of less than 8.0. The light chain framework amino acids, when the light chain is kappa, yield a calculated isoelectric point of less than 6.5. The isoelectric point of the caninized antibodies as a whole, i.e. heavy and light chain combined, due to the framework amino acids, and when the light chain is kappa, is less than 8.0. In comparison, the framework amino acids of human IgG1 heavy chains typically yield isoelectric points of greater than 8.0. The framework amino acids of human kappa light chains typically yield isoelectric points of greater than 6.5. The framework amino acids of whole human IgG1/k antibodies typically yield isoelectric points of greater than 8.0.

Example 15

CDR-Grafting to Create Humanized Monoclonal Antibodies

Each murine variable heavy and variable light chain antibody gene sequence (as set forth in Table 16) was separately aligned against 44 human immunoglobulin germline variable heavy chain or 46 germline variable light chain sequences (derived from NCBI Ig Blast website which is well known to those skilled in the art) using Vector NTI software. Human variable domain sequences having the highest overall homology to the original murine sequences were selected for each heavy chain and light chain antibody sequence to provide the framework (FW) 1, 2 and 3 sequences for CDR-grafting purposes. Identification of a suitable human variable heavy and light chain FW4 region (also known as the "joining" region) was accomplished by separately aligning each murine heavy chain and light chain FW4 region with 6 human immunoglobulin germline joining heavy chain and 5 germline joining light chain sequences in the NCBI database. In silico construction of complete CDR grafted variable domains was accomplished by substitution of human variable domain CDR sequences (derived from the NCBI website) with murine CDR sequences (derived from the murine antibodies) with addition of a FW4 region (derived from the NCBI website) to each 3' end. Further humanization may be accomplished by identification of back-mutations. Full length human Igs may be produced by expressing the variable domains of each CDR-grafted mAb with an in-frame human IgG constant domain. Mouse Anti-NGF mAb CDRs grafted onto human Ig frameworks (CDR-grafted Anti-NGF Abs) produced are those listed in Table 17.

TABLE 17

Mouse Anti-NGF mAb CDRs Humanized by CDR Grafting onto Human Ig Frameworks

| Name | Sequence (CDRs are underlined) |
|---|---|
| HU72 VH (CDR-GRAFT VH3-13/JH5) | EVQLVESGGGLVQPGGSLRLSCAASGFTFS<u>DYYM</u> <u>FW</u>VRQATGKGLEWVS<u>TISDGGSYTYYTDNVKGRF</u> TISRENAKNSLYLQMNSLRAGDTAVYYCAR<u>DWSD</u> <u>SEGFAY</u>WGQGTLVTVSS (SEQ ID NO: 165) |

TABLE 17-continued

Mouse Anti-NGF mAb CDRs Humanized by CDR Grafting onto Human Ig Frameworks

| Name | Sequence (CDRs are underlined) |
|---|---|
| Hu73 VH (CDR-GRAFT VH1-18/JH6) | QVQLVQSGAEVKKPGASVKVSCKASGYTFT<u>NYWM</u><br><u>H</u>WVRQAPGQGLEWMG<u>RIDPYGGGTKHNEKFKRR</u>V<br>TMTTDTSTSTAYMELRSLRSDDTAVYYCAR<u>SGYD</u><br><u>YYFDV</u>WGQGTTVTVSS (SEQ ID NO: 166) |
| HU77 VH (CDR-GRAFT VH1-69/JH6) | QVQLVQSGAEVKKPGSSVKVSCKASGFNIK<u>DTYI</u><br><u>Y</u>WVRQAPGQGLEWMG<u>RIDPANGNTIYASKFQG</u>RV<br>TITADKSTSTAYMELSSLRSEDTAVYYCAR<u>YGYY</u><br><u>AY</u>WGQGTTVTVSS (SEQ ID NO: 167) |
| HU80 VH (CDR-GRAFT VH1-18/JH6) | QVQLVQSGAEVKKPGASVKVSCKASGFNIK<u>DTYI</u><br><u>Y</u>WVRQAPGQGLEWMG<u>RIDPANGNTIYASKFQG</u>RV<br>TMTTDTSTSTAYMELRSLRSDDTAVYYCAR<u>YGYY</u><br><u>AY</u>WGQGTTVTVSS (SEQ ID NO: 168) |
| HU81 VH (CDR-GRAFT VH3-15/JH1) | EVQLVESGGGLVKPGGSLRLSCAASGFTFS<u>NHYM</u><br><u>Y</u>WVRQAPGKGLEWVG<u>SISDGGAYTFYPDTVKGR</u>F<br>TISRDDSKNTLYLQMNSLKTEDTAVYYCTT<u>EESA</u><br><u>NNGFAFW</u>GQGTLVTVSS (SEQ ID NO: 169) |
| HU82 VH (CDR-GRAFT VH2-26/JH6) | QVTLKESGPVLVKPTETLTLTCTVSGFSLT<u>GYNI</u><br><u>N</u>WIRQPPGKALEWLA<u>MIWGYGDTDYNSALKSR</u>LT<br>ISKDTSKSQVVLTMTNMDPVDTATYYCARD<u>HYGG</u><br><u>NDWYFDV</u>WGQGTTVTVSS (SEQ ID NO: 170) |
| HU72 VL (CDR-GRAFT 01/JK2) | DIVMTQTPLSLPVTGPEPASISC<u>RSSQSIVQSNG</u><br><u>NTYLE</u>WYLQKPGQSPQLLIY<u>KVSNRFS</u>GVPDRFS<br>GSGSGTDFTLKISRVEAEDVGVYYC<u>FQGSHVPFT</u><br>FGQGTKLEIKR (SEQ ID NO: 171) |
| HU73 VL (CDR-GRAFT L22/JK2) | DIQMIQSPSFLSASVGDRVSIIC<u>RASENIYSFLA</u><br>WYLQKPGKSPKLFLY<u>NANTLAEG</u>VSSRFSGRGSG<br>TDFTLTIISLKPEDFAAYYC<u>QHHFGTPFT</u>FGQGT<br>KLEIKR (SEQ ID NO: 172) |
| HU77 VL (CDR-GRAFT 01/JK2) | DIVMTQTPLSLPVTGPEPASISC<u>KSTKSLLNGDG</u><br><u>FTYLD</u>WYLQKPGQSPQLLIY<u>LVSNRFS</u>GVPDRFS<br>GSGSGTDFTLKISRVEAEDVGVYYC<u>FESNYLFTF</u><br>GQGTKLEIKR (SEQ ID NO: 173) |
| HU80 VL (CDR-GRAFT 01/JK2) | DIVMTQTPLSLPVTGPEPASISC<u>KSTKSLLNGDG</u><br><u>FTYLD</u>WYLQKPGQSPQLLIY<u>LVSNRFS</u>GVPDRFS<br>GSGSGTDFTLKISRVEAEDVGVYYC<u>FESNYLFTF</u><br>GQGTKLEIKR (SEQ ID NO: 174) |
| HU81 VL (CDR-GRAFT 01/JK2) | DIVMTQTPLSLPVTGPEPASISC<u>RSSQSILHSNG</u><br><u>NTYLE</u>WYLQKPGQSPQLLIY<u>RVSNRFS</u>GVPDRFS<br>GSGSGTDFTLKISRVEAEDVGVYYC<u>FQGAHVPFT</u><br>FGQGTKLEIKR (SEQ ID NO: 175) |
| HU82 VL (CDR-GRAFT 08/JK2) | DIQMTQSPSSLSASVGDRVTITC<u>RASQDITNYLN</u><br>WYQQKPGKAPKLLIY<u>YTSRLHS</u>GVPSRFSGSGSG<br>TDFTFTISSLQPEDIATYYC<u>QQGKTLPRT</u>FGQGT<br>KLEIKR (SEQ ID NO: 176) |

Example 16

Method for Constructing Full-Length Mouse/Canine Chimeric and Caninized Antibodies Using conventional molecular biology techniques, a cDNA fragment encoding the canine IgG1 constant region (which was obtained from the IMGT®, the International ImMunoGeneTics information system, which is the global reference in immunogenetics and immunoinformatics, created in by Marie-Paule Lefranc (Université Montepellier 2 and CNRS)) was synthesized and ligated to the 3' end of each of the heavy chain variable domains derived from murine anti-NGF monoclonal antibodies PR-1254972, PR-1254973, PR-1254977, PR-1254981, PR-1254982. For these same anti-NGF mAbs, a cDNA fragment encoding the canine kappa constant region obtained from U.S. Pat. No. 5,852,183A, (Sequence ID No. 54) was synthesized and ligated to the 3' end of each of the light chain variable domains. The complete canine IgG heavy chain constant domain nucleotide sequence and amino acid sequence is shown as SEQ ID NO: 51 and SEQ ID NO: 52, respectively. The complete canine kappa light chain constant domain nucleotide sequence and amino acid sequence is shown as SEQ ID NO: 53 and SEQ ID NO: 54, respectively. Complete heavy chain and light chain chimeric cDNAs were ligated into the pHybE expression plasmid; the sequences of these chimeric mAbs are in Table 18 below.

TABLE 18

Mouse/Canine Chimeric Antibody Sequences

| Name | Sequence (CDRs are underlined) |
|---|---|
| PR-1290646 light chain amino acid sequence | DVLMTQTPLSLPVSLGDQASISC<u>RSSQSIVQSNGNTYL</u><br><u>E</u>WYLQKPGQSPKLLIY<u>KVSNRFS</u>GVPDRFSGSGSGTDF<br>TLKISREAEDLGVYYC<u>FQGSHVPFT</u>FGSGTKLEIKRND<br>AQPAVYLFQPSPDQLHTGSASVVCLLNSFYPKDINVKW<br>KVDGVIQDTGIQESVTEQDKDSTYSLSSTLTMSSTEYL<br>SHELYSCEITHKSLPSTLIKSFQRSECQRVD<br>(SEQ ID NO: 194) |
| PR-1290646 heavy chain amino acid sequence | EVHLVESGGGLVKPGGFLILSCAASGFTFS<u>DYYMF</u>WIR<br>QTPGKRLEWVA<u>TISDGGSYTYYTDNVKGR</u>FTISRDNVK<br>NNLYLQMSHLKSADTAMYYCAR<u>DWSDSEGFAY</u>WGQGTL<br>VTVSAASTTAPSVFPLAPSCGSTSGSTVALACLVSGYF<br>PEPVTVSWNSGSLTSGVHTFPSVLQSSGLHSLSSMVTV<br>PSSRWPSETFTCNVVHPASNTKVDKPVFNECRCTDTPP<br>CPVPEPLGGPSVLIFPPKPKDILRITRTPEVTCVVLDL<br>GREDPEVQISWFVDGKEVHTAKTQSREQQFNGTYRVVS<br>VLPIEHQDWLTGKEFKCRVNHIDLPSPIERTISKARGR<br>AHKPSVYVLPPSPKELSSSDTVSITCLIKDFYPPDIDV<br>EWQSNGQQEPERKHRMTPPQLDEDGSYFLYSKLSVDKS<br>RWQQGDPFTCAVMHETLQNHYTDLSLSHSPGK<br>(SEQ ID NO: 195) |
| PR-1290654 light chain amino acid sequence | DIQMTQSPASLSASVGETVTVTC<u>RASENIYSFLA</u>WHQQ<br>KQGKSPQLLVY<u>NANTLAEG</u>VPSRFSGSGSGTQFSLKIN<br>SLQPEDFGSYYC<u>QHHFGTPFT</u>FGSGTKLEIKRNDAQPA<br>VYLFQPSPDQLHTGSASVVCLLNSFYPKDINVKWKVDG<br>VIQDTGIQESVTEQDKDSTYSLSSTLTMSSTEYLSHEL<br>YSCEITHKSLPSTLIKSFQR SECQRVD<br>(SEQ ID NO: 196) |
| PR-1290654 heavy chain amino acid sequence | QVQLQQPGAELVKPGASVKLSCKASGYTFT<u>NYWMH</u>WVK<br>QRPGQGLEWIG<u>RIDPYGGGTKHNEKFKR</u>KATVTADKSS<br>STAYILLSSLTSEDSAVYYC<u>TRSGYDYYFDV</u>WGTGTTV<br>TVSSASTTAPSVFPLAPSCGSTSGSTVALACLVSGYFP<br>EPVTVSWNSGSLTSGVHTFPSVLQSSGLHSLSSMVTVP<br>SSRWPSETFTCNVVHPASNTKVDKPVFNECRCTDTPPC<br>PVPEPLGGPSVLIFPPKPKDILRITRTPEVTCVVLDLG<br>REDPEVQISWFVDGKEVHTAKTQSREQQFNGTYRVVSV<br>LPIEHQDWLTGKEFKCRVNHIDLPSPIERTISKARGRA<br>HKPSVYVLPPSPKELSSSDTVSITCLIKDFYPPDIDVE<br>WQSNGQQEPERKHRMTPPQLDEDGSYFLYSKLSVDKSR<br>WQQGDPFTCAVMHETLQNHYTDLSLSHSPGV<br>(SEQ ID NO: 197) |
| PR-1290656 light chain amino acid sequence | DVVLTQTPLSLPVNIGDQASISCKST<u>KSLLNGDGFTYL</u><br><u>D</u>WYLQKPGQSPQLLIY<u>LVSNRFS</u>GVPDRFSGSGSGTDF<br>TLKISRVEAEDLGVYYC<u>FESNYLFT</u>FGSGTKLEMKRND<br>AQPAVYLFQPSPDQLHTGSASVVCLLNSFYPKDINVKW<br>KVDGVIQDTGIQESVTEQDKDSTYSLSSTLTMSSTEYL<br>SHELYSCEITHKSLPSTLIKSFQRSECQRVD<br>(SEQ ID NO: 198) |
| PR-1290656 heavy chain amino acid sequence | EVQLQQSGAELVKPGASVKLSCTASGFNIK<u>DTYIY</u>WVK<br>QRPEQGLEWIG<u>RIDPANGNTIYASKFQG</u>KASITADTSS<br>NTAYMQLSSLTSGDTAVYYCAG<u>YGYYAY</u>WGQGTTLVS<br>SASTTAPSVFPLAPSCGSTSGSTVALACLVSGYFPEPV<br>TVSWNSGSLTSGVHTFPSVLQSSGLHSLSSMVTVPSSR<br>WPSETFTCNVVHPASNTKVDKPVFNECRCTDTPPCPVP |

TABLE 18-continued

Mouse/Canine Chimeric Antibody Sequences

| Name | Sequence (CDRs are underlined) |
|---|---|
| | EPLGGPSVLIFPPKPKDILRITRTPEVTCVVLDLGRED<br>PEVQISWFVDGKEVHTAKTQSREQQFNGTYRVVSVLPI<br>EHQDWLTGKEFKCRVNHIDLPSPIERTISKARGRAHKP<br>SVYVLPPSPKELSSSDTVSITCLIKDFYPPDIDVEWQS<br>NGQQEPERKHRMTPPQLDEDGSYFLYSKLSVDKSRWQQ<br>GDPFTCAVMHETLQNHYTDLSLSHSPGK<br>(SEQ ID NO: 199) |
| PR-1290657<br>light chain<br>amino acid<br>sequence | DVLMTQTPLSLPVSLGDQASISC<u>RSSQSILHSNGNTYL</u><br><u>EWYLQKPGQSPNLLIY</u><u>RVSNRFS</u>GVPDRFSGSGSGTDF<br>TLKISRVEAEDLGVYYCF<u>QGAHVPFT</u>FGSGTKLEIKRN<br>DAQPAVYLFQPSPDQLHTGSASVVCLLNSFYPKDINVK<br>WKVDGVIQDTGIQESVTEQDKDSTYSLSSTLTMSSTEY<br>LSHELYSCEITHKSLPSTLI KSFQRSECQRVD<br>(SEQ ID NO: 200) |
| PR-1290657<br>heavy chain<br>amino acid<br>sequence | EVQLVESGGGAVKPGGSLTLSCAASGFTFS<u>NHYMYW</u>VR<br>QTPEKRLEWVA<u>SISDGGAYTFYPDTVKG</u>RFTISRDNVN<br>NNLYLQMRHLKSEDTAMYYC<u>TREESANNGFAF</u>WGQGTL<br>VTVSAASTTAPSVFPLAPSCGSTSGSTVALACLVSGYF<br>PEPVTVSWNSGSLTSGVHTFPSVLQSSGLHSLSSMVTV<br>PSSRWPSETFTCNVVHPASNTKVDKPVFNECRCTDTPP<br>CPVPEPLGGPSVLIFPPKPKDILRITRTPEVTCVVLDL<br>GREDPEVQISWFVDGKEVHTAKTQSREQQFNGTYRVVS<br>VLPIEHQDWLTGKEFKCRVNHIDLPSPIERTISKARGR<br>AHKPSVYVLPPSPKELSSSDTVSITCLIKDFYPPDIDV<br>EWQSNGQQEPERKHRMTPPQLDEDGSYFLYSKLSVDKS<br>RWQQGDPFTCAVMHETLQNHYTDLSLSHSPGV<br>(SEQ ID NO: 201) |

The canine IgG1 constant region nucleotide sequence described above was also ligated to the 3' end of each of the cDNAs encoding heavy chain variable domains derived from caninized anti-NGF monoclonal antibodies 72.2 VH, 72.3 VH, 72.4 VH, 73.2 VH, 73.4 VH, 77.2 VH, 77.3 VH, 77.4 VH, 81.2 VH, 81.4 VH, 81.2B, 81.4B, 81.5B, 81.6B, 82.2 VH, 82.4 VH. The canine kappa light chain constant domain nucleotide sequence described above was also ligated to the 3' end of each of the cDNAs encoding light chain variable domains derived from caninized anti-NGF monoclonal antibodies 72.2 VL, 72.4 VL, 73.2 VL, 73.4 VL, 77.2 VL, 77.4 VL, 81.2 VL, 81.4 VL, 82.2 VL.

Full-length chimeric or caninized antibodies were transiently expressed in 293-6E cells by co-transfection of combinations of heavy and light chain pHybE plasmids. Table 20 highlights all possible combination of caninized heavy and light chains that may be combined to produce a caninized antibody per the name in the table (Table 20). In Table 20, the heavy chain plasmids encoding caninized versions of murine heavy chains are listed on the top line and proceed rightward. The light chain plasmids encoding caninized versions of murine light chains are listed on the left-hand column and proceed downward. At each point where these boxes intersect, a name has been indicated to describe a potential resulting caninized antibody.

Example 17

Caninized Monoclonal Antibody Expression and Purification

Selected heavy chain and light chain mouse/canine chimeric and caninized antibody plasmids were co-transfected into 293-6e cells in suspension and allowed to grow for 7-8 days. Cell supernatants were harvested, centrifuged, and filtered. For each expressed antibody, supernatant was mixed with an equal volume of Pierce binding buffer to perform Protein A Sepharose affinity chromatography according to manufacturers instructions (GE Healthcare #17-1279-04). Although according to several sources canine IgGs bind directly to Protein A moderately well (GE Healthcare Antibody Purification Handbook package insert; Scott, M. A., et. al., Vet Immunol-Immunopatho, 59:205, 1997; Warr, G. W and Hart, I. R., Am J Vet Res, 40:922, 1979; Thermo Scientific Pierce Antibody Production and Purification Technical Handbook) the monoclonal canine mAbs did not quantitatively bind to Protein A and therefore could not be purified from supernatants without modification to the Protein A purification methodology.

To allow quantitative binding of canine IgGs to Protein A, supernatants were concentrated and mixed with an equal volume of Pierce binding buffer (Thermo #21007). To the concentrated and diluted supernatants, NaCl was added to a final concentration of 2.5 M. NaCl-adjusted supernatant was loaded onto Protein A Sepharose by continuous over-night loading, washed with Pierce binding buffer, and eluted using Pierce elution buffer (Thermo #21004). The eluates were neutralized by dropwise addition of 1M Tris pH 8.0; following this the neutralized antibodies were dialyzed into PBS and amounts of antibody were quantified spectrophotometrically by $OD_{280}$. The amount purified was mathematically divided by the total volume of cell supernatant purified to determine the overall estimated expression levels in ug/mL. The isolation and purification of theses canine IgG1/k mAbs allowed analytical characterization studies of the mAbs to be completed.

For purification of large-scale cell supernatants (10-15 L), cell supernatants were concentrated, then mixed with Pierce binding buffer A (Thermo, catalog #21001) in a 1 to 1 ratio. To this mixture, 5 M NaCl was added to 1.3 M final concentration. The pH of the mixture was adjusted to 8.5 with 10 N NaOH. The pH-adjusted cell supes were loaded onto a Protein A MabSelect SuRe (GE Healthcare, catalog #17-5438-03) chromatography column and eluted using two steps. The first step of the elution was performed using 20 mM Tris, 25 mM NaCl, pH 8.0, 7.4 mS/cm. Fractions containing antibodies were identified by $OD_{280}$ and size exclusion chromatography. To quantitatively isolate the remaining antibody bound to the Protein A column, the second step elution was performed using Pierce elution buffer (Thermo, catalog #21004), pH 2.7, 3.7 mS/cm, and fractions containing antibodies were identified by $OD_{280}$ and size exclusion chromatography. All fractions containing antibodies were neutralized using 2M Tris pH 8.5, and then dialyzed into PBS. The method employed to purify large volumes of cell supernatant containing canine monoclonal antibodies (ex. 10-15 L) differs from the method typically employed to purify human antibodies from large volumes. For human antibodies, Protein A purification is typically accomplished with cell supernatant binding conditions of pH 7.0 to 8.3 and 15 to 20 mS/cm, washing with similar conditions (1×PBS) and a 1 step elution of human antibodies with 0.1 M acetic acid, 0.15 M sodium chloride, pH 2.7 at 15 to 20 mS/cm or Thermo IgG elution buffer, pH 2.7, at 15 mS/cm.

Purified canine antibodies were analyzed by mass spectroscopy (MS) to confirm the expressed antibody protein molecular weight matched the expected weight based on amino acid sequence. In addition, canine antibodies were analyzed by size exclusion chromatography (SEC) to determine the percent monomer. This data indicated that mouse/canine chimierc IgG1/k mAbs may be expressed transiently in 293-6e cells and are 81% or greater monomeric following purification. This data also indicated that caninized IgG1/k mAbs may be expressed transiently in 293-6e cells and in most cases are 80% or greater monomeric following purification. In some cases, expression of protein may not be detected and in some cases purified caninized mAb is between 24 and 34% monomeric. The data is summarized in Tables 19 and 20.

TABLE 19

Mouse/Canine Chimeric Monoclonal Antibody Characterization Data

| Hybridoma Moniker | Name of Mouse/Canine Chimeric Version | Moniker of Mouse/Canine Chimeric Version | Estimated Expression Level in Cell Supernatants (ug/mL) | % Monomeric mAb |
|---|---|---|---|---|
| PR-1254972 | Mu72 Canine IgG1/k Chimera | PR-1290646 | 3.2 | 97 |
| PR-1254973 | Mu73 Canine IgG1/k Chimera | PR-1290654 | 7 | 88.3 |
| PR-1254977 | Mu77 Canine IgG1/k Chimera | PR-1290656 | 0.3 | 82.4 |
| PR-1254981 | Mu81 Canine IgG1/k Chimera | PR-1290657 | 0.9 | 81 |
| PR-1254982 | Mu82 Canine IgG1/k Chimera | PR-1290658 | 11.9 | 92.3 |

TABLE 21

Caninized Monoclonal Antibody Characterization Data

| Name | Moniker | Lot | Estimated Expression Level in Cell Supernatants (ug/mL) | % Monomeric mAb |
|---|---|---|---|---|
| 72.3 Canine IgG1/k | PR-1313524 | 1804091 | 2.63 | 88.3 |
| 72.4 Canine IgG1/k | PR-1314949 | 1805928 | 1.6 | 81.5 |
| 73.2 Canine IgG1/k | PR-1313520 | 1810546 | 13.4 | 96.5 |
| 73.4 Canine IgG1/k | PR-1314950 | 1805932 | 1.8 | 90 |
| 77.3 Canine IgG1/k | N/A | N/A | 0.7 | 24.8 |
| 77.4 Canine IgG1/k | N/A | N/A | 1 | 34.6 |
| 81.2 Canine IgG1/k | N/A | No mAb detected | No mAb detected | N/A |
| 81.4 Canine IgG1/k | N/A | No mAb detected | No mAb detected | N/A |
| 82.3 Canine IgG1/k | PR-1313519 | 1810585 | 4.4 | 80.7 |
| 82.4 Canine IgG1/k | PR-1313521 | 1816320 | 9.8 | 94.2 |

Example 18

Affinity Analysis of Canine Antibodies

Purified mouse/canine chimeric antibodies and caninized antibodies were analyzed for affinity to canine NGF using a Biacore T100 instrument. Goat anti Canine IgG (Southern Biotech) was immobilized at 5000-10000 RU on a CM5 chip using an amine coupling procedure according to the manufacturer's instructions (Biacore). Canine NGF was injected at 50 uL/min at a concentration range of 50-0.156 nM for the mouse/canine chimeric antibodies or 10-0.156 nM for the caninized antibodies. The association rate was monitored for 5 min and the dissociation rate was monitored

TABLE 20

Production of Caninized Antibodies by Combinations of Caninized Heavy and Light Chains

| Heavy chain | Light chain | | | | | | |
|---|---|---|---|---|---|---|---|
| | 72.2 VH | 72.3 VH | 72.4 VH | 73.2 VH | 73.4 VH | 77.2 VH | 77.3 VH |
| 72.2 VL | 72VHv2/72VLv2 | 72.3 CaIgG1/k | 72VHv4/72VLv2 | 73.5 CaIgG1/k | 73VHv4/72VLv2 | 77VHv2/72VLv2 | 77.5 CaIgG1/k |
| 72.4 VL | 72VHv2/72VLv4 | 72VHv3/72VLv4 | 72.4 CaIgG1/k | 73VHv2/72VLv4 | 73VHv4/72VLv4 | 77VHv2/72VLv4 | 77VHv3/72VLv4 |
| 73.2 VL | 72VHv2/73VLv2 | 72.5 CaIgG/k | 72VHv4/73VLv2 | 73.2 CaIgG1/k | 73VHv4/73VLv2 | 77VHv2/73VLv2 | 77.6 CaIgG1/k |
| 73.4 VL | 72VHv2/73VLv4 | 72VHv3/73VLv4 | 72VHv4/73VLv4 | 73VHv2/73VLv4 | 73.4 CaIgG/k | 77VHv2/73VLv4 | 77VHv3/73VLv4 |
| 77.2 VL | 72VHv2/77VLv2 | 72.6 CaIgG/k | 72VHv4/77VLv2 | 73VHv2/77VLv2 | 73VHv4/77VLv2 | 77VHv2/77VLv2 | 77.3 CaIgG1/k |
| 77.4 VL | 72VHv2/77VLv4 | 72VHv3/77VLv4 | 72VHv4/77VLv4 | 73VHv2/77VLv4 | 73VHv4/77VLv4 | 77VHv2/77VLv4 | 77VHv3/77VLv4 |
| 81.2 VL | 72VHv2/81VLv2 | 72.7 CaIgG/k | 72VHv4/81VLv2 | 73VHv2/81VLv2 | 73VHv4/81VLv2 | 77VHv2/81VLv2 | 77.7 CaIgG1/k |
| 81.4 VL | 72VHv2/81VLv4 | 72VHv3/81VLv4 | 72VHv4/81VLv4 | 73VHv2/81VLv4 | 73VHv4/81VLv4 | 77VHv2/81VLv4 | 77VHv3/81VLv4 |
| 82.2 VL | 72VHv2/82VLv2 | 72VHv3/82VLv2 | 72VHv4/82VLv2 | 73VHv2/82VLv2 | 73VHv4/82VLv2 | 77VHv2/82VLv2 | 77VHv3/82VLv2 |
| 82.3 VL | 72VHv2/82VLv3 | 72.8 CaIgG/k | 72VHv4/82VLv3 | 73VHv2/82VLv3 | 73VHv4/82VLv3 | 77VHv2/82VLv3 | 77.8 CaIgG1/k |
| 82.4 VL | 72VHv2/82VLv4 | 72VHv3/82VLv4 | 72VHv4/82VLv4 | 73VHv2/82VLv4 | 73VHv4/82VLv4 | 77VHv2/82VLv4 | 77VHv3/82VLv4 |

| Heavy chain | Light chain | | | | |
|---|---|---|---|---|---|
| | 77.4 VH | 81.2 VH | 81.4 VH | 82.2 VH | 82.4 VH |
| 72.2 VL | 77VHv4/72VLv2 | 81.5 CaIgG1/k | 81VHv4/72VLv2 | 82.5 CaIgG1/k | 82VHv4/72VLv2 |
| 72.4 VL | 77VHv4/72VLv4 | 81VHv2/72VLv4 | 81VHv4/72VLv4 | 82VHv2/72VLv4 | 82VHv4/72VLv4 |
| 73.2 VL | 77VHv4/73VLv2 | 81.6 CaIgG1/k | 81VHv4/73VLv2 | 82.6 CaIgG1/k | 82VHv4/73VLv2 |
| 73.4 VL | 77VHv4/73VLv4 | 81VHv2/73VLv4 | 81VHv4/73VLv4 | 82VHv2/73VLv4 | 82VHv4/73VLv4 |
| 77.2 VL | 77VHv4/77VLv2 | 81.7 CaIgG1/k | 81VHv4/77VLv2 | 82.7 CaIgG1/k | 82VHv4/77VLv2 |
| 77.4 VL | 77.4 CaIgG1/k | 81VHv2/77VLv4 | 81VHv4/77VLv4 | 82VHv2/77VLv4 | 82VHv4/77VLv4 |
| 81.2 VL | 77VHv4/81VLv2 | 8.12 CaIgG1/k | 81VHv4/81VLv2 | 82.8 CaIgG1/k | 82VHv4/81VLv2 |
| 81.4 VL | 77VHv4/81VLv4 | 81VHv2/81VLv4 | 81.4 CaIgG1/k | 82VHv2/81VLv4 | 82VHv4/81VLv4 |
| 82.2 VL | 77VHv4/82VLv2 | 81VHv2/82VLv2 | 81VHv4/82VLv2 | 82VHv2/82VLv2 | 82VHv4/82VLv2 |
| 82.3 VL | 77VHv4/82VLv3 | 81.8 CaIgG1/k | 81VHv4/82VLv3 | 82.3 CaIgG1/k | 82VHv4/82VLv3 |
| 82.4 VL | 77VHv4/82VLv4 | 81VHv2/82VLv4 | 81VHv4/82VLv4 | 82VHv2/82VLv4 | 82.4 CaIgG1/k | for 10-20 min. The chip surface was regenerated using 50-75 uL 10 mM glycine pH 1.5 at a flow rate of 50-100 uL/min. Data was analyzed using Biaevaluation T100 software version 2.0.2, software, GE Healthcare Life Sciences (Piscataway, N.J.). Overall affinity parameters established for mouse/canine chimeric antibodies is summarized in Table 22 and for caninized antibodies in Table 23. This data indicates that the isolated mouse/canine chimeric anti-NGF mAbs have fast on-rates (from greater than $2 \times 10^6$) and slow off-rates (from less than $3 \times 10^{-3}$). The overall $K_D$s of the mouse/canine anti-NGF mAbs range from about 1300 pM to 1.6 pM. This data also indicates that the isolated caninized chimeric anti-NGF mAbs have fast on-rates (from greater than $6 \times 10^6$) and slow off-rates (from less than $2 \times 10^{-4}$). The overall $K_D$s of the caninized anti-NGF mAbs range from about 42 pM to 1.2 pM.

TABLE 22

Affinity Parameters of Mouse/Canine Chimeric Monoclonal Antibodies to Canine NGF

| Name | Moniker | On-rate (1/M·S) | Off-rate (1/S) | Overall Affinity (M) |
|---|---|---|---|---|
| Mu72 Canine IgG1/k Chimera | PR-1290646 | $2.9 \times 10^6$ | $3.8 \times 10^{-3}$ | $1.3 \times 10^{-9}$ |
| Mu73 Canine IgG1/k Chimera | PR-1290654 | $6.3 \times 10^6$ | $9 \times 10^{-5}$ | $1.4 \times 10^{-11}$ |
| Mu77 Canine IgG1/k Chimera | PR-1290656 | $9.1 \times 10^6$ | $1.9 \times 10^{-4}$ | $2.1 \times 10^{-11}$ |
| Mu81 Canine IgG1/k Chimera | PR-1290657 | $4.2 \times 10^6$ | $3.5 \times 10^{-4}$ | $8.2 \times 10^{-11}$ |
| Mu82 Canine IgG1/k Chimera | PR-1290658 | $8.7 \times 10^6$ | $1.4 \times 10^{-5}$ | $1.6 \times 10^{-12}$ |

TABLE 23

Affinity Parameters of Caninized Monoclonal Antibodies to Canine NGF

| Name | | On-rate (1/M · s) | Off-rate (1/s) | Overall affinity (M) |
|---|---|---|---|---|
| 73.2 canine IgG1/k PR-13113520 | Expt 1 | $6.3 \times 10^6$ | $2.8 \times 10^{-4}$ | $4.4 \times 10^{-11}$ |
| | Expt 2 | $6.9 \times 10^6$ | $2.9 \times 10^{-4}$ | $4.2 \times 10^{-11}$ |
| | Average | $6.6 \times 10^6$ | $2.9 \times 10^{-4}$ | $4.3 \times 10^{-11}$ |
| 82.3 canine IgG1/k PR-13113519 | Expt 1 | $8.2 \times 10^6$ | $2 \times 10^{-5}$ | $2.4 \times 10^{-12}$ |
| | Expt 2 | $8.5 \times 10^6$ | $1.3 \times 10^{-5}$ | $1.6 \times 10^{-12}$ |
| | Average | $8.4 \times 10^6$ | $1.7 \times 10^{-5}$ | $2 \times 10^{-12}$ |
| 82.4 canine IgG1/k PR-13113521 | Expt 1 | $8.6 \times 10^6$ | $1.1 \times 10^{-5}$ | $1.2 \times 10^{-12}$ |
| | Expt 2 | $7.7 \times 10^6$ | $1.2 \times 10^{-5}$ | $1.5 \times 10^{-12}$ |
| | Average | $8.2 \times 10^6$ | $1.2 \times 10^{-5}$ | $1.4 \times 10^{-12}$ |

Example 19

Characterization of Canine Antibodies by the TF-1 Cell Proliferation Potency Assay Purified mouse/canine chimeric antibodies and caninized antibodies were characterized using the TF-1 Cell Proliferation Potency Assay (described previously) using 70 pM canine NGF in the assay. The summarized potency data is in Tables 20 and 21. The data shows that in the presence of 70 pM canine NGF, all of the mouse/canine chimeric anti-NGF antibodies display sub-nM potencies, and all display potencies of less than 50 pM. The data shows that in the presence of 70 pM canine NGF, some of the caninized anti-NGF antibodies have no neutralization potency on 70 pM canine NGF. Some caninized mAbs have sub-nM potencies, and some have potencies of less than 20 pM.

TABLE 24

Potency of Mouse/Canine Chimeric NGF Monoclonal Antibodies on Canine NGF-Induced TF-1 Cell Proliferation

| Name | Moniker | Lot | $IC_{50}$ (nM) |
|---|---|---|---|
| Mu72 Canine IgG1/k Chimera | PR-1290646 | 1785614 | 0.041 |
| Mu73 Canine IgG1/k Chimera | PR-1290654 | 1785658 | 0.008 |
| Mu77 Canine IgG1/k Chimera | PR-1290656 | 1785699 | 0.028 |
| Mu81 Canine IgG1/k Chimera | PR-1290657 | 1778832 | 0.012 |
| Mu82 Canine IgG1/k Chimera | PR-1290658 | 1785732 | 0.007 |

TABLE 25

Potency of Caninized NGF Monoclonal Antibodies on Canine NGF-Induced TF-1 Cell Proliferation (N/A = not applicable)

| Name | Moniker | Lot | $IC_{50}$ (nM) |
|---|---|---|---|
| 72.3 Canine IgG1/k | PR-1313524 | 1804091 | 0 |
| 72.4 Canine IgG1/k | PR-1314949 | 1805928 | 0 |
| 73.2 Canine IgG1/k | PR-1313520 | 1810546 | 0.422 |
| 73.4 Canine IgG1/k | PR-1314950 | 1805932 | 0 |
| 77.3 Canine IgG1/k | N/A | N/A | 0.625 |
| 77.4 Canine IgG1/k | N/A | N/A | 0 |
| 82.3 Canine IgG1/k | PR-1313519 | 1810585 | 0.017 |
| 82.4 Canine IgG1/k | PR-1313521 | 1816320 | 0.016 |

Example 20

Characterization of Solubility and Stability of Caninized Anti-NGF Antibodies

Stock solutions of two caninized anti-NGF antibodies (73.2 canine IgG1/k and 82.4 canine IgG1/k) were obtained. [Are these the canonized Abs produced in Ex. 13?] The antibodies were formulated in phosphate buffer saline (PBS) at concentrations below 5 mg/ml (PBS contains, but is not limited to, the following ingredients: 15 mM phosphate buffer and 150 mM sodium chloride at pH 7.4).

Solubility:

The solubility of the caninized antibodies at high concentrations in PBS were evaluated by concentrating the antibodies with Amicon 30K molecular weight cutoff centrifuge spin filters. The final concentrations were determined by UV absorbance.

At room temperature, 73.2 canine IgG1/k was soluble to at least 54 mg/ml and 82.4 canine IgG1/k was soluble to at least 83 mg/ml. When stored at 5° C. for 5 hours at those concentrations, 73.2 canine IgG1/k formed a gel layer at the bottom of the container while 82.4 canine IgG1/k remained as a uniform solution. When re-equilibrated to room temperature, 73.2 canine IgG1/k became a uniform solution. When 73.2 canine IgG1/k was diluted to 27 mg/ml, it remained as a uniform solution at 5° C.

In comparison, adalimumab, a human antibody, demonstrated a solubility of at least 150 mg/ml at 5° C. and at room temperature. This was observed in a formulation with a pH of 7 and with a sodium chloride concentration of 150 mM. The observations are described in Table 26.

TABLE 26

Solubility of 73.2 canine IgG1/k, 82.4 canine IgG1/k, and human antibody adalimumab in PBS.

| Antibody | Room temperature solubility (mg/ml) | Observations when placed at 5° C. |
|---|---|---|
| 73.2 canine IgG1/k | ≥54 | Gel layer formed at container bottom* |
| 82.4 canine IgG1/k | ≥83 | Remained as solution |
| adalimumab | ≥150 | Remained as solution |

*returned to uniform solution when brought back to room temperature; when diluted to 27 mg/ml, remained as uniform solution at 5° C.

The solubility of 73.2 canine IgG1/k 82.4 canine IgG1/k was also evaluated in 15 mM histidine buffer pH 6.0. This is a buffer typically used to formulate human therapeutic antibodies. The PBS buffer comprising the stock solutions of 73.2 canine IgG1/k and 82.4 canine IgG1/k were exchanged with the histidine buffer using Amicon 30K molecular weight cutoff centrifuge spin filters. Following buffer exchange, the antibodies exhibited white precipitation and solubilities of less than 2 mg/ml at room temperature, as determined by UV absorbance. In comparison, the human antibody adalimumab was observed to reach a concentration of at least 150 mg/ml in 15 mM histidine buffer pH 6.0 at room temperature. These observations are summarized in Table 27.

TABLE 27

Solubility of anti-NGF caninized antibodies 73.2 canine IgG1/k, 82.4 canine IgG1/k and human antibody adalimumab in 15 mM histidine buffer pH 6.0.

| Antibody | Room temperature solubility (mg/ml) | Observations |
|---|---|---|
| 73.2 canine IgG1/k | <2 | White precipitate observed |
| 82.4 canine IgG1/k | <2 | White precipitate observed |
| adalimumab | ≥150 | Remained as solution |

Freeze-Thaw Stability

An assessment of the freeze-thaw (FT) stability of 73.2 canine IgG1/k and 82.4 canine IgG1/k in PBS, and after dilution with PBS to 1 mg/ml, was performed. Both antibodies were frozen at −80° C. for at least 4 hours. They were then thawed in a 30° C. water bath (this constitutes one freeze-thaw cycle). Stability was assessed for four freeze-thaw cycles by size exclusion HPLC (SEC). The freeze-thaw analysis is summarized in Table 28.

TABLE 28

Freeze-thaw stability of 73.2 canine IgG1/k and 82.4 canine IgG1/k at 1 mg/ml in PBS.

| Antibody | Species | Pre-FT | Post FT#1 | Post FT#2 | Post FT#4 |
|---|---|---|---|---|---|
| 73.2 canine IgG1/k | Monomer | 97.4 | 97.3 | 97.3 | 97.2 |
| | Aggregate | 1.7 | 1.8 | 1.8 | 1.8 |
| | Fragment | 0.9 | 0.9 | 0.9 | 1 |
| 82.4 canine IgG1/k | Monomer | 96.6 | 96.6 | 96.6 | 96.1 |
| | Aggregate | 2.9 | 2.9 | 2.9 | 3.2 |
| | Fragment | 0.5 | 0.5 | 0.5 | 0.7 |

Storage Stability and Accelerated Stability:

The stability of 73.2 canine IgG1/k and 82.4 canine IgG1/k when formulated at a concentration of 10 mg/mL and within a pH range of 5 to 8 and at low (~7.5 mM) and high (~>150 mM) ionic strengths was assessed. Stability at these conditions was assessed by monitoring the stability of the antibodies in the following buffers and salt concentrations: (A) 15 mM acetate pH 5; (B) 15 mM acetate pH 5+150 mM NaCl; (C) 15 mM histidine pH 6+150 mM NaCl; (D) 15 mM phosphate pH 7.4; (E) PBS pH 7.4; (F) 15 mM Tris pH 7.5; (G) 15 mM Tris pH 8.0. Sodium azide (0.02%) was added to all buffers as an anti-microbial agent.

Stock solutions of 73.2 canine IgG1/k and 82.3 canine IgG1/k in PBS were concentrated up to 15 mg/ml using 30K molecular weight cutoff centrifuge spin filters. They were then dialyzed against the buffers listed above for 18 hours using mini-dialysis 1 kDa molecular weight cut-off dialysis tubes (GE Healthcare). Following dialysis, samples were diluted with the respective buffers to a final concentration of 10 mg/ml. 150 µl of each sample was aliquoted to cryovials which were then stored at 40° C. or 5° C. Samples were analysed at time=0 hours (T0), at 7 days (T7d), and at 21 days (T21d) and stability was assessed by SEC.

After 21 days at 40° C., accelerated stability testing showed that 73.2 canine IgG1/k and 82.3 canine IgG1/k have much greater fragmentation at pH values below 7.4 than at pH values above 7.4. In comparison, the human antibody adalimumab, exhibited less fragmentation within the pH range 4 to 8 over 21 days at 40° C. In particular, the fragmentation of adalimumab at pH 6 was much less than the fragmentation of 73.2 canine IgG1/k or 82.4 canine IgG1/k at pH 6. Also, adalimumab at the higher stress condition of pH 4 showed equal or less fragmentation compared to 73.2 canine IgG1/k or 82.4 canine IgG1/k at the lower stress condition of pH 5. The results of the stability analyses and fragmentation profiles are shown, respectively, in Tables 25 and 26. These data suggest that canine IgG1/k monoclonal antibodies have a different degradation profile compared to that of human IgG1/k monoclonal antibodies. Specifically, the fragmentation appears to be more extensive for canine IgG1/k antibodies than for human antibodies at pH 6 and below.

TABLE 29

Stability data from SEC for 73.2 canine IgG1/k, 82.4 canine IgG1/k and human antibody adalimumab in different formulations at 7 and 21 days at 5° C. and at 40° C.

| Buffer | Percentage Monomer | | | Percentage Aggregate | | | Percentage Fragment | | |
|---|---|---|---|---|---|---|---|---|---|
| | T0 | T7d | T21d | T0 | T7d | T21d | T0 | T7d | T21d |
| 73.2 canine IgG1/k at 5° C. | | | | | | | | | |
| A (pH 5) | 94.6 | 91.4 | 90.3 | 2.9 | 3.1 | 3.4 | 2.6 | 5.5 | 6.2 |
| B (pH 5) | 95.2 | 98.2 | 98.2 | 3.4 | 0.4 | 0.5 | 1.4 | 1.4 | 1.3 |
| C (pH 6) | 93.9 | 98.0 | 97.8 | 4.4 | 0.5 | 0.7 | 1.8 | 1.5 | 1.5 |
| D (pH 7.4) | 94.3 | 97.9 | 97.7 | 4.7 | 0.6 | 0.8 | 1.0 | 1.5 | 1.5 |
| E (pH 7.4) | 94.5 | 97.9 | 97.8 | 4.5 | 0.5 | 0.8 | 1.0 | 1.6 | 1.5 |
| F (pH 7.5) | 94.5 | 98.0 | 97.8 | 4.0 | 0.5 | 0.8 | 1.6 | 1.5 | 1.5 |
| G (pH 8.0) | 93.7 | 97.8 | 97.6 | 4.6 | 0.7 | 0.9 | 1.7 | 1.5 | 1.5 |
| 73.2 canine IgG1/k at at 40° C. | | | | | | | | | |
| A (pH 5) | 94.6 | 81.3 | 79.0 | 2.9 | 4.5 | 5.1 | 2.6 | 14.2 | 15.9 |
| B (pH 5) | 95.2 | 92.1 | 90.9 | 3.4 | 0.6 | 1.2 | 1.4 | 7.4 | 7.8 |
| C (pH 6) | 93.9 | 94.4 | 91.6 | 4.4 | 0.6 | 1.1 | 1.8 | 5.0 | 7.3 |
| D (pH 7.4) | 94.3 | 97.5 | 96.6 | 4.7 | 0.9 | 1.6 | 1.0 | 1.5 | 1.8 |
| E (pH 7.4) | 94.5 | 98.0 | 97.3 | 4.5 | 0.6 | 1.1 | 1.0 | 1.4 | 1.6 |
| F (pH 7.5) | 94.5 | 97.5 | 96.3 | 4.0 | 0.9 | 1.8 | 1.6 | 1.6 | 1.9 |
| G (pH 8.0) | 93.7 | 97.0 | 95.2 | 4.6 | 1.2 | 2.6 | 1.7 | 1.8 | 2.2 |

TABLE 29-continued

Stability data from SEC for 73.2 canine IgG1/k, 82.4 canine IgG1/k and human antibody adalimumab in different formulations at 7 and 21 days at 5° C. and at 40° C.

82.4 canine IgG1/k at 5° C.

| | | | | | | | | | |
|---|---|---|---|---|---|---|---|---|---|
| A (pH 5) | 96.7 | 98.1 | 98.7 | 2.3 | 1.3 | .8 | 1.0 | 0.5 | 0.5 |
| B (pH 5) | 96.3 | 97.2 | 97.3 | 2.4 | 2.3 | 2.3 | 1.3 | 0.5 | 0.4 |
| C (pH 6) | 97.0 | 97.1 | 97.1 | 2.6 | 2.3 | 2.3 | 0.4 | 0.6 | 0.6 |
| D (pH 7.4) | 96.4 | 97.0 | 97.1 | 2.5 | 2.4 | 2.5 | 1.0 | 0.5 | 0.4 |
| E (pH 7.4) | 96.7 | 96.8 | 96.8 | 2.8 | 2.5 | 2.6 | 0.5 | 0.7 | 0.6 |
| F (pH 7.5) | 96.8 | 97.1 | 96.9 | 2.9 | 2.5 | 2.5 | 0.2 | 0.5 | 0.6 |
| G (pH 8.0) | 96.6 | 96.9 | 96.9 | 2.5 | 2.5 | 2.5 | 0.9 | 0.6 | 0.6 |

82.4 canine IgG1/k at 40° C.

| | | | | | | | | | |
|---|---|---|---|---|---|---|---|---|---|
| A (pH 5) | 96.7 | 93.1 | 87.8 | 2.3 | 2.8 | 4.2 | 1.0 | 4.1 | 8.0 |
| B (pH 5) | 96.3 | 93.3 | 91.3 | 2.4 | 2.5 | 3.1 | 1.3 | 4.3 | 5.6 |
| C (pH 6) | 97.0 | 94.1 | 92.5 | 2.6 | 2.3 | 2.7 | 0.4 | 3.5 | 4.8 |
| D (pH 7.4) | 96.4 | 93.5 | 93.8 | 2.5 | 3.4 | 3.3 | 1.0 | 3.1 | 2.9 |
| E (pH 7.4) | 96.7 | 95.1 | 93.6 | 2.8 | 2.4 | 2.6 | 0.5 | 2.5 | 3.8 |
| F (pH 7.5) | 96.8 | 93.4 | 923.6 | 2.9 | 2.6 | 3.0 | 0.2 | 4.0 | 0.5 |
| G (pH 8.0) | 96.6 | 94.8 | 92.7 | 2.5 | 2.8 | 3.5 | 0.9 | 2.4 | 0.4 | adalimumab at 40° C.

| PH | Percentage Monomer | | | Percentage Aggregate | | | Percentage Fragment | | |
|---|---|---|---|---|---|---|---|---|---|
| | T0 | T7d | T21d | T0 | T7d | T21d | T0 | T7d | T21d |
| 4 | 99 | 98 | 95 | <1 | <2 | 0.5 | <1 | <2 | 4.5 |
| 6 | 99 | 99 | 99 | <1 | <1 | 0.3 | <1 | <1 | 0.7 |
| 8 | 99 | 98 | 98 | <1 | <2 | 1.2 | <1 | <2 | 0.8 |

TABLE 30

Fragmentation profile from SEC for 73.2 canine IgG1/k, 82.4 canine IgG1/k and human antibody adalimumab in different formulations at 21 days and at 40° C.

| Antibody | Buffer | Increase in Percent Fragmentation over 21 days at 40° C. |
|---|---|---|
| 73.2 canine IgG1/k | A (pH 5) | 13.3 |
| | B (pH 5) | 6.4 |
| | C (pH 6) | 5.5 |
| | D (pH 7.4) | 0.8 |
| | E (pH 7.4) | 0.6 |
| | F (pH 7.5) | 0.3 |
| | G (pH 8.0) | 0.5 |
| 82.4 canine IgG1/k | A (pH 5) | 7.0 |
| | B (pH 5) | 4.3 |
| | C (pH 6) | 4.4 |
| | D (pH 7.4) | 1.9 |
| | E (pH 7.4) | 3.3 |
| | F (pH 7.5) | 0.3 |
| | G (pH 8.0) | −0.5 |
| adalimumab | pH 4 | <4.5 |
| | pH 6 | <0.7 |
| | pH 8 | <0.8 |

Example 21

Canine Single Dose PK Study and Antigen Bridging Assay for PK Serum Sample Analysis The serum levels of 73.2 canine IgG1/k and 82.4 canine IgG1/k were analyzed following a single dose of 4.5 mg/kg (intravenous or subcutaneous) in mongrel dogs. Following the injection, 13 samples of venous blood were collected over 672 hours. Blood samples were allowed to clot and the serum removed for antibody quantitation.

An NGF bridging assay was developed to quantitate canine anti-NGF mAbs in serum. Streptavidin-coated 96-well plates (MSD #L11SA-1) were blocked with Blocker A (MSD #R93BA-4). Canine anti-NGF antibody present in serum (or in PBS) was mixed with equi-molar ratios of biotin-tagged NGF and Sulfo-tagged NGF (Sulfo Reagent MSD #R91AN-1) and incubated to form an NGF+antibody complex. The final concentration of the biotin-tagged NGF and sulfo-tagged NGF in the assay was between 1-2 nM. NGF-antibody complexes were added to the streptavidin-coated plate and allowed to bind for 60 minutes. Following incubation, plates were washed with PBS plus 0.05% Tween-20, and bound NGF-antibody complexes were detected in Read Buffer T (MSD #R92TC-1) on an MSD SECTOR Imager 6000. Data was quantitated to estimate the total amount of antibody in ug/mL of a sample liquid and is provided below in Tables 27-30.

TABLE 31

Serum Concentrations of 82.4 canine IgG1/k Following a Single Subcutaneous Dose

| Hours post injection | Dog # | | | | |
|---|---|---|---|---|---|
| | 1073305 | 1072602 | 1072104 | 1072306 | 1072105 |
| | | | ug/mL | | |
| 0 | 0.0 | 0.0 | 0 | 0 | 0.1 |
| 0.25 | 2.6 | 0.4 | 0.0 | 2.24 | 0.1 |
| 1 | 9.0 | 2.2 | 0.9 | 9.07 | 0.4 |
| 8 | 31.5 | 17.7 | 13.8 | 32.55 | 12.8 |
| 12 | 41.1 | 20.5 | 18.7 | 33.31 | 24.5 |
| 24 | 42.2 | 25.6 | 23.2 | 35.73 | 23.8 |
| 48 | 52.3 | 37.2 | 36.3 | 41.35 | 35.3 |
| 72 | 51.2 | 41.1 | 34.4 | 38.91 | 36.8 |
| 144 | 47.1 | 42.6 | 35.2 | 33.46 | 36.7 |
| 240 | 39.0 | 32.4 | 29.0 | 26.03 | 31.7 |
| 336 | 30.9 | 28.2 | 24.1 | 19.99 | 26.8 |
| 504 | 20.1 | 18.3 | 16.0 | 11.03 | 18.6 |
| 672 | 16.3 | 12.8 | 10.4 | 5.81 | 5.4 |

TABLE 32

Serum Concentrations of 82.4 canine IgG1/k Following a Single Intravenous Dose

| Hours post injection | Dog # | | | | |
|---|---|---|---|---|---|
| | 1072705 | 1073804 | 1073303 | 1073903 | 1074502 |
| | | | ug/mL | | |
| 0 | 0 | 0 | 0 | 0 | 0 |
| 0.25 | 102.6 | 83.1 | 84.0 | 80.1 | 81.7 |
| 1 | 106.7 | 70.1 | 87.4 | 74.1 | 81.9 |
| 8 | 88.4 | 65.7 | 68.1 | 67.4 | 68.9 |
| 12 | 91.5 | 61.6 | 62.6 | 62.1 | 59.3 |
| 24 | 87.4 | 60.0 | 57.2 | 53.9 | 53.0 |
| 48 | 76.6 | 49.9 | 52.6 | 50.9 | 50.2 |
| 72 | 60.3 | 49.1 | 46.0 | 40.8 | 44.6 |
| 144 | 45.7 | 43.1 | 36.1 | 35.7 | 36.0 |
| 240 | 37.2 | 34.4 | 32.6 | 24.3 | 32.6 |
| 336 | 31.7 | 32.7 | 24.8 | 20.6 | 20.1 |

TABLE 32-continued

Serum Concentrations of 82.4 canine IgG1/k Following a Single Intravenous Dose

| Hours post injection | Dog # | | | | |
|---|---|---|---|---|---|
| | 1072705 | 1073804 | 1073303 | 1073903 | 1074502 |
| | ug/mL | | | | |
| 504 | 23.5 | 17.4 | 18.5 | 12.2 | 12.8 |
| 672 | 15.2 | 10.7 | 12.5 | 7.3 | 8.3 |

TABLE 33

Serum Concentrations of 73.2 canine IgG1/k Following a Single Subcutaneous Dose

| Hours post injection | Dog # | | | |
|---|---|---|---|---|
| | 1072607 | 1074307 | 1072606 | 1074503 |
| | ug/mL | | | |
| 0 | 0 | 0 | 0 | 0 |
| 0.25 | 0 | 0 | 2.1 | 0 |
| 1 | 1.0 | 5.9 | 4.7 | 0.0 |
| 8 | 18.6 | 31.3 | 18.7 | 7.4 |
| 12 | 22.7 | 32.5 | 21.3 | 8.7 |
| 24 | 26.8 | 33.2 | 24.2 | 12.0 |
| 48 | 33.7 | 35.9 | 28.4 | 16.2 |
| 72 | 35.0 | 37.6 | 30.7 | 19.4 |
| 144 | 34.9 | 37.4 | 30.2 | 21.8 |
| 240 | 31.6 | 31.8 | 26.8 | 22.0 |
| 336 | 24.4 | 24.7 | 22.6 | 16.5 |
| 504 | 15.3 | 14.3 | 13.8 | 10.6 |
| 672 | 6.8 | 9.2 | 5.1 | 5.4 |

TABLE 34

Serum Concentrations of 73.2 canine IgG1/k Following a Single Intravenous Dose

| Hours post injection | Dog # | | |
|---|---|---|---|
| | 1072804 | 1073304 | 1072604 |
| | ug/mL | | |
| 0 | 0 | 0 | 0 |
| 0.25 | 93.6 | 33.2 | 108.5 |
| 1 | 86.3 | 30.8 | 103.1 |
| 8 | 76.9 | 22.1 | 85.4 |
| 12 | 72.1 | 21.4 | 80.5 |
| 24 | 63.0 | 17.1 | 68.0 |
| 48 | 54.6 | 14.6 | 56.8 |
| 72 | 49.4 | 13.5 | 50.8 |
| 144 | 41.4 | 10.2 | 41.4 |
| 240 | 35.4 | 8.9 | 30.8 |
| 336 | 30.5 | 6.3 | 20.9 |
| 504 | 22.2 | 4.0 | 3.4 |
| 672 | 14.8 | 3.4 | 0.0 |

Example 22

Pharmacokinetic Analysis of Serum Concentration Data

Pharmacokinetic parameters for both intravenous (IV) and subcutaneous (SC) dosing routes were calculated for each animal using WinNonlin software (Pharsight Corporation, Mountain View, Calif.) by noncompartmental analysis. Other calculations, e.g. mean, standard deviation (SD), and percent subcutaneous bioavailability (F: %) were carried out using Microsoft Excel software (Microsoft Corporation Redmond, Wash.). The data is shown in Table 35 and 36.

TABLE 35

Pharmacokinetic Analysis of 73.2 canine IgG1/k Following a Single Intravenous Dose

| IV | | | SC | | | |
|---|---|---|---|---|---|---|
| T½ (day) | Vss (mL/kg) | Cl (mL/h/kg) | T½ (day) | Cmax (ug/mL) | Tmax (day) | % F |
| 14.8* | 71 | 0.15 | 8.0* | 31.3 | 4.8 | 51 |

*Harmonic Mean

TABLE 36

Pharmacokinetic Analysis of 82.4 canine IgG1/k Following a Single Intravenous Dose

| IV | | | SC | | | |
|---|---|---|---|---|---|---|
| T½ (day) | Vss (mL/kg) | Cl (mL/h/kg) | T½ (day) | Cmax (ug/mL) | Tmax (day) | % F |
| 10.9* | 73 | 0.19 | 11.6* | 41.9 | 3.0 | 94 |

*Harmonic Mean

The data indicates that canine mAbs 73.2 and 82.4 have a half-life of about 8 to about 15 days when dosed IV or SC, suggesting that these molecules exhibit mammalian antibody-like half-lives and overall PK parameters.

Example 23

ELISA for Titering Canine Antibodies

To quantitate canine antibodies in cell supernatants (or other liquids), high-binding EIA plates (Costar #9018) were coated with polyclonal goat anti-dog IgG antibodies (Rockland #604-1102) at 4 ug/ml in PBS. After blocking with 2% non-fat milk in PBS, canine monoclonal antibodies were added to the plates and the plates were washed with PBS plus 0.05% Tween-20. Bound canine mAbs were detected with HRP-tagged goat anti-dog IgG antibodies (Rockland #604-1302) at 0.1 ug/ml. Plates were washed with PBS plus 0.05% Tween-20. Canine mAbs were detected by addition of TMB substrate (Neogen #308177), and the reaction was stopped with 1N HCl. Bound canine antibodies were quantitated by absorption at 450 nM to estimate the total amount of antibody in ug/mL of a sample liquid.

The present disclosure incorporates by reference in their entirety techniques well known in the field of molecular biology. These techniques include, but are not limited to, techniques described in the following publications:

Ausubel, F. M. et al. eds., *Short Protocols In Molecular Biology* (4th Ed. 1999) John Wiley & Sons, NY. (ISBN 0-471-32938-X).

Lu and Weiner eds., *Cloning and Expression Vectors for Gene Function Analysis* (2001) BioTechniques Press. Westborough, Mass. 298 pp. (ISBN 1-881299-21-X).

Kontermann and Dubel eds., *Antibody Engineering* (2001) Springer-Verlag. New York. 790 pp. (ISBN 3-540-41354-5).

Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4).

Sambrook, J. et al. eds., *Molecular Cloning: A Laboratory Manual* (2d Ed. 1989) Cold Spring Harbor Laboratory Press, NY. Vols. 1-3. (ISBN 0-87969-309-6).

Winnacker, E. L. *From Genes To Clones: Introduction To Gene Technology* (1987) VCH Publishers, NY (translated by Horst Ibelgaufts). 634 pp. (ISBN 0-89573-614-4).

All references, publications, and patent applications disclosed herein are hereby incorporated by reference in their entirety.

Although a number of embodiments, aspects and features have been described above, it will be understood by those skilled in the art that modifications and variations of the described embodiments and features may be made without departing from the present disclosure or the disclosure as defined in the appended claims.

What is claimed is:

1. An antibody comprising:

(a) a heavy chain variable region comprising an amino acid sequence having a sequence of SEQ ID NO: 192 and complementary determining regions (CDRs) consisting of SEQ ID NOS: 79, 80, and 81; and (b) a light chain variable region comprising an amino acid sequence having a sequence of SEQ ID NO: 193 and CDRs consisting of SEQ ID NOS: 82, 83 and 84.

2. The antibody of claim 1, wherein the antibody comprises a heavy chain human immunoglobulin constant domain selected from the group consisting of IgM constant domain, IgG4 constant domain, IgG1 constant domain, IgE constant domain, IgG2 constant domain, IgG3 constant domain, and IgA constant domain.

3. The antibody of claim 1, wherein the antibody comprises a heavy chain canine immunoglobulin constant domain selected from the group consisting of IgM constant domain, IgG4 constant domain, IgG 1 constant domain, IgE constant domain, IgG2 constant domain, IgG3 constant domain, and IgA constant domain.

4. The antibody of claim 1, wherein the antibody comprises a heavy chain feline immunoglobulin constant domain.

5. The antibody of claim 1, wherein the antibody comprises a heavy chain equine immunoglobulin constant domain.

6. The antibody of claim 1, comprising a constant region having an amino acid sequence selected from the group consisting of SEQ ID NO: 52 and SEQ ID NO: 54.

7. The antibody of claim 1, wherein the antibody is selected from the group consisting of: an immunoglobulin molecule, disulfide linked Fv, monoclonal antibody, scFv, chimeric antibody, single domain antibody, CDR-grafted antibody, diabody, humanized antibody, caninized mAb, canine mAb, feline mAb, felinized mAb, equine mAb, equinized mAb, a multispecific antibody, a Fab, a dual specific antibody, a DVD-Ig, a Fab', a bispecific antibody, an F(ab')2, and an Fv.

8. The antibody of claim 1, wherein the antibody neutralizes NGF.

9. A pharmaceutical or diagnostic composition comprising an antibody of claim 1, and a pharmaceutically acceptable carrier, diluent or excipient.

10. The pharmaceutical composition of claim 9, comprising a therapeutically effective amount of the antibody.

11. The pharmaceutical composition of claim 9, comprising at least one preservative, wherein the preservative is methylparaben, propylparaben, benzyl alcohol, chlorobutanol or benzalkonium chloride.

12. The pharmaceutical composition of claim 9, wherein the pH of the composition is between 7.0 and 8.0.

13. The pharmaceutical composition of claim 9, wherein the composition has a half-life of from about 8.0 to about 15.0 days when dosed intravenously or subcutaneously.

* * * * *